(12) United States Patent
Timmers et al.

(10) Patent No.: US 8,431,564 B2
(45) Date of Patent: Apr. 30, 2013

(54) RING-ANNULATED DIHYDROPYRROLO[2,1-α]ISOQUINOLINES

(75) Inventors: Cornelis Marius Timmers, Oss (NL); Hubert Jan Jozef Loozen, Oss (NL); Herman Thijs Stock, Oss (NL)

(73) Assignee: Merck Sharp & Dohme B.V., Oss (NL)

( * ) Notice: Subject to any disclaimer, the term of this patent is extended or adjusted under 35 U.S.C. 154(b) by 295 days.

(21) Appl. No.: 12/844,007

(22) Filed: Jul. 27, 2010

(65) Prior Publication Data
US 2011/0028450 A1 Feb. 3, 2011

Related U.S. Application Data

(60) Provisional application No. 61/229,475, filed on Jul. 29, 2009.

(51) Int. Cl.
| | | |
|---|---|---|
| C07D 471/00 | (2006.01) |
| C07D 491/00 | (2006.01) |
| C07D 498/00 | (2006.01) |
| C07D 513/00 | (2006.01) |
| C07D 515/00 | (2006.01) |
| A61K 31/00 | (2006.01) |
| A61K 31/553 | (2006.01) |
| A61K 31/554 | (2006.01) |
| A61K 31/55 | (2006.01) |
| A61K 31/54 | (2006.01) |
| A61K 31/535 | (2006.01) |
| A61K 31/44 | (2006.01) |
| A61K 31/50 | (2006.01) |

(52) U.S. Cl.
USPC ............ 514/210.21; 514/211.08; 514/211.09; 514/212.01; 514/218; 514/222.2; 514/228.8; 514/278; 514/285; 514/287; 514/247; 546/70

(58) Field of Classification Search .................. None
See application file for complete search history.

(56) References Cited

FOREIGN PATENT DOCUMENTS

| WO | 00/08015 A2 | 2/2000 |
|---|---|---|
| WO | 02/09706 A1 | 2/2002 |
| WO | 03/004028 A1 | 1/2003 |
| WO | 2004/014917 A2 | 2/2004 |
| WO | 2004/031182 A1 | 4/2004 |
| WO | 2004/056780 A2 | 7/2004 |
| WO | 2005/087765 A1 | 9/2005 |
| WO | 2006/117023 A1 | 11/2006 |
| WO | 2006/117368 A1 | 11/2006 |
| WO | 2006/117370 A1 | 11/2006 |
| WO | 2006/117371 A1 | 11/2006 |

OTHER PUBLICATIONS

Marx, MA. et al. Synthetic Design for Combinatorial Chemistry. Solution and Polymer-Supported Synthesis of Polycyclic Lactams by Intramolecular Cyclization of Azomethine Ylides. J. Am. Chem. Soc. 1997, vol. 119, p. 6153, left column, line 10, p. 6160, table 3, entry 1.*
Armstrong, RW. et al. Multiple-Component Condensation Strategies for Combinatorial Library Synthesis. Acc. Chem. Res. 1996, vol. 29, p. 123, paragraph 3, lines 1-5, p. 131, conclusion, lines 9-12.*
M. A. Marx et al., J. Am. Chem. Soc., vol. 119, pp. 6153-6167 (1997).
Written Opinion for U.S. Appl. No. 12/844,007; mailed; issued Jan. 31, 2012.

* cited by examiner

*Primary Examiner* — Rita Desai
*Assistant Examiner* — Ben S Michelson
(74) *Attorney, Agent, or Firm* — Kendrick L. Vidale; John C. Todaro

(57) ABSTRACT

The invention relates to ring-annulated dihydropyrrolo[2,1-a]isoquinoline compounds according to general Formula I

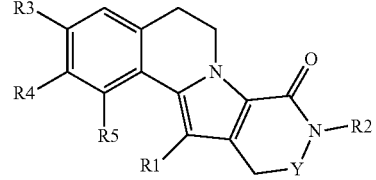

Formula I or a pharmaceutically acceptable salt thereof. The compounds can be used for the treatment of infertility.

12 Claims, No Drawings

RING-ANNULATED DIHYDROPYRROLO[2,1-α]ISOQUINOLINES

The present invention relates to ring-annulated dihydropyrrolo[2,1-c]isoquinoline derivatives, to pharmaceutical compositions comprising the same and to the use of said compounds for the manufacture of medicaments for the treatment of infertility.

Gonadotropins serve important functions in a variety of bodily functions including metabolism, temperature regulation and the reproductive process. Gonadotropins act on specific gonadal cell types to initiate ovarian and testicular differentiation and steroidogenesis. The pituitary gonadotropin FSH (follicle stimulating hormone), for example, plays a pivotal role in the stimulation of follicle development and maturation whereas LH (luteinizing hormone) induces ovulation (Sharp, R. M. *Clin Endocrinol.* 33, 787-807 (1990); Dorrington and Armstrong, *Recent Prog. Horm. Res.* 35, 301-342 (1979)). Currently, FSH is applied clinically for ovarian stimulation, i.e. controlled ovarian stimulation for in vitro fertilisation (IVF) and induction of ovulation in infertile anovulatory women (Insler, V., Int. *J. Fertility* 33, 85-97 (1988), Navot and Rosenwaks, *J. Vitro Fert. Embryo Transfer* 5, 3-13 (1988)), as well as for male hypogonadism and male infertility.

The gonadotropin FSH is released from the anterior pituitary under the influence of gonadotropin-releasing hormone and estrogens, and from the placenta during pregnancy. In the female, FSH acts on the ovaries promoting development of follicles and is the major hormone regulating secretion of estrogens. In the male, FSH is responsible for the integrity of the seminiferous tubules and acts on Sertoli cells to support gametogenesis. Purified FSH is used clinically to treat infertility in females and for some types of failure of spermatogenesis in males. Gonadotropins destined for therapeutic purposes can be isolated from human urine sources and are of low purity (Morse et al, *Amer. J. Reproduct. Immunol. and Microbiology* 17, 143 (1988)). Alternatively, they can be prepared as recombinant gonadotropins. Recombinant human FSH is available commercially and is being used in assisted reproduction (Olijve et al. *Mol. Hum. Reprod.* 2, 371-381 (1996); Devroey et al. *Lancet* 339, 1170-1171 (1992)).

The actions of the FSH hormone are mediated by a specific membrane receptor that is a member of the large family of G-protein coupled receptors. These receptors consist of a single polypeptide with seven transmembrane domains and are able to interact with the Gs protein, leading to the activation of adenylate cyclase.

The FSH receptor (FSHR) is a highly specific target in the ovarian follicle growth process and is exclusively expressed in the ovary. Low molecular weight FSHR agonists can be used for the same clinical purposes as native FSH, i.e. for the treatment of infertility and for controlled ovarian stimulation preceeding in vitro fertilisation.

Certain tetrahydroquinoline derivatives have recently been disclosed in the International Application WO 2003/004028 (AKZO NOBEL N.V.) as FSHR modulating substances, either having agonistic or antagonistic properties.

Low molecular weight FSH mimetics with agonistic properties were disclosed in the International Application WO 2000/08015 (Applied Research Systems ARS Holding N.V.); WO 2004/031182 (Applied Research Systems ARS Holding N.V.); WO 2002/09706 (Affymax Research Institute); WO 2005/087765 (Arena Pharmaceuticals, Inc); WO 2006/117368 (AKZO NOBEL N.V.); WO 2006/117370 (AKZO NOBEL N.V.); WO 2006/117371 (AKZO NOBEL N.V.) and in WO 2006/117023 (AKZO NOBEL N.V.).

There clearly is a need for low molecular weight hormone mimetics that selectively activate the FSH receptor.

To that aim, the present invention provides ring-annulated dihydropyrrolo[2,1-a]isoquinoline derivatives.

More specifically, the present invention provides ring-annulated dihydropyrrolo[2,1-c]isoquinoline compounds according to formula I

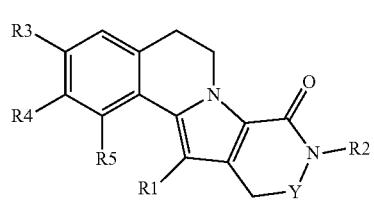

Formula I or a pharmaceutically acceptable salt thereof.

In this Formula R1 through R5 have the following definitions:

R1 is phenyl, (2-5C)heteroaryl, (3-6C)cycloalkyl, (1-6C)alkyl, (2-5C)heterocycloalkyl or (2-5C)heterocycloalkenyl, each optionally substituted with one or more (1-3C)alkyl or halogen; or
R1 is halogen
R2 is H or (1-4C)alkyl;
R3 is hydroxyl, (1-3C)alkoxy; (1-3C)alkylthio or (1-4C)alkyl;
R4 is (1-5C)heteroaryl, (2-5C)heterocycloalkyl or (2-5C)heterocycloalkenyl, each optionally substituted with one or more hydroxy, cyano, halogen, (1-3C)alkoxy or (1-6C)alkyl, the alkyl group optionally substituted with one or more hydroxy or fluorine; or
R4 is halogen, nitro, cyano, amino, carboxylic acid or N-hydroxy-imidamide; or
R4 is (1-6C)alkyl, (2-6C)alkenyl, (2-6C)alkynyl, (3-6C)cycloalkyl, (1-6C)alkoxy, (1-6C)alkylthio, (1-6C)alkylOC(O)(1-6C)alkyl, each optionally substituted with hydroxy hydroxy, oxo, cyano or fluorine; or
R4 is —NH(CO)R6, —NHSO2R6, —NHR6, —C(O)N(R7)R8, —C(O)OR6, —S(O)R6 or —SO2R6;
R5 is H or halogen;
R6 is (1-6C)alkyl, (2-6C)alkenyl or (2-5C)heteroaryl, each optionally substituted with one or more (1-3C)alkyl, (1-3C)alkoxy, hydroxy or halogen; or
R6 is (di)[(1-4C)alkyl]amino(1-4C)alkyl, (di)[(1-4C)alkyl]aminoC(O)(1-4C)alkyl or (2-5C)heterocycloalkyl(1-4C)alkyl, the heterocycloalkyl group optionally substituted with one or more (1-4C)alkyl, oxo, hydroxy, fluorine or (di)[(1-4C)alkyl]amino(1-4C)alkyl;
Y is a bond, Y is $(CH_2)_n$ or Y is $X(CH_2)_m$, wherein one or more of the hydrogen atoms in the $(CH_2)_n$ or $(CH_2)_m$ groups in Y may optionally be substituted with (1-3C)alkyl, fluorine or hydroxy;
X is O, S or NR9;
R7 is hydrogen or (1-6C)alkyl, optionally substituted with one or more hydroxyl groups;
R8 is hydrogen, (1-6C)alkyl, (1-6C)alkenyl or (2-5C)heteroaryl, each optionally substituted with one or more (1-3C) alkyl, (1-3C)alkoxy, hydroxy or halogen; or
R8 is (2-5C)heterocycloalkyl(1-4C)alkyl, the heterocycloalkyl group optionally substituted with (1-4C)alkyl or (di)[(1-4C)alkyl]amino(1-4C)alkyl; or
R7 and R8 can form, together with the interconnecting nitrogen, a (2-5)heterocycloalkyl group, optionally substituted with hydroxy, (1-6C)alkoxycarbonyl or (1-6C)alkyl, the alkyl group optionally substituted with one or more hydroxy or fluorine;

R9 is hydrogen or R10-carbonyl;

R10 is (1-3C)alkyl, optionally substituted with halogen;

n is 0-4; and m is 2 or 3.

The ring-annulated dihydropyrrolo[2,1-c]isoquinoline derivatives according to the present invention are potent FSH receptor activators and can be used for the same clinical purposes as native FSH since they behave like agonists, with the advantage that they may be prepared synthetically, may display altered stability properties and may be administered differently.

Thus, the FSH-receptor agonists of the present invention may be used for the treatment of fertility disorders e.g. controlled ovarian stimulation and IVF procedures.

The term (1-3C)alkyl as used in the definition means an alkyl group having 1-3 carbon atoms, being methyl, ethyl, n-propyl or isopropyl.

The term (1-4C)alkyl as used in the definition means a branched or unbranched alkyl group having 1-4 carbon atoms, being methyl, ethyl, n-propyl, isopropyl, butyl, isobutyl, sec-butyl and tert-butyl.

The term (1-6C)alkyl means a branched or unbranched alkyl group having 1-6 carbon atoms, for example methyl, ethyl, n-propyl, isopropyl, butyl, tert-butyl, n-pentyl and n-hexyl. (1-5C)Alkyl groups are preferred, (1-4C)alkyl being the most preferred.

The term (3-6C)cycloalkyl means a cycloalkyl group having 3-6 carbon atoms, such as cyclopropyl, ethylcyclopropyl, cyclobutyl, methylcyclobutyl, cyclopentyl and cyclohexyl.

The term (2-6C)alkenyl means a branched or unbranched alkenyl group having 2-6 carbon atoms, such as ethenyl, 2-butenyl, and n-pentenyl.

The term (2-6C)alkynyl means a branched or unbranched alkynyl group having 2-6 carbon atoms, such as ethynyl, propynyl and n-pentynyl.

The term (1-6C)alkoxyC(O)(1-6C)alkyl means an alkoxycarbonyl group as defined attached to an alkyl group containing 1-6 carbon atoms with the same meaning as previously defined.

The term (di)[(1-4C)alkyl]amino(1-4C)alkyl as used herein means a (di)alkylamino group, the alkyl group(s) of which each contain(s) 1-4 carbon atoms with the same meaning as previously defined, connected via the amino group to an alkyl group which contains 1-4 carbon atoms with the same meaning as previously defined.

The term (di)[(1-4C)alkyl]aminoC(O)(1-4C)alkyl as used herein means a (di)alkylaminocarbonyl group, the alkyl group(s) of which each contain(s) 1-4 carbon atoms with the same meaning as previously defined, connected via the amino carbonyl group to an alkyl group which contains 1-4 carbon atoms with the same meaning as previously defined.

The term (2-5C)heterocycloalkyl(1-4C)alkyl means a heterocycloalkylalkyl group, the heterocycloalkyl group of which contains 2-5 carbon atoms, preferably 3-5 carbon atoms, with the same meaning as previously defined and the alkyl group of which contains 1-4 carbon atoms with the same meaning as previously defined.

The term (1-6C)alkoxy means an alkoxy group having 1-6 carbon atoms, the alkyl moiety having the same meaning as previously defined. (1-3C)Alkoxy groups are preferred.

The term (1-3C)alkoxy means an alkoxy group having 1-3 carbon atoms, the alkyl moiety having the same meaning as previously defined.

The term (1-3C)alkylthio means an alkylthio group having 1-3 carbon atoms, the alkyl group of which contains 1-3 carbon atoms with the same meaning as previously defined.

The term (1-3C)alkylcarbonyl means an alkylcarbonyl group the alkyl group of which contains 1-3 carbon atoms.

The term (1-6C)alkylthio means an alkylthio group having 1-6 carbon atoms, the alkyl group of which contains 1-6 carbon atoms with the same meaning as previously defined. Preferred is (1-3C)alkylthio.

The term (2-5C)heteroaryl means an aromatic group having 2-5 carbon atoms and 1-3 heteroatoms selected from N, O and S, like but not limited to imidazolyl, thiadiazolyl, pyrazinyl, pyrazolyl, pyrimidinyl, pyridinyl, thienyl or furyl. Preferred number of heteroatoms is one or two. Preferred heteroaryl groups are thienyl, thiazolyl, oxazolyl, and pyridinyl. The (2-5C)heteroaryl group may be attached via a carbon atom or a nitrogen, if feasible. Preferably attachment is via the carbon atom. N-containing heteroaryl groups include their corresponding N-oxide derivatives where appropriate.

The term (1-5C)heteroaryl means an aromatic group having 1-5 carbon atoms and 1-4 heteroatoms selected from N, O and S, like but not limited to imidazolyl, thiadiazolyl, pyridinyl, pyrimidinyl, thienyl, triazolyl, tetrazolyl, oxazolyl, imidazolyl, pyrazolyl or furyl. Preferred number of heteroatoms is one or two. Preferred heteroaryl groups are thiazolyl, oxazolyl, triazolyl, tetrazolyl, pyrazolyl, pyrazinyl and pyridinyl. The (1-5C)heteroaryl group may be attached via a carbon atom or a nitrogen, if feasible. Preferably attachment is via the carbon atom. N-containing heteroaryl groups include their corresponding N-oxide derivatives where appropriate.

The term (2-5C)heterocycloalkyl means a heterocycloalkyl group having 2-5 carbon atoms, including 1-3 heteroatoms selected from N, O and/or S, which may be attached via a nitrogen if feasible, or a carbon atom. Preferred number of heteroatoms is one or two. Preferred heterocycloalkyl groups are tetrahydro-2H-pyran-4-yl and tetrahydro-2H-thiopyran-4-yl.

The term (2-5C)heterocycloalkenyl means a heterocycloalkenyl group having 2-5 carbon atoms, including 1-3 heteroatoms selected from N, O and/or S, which may be attached via a nitrogen if feasible, or a carbon atom. Preferred number of heteroatoms is one or two. Preferred heterocycloalkyl groups are 3,6-dihydro-2H-pyran-4-yl and 3,6-dihydro-2H-thiopyran-4-yl.

The term (1-6C)alkoxycarbonyl means an alkoxycarbonyl group, the alkoxy group of which contains 1-6 carbon atoms with the same meaning as previously defined, connected via a carbonyl group.

The term halogen means fluorine, chlorine, bromine or iodine.

The term "substituted" means that one or more hydrogens on the designated atom is/are replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional i.e. with or without substitution with the specified groups, radicals or moieties.

In the above definitions with multifunctional groups the attachment point is at the last group unless otherwise indicated.

The term pharmaceutically acceptable salt represents those salts which are, within the scope of medical judgement, suitable for use in contact for the tissues of humans and lower animals without undue toxicity, irritation, allergic response and the like, and are commensurate with a reasonable benefit/risk ratio. Pharmaceutically acceptable salts are well known in the art. They may be obtained during the final isolation and purification of the compounds of the invention, or separately by reacting the free base function with a suitable mineral acid such as hydrochloric acid, phosphoric acid, or sulfuric acid, or with an organic acid such as for example ascorbic acid, citric acid, tartaric acid, lactic acid, maleic acid, malonic acid, fumaric acid, glycolic acid, succinic acid, propionic acid, acetic acid, methanesulfonic acid, and the like. The acid function can be reacted with an organic or a mineral base, like amines, sodium hydroxide, potassium hydroxide or lithium hydroxide.

In one aspect the invention relates to compounds of formula I wherein R1 is phenyl or (2-5C)heteroaryl, both optionally substituted with (1-3C)alkyl or halogen.

In another aspect the invention relates to compounds of formula I wherein R4 is (1-5C)heteroaryl, optionally substituted with (1-3C)alkyl, (1-3C)alkoxy, hydroxy or halogen; or R4 is nitro, (1-6C)alkyl, (1-6C)alkoxy, (1-6C)alkylthio, —NH(CO)R6 or —C(O)N(R7)R8.

In another aspect the invention relates to compounds of formula I wherein R4 is (1-5C) heteroaryl, optionally substituted with (1-3C)alkyl or halogen; or R4 is nitro, cyano, (1-6C)alkyl, (1-6C)alkoxy, (1-6C)alkylthio, —SO$_2$R6, —C(O)R6, —C(O)NR7R8 or —NH(CO)R6.

In another aspect the invention relates to compounds of formula I wherein R4 is (1-5C) heteroaryl, optionally substituted with (1-3C)alkyl or halogen; or R4 is nitro, (1-6C)alkyl, (1-6C)alkoxy, (1-6C)alkylthio, or —NH(CO)R6.

In another aspect the invention relates to compounds of formula I wherein R5 is H.

In another aspect the invention relates to compounds of formula I wherein R6 is (1-6C)alkyl or (2-5C)heteroaryl, both optionally substituted with one or more (1-3C)alkyl, (1-3C) alkoxy, hydroxy or halogen.

In yet another aspect the invention relates to compounds of formula I wherein R6 is (1-3C)alkyl.

In still another aspect the invention relates to compounds of formula I wherein R3 is (1-3C)alkoxy.

In another aspect the invention relates to compounds of formula I wherein Y is a bond, Y is (CH$_2$)$_n$ or Y is X(CH$_2$)$_m$, wherein one or more of the hydrogen atoms in the (CH$_2$)$_n$ or (CH$_2$)$_m$ groups in Y may optionally be substituted with (1-3C) alkyl.

In still another aspect the invention relates to compounds of formula I wherein Y is (CH$_2$)$_n$ or Y is X(CH$_2$)$_m$, wherein one or more of the hydrogen atoms in the (CH$_2$)$_n$ or (CH$_2$)$_m$ groups in Y may optionally be substituted with (1-3C)alkyl.

In another aspect the invention relates to compounds of formula I wherein Y is (CH$_2$)$_3$.

In yet another aspect the invention relates to compounds of formula I wherein Y is X(CH$_2$)$_2$.

In another aspect the invention relates to compounds of formula I wherein R7 and R8 are independently H, (1-6C) alkenyl or (1-6C)alkyl, optionally substituted with one or more hydroxyl groups.

In another aspect the invention relates to compounds of formula I wherein R7 is H, and R8 is (1-6C)alkenyl or (1-6C) alkyl, optionally substituted with one or more hydroxyl groups.

In another aspect the invention relates to compounds of formula I wherein R7 and R8 are independently H or (1-6C) alkyl, optionally substituted with one or more hydroxyl groups.

In another aspect the invention relates to compounds of formula I wherein n is 1-4.

In another aspect the invention relates to compounds of formula I wherein R1 is thienyl or thiazolyl.

In another aspect the invention relates to compounds of formula I wherein the annulated ring is a 7, 8 or 9-membered heterocyclic ring.

In yet another aspect the invention relates to compounds of formula I wherein the optionally substituted heteroaryl in R4 is selected from thiazolyl, oxazolyl, tetrazolyl, pyrazolyl, pyrazinyl and pyridinyl.

In still another aspect the invention relates to compounds of formula I wherein the optionally substituted heteroaryl in R1 is selected from thienyl, thiazolyl, oxazolyl, and pyridinyl.

The invention also relates to those compounds wherein all specific definitions for R1 through R5 as well as the definitions of the subgroups R6 trough R10, Y, X and m and n in the various aspects of the invention as defined hereabove occur in any combination within the definition of the ring-annulated dihydropyrrolo[2,1-c]isoquinoline compound of formula I.

All compounds of the invention have a pEC$_{50}$ in the CHO-hFSHR (luciferase) assay of at least 5.

In another aspect the invention relates to compounds of formula I which have a pEC$_{50}$ in the CHO-hFSHR (luciferase) assay of more than 7. In yet another aspect the invention relates to compounds of formula I which have a pEC$_{50}$ in the CHO-hFSHR (luciferase) assay of more than 8.

The term EC$_{50}$ means the concentration of the test compound that elicits half-maximal (50%) stimulation compared to the compound's maximally attainable effect. pEC$_{50}$ is the negative log of EC$_{50}$. The values can be determined e.g. in a cell line transfected with a FSH receptor gene and cotransfected with a cAMP responsive element/promoter directing the expression of a reporter gene. For the determination a software program such as MathIQ (version 2.0, ID Business Solutions Limited) can be used.

Compounds according to the invention are unknown in literature. From a synthetic point of view they can be regarded as dihydropyrrolo[2,1-a]isoquinolines to which additional homocyclic and heterocyclic rings have been annulated.

The synthetic methodology has been disclosed in chemical literature which enables construction of substituted dihydropyrrolo[2,1-a]isoquinolines by making use of so called dipolar cycloaddition reactions of azomethine ylids and munchnones. The chemical base hereof finds its origin in pioneering work of Huisgen et al. (R. Huisgen, H. Gotthardt, H. Bayer, F. Schaefer, *Chem. Ber.* 103, 2611 (1970); H. Gotthardt, R. Huisgen., *Chem. Ber.* 103, 2626 (1970)) and application to the scaffold mentioned was described several years later by Hershenson (*J. Org. Chem.* 40, 740 (1975). The methodology has since then become an indispensable tool in construction of complex molecules (I. Coldham, R. Hufton, *Chem. Rev.* 105, 2765 (2005)), and upon that time a significant amount of literature has become available on applications towards synthesizing for example alkoxyaryl-substituted dihydropyrrolo[2,1-a]isoquinolines, predominantly in the area of antitumor compounds related to the natural product class of Lamellarins and synthetic derivatives thereof. A number of references illustrate the scope of that work (C. Ridley, M. Venkata, R.

Ami Reddy, G. Rocha, F. Bushman, D. Faulkner, *Bioorg. Med. Chem. Lett.* 10, 3285 (2002); M. Banwell, B. Flynn, D. Hockkless, *Chem. Comm.* 2259 (1997); C. Bailly, WO2004/014917; P. Cironi, I. Manznares, F. Alberico, M. Alvarez, *Org. Lett.* 5, 2959 (2003); S. Handy, Y. Zhang, H. Bregman, *J. Org. Chem.* 69, 2362 (2004); C. Olsen, N. Parera, F. Alberico, M. Alvarez, *Tetrahedron Lett.* 46, 2041 (2005); D. Pla, A. Marchal, C. Olsen, F. Alberico, M. Alvarez, *J. Org. Chem.* 70, 8231 (2005); S. Ruchirawat, T. Mutarapat, *Tetrahedron Lett.* 42, 1205 (2001); P. Ploypradith, W. Jinaglueng, C. Pavaro, S. Ruchirawat, *Tetrahedron Lett.* 44, 1363 (2003); P. Ploypradith, C. Mahidol, P. Sahakitpichan, S. Womgbundit, R. Ruchirawat, *Angew. Chem. Int. Ed.* 43, 866 (2004); F. Ishibash, Y. Miyazaki, M. Iwao, *Tetrahedron* 53, 5951 (1997); F. Ishibashi, S. Tanabe, T. Oda, M. Iwao, *J. Nat. Prod.* 65, 500 (2000)).

In order to arrive at the specific compounds of the invention two different approaches may be applied. First, 1,3-dipolar intramolecular cycloaddition reactions (starting from suitably functionalized isoquinoline-1-carboxylic acids) are applied to achieve direct entry into the desired ring-annulated dihydropyrrolo[2,1-a]isoquinolines (scheme I, sequence II→V→I).

The substrates of general formula V, required for intramolecular cycloaddition to I, are accessible from the acetylenic modules of general structure III. Commercially available materials can generally be used to obtain them in a few routine steps (cf IV→III), well known to those of skill in the art. In the case X=O or S, 1,2-ethane- or 1,3-propane-diols or 1,2-ethane- or 1,3-propane-mercapto-ethanols (in which the length of the alkyl chain determines the size of the annulated ring) are used as starting materials, which upon reaction with propargyl bromides under basic conditions, followed by conversion of the resulting terminal alcohols into e.g. the corresponding mesylates and subsequent substitution of the mesylates by amines, provide the required alkyne derivatives of general formula IV (X=O,S; Y=X—$(CH_2)_m$; m=2, 3).

In the case X=NR9, generally orthogonally protected aminoalcohols are the preferred starting materials. A convenient protection for the alcohol is e.g. a silyl group, and for nitrogen a Boc group is preferred. In that case, upon reaction with propargyl bromides under basic conditions, introduction of an alkynylmethylene group at nitrogen is achieved. After deprotection of the alcohol group, conversion into amines IV (X=NR9; Y=X—$(CH_2)_m$; m=2, 3) as described above, can be effectuated.

General Formula

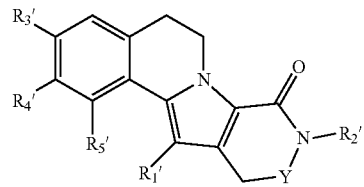

optionally one or more hydrogens of $CH_2$ groups in Y are substituted by (1-3C) alkyl I-a Y = bond
I-b Y = $(CH_2)_n$ n = 1-4
I-c Y = $X(CH_2)_m$ m = 2, 3
X = O, S, NR9

Scheme I

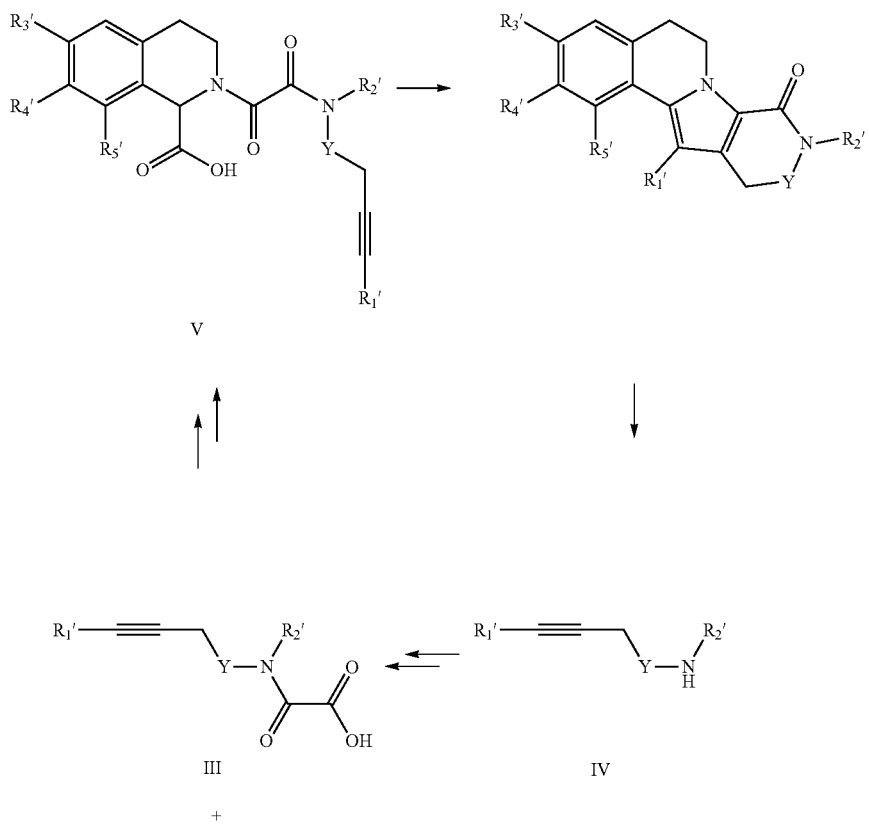

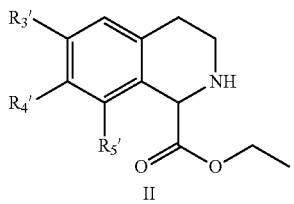

II

I-a Y = bond
I-b Y = (CH$_2$)$_n$   n = 1-4
I-c Y = X(CH$_2$)$_m$   m = 2, 3
   X = O, S, NR9 optionally one or more
hydrogens of CH$_2$ groups in Y
are substituted by (1-3C)alkyl In the case Y=bond, or (CH$_2$)$_n$, hydroxyalkyl-acetylenes are used, in which the length of the alkyl chain determines the size of the annulated ring. Hydroxyalkyl acetylenes are converted into e.g. the corresponding mesylates and reacted with appropriate amines to yield compounds of general formula IV (Y=bond or (CH$_2$)$_n$).

Compounds IV are converted into the oxalates III by treatment with ethyloxalyl chloride, saponified and coupled to isoquinoline esters II via standard amide condensation reactions, known to those skilled in the art. After saponification of the resulting derivatives, compounds of general formula V are obtained. Submitting V to typical cyclization conditions (like heating in acetic anhydride) the required structures I are obtained. In order to synthesize the molecules of choice, as claimed in general formula I, either the desired specific substituents are in place during synthesis (in that case R1'=R1, R2'=R2, R3'=R3, etc.) or alternatively, depending on the strategy of synthesis, R1'-R10' are separately converted at any convenient stage of the synthetic process into the desired R1-R10 (as defined in the claims of the invention) by one or more additional steps.

Isoquinolines II are available by Bishler-Napieralsky type reactions from appropriately substituted carbamoylated phenethylamines and glyoxalic acid, according to published procedures (S. Bajusz, WO93/12091; W. Z. Li, Y-Q Wang, *Org. Lett.* 5, 2931 (2003); D. Ma, W. Wu, G. Yang, J. Li, J. Li, Q. Ye, *Bioorg. Med. Chem. Lett.* 14, 47 (2004), B. A. Bunin, J. M. Dener, D. Kelly, N. A. Paras, J. D. Tario, S. P. Tushup, *J. Comb. Chem.* 6, 487 (2004); Z. Zalan, T. Martinez, L. Lazar, R. Sillanpaa, F. Fulop, *Tetrahedron* 6, 2883 (2006); J. J. Li, *Bioorganic Med. Chem. Lett.* 15, 1799 (2005); S. W. Youn, *J. Org. Chem.* 71, 2521 (2006); I. Schuster, A. Sztojkov, L. Fulop, *Lett. Org. Chem.* 4, 102 (2007); W. K. Anderson, H. McPherson, S, New, A. Rick, *J. Med. Chem.* 27, 1321 (1984)), and are subsequently converted into the corresponding ethyl esters by standard esterification procedures, well known to those skilled in the art.

Specifically substituted phenethyl amines are either commercially available or may be readily synthesized by known routine procedures from the corresponding aryl precursors via chloromethylation and cyanation, followed by reduction to the phenethyl amines. In an alternative fashion, aryl aldehydes can be converted by the so-called Henry reaction, leading to nitro-olefins, followed by two-step reduction of the nitro moiety and the unsaturated bond to the desired phenethyl amines.

Substituents R3-R5 according to the claims can be introduced from R3'-R5' halogens like bromides, iodides and chlorides or from active esters of phenol, such as triflates, tosylates etc., by means of organometallic techniques, belonging to the routine tool box of modern organic chemistry (Suzuki et al., *Chem. Comm.* 4759 (2005); Bach et al., *Tetrahedron* 61, 2245 (2005); Rossi et al., *Synthesis,* 2419 (2004); Muci and Buchwald, Practical Palladium Catalysts for C—N and C—O bond formation in *Topics in current Chemistry-Cross coupling Reactions*, Vol. 219, N. Miyaura., Ed., Springer Verlag, Heidelberg, 131-209, (2002); Hartwig, Palladium-catalyzed Amination of Aryl Halides and Related Reactions in *Handbook of Organopalladium Chemistry for Organic Synthesis*, Vol. 1, 1051-1096 (2002), E. Negishi Ed., J. Wiley & Sons, New York; Schlummer et al., *Advanced Synthesis and Catalysis* 46, (13-15) 1599 (2004), Transition Metals for Organic Synthesis; M. Beller, C. Bolm, Ed., Wiley-VCH Verlag GmbH & Co, Weinheim, Germany), like Ullmann, Suzuki, Stille, Sonogashira, Heck and Buchwald protocols. In this way an efficient access is achieved to heteroaryl and aryl substituents. In a similar way, new carbon carbon single, double and triple bonds are introduced as well as nitrogen atoms and nitriles. Acetylenes, azides and nitriles thus formed similarly serve as functionalities for new heterocyclic structures by applying cycladditions.

Phenolic substituents at R3'-R5' (vide supra) can be obtained by deprotection of e.g. their corresponding methyl ethers (e.g. R4'=OMe) by known procedures using Lewis acids like BCl$_3$, AlCl$_3$, BBr$_3$, etc. and may be used for constructing alternative ether substituents.

Substituents R1' (see Scheme II) can be introduced onto the acetylene before carrying out the intramolecular cycloaddition reaction, but alternatively, if a terminal acetylene is employed (IV, R1'=H→III, R1'=H) the structures I (R1'=H) are obtained. These can be converted into the 1-substituted bromides (I, R1'=Br) by e.g. N-bromosuccinimide and subsequently coupled under typical organometallic conditions (vide supra, references) to 1-arylated or alkylated structures of general formula I.

Moreover, if both R1' and R4' are bromine, regioselective coupling on I (R1'=R4'=Br) is possible to selectively and sequentially introduce new substituents independently at C9 and C1 of the dihydropyrroloisoquinoline scaffold from a common precursor, as shown in Scheme II.

Scheme II

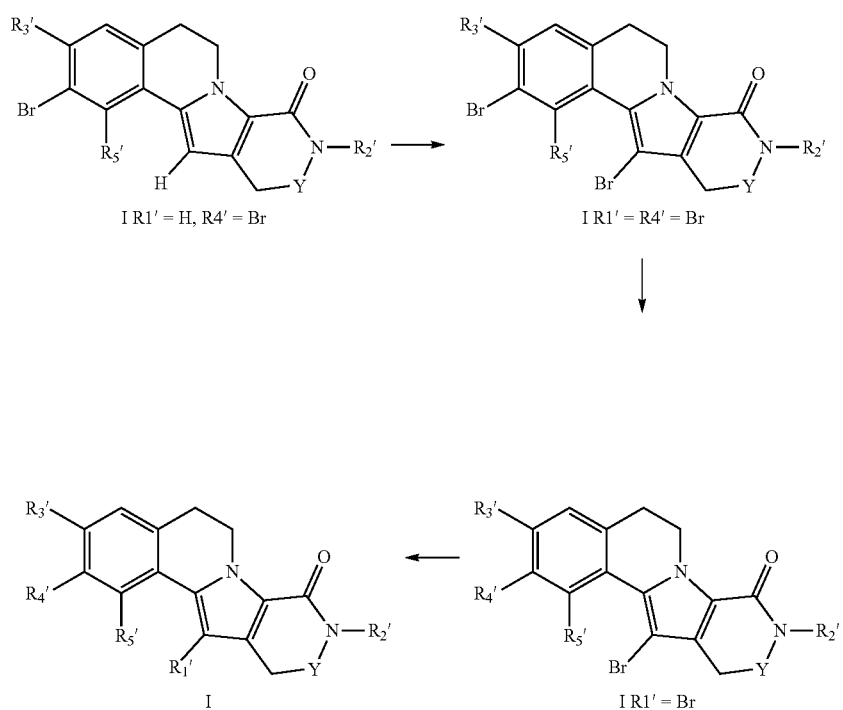

Alternatively, compounds of general formula I are accessible by regioselective intermolecular dipolar cycloaddition reactions (see Scheme III) of suitably functionalized acetylenes of general formula VIII or XI, leading to dihydropyrrolo[2,1-a]isoquinolines with tailor-made functionality at the C2,C3 position (IX or XII). The C2,C3-moieties can be step-wise elaborated to amino acid derivatives (X or XIII) which can be cyclized by several lactamization methods, well known to those skilled in the art, to the desired annulated compounds I-a or I-b.

Thus, treatment of protected aryl-acetylenic aldehydes VIII with isoquinoline derivatives VII under proper conditions leads, after deprotection of the aldehyde moiety, to the desired 2,3-substituted substrates IX. The aldehyde function at C2 thus delivered can be converted under suitable conditions into amines X. After saponification of the esters the amino acids are closed to annulated lactams I-a under standard peptide bond forming conditions, well known to those of skill in the art.

In a related way, acetylenes bearing a mesylated chain (XI) are converted into substrates XII, which upon amination (XIII) and saponification, followed by ring closure as described above, lead to the ring-annulated structures (I-b, $Y=(CH_2)_2$).

Scheme III

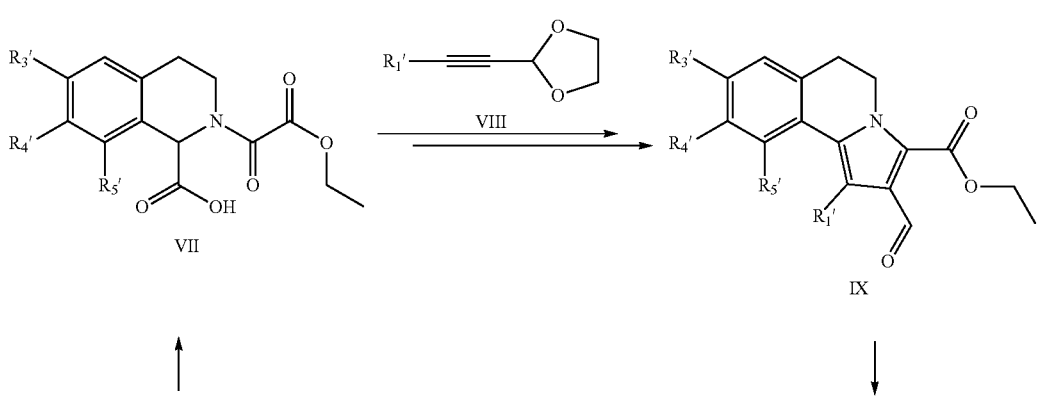

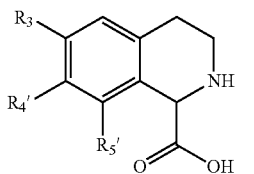

VI

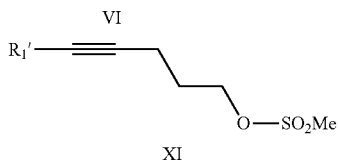

XI

+ VII ↓

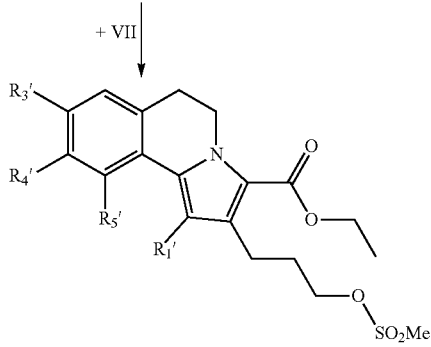

XII

↓

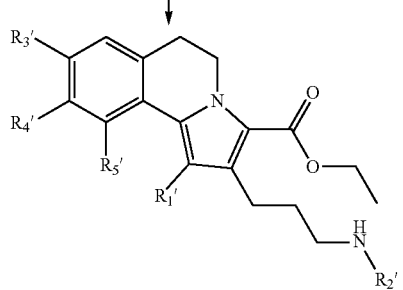

XIII

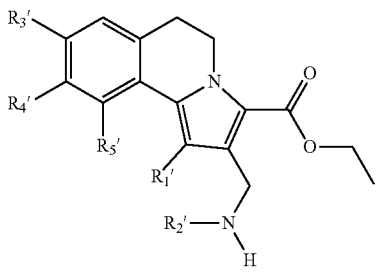

X

↓↓

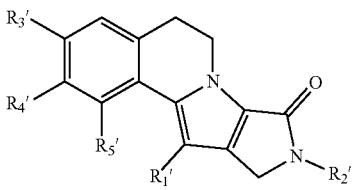

I-a Y = bond

→

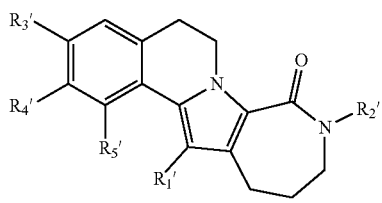

I-b Y = (CH$_2$)$_2$

The compounds of the invention may form hydrates or solvates. It is known to those of skill in the art that charged compounds form hydrated species when lyophilized with water, or form solvated species when concentrated in a solution with an appropriate organic solvent. The compounds of this invention include the prodrugs, hydrates or solvates of the compounds listed.

A discussion of prodrugs is provided in T. Higuchi and V. Stella, Pro-drugs as Novel Delivery Systems (1987) 14 of the A.C.S. Symposium Series, and in Bioreversible Carriers in Drug Design, (1987) Edward B. Roche, ed., American Pharmaceutical Association and Pergamon Press. The term "prodrug" means a compound (e.g, a drug precursor) that is transformed in vivo to yield a compound of Formula (I) or a pharmaceutically acceptable salt, hydrate or solvate of the compound. The transformation may occur by various mechanisms (e.g. by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is H$_2$O.

The compounds of Formula I can form salts which are also within the scope of this invention. Reference to a compound of Formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula I may be formed, for example, by reacting a compound of Formula I with an amount of acid or base, such as an equivalent amount, in a medium such as one in which the salt precipitates or in an aqueous medium followed by lyophilization.

The compounds of Formula I may contain asymmetric or chiral centers, and, therefore, exist in different stereoisomeric forms. It is intended that all stereoisomeric forms of the compounds of Formula I as well as mixtures thereof, including racemic mixtures, form part of the present invention. In addition, the present invention embraces all geometric and positional isomers. For example, if a compound of Formula I incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g. chiral auxiliary such as a chiral alcohol or Mosher's acid chloride), separating the diastereomers and converting (e.g. hydrolyzing) the individual diastereomers to the corresponding pure enantiomers. Also, some of the compounds of Formula I may be atropisomers (e.g. substituted biaryls) and are considered as part of this invention. Enantiomers can also be separated by use of chiral HPLC column.

It is also possible that the compounds of Formula I may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2$H, $^3$H, $^{13}$C, $^{14}$C, $^{15}$N, $^{18}$O, $^{17}$O, $^{18}$F, and $^{36}$Cl, respectively.

Certain isotopically-labelled compounds of Formula (I) (e.g., those labeled with $^3$H, $^{14}$C, $^{18}$F and $^{11}$C) are useful in compound and/or substrate tissue distribution assays. Tritiated (i.e., $^3$H) and carbon-14 (i.e., $^{14}$C) isotopes are particularly preferred for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labelled compounds of Formula (I) can generally be prepared by following procedures analogous to those disclosed in the Schemes and/or in the Examples hereinbelow, by substituting an appropriate isotopically labelled reagent for a non-isotopically labelled reagent.

The ring-annulated dihydropyrrolo[2,1-c]isoquinoline compounds of the invention were found to stimulate the FSH receptor. Methods to determine receptor binding, as well as in vitro and in vivo assays to determine biological activity, of gonadotropins are well known. In general, expressed receptor is incubated with the compound to be tested and binding or stimulation or inhibition of a functional response is measured.

To measure a functional response, isolated DNA encoding the FSH receptor gene, preferably the human receptor, is expressed in suitable host cells. Such a cell might be the Chinese Hamster Ovary cell, but other cells are also suitable. Preferably the cells are of mammalian origin (Jia et al, *Mol. Endocrin.*, 5, 759-776, (1991)).

Methods to construct recombinant FSH receptor expressing cell lines are well known in the art (Sambrook et al., Molecular Cloning: a Laboratory Manual, Cold Spring Harbor Laboratory Press, Cold Spring Harbor). Expression of receptor is attained by expression of the DNA encoding the desired protein. Techniques for site directed mutagenesis, ligation of additional sequences, PCR, and construction of suitable expression systems are all, by now, well known in the art. Portions, or all, of the DNA encoding the desired protein can be constructed synthetically using standard solid phase techniques, preferably to include restriction sites for ease of ligation. Suitable control elements for transcription and translation of the included coding sequence can be provided to the DNA coding sequences. As is well known, expression systems are now available which are compatible with a wide variety of hosts, including prokaryotic hosts such as bacteria and eukaryotic hosts such as yeast, plant cells, insect cells, mammalian cells, avian cells and the like.

Cells expressing the receptor are then incubated with the test compound to observe binding of the test compound, or stimulation of a functional response. Alternatively, isolated cell membranes containing the expressed receptor may be used to measure binding of the test compound.

For measurement of binding, radioactive or fluorescent compounds may be used. Such compounds are also part of the invention.

In the alternative also competition binding assays may be performed.

Another assay involves screening for FSH receptor agonistic compounds by determining stimulation of receptor mediated cAMP accumulation. Thus, such a method involves expression of the receptor in a host cell and exposing the cell to the test compound. The amount of cAMP is then measured. The level of cAMP will be increased, by the stimulating effect of the test compound upon binding to the receptor.

For the measurement of intrinsic activity human recombinant FSH can be used as a reference compound.

In addition to direct measurement of e.g. cAMP levels in the exposed cell, cells lines can be used which in addition to transfection of DNA encoding the FSH receptor are also transfected with a second DNA encoding a reporter gene the expression of which responds to the level of cAMP. Such reporter genes might be cAMP inducible or might be constructed in such a way that they are connected to novel cAMP responsive elements. In general, reporter gene expression might be controlled by any response element reacting to changing levels of cAMP. Suitable reporter genes are e.g. LacZ, alkaline phosphatase, firefly luciferase and green fluorescence protein. The principles of such transactivation assays are well known in the art and are described e.g. in Stratowa, Ch., Himmler, A. and Czernilofsky, A. P., *Curr. Opin. Biotechnol.*, 6, 574-581 (1995).

The present invention also relates to a pharmaceutical composition comprising a ring-annulated dihydropyrrolo[2,1-a]isoquinoline derivative or pharmaceutically acceptable salts thereof having the general formula I in admixture with pharmaceutically acceptable auxiliaries and optionally other therapeutic agents.

The auxiliaries must be "acceptable" in the sense of being compatible with the other ingredients of the composition and not deleterious to the recipients thereof.

Compositions include e.g. those suitable for oral, sublingual, subcutaneous, intravenous, intramuscular, nasal, local, or rectal administration, and the like, all in unit dosage forms for administration.

For oral administration, the active ingredient may be presented as discrete units, such as tablets, capsules, powders, granulates, solutions, suspensions, and the like.

For parenteral administration, the pharmaceutical composition of the invention may be presented in unit-dose or multi-dose containers, e.g. injection liquids in predetermined amounts, for example in sealed vials and ampoules, and may also be stored in a freeze dried (lyophilized) condition requiring only the addition of sterile liquid carrier, e.g. water, prior to use.

Mixed with such pharmaceutically acceptable auxiliaries, e.g. as described in the standard reference, Gennaro, A. R. et al., *Remington: The Science and Practice of Pharmacy* (20th Edition., Lippincott Williams & Wilkins, 2000, see especially Part 5: Pharmaceutical Manufacturing), the active agent may be compressed into solid dosage units, such as pills, tablets, or be processed into capsules or suppositories. By means of pharmaceutically acceptable liquids the active agent can be applied as a fluid composition, e.g. as an injection preparation, in the form of a solution, suspension, emulsion, or as a spray, e.g. a nasal spray.

For making solid dosage units, the use of conventional additives such as fillers, colorants, polymeric binders and the like is contemplated. In general any pharmaceutically acceptable additive which does not interfere with the function of the active compounds can be used. Suitable carriers with which the active agent of the invention can be administered as solid compositions include lactose, starch, cellulose derivatives and the like, or mixtures thereof, used in suitable amounts. For parenteral administration, aqueous suspensions, isotonic saline solutions and sterile injectable solutions may be used, containing pharmaceutically acceptable dispersing agents and/or wetting agents, such as propylene glycol or butylene glycol.

The pharmaceutical composition might also include additional therapeutically active agents, in particular those that are to be used in the same regimen. Such agents include but are not limited to other gonadotropin agonists and GnRH modulators.

The invention further includes a pharmaceutical composition, as hereinbefore described, in combination with packaging material suitable for said composition, said packaging material including instructions for the use of the composition for the use as hereinbefore described.

The exact dose and regimen of administration of the active ingredient, or a pharmaceutical composition thereof, may vary with the particular compound, the route of administration, and the age and condition of the individual subject to whom the medicament is to be administered.

In general, parenteral administration requires lower dosages than other methods of administration which are more dependent upon absorption. However, a suitable dosage for humans may be 0.05-25 mg per kg body weight. The desired dose may be presented as one dose or as multiple subdoses administered at appropriate intervals throughout the day, or, in case of female recipients, as doses to be administered at appropriate daily intervals throughout the menstrual cycle. The dosage as well as the regimen of administration may differ between a female and a male recipient.

The compounds according to the invention can be used in therapy. They can be used for the same clinical purposes as the native FSH.

A further aspect of the invention resides in the use of ring-annulated dihydropyrrolo[2,1-a]isoquinoline compounds having the general formula I for the manufacture of a medicament to be used for the treatment of disorders responsive to FSH receptor mediated pathways, preferably for the treatment of fertility disorders. Thus, patients in need thereof can be administered with suitable amounts of the compounds according to the invention.

In yet another aspect the invention resides in the use of ring-annulated dihydropyrrolo[2,1-a]isoquinoline compounds having the general formula I for the manufacture of a medicament to be used for the treatment of infertility. In particular the compounds can be used to induce ovulation (OI) or in controlled ovarian stimulation (COS) protocols.

The invention is illustrated by the following examples.

EXAMPLES

General Comments

The following abbreviations are used in the examples: DIPEA=N,N-diisopropylethyl amine, HATU=O-(7-azabenzotriazole-1-yl)-N,N,N',N'-tetramethyl-uronium hexafluorophosphate, DMF=N,N-dimethyl-formamide, DME=1,2-dimethoxyethane, THF=tetrahydrofuran, Boc=t-butoxycarbonyl, NMP=N-methylpyrrolidone, TBTU=O-benzotriazol-1-yl-N,N,N,N'-tetrabutyluronium tetrafluoroborate, hexafluorophosphate, DMAP=4-(dimethylamino) pyridine.

The names of the products described in the examples were generated using the Chem Draw Ultra program. The names of the annulated tetracyclic target structures of the invention were generated with ACD/NAME program (Advanced Chemistry Development Inc.).

Microwave reactions were carried out on a Biotage (model: Initiator) microwave oven with autosampler.

Thin Layer Chromatography (TLC) was conducted on Merck TLC plates (5×10 cm) silica gel 60 $F_{254}$.

Example 1

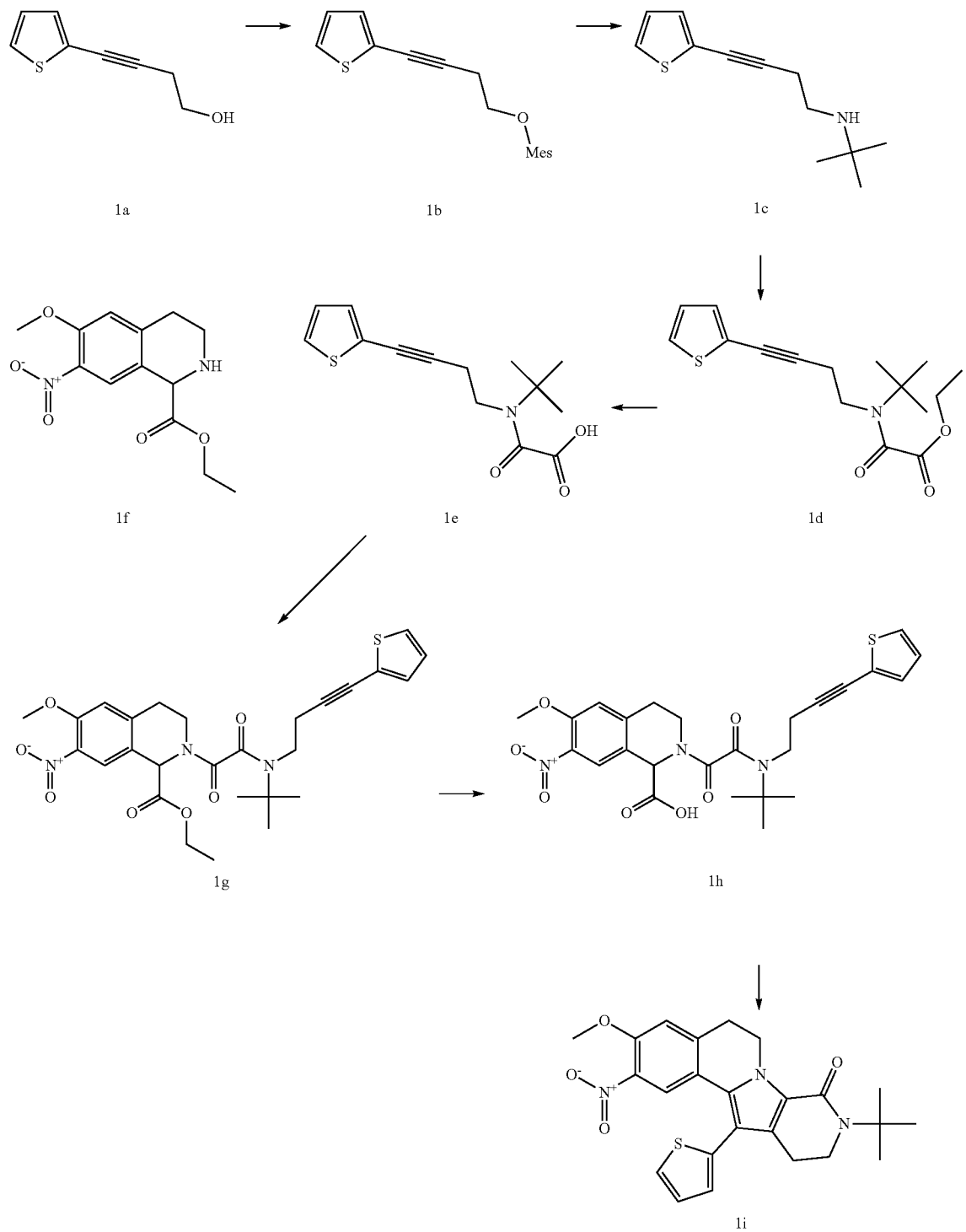

4-(thiophen-2-yl)but-3-yn-1-ol (1a)

To a solution of 1.2 g of 2-bromothiophene and 0.9 g of butynol in 15 ml of degassed dioxane were added 100 mg of PdCl$_2$(PheCN)$_2$, 50 mg of CuI, 1 ml of diisopropyl amine, 750 µl of a 1M solution of tri-tert-butyl phosphine in toluene. The mixture was stirred under N$_2$ atmosphere for 16 hr and then diluted with 50 ml of water and extracted with ethyl acetate. The organic layers were combined and washed with water, dried and concentrated. The residue was chromatographed using a gradient of heptane/ethyl acetate as eluent, to provide 850 mg of 1a; R$_f$ (heptane/ethyl acetate 1/1) 0.50. NMR (CDCl$_3$) δ 1.83 (t, 1, OH), 2.72 (t, 2, CH$_2$), 3.83 (q, 2, CH$_2$), 6.95, 7.16, 7.20 (3×m, 3, thiophene-H).

4-(thiophen-2-yl)but-3-ynyl methanesulfonate (1b)

To a solution of 750 mg of 1a and 1 ml of triethyl amine in 15 ml of diethyl ether, was added dropwise at 0° C. 400 µl of methanesulfonyl chloride in 5 ml of diethyl ether. The reaction mixture was stirred for ½ hr and then diluted with 30 ml of water and 5 ml of 1M $K_2CO_3$. The product was extracted with diethyl ether and the combined extracts were once washed with water, dried and concentrated, to provide 1.2 g of mesylate 1b; $R_f$ 0.50 (heptane/ethyl acetate 1/1), MS-ESI: [M+1] 231.07.

NMR ($CDCl_3$) δ 2.82 (t, 2, $CH_2$), 3.08 (s, 3, $CH_3SO_2$), 4.38 (t, 2, $CH_2$), 6.96, 7.16 and 7.22 (3×m, 3, thiophene-H).

N-tert-butyl-4-(thiophen-2-yl)but-3-yn-1-amine (1c)

A solution of 1 g of 1b in 10 ml of tert-$BuNH_2$ was stirred overnight at RT. The mixture, consisting of desired product as well as elimination product, was concentrated, diluted with 20 ml of 5% $NaHCO_3$ and extracted with ether. The extract was dried and concentrated (45° C./100 mm). The residue (~450 mg) containing 1c was used without further purification in the next step;

MS-ESI: [M+1] 208.20.

ethyl 2-(tert-butyl(4-(thiophen-2-yl)but-3-ynyl) amino)-2-oxoacetate (1d)

A solution of 200 µl of ethyloxalyl chloride in 1 ml of diethyl ether was added dropwise at 0° C. to a solution of 450 mg of 1c (contaminated with elimination products from previous reaction) and 200 µl of triethyl amine in 5 ml of ether. The reaction mixture was stirred for 20 min and then diluted with 10 ml of 1M $K_2CO_3$ and stirred for 5 min. The product was extracted with ethyl acetate and the extracts were washed once with water, dried and concentrated. The crude material was passed through a short silica column, using a gradient of heptane/ethyl acetate, as eluent, to provide 120 mg of 1d as colorless oil;

MS-ESI: [M+1] 308.15; $R_f$ (heptane/ethyl acetate 2/1) 0.50. NMR ($CDCl_3$) δ 1.37 (t, 3, $OC_2H_5$), 1.52 (s, 9, tert$C_4H_9$), 2.77 (m, 2, $CH_2$), 3.52 (m, 2, $CH_2$), 4.34 (q, 4, $OC_2H_5$), 6.95, 7.13, 7.21 (3×s, 3, thiophene-H).

2-(tert-butyl(4-(thiophen-2-yl)but-3-ynyl)amino)-2-oxoacetic acid (1e)

A solution of 100 mg of 1d in 1 ml of dioxane was mixed with a solution of 40 mg of KOH in 400 µl of water and stirred for 16 hr at RT. The mixture was diluted with 5 ml of water and acidified to pH3 with 0.5 N HCl. The product was extracted with ethyl acetate and the extracts were washed once with sat. NaCl, dried and concentrated, to provide 65 mg of essentially pure 1e as colorless oil; MS-ESI: [M+1] 280.16; NMR ($CDCl_3$) δ 1.54 (s, 9, tert$C_4H_9$), 2.80 (m, 2, CH2), 4.10 (bm, 2, CH2), 6.94, 7.13, 7.20 (3×m, 3, thiophene-H).

ethyl 2-(2-(tert-butyl(4-(thiophen-2-yl)but-3-ynyl) amino)-2-oxoacetyl)-6-methoxy-7-nitro-1,2,3,4-tetrahydroisoquinoline-1-carboxylate (1g)

To a solution of 65 mg of 1e and 85 mg of nitroester 1f (see example 5) in 1 ml of DMF was added 60 mg of N-ethyl morpholine and 120 mg of TBTU. The mixture was stirred for 2 hr and then diluted with 5% $NH_4Cl$ solution and stirred for an additional 10 min. The product was extracted into ethyl acetate. The organic layer was washed once with water, dried and concentrated. The crude material was chromatographed over silica gel, using a gradient of heptane/acetone as eluent, to provide 105 mg of 1g as amorphous material; $R_f$ 0.60 (heptane/acetone 1/1). NMR ($CDCl_3$) δ 1.28 (t, 3, $OC_2H_5$), 1.58 (s, 9, tert-$C_4H_9$), 2.70-2.82 (bm, 1, CH), 2.90-3.03 (bm, 2, $CH_2$), 3.07-3.15 (bm, 1, CH), 3.60-3.80 (bm, 4, 2×$CH_2$), 4.25 (m, 2, $OC_2H_5$), 5.88 (s, 1, $CHCOOC_2H_5$), 3.96 (s, 3, $OCH_3$), 6.83, 8.15 (2×s, 2, Ar—H), 6.93 (7.12, 7.19 (3×m, 3, thiophene-H).

2-(2-tert-butyl(4-thiophen-2-yl)but-3-ynyl)amino)-2-oxoacetyl)-6-methoxy-7-nitro-1,2,3,4-tetrahydroiso-quinoline-1-carboxylic acid (1h)

To a solution of 100 mg of 1g in in 2 ml of dioxane was added 60 mg of KOH in 500 µl of water. The mixture was stirred for 3 hr at RT and then diluted with 3 ml of water and acidified with 0.5N HCl. The product was extracted with ethyl acetate. The organic layer was washed once with water, dried and concentrated, to give 65 mg of essentially pure 1 h. NMR ($CDCl_3$) δ 1.58 (s, 9, tert$C_4H_9$), 2.70-2.83 (bm, 1, CH), 2.87-3.00 (bm, 2, CH2), 3.07-3.15 (bm, 1, CH), 3.65-3.81 (bm 4, 2×$CH_2$), 3.95 (s, 3, $OCH_3$), 5.87 (s, 1, CHCOOH), 6.82, 8.18 (2×s, 2, Ar—H). 6.94, 7.13, 7.20 (3×m, 3, thiophene-H).

9-tert-butyl-3-methoxy-2-nitro-12-(2-thienyl)-5,6,10,11-tetrahydropyrido[4',3':4,5]pyrrolo[2,1-a]isoquinolin-8(9H)-one (1i)

A solution of 65 mg of 1h in 1 ml of acetic anhydride was heated at 100° C. for 3 hr. The mixture was cooled and diluted with 3 ml of water and stirred for 1 hr at RT. The reaction mixture was then neutralized by addition of cold conc. aq. $NH_4OH$ solution and the product was extracted with ethyl acetate. The organic layer was washed once with water, dried, concentrated and the residue was treated with diethyl ether, to provide 35 mg of 1i as yellow crystalline material; Mp 226-227° C., MS-ESI: [M+1]452.17; $R_f$ (heptane/acetone 1/1) 0.60. NMR ($CDCl_3$) δ 1.53 (s, 9, tert$C_4H_9$), 2.67, 3.10, 3.58, 4.72 (4×t, 8, 4×$CH_2$), 3.95 (s, 3, $OCH_3$), 6.92 and 7.78 (2×s, 2, Ar—H), 6.98, 7.12 and 7.38 (3×m, 3, thiophene-H).

hFSHRago (CHO luc) $pEC_{50}$=7.00.

Example 2
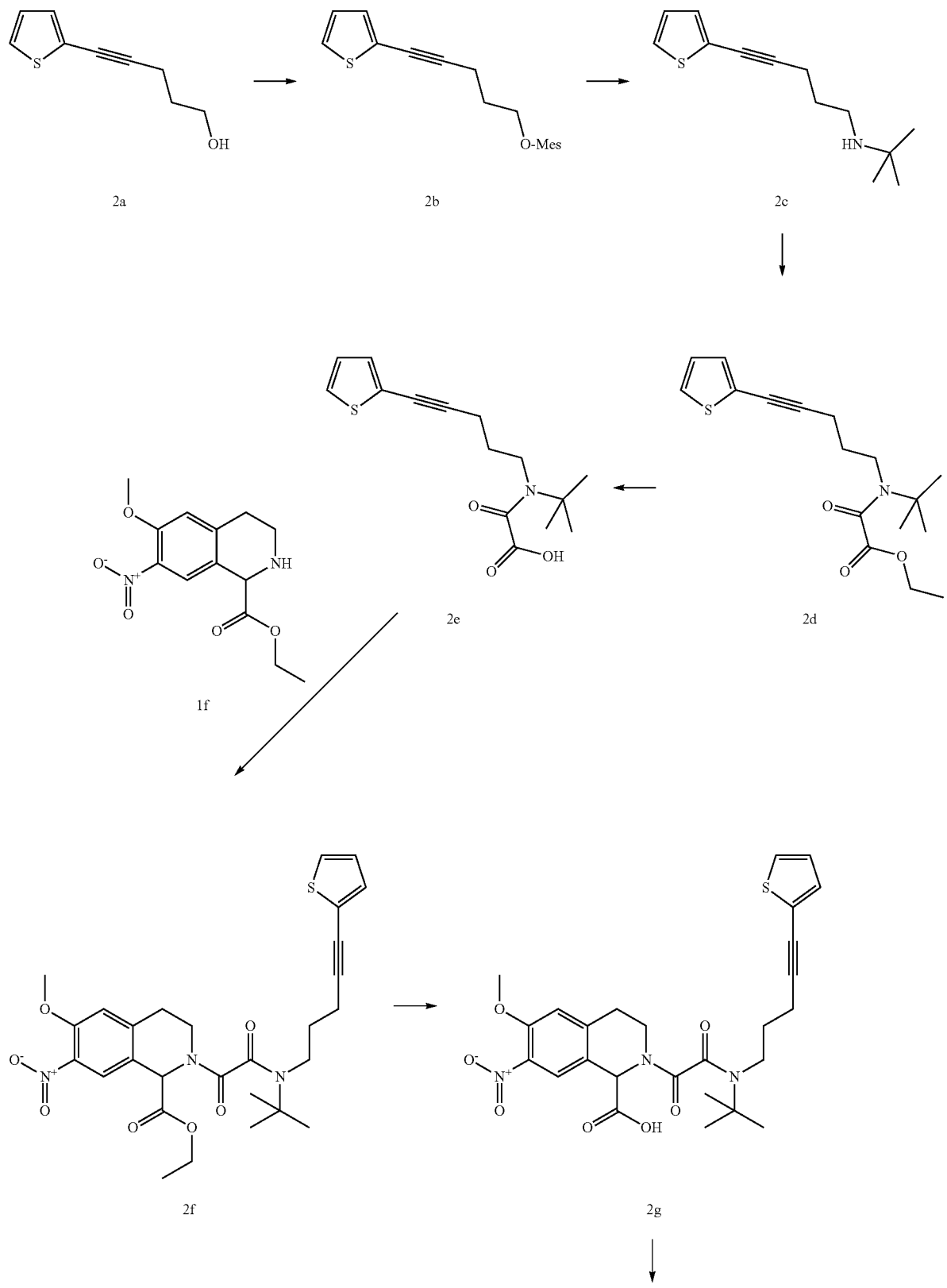

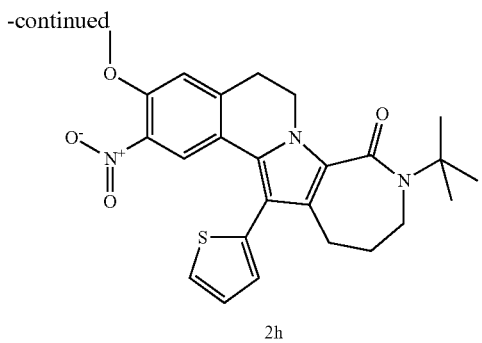

2h

5-(thiophen-2-yl)pent-4-yn-1-ol (2a)

A solution of 120 mg of 2-iodothiophene, 140 mg of pentynol, 200 μA of diisopropyl amine, in 1.5 ml of degassed dioxane was charged with 10 mg of CuI, 20 mg of $PdCl_2$ (benzonitrile)$_2$ and 150 μl of a 1M solution of tri-tert-butyl phosphine in toluene. The mixture was stirred under $N_2$ atmosphere for 16 hr. The mixture was concentrated and the residue was applied to a silica column and eluted with a gradient of heptane/ethyl acetate. This gave 145 mg of 2a as a colorless oil.

$R_f$(heptane/ethyl acetate 1/1) 0.50;
MS-ESI: [M+1] 167.08

5-(thiophen-2-yl)pent-4-ynyl methanesulfonate (2b)

To a solution of 145 mg of 2a and 200 μl of triethyl amine in 2 ml of dichloromethane was added dropwise at 0° C. 80 μl of methanesulfonyl chloride in 1 ml of dichloromethane. The reaction mixture was stirred for ½ hr and then diluted with 10 ml of water and extracted with dichloromethane. The organic layer was washed with 1M $K_2CO_3$, dried and concentrated, to provide 210 mg of essentially pure 2b as an oil; $R_f$(heptane/ethyl acetate 1/1) 0.55. NMR (CDCl$_3$): δ 2.03 (m, 2, CH$_2$), 2.60 (t, 2, CH$_2$), 4.40 (t, 2, CH$_2$), 3.03 (s, 3, CH$_3$SO$_2$), 6.95, 7.13, 7.20 (3×m, 3, thiophene-H).

N-tert-butyl-5-(thiophen-2-yl)pent-4-yn-1-amine (2c)

A mixture of 210 mg of 2b and 5 ml of tert-butyl amine was stirred for 4 days. The reaction mixture was concentrated and the residue was treated with 20 ml of 1M $K_2CO_3$ and the product was extracted into ethyl acetate. The organic layer was washed once with water, dried and concentrated, to provide 250 mg of 2c as a colorless oil.

MS-ESI: [M+1], 222.18.

ethyl 2-(tert-butyl(5-(thiophen-2-yl)pent-4-ynyl)amino)-2-oxoacetate (2d)

To a solution of 200 mg of 2c and 400 μl of triethyl amine in 6 ml of diethyl ether was added dropwise at 0° C. 200 μl of ethyl oxalyl chloride. The mixture was stirred for 15 min and then 20 ml of ice water was added and stirring was prolonged for 10 min. The product was extracted into ethyl acetate and the organic layer was washed with 1M $K_2CO_3$, dried and concentrated, to give 300 mg of essentially pure 2d; $R_f$(heptane/ethyl acetate 1/1) 0.66;
MS-ESI: [M+1]: 322.20.

NMR (CDCl$_3$) δ 1.34 (t, 3, OCH$_2$CH$_3$), 1.50 (s, 9, tertC$_4$H$_9$), 4.28 (q, 2, OCH$_2$CH$_3$), 1.94 (m, 2, CH$_2$) 2.40 (t, 2, CH$_2$), 3.40 (t, 2, CH$_2$), 6.94, 7.12, 7.19 (3×m, 3, thiophene-H).

2-(tert-butyl(5-(thiophen-2-yl)pent-4-ynyl)amino)-2-oxoacetic acid (2e)

To a solution of 300 mg of 2d in 6 ml of dioxane was added a solution of 200 mg of KOH in 2 ml of water. The mixture was stirred at 50° C. for 1 hr. After cooling to RT, 25 ml of water was added and the reaction mixture was acidified to pH3 by addition of 0.5N HCl. The product was extracted into ethyl acetate. The organic layer was washed once with water, dried and concentrated, to provide 240 mg of 2e as colorless oil;

MS-ESI: [M+1] 294.17.
$R_f$(CH$_2$Cl$_2$-methanol 1/1) 0.50. NMR (CDCl$_3$): δ 1.50 (s, 9, tertC$_4$H$_9$), 1.98 (m, 2, CH2), 2.45 (t, 2, CH$_2$), 3.70 (t, 2, CH2), 6.93, 7.11, 7.18 (3×m, 3, thiophene-H)

ethyl 2-(2-(tert-butyl(5-(thiophen-2-yl)pent-4-ynyl)amino)-2-oxoacetyl)-6-methoxy-7-nitro-1,2,3,4-tetrahydroisoquinoline-1-carboxylate (2f)

To a mixture of 240 mg of 2e and 240 mg of 1f in 3 ml of DMF was added 200 μl of N-ethyl morpholine and 400 mg of TBTU. The reaction mixture was stirred for 2 hr. Then 20 ml of 5% NH$_4$Cl was added and stirred for 15 min. The product was extracted into ethyl acetate. The combined extracts were washed twice with water, dried and concentrated. The residue was purified by passing through a silica column (heptane/acetone gradient) to provide 330 mg of yellowish amorphous 2f:

MS-ESI: [M+1] 556.22.
$R_f$(heptane/acetonel/1) 0.60. NMR (CDCl$_3$): δ 1.29 (t, 3, OC$_2$H$_5$), 1.58 (s, 9, tert-C$_4$H$_9$), 3.96 (s, 3, OCH$_3$), 4.22 (m, 2, OCH$_2$CH$_3$), 1.93, 2.10 (2×m, 2, CH$_2$), 2.36, 2.45 (2×m, 2, CH$_2$), 2.93, 3.10 (2×m, 2, CH$_2$), 3.46, 3.61 (2×m, 2, CH$_2$), 3.72, 3.78 (2×m, 2, CH$_2$), 5.82 (s, 1, CHCOOC$_2$H$_5$), 6.84, 8.12 (2×s, 2, Ar—H), 6.93, 7.10, 7.18 (3×m̄, 3, thiophene-H).

2-(2-tert-butyl(5-thiophen-2-yl)pent-4-ynyl)amino)-2-oxoacetyl)-6-methoxy-7-nitro-1,2,3,4-tetrahydroisoquinoline-1-carboxylic acid (2g)

To a solution of 340 mg of 2f in 8 ml of dioxane was added a solution of 240 mg of KOH in 2 ml of water and the mixture was stirred for 2 hr at RT. Then 10 ml of water was added and the mixture was made slightly acidic by addition of 0.5 N HCl. The product was extracted with ethyl acetate and the organic layer was washed once with water, dried and concentrated, to give 320 mg of the acid 2g.

MS-ESI: [M+1] 528.25.

$R_f$ (heptane/acetone 1/1) 0.20. NMR (CDCl$_3$) δ 1.65 (s, 9, tertC$_4$H$_9$), 3.95 (s, 3, OCH$_3$), 5.81 (s, 1, CHCOOH), 6.82, 8.07 (2×s, 2, Ar—H). 6.93, 7.08, 7.18 (3×m, 3, thiophene-H).

9-tert-butyl-2-nitro-3-methoxy-13-(2-thienyl)-5,6,9,10,11,12-hexahydro-8H-azepino[4',3':4,5]pyrrolo[2,1-a]isoquinolin-8-one (2h)

A solution of 300 mg of 2g and 500 mg of anhydrous sodium acetate in 5 ml of acetic acid was heated at 100° C. for ½ hr. The mixture was cooled, diluted with 15 ml of water and stirred for 1 hr at ambient temperature. The reaction mixture was then neutralized by addition of cold conc. ammonia and the product was extracted into ethyl acetate. The organic layer was washed with water, dried, concentrated and the residue was triturated with cold ether/heptane (2/1, v/v), to provide 210 mg of yellow crystalline 2h.

Mp 279-280° C.; $R_f$ 0.60 (heptane/acetone 1/1).

NMR (CDCl$_3$): δ 1.53 (s, 9, tert-C$_4$H$_9$), 1.89 (m, 2, CH$_2$), 2.58 (t, 2, CH$_2$), 3.02 (t, 2, CH$_2$), 3.43 (t, 2, CH$_2$), 4.53 (t, 2, CH$_2$) 3.95 (s, 3, OCH$_3$) 6.90, 7.57 (2×s, 2, Ar—H), 6.95, 7.14, 7.42 (3×m, 3, thiophene-H).

hFSHRago (CHO luc) pEC$_{50}$=7.46

Example 3

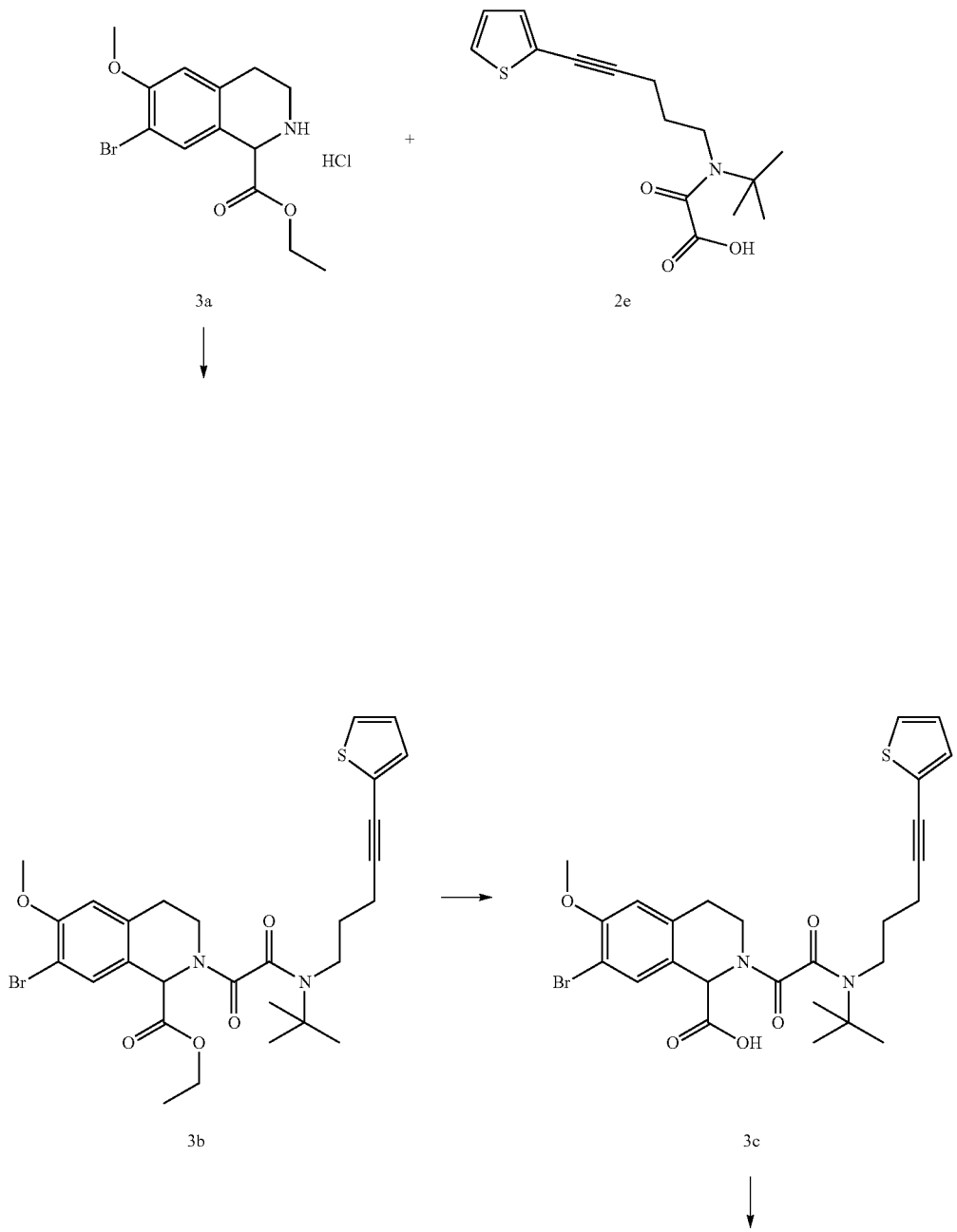

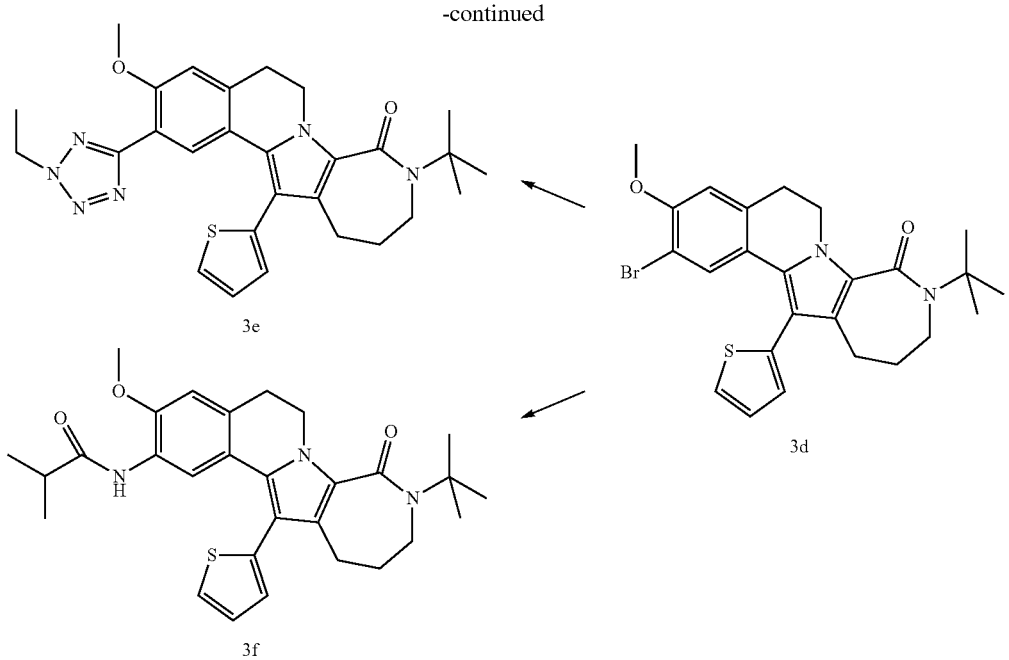

ethyl 7-bromo-2-(2-(tert-butyl(5-(thiophen-2-yl)
pent-4-ynyl)amino)-2-oxoacetyl)-6-methoxy-1,2,3,4-
tetrahydroisoquinoline-1-carboxylate (3b)

A mixture of 1.60 g of 2e, 2g of 3a, 1.8 ml of N-ethyl morpholine, 8 ml of DMF and 3.3 g of TBTU was stirred for 2 hr. The reaction mixture was diluted with 5% NH$_4$Cl and extracted with ethyl acetate. The organic layer was washed successively with 0.5N HCl, 0.5N NaOH and water, then dried and concentrated to provide 3.1 g of 3b as colorless amorphous material;

R$_f$ 0.55 (heptane/ethyl acetate 1/1);
MS-ESI: [M+1] 589.23 and 591.21.

7-bromo-2-(2-(tert-butyl(5-(thiophen-2-yl)pent-4-
ynyl)amino)-2-oxoacetyl)-6-methoxy-1,2,3,4-tet-
rahydroisoquinoline-1-carboxylic acid (3c)

A solution of 3.1 g of 3b in 30 ml of dioxane and a solution of 1.5 g of KOH in 10 ml of water were mixed and stirred for 3 hr at RT. 75 ml of water was added and the mixture was acidified with 0.5N HCl to pH3. The product was extracted with ethyl acetate. The material 3c which remained after washing, drying and concentration was used, as such, in the cyclization step.

MS-ESI: [M+1] 563.13 and 561.12

9-tert-butyl-2-bromo-3-methoxy-13-(2-thienyl)-5,6,
9,10,11,12-hexahydro-8H-azepino[4',3':4,5]pyrrolo
[2,1-a]isoquinolin-8-one (3d)

A solution of 2.9 g of 3c in 30 ml of acetic anhydride and 3 g of sodium acetate was heated with stirring at 100° C. for ½ hr. The mixture was cooled to RT. Then, 100 ml of water was added and stirring was prolonged for 1 hr. The reaction mixture was neutralized by dropwise addition of cold conc. aq. NH$_4$OH solution, the product was extracted with ethyl acetate and the organic layer was washed, dried and concentrated. The residue was treated with diisopropyl ether, to provide 2.2 g of 3d as white crystalline material; Mp 232-233° C.; MS-ESI: [M+1] 499.15 and 501.19. R$_f$(heptane/ethyl acetate 1/1) 0.50

NMR (CDCl$_3$) δ 1.53 (s, 9, tertC$_4$H$_9$), 1.88 (m, 2, CH$_2$), 2.58 (t, 2, CH$_2$), 3.02 (t, 2, CH$_2$), 3.43 (t, 2, CH$_2$), 3.88 (s, 3, OCH$_3$) 4.50 (t, 2, CH$_2$), 6.72, 7.21 (2×s, 2, Ar—H), 6.83, 7.14, 7.41 (3×m, 3, thiophene-H).

9-tert-butyl-2-(2-ethyl-2H-tetrazol-5-yl)-3-methoxy-
13-(2-thienyl)-5,6,9,10,11,12-hexahydro-8H-azepino
[4',3':4,5]pyrrolo[2,1-a]isoquinolin-8-one (3e)

To a solution of 235 mg of 3d and 235 mg of 2-ethyl-5-tributylstannyl tetrazole in 6 ml of degassed toluene was added 30 mg of Pd(PPh)$_4$ and the mixture was heated under N$_2$ atmosphere for 48 hr at 110° C. The reaction mixture was applied onto a silica column and chromatographed using a gradient of toluene/ethyl acetate as eluent and the isolated product was treated with diethyl ether providing 155 mg of crystalline white 3e.

Mp: 235-237° C.
R$_f$(heptane/ethyl acetate 1/1): 0.27
NMR (CDCl$_3$) δ 1.52 (s, 9, tertC$_4$H$_9$), 1.62 (t, 3, C$_2$H$_5$), 1.87 (m, 2, CH$_2$), 2.60 (t, 2, CH$_2$), 3.12 (t, 2, CH$_2$), 3.43 (t, 2, CH$_2$), 4.52 (t, 2, CH$_2$), 4.64 (q, 2, C$_2$H$_5$), 3.92 (s, 3, OCH$_3$), 6.87, 7.72 (2×s, 2, Ar—H), 6.98, 7.10, 7.47 (3×m, 3, thiophene-H). MS-ESI: [M+1] 517.30.
hFSHRago (CHO luc) pEC$_{50}$=7.44

9-tert-butyl-2-isobutyramido-3-methoxy-13-(2-thie-
nyl)-5,6,9,10,11,12-hexahydro-8H-azepino[4',3':4,5]
pyrrolo[2,1-a]isoquinolin-8-one (3f)

A mixture of 250 mg of 3d, 110 mg of isobutyramide, 230 mg of K$_3$PO$_4$, 15 mg of Pd$_2$ dba$_3$ and 20 mg of di-tert-butyl (2',4',6'-triisopropyl-3,4,5,6-tetramethylbiphenyl-2-yl)phosphine in 3 ml of degassed tert-butanol was heated under nitrogen atmosphere for 16 hr at 100° C. The reaction mixture was cooled and diluted with 20 ml of water. The product was extracted into ethyl acetate. The extract was washed with water, dried, concentrated and the product was purified by chromatography over silica gel, using a gradient of heptane/ethyl acetate as eluent, to provide 120 mg of 3f. The sample was crystallized from ethyl acetate; MS-ESI: [M+1] 506.25. NMR (CDCl$_3$) δ 1.18 (d, 6, isoC$_3$H$_7$), 1.58 (s, 9, tertC$_4$H$_9$), 1.89 (m, 2, CH$_2$), 2.44 (m, 1, CH), 2.58 (t, 2, CH$_2$), 3.01 (t, 2, CH$_2$), 3.42 (t, 2, CH$_2$), 3.86 (s, 3, OCH$_3$), 4.50 (t, 2, CH$_2$), 6.70 (s, 1 ArH) and 7.46 (bs, 1, ArH), 7.00, 7.18 and 7.38 (3×m, 3, thiophene-H), 8.08 (bs, 1, NH).

Mp: 226-227° C.

hFSHRago (CHO luc) pEC$_{50}$=6.90

Example 4

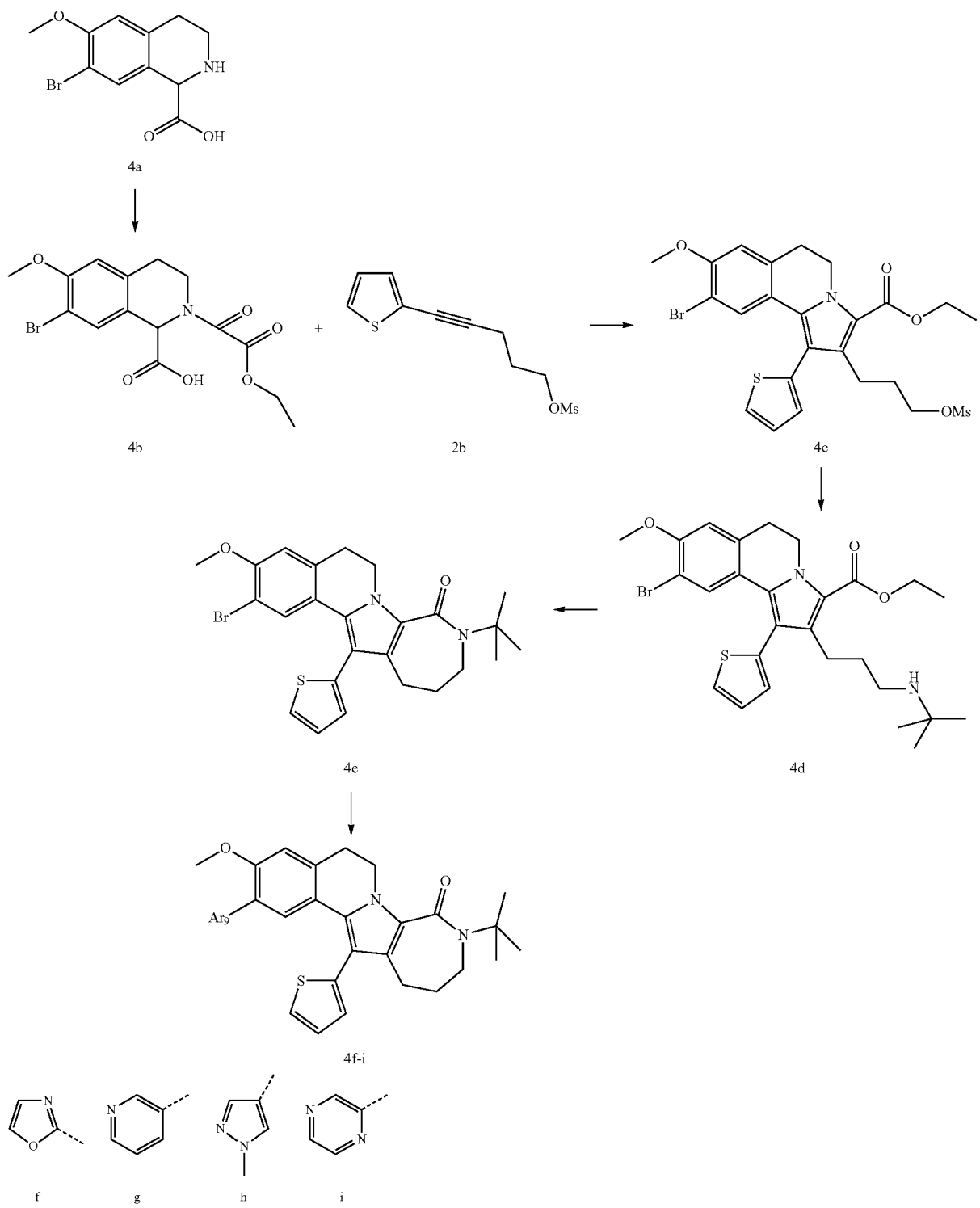

7-bromo-2-((2-ethoxy-2-oxoacetyl)-6-methoxy-1,2, 3,4-tetrahydroisoquinoline-1-carboxylic acid (4b) and ethyl 9-bromo-8-methoxy-2-(3-(methylsulfonyloxy)propyl)-1-(thiophen-2-yl)-5,6-dihydropyrrolo [2,1-a]isoquinoline-3-carboxylate (4c)

A mixture of 3.3 g of 4a and 1.57 g of ethyl oxalyl chloride in 50 ml of THF was heated at reflux for 1 hr, delivering a clear solution of 4b. The reaction mixture was concentrated under reduced pressure and then dissolved in 8 ml of acetic anhydride, upon which 3.1 g of 2b was added. The mixture was heated in a microwave reactor at 140° C. for 15 minutes. The reaction mixture was diluted with toluene and concentrated in vacuo. The residue was treated with abs ethanol to give 5.7 g of 4c; MS-ESI: [M+1] 576.94 and 569.96.

ethyl 9-bromo-2-(3-(tert-butylamino)propyl)-8-methoxy-1-(thiophen-2-yl)-5,6-dihydropyrrolo[2,1-a] isoquinoline-3-carboxylate (4d)

To a solution of 2.5 g of 4c in 25 ml of NMP was added 2.5 ml of tert-butyl amine. The mixture was heated for 30 min at 120° C. in a microwave oven. The reaction mixture was cooled and diluted with 150 ml of 5% $NH_4Cl$ solution and the product was extracted with ethyl acetate. The organic layer was washed with water, dried, concentrated and the residue was treated with diethyl ether, to provide 1.6 g of 4d; MS-ESI: [M+1] 547 and 545.

NMR (DMSO-$d^6$) δ 1.23 (s, 9, tertC$_4$H$_9$), 1.36 (t, 3, OC$_2$CH$_5$), 1.82 (m, 2, CH$_2$), 2.62 (t, 2, CH$_2$), 2.66 (m, 2, CH$_2$) 3.06 (t, 2, CH$_2$) 3.84 (s, 3, OCH$_3$), 4.30 (q, 2, OC$_2$CH$_5$), 4.53 (t, 2, CH$_2$), 6.96 and 7.12 (2×s, 2, Ar—H), 7.06, 7.24, 7.75 (3×m, 3, thiophene-H).

9-tert-butyl-2-bromo-3-methoxy-13-(2-thienyl)-5,6, 9,10,11,12-hexahydro-8H-azepino[4',3':4,5]pyrrolo [2,1-a]isoquinolin-8-one A solution of 1.6 g of 4d in 50 ml of ethanol was mixed with 6 ml of 2N NaOH and stirred at 65° C. for 5 hr. The mixture was cooled and neutralized by addition of 6 ml of 2N HCl. Then, 1 ml of DiPEA was added, the reaction mixture was concentrated in vacuo and residual solvents were removed by repeated coevaporation with ethanol. The residue was taken up in 50 ml of NMP and 2.5 ml of diisopropylethyl amine and 1.7 g of HATU were added. The mixture was stirred for 16 hr. Then, 200 ml of water was added and the product was extracted into ethyl acetate. The organic layer was washed several times with water, dried, concentrated and chromatographed, using a gradient of heptane/ethyl acetate as eluent. The material isolated was triturated with diisopropyl ether, to provide 1.02 g of 4e. MS-ESI: [M+1] 499.02 and 501.01.

9-tert-butyl-2-(oxazol-2-yl)-3-methoxy-13-(2-thienyl)-5,6,9,10,11,12-hexahydro-8H-azepino[4',3':4,5] pyrrolo[2,1-a]isoquinolin-8-one (4f)

A solution of 300 mg of 4e and 430 mg of 2-tributylstannyl oxazole in 2 ml of degassed toluene was heated in a microwave oven under N$_2$ for 3 hr at 150° C. The reaction mixture was concentrated and chromatographed over SiO$_2$ (using a gradient of heptane/ethyl acetate as eluent). Product fractions were pooled, concentrated and triturated with diethyl ether, to provide 185 mg of 4f;

MS-ESI: [M+1] 488.13; Mp 230-231° C. NMR (CDCl$_3$) δ 1.53 (s, 9, tertC$_4$H$_9$), 1.89 (m, 2, CH$_2$), 2.60, 3.11, 3.44, 4.53 (4×m, 8, 4×CH$_2$), 3.98 (s, 3, OCH$_3$), 6.87, 7.72 (2×s, 2, Ar—H), 7.19 and 7.54 (2×d, 2, oxazole-H), 6.98, 7.13 and 7.39 (3×m, 3, thiophene-H).

hFSHRago (CHO luc) pEC$_{50}$=7.94.

9-tert-butyl-2-(pyridin-3-yl)-3-methoxy-13-(2-thienyl)-5,6,9,10,11,12-hexahydro-8H-azepino[4',3':4,5] pyrrolo[2,1-a]isoquinolin-8-one (4g)

A solution of 57 mg of 4e and 84 mg of 3-tributylstannylpyridine in 3 ml of degassed toluene was heated under nitrogen atmosphere in a microwave oven for 30 minutes at 150° C. The reaction mixture was concentrated and the residue was chromatographed on silica (using a gradient of heptane ethyl acetate as eluent). The product thus isolated was treated with diethyl ether, to give 44 mg of 4g. MS-ESI: [M+1], 498.3. NMR (CDCl$_3$) δ 1.54 (s, 9, tertC$_4$H$_9$), 1.89 (m, 2, CH$_2$), 2.60, 3.12, 3.44 and 4.54 (4×t, 8, 4×CH$_2$), 3.82 (s, 3, OCH$_3$), 6.83, 7.07 (2×s, 2, Ar—H), 6.95, 7.12 and 7.40 (3×m, 3, thiophene-H), 7.12, 7.63, 8.46 and 8.49 (4×m, 4, pyridine-H).

hFSHRago (CHO luc) pEC$_{50}$=8.38.

9-tert-butyl-2-((1-methyl-pyrazol)-3-yl)-3-yl)-3-methoxy-13-(2-thienyl)-5,6,9,10,11,12-hexahydro-8H-azepino[4',3':4,5]pyrrolo[2,1-a]isoquinolin-8-one (4h)

A solution of 67 mg of 4e, 55 mg of K$_2$CO$_3$ and 56 mg of 1-methyl-4-(4,4,5,5-tetramethyl-1,3,2-dioxaborolan-2-yl-1H-pyrazole in 3 ml of degassed 90% aq. dimethoxyethane was heated in a microwave oven under N$_2$ atmosphere for 1 hr at 150° C. The reaction mixture was diluted with water and the product was extracted into ethyl acetate. The organic layer was washed, dried, concentrated and the product was purified by preparative HPLC, using a gradient of CH$_3$CN-water. The product fractions were pooled and freeze-dried, to give 17 mg of 4h.

MS-ESI: [M+1] 501.4. NMR (CDCl$_3$) δ 1.53 (s, 9, tertC$_4$H$_9$), 1.90 (m, 2, CH$_2$), 2.60, 3.16, 3.44 and 5.51 (4×t, 8, 4×CH$_2$) 3.88 and 3.90 (2×s, 6, N—CH$_3$+OCH$_3$), 6.77 and 7.63 (2×s, 2, Ar—H), 7.28 and 7.34 (2×s, 2, pyrazole-H), 6.98, 7.18 and 7.45 (3×m, 3, thiophene-H).

hFSHRago (CHO luc) pEC$_{50}$=7.19.

9-tert-butyl-2-(pyrazin-2-yl)-13-(2-thienyl)-5,6,9,10, 11,12-hexahydro-8H-azepino[4',3':4,51]pyrrolo[2,1-a]isoquinolin-8-one (4i)

A solution of 65 mg of 4e and 65 mg of 2-tributylstannyl pyrazine in 3 ml of degassed toluene was heated under nitrogen atmosphere in a microwave oven for 30 minutes at 150° C. The reaction mixture was concentrated and purified by preparative HPLC (using gradient of acetonitrile/water as eluent). The product fractions were concentrated and taken up in ethyl acetate. The organic layer was washed with water, dried, concentrated and the residue was treated with diethyl ether, to provide 27 mg of 4i;

MS-ESI: [M+1] 499.4 NMR (CDCl$_3$) δ 1.54 (s, 9, tertC$_4$H$_9$), 1.88 (m, 2, CH$_2$), 2.60, 3.33, 3.44, 4.55 (4×m, 8, 4 CH$_2$), 3.88 (s, 3, OCH$_3$), 6.86 and 7.52 (2×s, 2, Ar—H), 7.06, 7.10 and 7.35 3×m, 3, thiophene-H), 8.37, 8.49 and 8.85 (3×bm, 3, pyrazine-H). hFSHRago (CHO luc) pEC$_{50}$=7.86.

Example 5

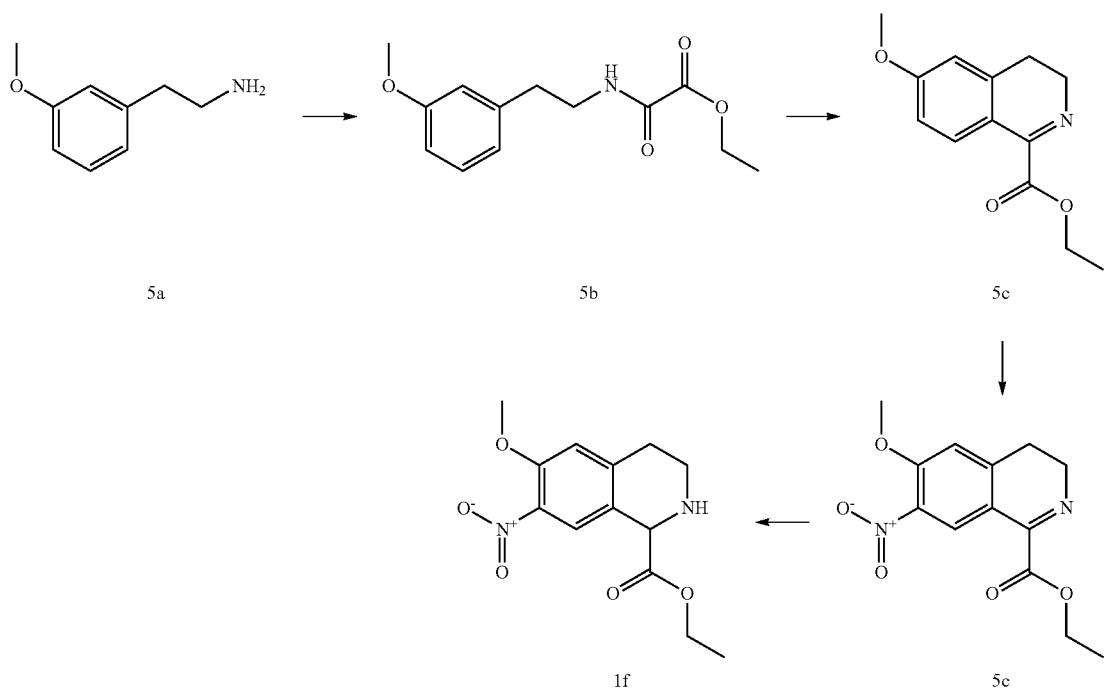

ethyl 2-(3-methoxyphenethylamino)-2-oxoacetate (5b)

To a solution of 60 g of 2-(3-methoxyphenyl)-ethyl amine (5a) and 77 g of DiPEA in 750 ml of dichloromethane was added dropwise at 0° C., 57 g of ethyloxalyl chloride. After stirring for an additional ½ h the reaction mixture was quenched by addition of water. The organic layer was washed with 1N aq. HCl and water and then dried and concentrated. The residue was chromatographed, using a gradient of heptane/ethyl acetate as eluent and provided 97.5 g of N-[2-(3-methoxyphenyl)-ethyl]oxalamic acid ethylester 5b;

MS-ESI: [M+1] 252.22. NMR (CDCl$_3$) δ 1.38 (t, 3, OC$_2$CH$_5$), 2.83 (t, 2, CH$_2$), 3.60 (m, 2, CH$_2$), 4.33 (q, 2, OC$_2$CH$_5$), 3.80 (s, 3, OCH$_3$), 6.75, 6.78, 6.80 and 7.22 (4×m, 4, Ar—H).

ethyl 6-methoxy-3,4-dihydroisoquinoline-1-carboxylate (5c)

A mixture of 160 ml of methanesulfonic acid and 45 g of P$_2$O$_5$ was heated with stirring at an oil bath for about ½ hr in order to obtain a homogeneous mixture. The mixture was cooled to RT and a solution of 46 g of N-[2-(3-methoxyphenyl)-ethyl]oxalamic acid ethylester, 5b, in 50 ml of CH$_2$Cl$_2$ was added and the temperature was raised again to 80° C., while distilling off the CH$_2$Cl$_2$. The mixture was kept for 16 hr at 80° C. in order to complete the cyclization reaction. Then the reaction mixture was cooled and poured into ice-water and was made alkaline by careful addition of solid K$_2$CO$_3$. The product was extracted into ethyl acetate. The organic layer was washed with water, dried, concentrated and the residue was chromatographed, using a gradient of heptane/ethyl acetate as eluent, to provide 35 g of 6-methoxy-3,4-dihydroisoquinoline-1-carboxylic acid ethyl ester 5c. MS-ESI: [M+1] 234.14. NMR (CDCl$_3$) δ 1.40 (t, 3, OC$_2$H$_5$), 2.72 (m, 2, CH$_2$), 3.85 (s and m, 5, CH$_2$ and OCH$_3$) 4.40 (q, 2, OC$_2$H$_5$), 6.70, 6.80 and 7.70 (3×m, 3, Ar—H).

ethyl 6-methoxy-7-nitro-3,4-dihydroisoquinoline-1-carboxylate (5d)

To a solution of 35 g of 6-methoxy-3,4-dihydroisoquinoline-1-carboxylic acid ethyl ester in 250 ml of concentrated sulphuric acid was added, at 0° C., 21 g of KNO$_3$ in portions over 5 min. The reaction mixture was stirred for 1 h and then poured with stirring onto 500 g of NaHCO$_3$. The resulting mixture was diluted with 2 l of ice-water and the product was extracted into dichloromethane. The organic layer was washed with water, dried, concentrated and the residue was treated with diethyl ether, to provide 34 g of 6-methoxy-7-nitro-3,4-dihydroisoquinoline-1-carboxylic acid ethyl ester, 5d MS-ESI: [M+1] 279.07. NMR (CDCl$_3$) δ 1.42 (t, 3, OCH$_2$CH$_3$), 2.82 (t, 2, CH$_2$), 3.94 (t, 2, CH$_2$), 4.46 (q, 2, OCH$_2$CH$_3$), 6.92 and 8.44 (2×s, 2, Ar—H).

ethyl 6-methoxy-7-nitro-1,2,3,4-tetrahydroisoquinoline-1-carboxylate (1f)

A solution of 34 g of 6-methoxy-7-nitro-3,4-dihydroisoquinoline-1-carboxylic acid ethyl ester in 300 ml of acetic acid was treated with 25 g NaCNBH$_3$ (added in several portions). The mixture was stirred for 2 h. The reaction mixture was poured onto 300 g of solid NaHCO$_3$ and 2 l of ice-water was carefully added with vigorous stirring. The product was extracted into dichloromethane. The organic layer was washed twice with water, dried and concentrated, to give 32g of essentially pure 6-methoxy-7-nitro-1,2,3,4-tetrahydroisoquinoline-1-carboxylic acid ethyl ester 1f. The compound is used as intermediate in the synthesis described in examples 1 and 2.

MS-ESI: [M+1] 281.12. NMR (CDCl$_3$) δ 1.30 (t, 3, OC$_2$H$_5$), 3.80 and 3.90 (2×m, 2, CH$_2$), 3.10 and 3.27 (2×m, 2, CH$_2$), 3.95 (s, 3, OCH$_3$), 4.26 (q, 2, C$_2$H$_5$), 4.47 (s, 1, CHCOOC$_2$H$_5$), 6.80 and 7.98 (2×s, 2, Ar—H).

Example 6

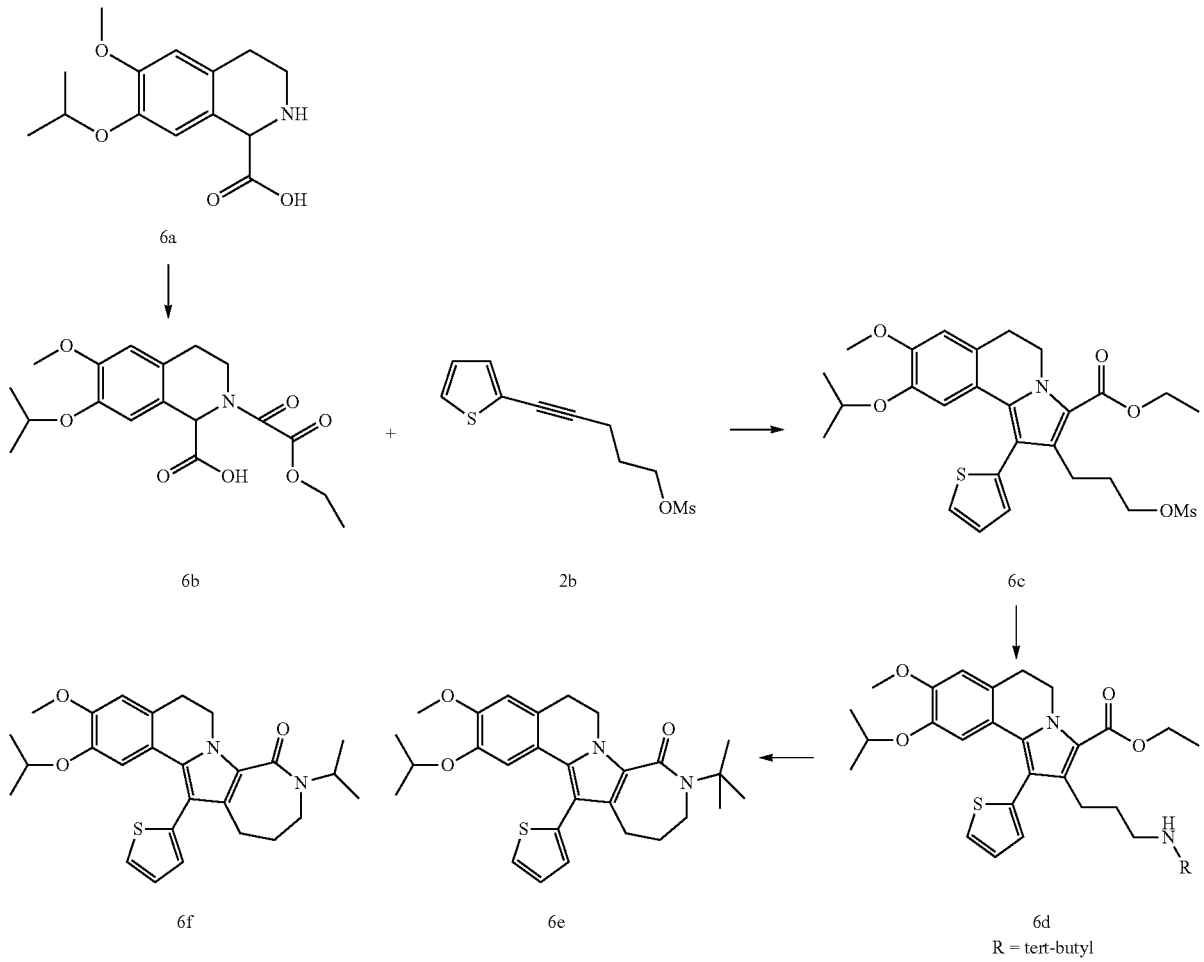

2-(2-ethoxy-2-oxoacetyl)-7-isopropoxy-6-methoxy-1,2,3,4-tetrahydroisoquinoline-1-carboxylic acid (6b)

A mixture of 3 g of 6a and 3 g of ethyloxalyl chloride in 30 ml of THF was heated under reflux for 2 h, after which a homogeneous solution was generated. The mixture was cooled and concentrated, the residue was dissolved in ethyl acetate and the organic material was washed twice with water, dried and concentrated, to give 3.4 g of 6b.

NMR (CDCl$_3$) δ 1.30 (m, 9, isopropyl+ethyl CH$_3$), 2.87 (m, 2, CH$_2$Ar), 4.37 (m, 3, C$_2$H$_5$+CHN), 4.52 (m, 1, CHN), 5.75 (s, 1, CHCOOH) 6.65 (s, 1, ArCH), 7.05 (ArCH).

ethyl 9-isopropoxy-8-methoxy-2-(3-(methylsulfonyloxy)propyl)-1-(thiophen-2-yl)-5,6-dihydropyrrolo[2,1-a]isoquinoline-3-carboxylate (6c)

A solution of 280 mg of 6b and 165 mg of 2b in 6 ml of acetic anhydride was heated in a microwave oven for 15 min at 140° C. The reaction mixture was cooled and residual solvents were removed by sequential coevaporation with toluene. The residue was purified by chromatography on silica gel, using a gradient of heptane/ethyl acetate as eluent, to provide 215 mg of 6c; MS-ESI: [M+1] 548.15.

NMR (CDCl$_3$) δ 1.12 (d, 6, isoC$_3$H$_7$), 1.40 (t, 3, OC$_2$H$_5$), 1.97 (m, 2, CH$_2$), 2.76 (m, 2, CH$_2$), 3.00 (t, 2, CH$_2$) 3.84 (s, 3, OCH$_3$), 3.92 (m, 1, CH), 4.18 (t, 2, CH$_2$) 4.37 (q, 2, OC$_2$H$_5$), 4.61 (bt, 2, CH$_2$), 3.92 (s, 3, OMes), 6.62 and 6.69 (2×s, 2, Ar—H), 6.96, 7.13 and 7.40 (3×m, 3, thiophene-H).

ethyl 2-(3-(tert-butylamino)propyl)-9-isopropoxy-8-methoxy-1-(thiophen-2-yl)-5,6-dihydropyrrolo[2,1-a]isoquinoline-3-carboxylate (6d)

A solution of 30 mg of 6c and 20 mg of tert-butyl amine in 1 ml of N-methylpyrolidone was heated in a microwave oven at 120° C. for 30 min. The reaction mixture was cooled, poured into 5 ml of water and extracted with ethyl acetate. The product was purified by chromatography over silica gel, using a gradient of CH$_2$Cl$_2$/methanol as eluent, to provide 25 mg of 6d;

MS-ESI: [M+1] 525.25.

9-tert-butyl-2-bromo-3-isopropoxy-13-(2-thienyl)-5, 6,9,10,11,12-hexahydro-8H-azepino[4',3':4,5]pyrrolo [2,1-a]isoquinolin-8-one (6e)

A solution of 35 mg of 6d in 5 ml of ethanol was mixed with a solution of 3 ml of 2N NaOH in water and stirred at 40° C. The mixture was neutralized to pH6 by addition of 0.5N HCl and concentrated in vacuo. The residue was taken up in 2 ml of NMP and 45 mg of DiPEA and 38 mg of HATU were added and the mixture was stirred at RT for 1 h. The reaction mixture was then diluted with 5% aq. $NH_4Cl$ and was extracted with ethyl acetate. The organic layer was dried, concentrated and the residue was purified by preparative HPLC, using a gradient of acetonitrile/water as eluent, to provide 6 mg of 6e, MS-ESI: [M+1] 479.26. NMR ($CDCl_3$) δ 1.14 (d, 6, iso-$C_3H_7$), 1.54 (s, 9, tert$C_4H_9$), 1.88 (m, 2, $CH_2$), 2.56, 2.98, 3.40, 4.48 (4xt, 8, 4x$CH_2$), 3.96 (m, 1, iso$C_3H_7$), 3.83 (s, 3, $OCH_3$), 6.68 and 6.70 (2xs, 2, Ar—H) 6.95, 7.11 and 7.38 (3xm, 3, thiophene-H).

hFSHRago (CHO luc) $pEC_{50}$=7.96.

9-isopropyl-2-bromo-3-isopropoxy-13-(2-thienyl)-5, 6,9,10,11,12-hexahydro-8H-azepino[4',3':4,5]pyrrolo [2,1-a]isoquinolin-8-one (6f)

In a similar way as described for 6e, compound 6f was prepared. MS-ESI: [M+1] 465.20. NMR ($CDCl_3$) δ 1.15 (d, 6, iso$C_3H_7$), 1.22 (d, 6, iso$C_3H_7$), 1.95 (m, 2, $CH_2$), 2.57, 3.00, 3.33, 4.47 (4xt, 8, 4x$CH_2$), 3.97 (m, 1, iso$C_3H_7$), 4.85 (m, 1, iso$C_3H_7$). 3.83 (s, 3, $OCH_3$), 6.69 and 6.71 (2xs, 2, Ar—H) 6.94, 7.10 and 7.38 (3xm, 3, thiophene-H).

hFSHRago (CHO luc) $pEC_{50}$=7.30.

Example 7

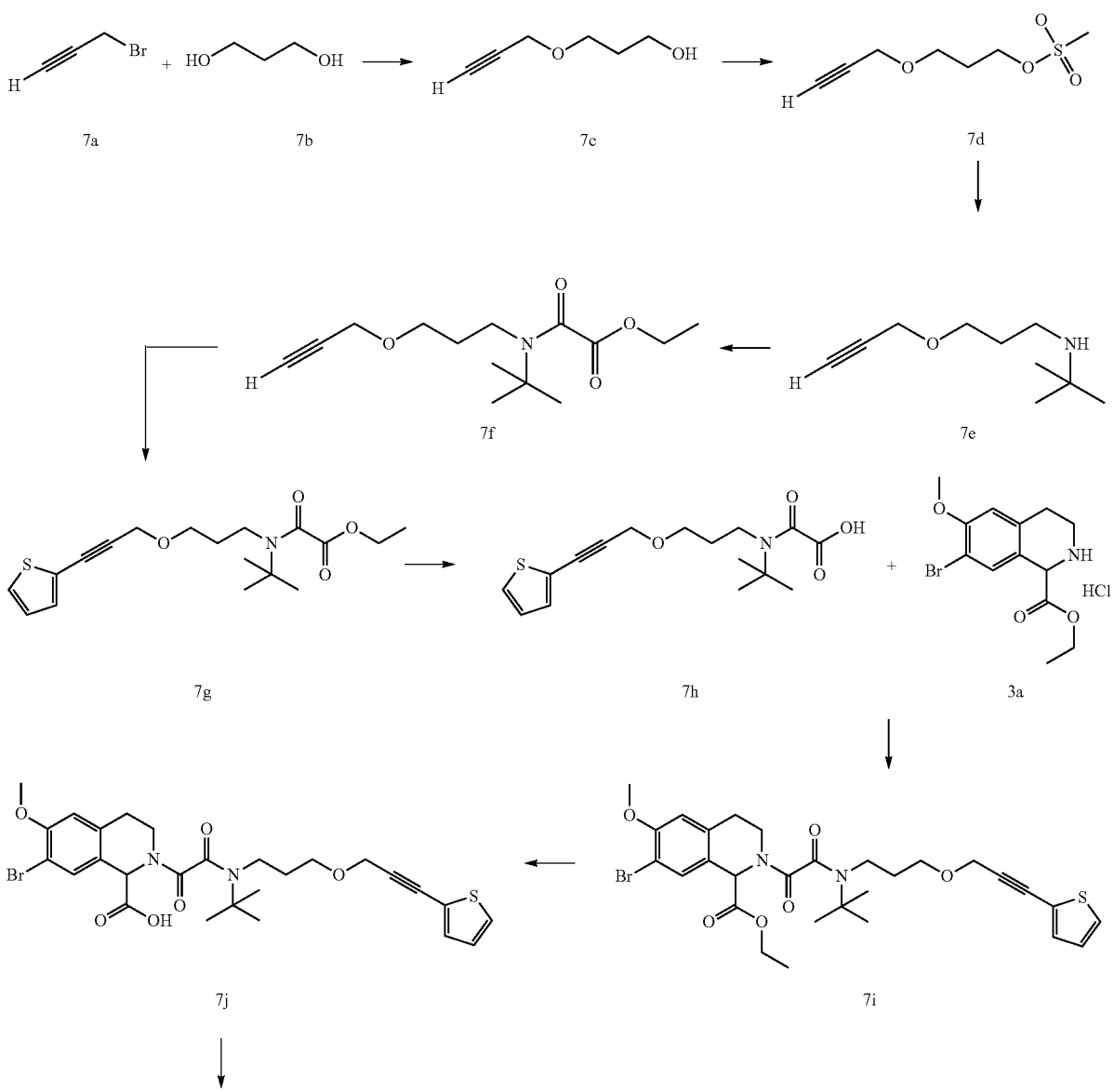

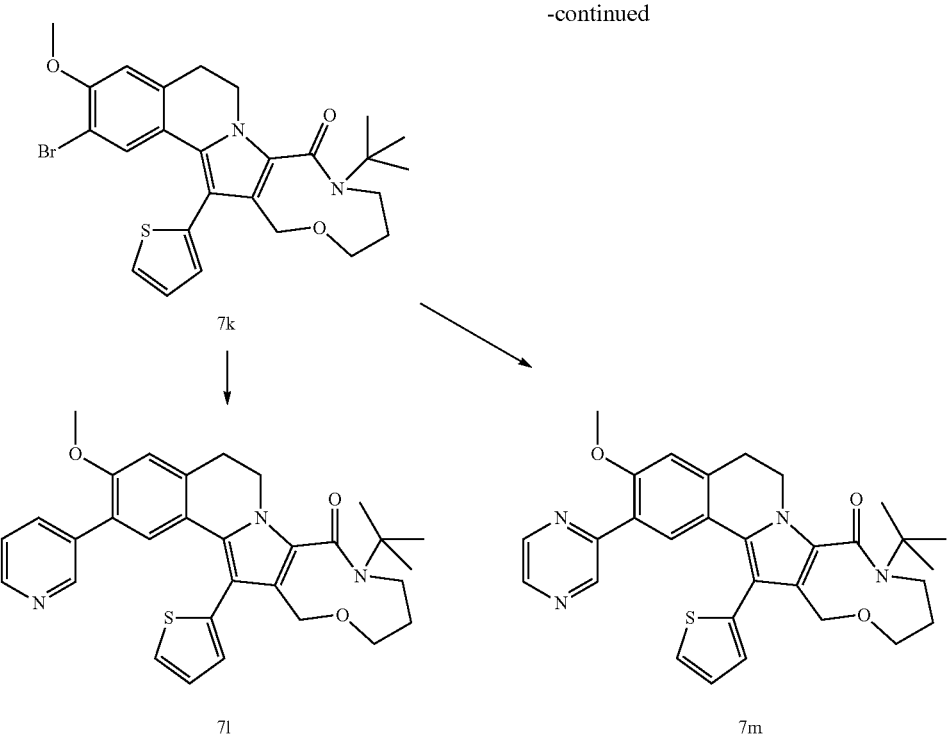

3-(prop-2-ynyloxy)propan-1-ol (7c)

A mixture of 2g of propane-1,3-diol and 2.95 g of propargyl bromide was treated with 3.75 g of KOH in small portions, while maintaining the temperature of the (quite vigorous) reaction mixture below 30° C. by external cooling. When the exotherm subsided the mixture was stirred for 1 hr at RT. The mixture was then diluted with water and extracted with ethyl acetate. The organic layer was dried, concentrated and the residue was passed through a silica column, using a gradient of heptane/acetone as eluent, to provide 1.9 g of 7c as an oil.

NMR (CDCl$_3$) δ 4.18 (s, 2, CH$_2$), 3.79 (m, 2, CH$_2$), 3.72 (m, 2, CH$_2$O), 2.45 (t, 1, acetylene-H), 1.87 (m, 2, CH$_2$).

Adapted to literature reference: R. W. Hoffmann, A. Hense, *Ann. Chemie*, 1283 (1996).

3-(prop-2-ynyloxy)propyl methanesulfonate (7d)

To a solution of 1.9 g of 7c in 15 ml diethyl ether and 3.5 ml triethyl amine was added, at 0° C., a solution of 1.4 ml of ethyloxalyl chloride in 5 ml of ether. The reaction mixture was stirred for 1 hr at 0° C. and then poured onto water and was subsequently extracted with ethyl acetate. The organic layer was washed once with 1M aq. K$_2$CO$_3$ and then dried and concentrated, to give 3.2 g of 7d as a colorless oil.

NMR (CDCl$_3$) δ 4.34 (t, 2, CH$_2$OSO$_2$), 4.17 (s, 2, CH$_2$), 3.02 (s, 3, CH$_3$), 2.45 (t, 1, acetylene-H), 2.05 (m, 2, —CH$_2$—). R$_f$ 0.50 (heptane/ethyl acetate 1/1).

N-tert-butyl-3-(prop-2-ynyloxy)propan-1-amine (7e)

A solution of 1 g of methane sulphonic acid and 1 g of 7d in 10 ml of tert-C$_4$H$_9$NH$_2$ was heated at 60° C. for 24 hr in a closed vial. The reaction mixture was concentrated and the residue was diluted with 15 ml of 1M aq. K$_2$CO$_3$. Then, the product was extracted with ethyl acetate. The organic layer was washed once with sat. NaCl solution, dried and concentrated to provide 830 mg of 7e as a yellowish oil.

NMR (CDCl$_3$) δ 1.50 (s, 9, tertC$_4$H$_9$), 1.75 (m, 2, CH$_2$), 2.42 (t, 1, acetylene-H), 2.66 (t, 2, CH$_2$), 3.60 (t, 2, CH$_2$), 4.14 (s, 2, CH$_2$).

ethyl 2-(tert-butyl(3-(prop-2-ynyloxy)propyl)amino)-2-oxoacetate (7f)

To a solution of 750 mg of 7e and 1 ml of triethyl amine in 10 ml of diethyl ether was added, at 0° C., a solution of 0.55 ml of ethyloxalyl chloride in 3 ml of diethyl ether. The mixture was stirred for 15 min and then quenched with 30 ml of water and was extracted with ethyl acetate. The organic layer was washed once with 1M aq. K$_2$CO$_3$ and once with water, dried, concentrated and chromatographed, to provide 1.0 g of 7f as an oil. R$_f$ (heptane/ethyl acetate 1/1) 0.6.

NMR (CDCl$_3$) δ 1.37 (t, 3, C$_2$H$_5$), 1.48 (s, 9, tert-C$_4$H$_9$), 4.30 (q, 2, C$_2$H$_5$), 4.10 (d, 2, CH$_2$), 3.49 (t, 2, CH$_2$), 3.38 (m, 2, CH$_2$), 2.42 (t, 1, acetylene-H), 1.93 (m, 2, CH$_2$).

ethyl 2-(tert-butyl(3-(3-(thiophen-2-yl)prop-2-ynyloxy)propyl)amino)-2-oxoacetate (7 g)

A solution of 300 mg of 7f, 200 µl of diisopropyl amine, 200 µl of a 1M solution of tributyl phosphine in toluene, in 4 ml of degassed dioxane, was charged with 21 mg of PdCl$_2$(benzonitrile)$_2$ and 10 mg of CuI. The mixture was stirred under nitrogen atmosphere for 16 hr. The mixture was then diluted with 30 ml of 5% NH$_4$Cl and was extracted with ethyl acetate. The organic layer was washed with water, dried, concentrated and the residue was chromatographed over silica gel (heptane/ethyl acetate 1/1) to provide 278 mg of 7g, as colorless oil.

NMR (CDCl$_3$) δ 1.35 (t, 3, C$_2$H$_5$), 1.49 (s, 9, tertC$_4$H$_9$), 1.96 (m, 2, CH$_2$), 3.37 (t, 2, CH$_2$), 3.52 (t, 2, CH$_2$), 4.31 (q, 2, CH$_2$CH$_5$), 4.34 (s, 2, CH$_2$), 6.98, 7.22, 7.28 (3×m, 3, thiophene H).

2-(tert-butyl(3-(3-(thiophen-2-yl)prop-2-ynyloxy)propyl)amino)-2-oxoacetic acid (7h)

A solution of 278 mg of 7g in 3 ml of dioxane was mixed with 170 mg of KOH in 1.5 ml of water and stirred at 55° C. for 1 hr. Then the reaction mixture was cooled and diluted with 10 ml of water and acidified to pH3 with 0.5N HCl. The product was extracted with ethyl acetate. The extract was washed with water, dried and concentrated, to provide 1.95 g of 7h, used without further purification in the next step.

NMR (CDCl$_3$) δ 1.50 (s, 9, tertC$_4$H$_9$), 1.98 (m, 2, CH$_2$), 3.60 (t, 2, CH$_2$), 3.78 (bm, 2, CH$_2$), 4.35 (s, 2, CH$_2$), 6.97, 7.22, 7.26 (3×m, 3, thiophene H).

ethyl 7-bromo-2-(2-(tert-butyl(3-(3-(thiophen-2-yl)prop-2-ynyloxy)propyl)amino)-2-oxoacetyl)-6-methoxy-1,2,3,4-tetrahydroisoquinoline-1-carboxylate (7i)

A solution of 195 mg of 7h, 233 mg of 3a and 0.4 ml of N-ethyl morpholine in 3 ml of DMF was stirred for 5 min. Then, 300 mg of TBTU was added and the reaction mixture was stirred for 2 h at RT. Next, 20 ml of 5% NH$_4$Cl was added and the product was extracted with ethyl acetate. The organic solution was washed with water, dried, concentrated and the crude material was chromatographed over silica gel, using a gradient of heptane/ethyl acetate as eluent, to provide 265 mg of 7l as an oil.

R$_f$ 0.45 (heptane/ethyl acetate 1/1);

NMR (CDCl$_3$) δ 1.27 (t, 3, C$_2$H$_5$), 1.54 (s, 9, tertC$_4$H$_9$), 1.98 and 2.10 (2×bm, 2, CH$_2$), 2.85 and 2.97 (2×dt, 2, CH$_2$), 3.40-3.60 (bm, 4, 2×CH$_2$), 3.70 (dd, 2, CH$_2$), 3.87 (s, 3, OCH$_3$), 4.15 (m, 2, CH$_2$CH$_3$), 4.33 (s, 2, CH$_2$), 5.72 (s, 1, C HCOOC$_2$H$_5$), 6.63 and 7.73 (2×s, 2, Ar—H), 6.96, 7.20 and 7.24 (3×m, 3, thiophene-H).

7-bromo-2-(2-(tert-butyl(3-(3-(thiophen-2-yl)prop-2-ynyloxy)propyl)amino)-2-oxoacetyl)-6-methoxy-1,2,3,4-tetrahydroisoquinoline-1-carboxylic acid (7j)

A solution of 265 mg of 7l in 3 ml of dioxane was mixed with a solution of 100 mg of KOH in 1.5 ml of water. The mixture was stirred for 1 hr at 50° C. (disappearance of the ester spot on TLC). Then, 6 ml of water was added and the reaction mixture was slightly acidified with 0.5N HCl. The product was extracted into ethyl acetate. The organic materials were washed with water, dried, concentrated and the product 7j was isolated in a quantity of 260 mg, which was used without further purification in the next step;

NMR (CDCl$_3$): δ 1.53 (s, 9, tertC$_4$H$_9$), 1.97 and 2.10 (2×m, 2, CH$_2$), 2.85 and 2.94 (2×m, 2, CH$_2$), 3.38-3.58 (bm, 4, 2×CH$_2$), 3.68 (t, 2, CH$_2$), 3.88 (s, 3, OCH$_3$), 4.31 (s, 2, CH$_2$), 5.75 (s, 1, CHCOOH), 6.63 and 7.71 (2×s, 2, Ar—H), 6.96, 7.20 and 7.27 (3×m, 3, thiophene-H).

2-bromo-9-tert-butyl-3-methoxy-15-(2-thienyl)-5,6,9,10,11,12-hexahydro[1,5]oxazonino[8',7':4,5]pyrrolo[2,1-a]isoquinolin-8(14H)-one (7k)

A solution of 257 mg of 7j in a mixture of 5 ml of acetic anhydride and 100 mg of sodium acetate was heated at 105° C. for 30 min. The reaction mixture was cooled, diluted with 20 ml of water and stirred for 1 hr at RT. Then, acetic acid was neuralized by addition of cold conc. ammonia. The product was extracted with ethyl acetate and the organic layer was washed twice with water, dried, concentrated and the crude material was purified by chromatography over silica gel, using a gradient of heptane/ethyl acetate. The material isolated was triturated with diethyl ether, to give 120 mg of 7k;

R$_f$ (toluene/acetone 7/3) 0.68.

NMR (CDCl$_3$) δ 1.58 (s, 9, tertC$_4$H$_9$), 1.70 and 1.90 (2×m, 2, CH$_2$), 2.96 and 3.12 (2×bm, 2, CH$_2$), 3.50 (bm, 2, CH$_2$), 3.70-3.85 (bm, 3, CH$_2$+CH), 4.33 (bm, 1, CH), 4.42 (d, 2, CH$_2$), 3.88 (s, 3, OCH$_3$), 6.72 and 7.28 (2×s, 2, Ar—H), 6.98, 7.12 and 7.38 (3×m, 3, thiophene-H).

9-tert-butyl-3-methoxy-2-pyridin-3-yl-15-(2-thienyl)-5,6,9,10,11,12-hexahydro[1,5]oxazonino[8',7':4,5]pyrrolo[2,1-a]isoquinolin-8(14H)-one (7l)

A solution of 60 mg of 7k, 28 mg of 3-pyridylboronic acid, 47 mg of K$_2$CO$_3$ and 13 mg of Pd(PPh$_3$)$_4$ in 2 ml of degassed 90% aq. dimethoxyethane was heated under N$_2$ atmosphere for 4 h. The reaction mixture was cooled, diluted with 20 ml of ethyl acetate and washed with 2N NaOH and water, dried and concentrated. The crude material was purified by chromatography over silica gel, using a gradient of toluene/acetone. The material thus isolated was treated with diethyl ether, to give 45 mg of 7l, as crystalline material;

MS-ESI: [M+1] 528.3

NMR (CDCl$_3$) δ 1.58 (s, 9, tertC$_4$H$_9$), 1.70 and 1.90 (2×bm, 2, CH$_2$), 3.05 and 3.22 (bm, 2, CH$_2$), 3.53 (bm, 2, CH$_2$) 3.76-3.86 (bm, 3, CH$_2$+CH), 4.40 (bm, 1, CH), 3.83 (s, 3, OCH$_3$), 4.45 (s, 2, CH$_2$), 6.83 and 7.13 (2×s, 2, Ar—H), 7.09, 7.22 and 7.37 (3×m, 3, thiophene-H), 7.00, 7.62, 8.46 and 8.53 (4×m, 4, pyridine-H)

Mp: 228-232° C.

hFSHRago (CHO luc) pEC$_{50}$=8.55

9-tert-butyl-3-methoxy-2-pyrazin-2-yl-15-(2-thienyl)-5,6,9,10,11,12-hexahydro[1,5]oxazonino[8',7':4,5]pyrrolo[2,1-a]isoquinolin-8(14H)-one (7m)

A solution of 60 mg of 7k and 125 mg of 2-tributylstannyl pyrazine and 13 mg of Pd(PPh$_3$)$_4$ was heated in 2 ml of degassed toluene, under N2 atmosphere for 16 hr. The reaction mixture was concentrated and the crude material was chromatographed over silica gel, using a gradient of toluene/ethyl acetate as eluent. The material thus isolated was treated with diethyl ether, to provide 13 mg of crystalline 7m; Mp 267-268° C.; MS-ESI: [M+1] 529.3.

NMR (CDCl$_3$) δ 1.58 (s, 9, tertC$_4$H$_9$), 1.70 and 1.90 (2×bm, 2, CH$_2$), 3.04 and 3.23 (bm, 2, CH$_2$), 3.45-3.67 (bm, 2, CH$_2$) 3.80 (bm, 3, CH$_2$+CH), 4.40 (bm, 1, CH), 3.88 (s, 3, OCH$_3$), 4.44 (d, 2, CH$_2$), 6.86 and 7.59 (2×s, 2, Ar—H), 7.02, 7.06, 7.21, (3×m, 3, thiophene-H), 8.37, 8.50 and 8.87 (3×m, 3, pyrazine-H).

hFSHRago (CHO luc) pEC$_{50}$=7.75

Example 8
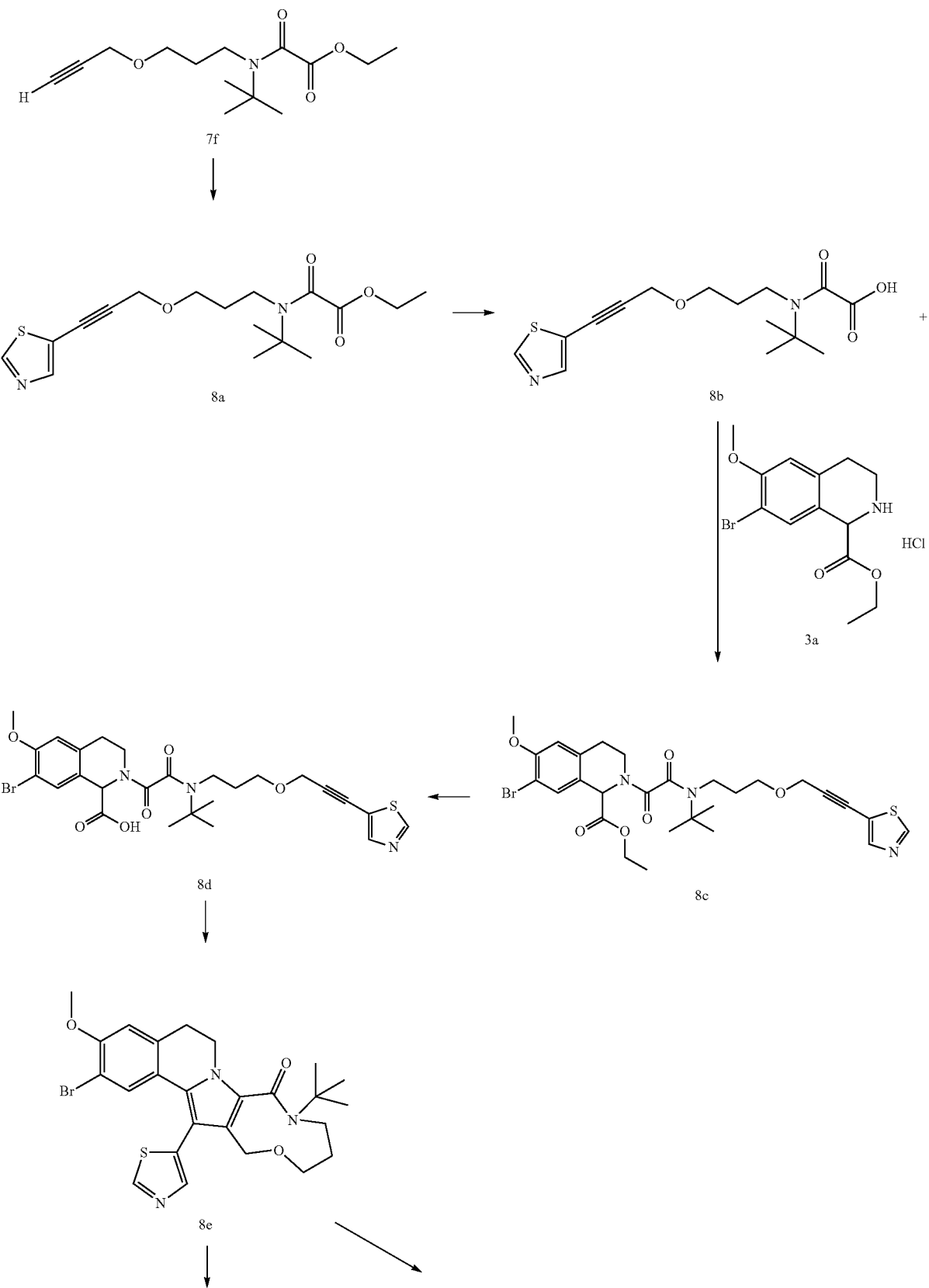

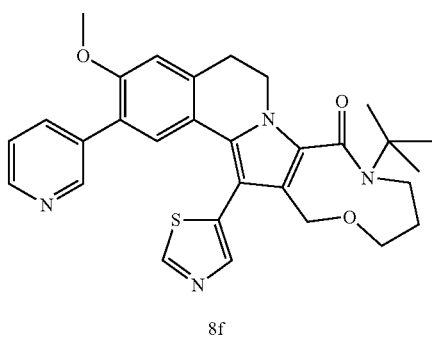

8f

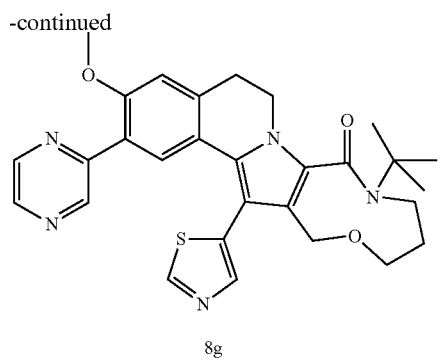

8g ethyl 2-(tert-butyl(3-(3-(thiazol-5-yl)prop-2-ynyloxy)propyl)amino)-2-oxoacetate (8a)

A solution of 300 mg of 7f, 330 mg of 5-bromothiazole, 300 μl of diisopropyl amine and 200 μl of a 1M solution of tributyl phosphine in toluene, in 4 ml of degassed dioxane was charged with 21 mg of PdCl$_2$ (benzonitrile)$_2$ and 10 mg of CuI. The mixture was stirred under nitrogen atmosphere for 16 hr. The mixture was diluted with 30 ml of 5% NH$_4$Cl and was extracted with ethyl acetate. The organic layer was washed with water, dried, concentrated and the residue was chromatographed over silica gel, using a gradient of heptane/ethyl acetate (1/1) as eluent, to provide 270 mg of N-tert-butyl-N-[3-(3-thiazol-5-yl-prop-2-ynyloxy)-propyl]oxalamic acid ethyl ester 8a, as colorless oil. R$_f$ (heptane/ethyl acetate 1/1) 0.40.

NMR (CDCl$_3$) δ 1.35 (t, 3, C$_2$H$_5$), 1.49 (s, 9, tertC$_4$H$_9$), 1.98 (m, 2, CH$_2$), 3.36 (m, 2, CH$_2$), 3.52 (m, 2, CH$_2$), 4.30 (q, 2, C$_2$H$_5$), 4.34 (s, 2, CH$_2$), 7.98 and 8.72 (2×s, 2, thiazole H).

2-(tert-butyl(3-(3-(thiazol-5-yl)prop-2-ynyloxy)propyl)amino)-2-oxoacetic acid (8b)

A solution of 272 mg of 8a in 3 ml of dioxane was mixed with 170 mg of KOH in 1.5 ml of water. The mixture was stirred for 1 h at 55° C. after which all starting material had disappeared, as judged by TLC analysis. The reaction mixture was cooled, diluted with 10 ml of water and acidified to pH3 by addition of cold 0.5N HCl. The product was extracted with ethyl acetate. The combined organic layers were washed once with water, dried and concentrated. The product 8b, 210 mg, thus obtained was used without further purification in the next step.

NMR (CDCl$_3$) δ 1.50 (s, 9, tertC$_4$H$_9$), 2.00 (m, 2, CH$_2$), 3.59 t, 2, CH$_2$), 3.75 (m, 2, CH2), 4.36 (s, 2, CH$_2$), 8.00 and 8.76 (2×s, 2, thiazole H).

ethyl 7-bromo-2-(2-(tert-butyl(3-(3-(thiazol-5-yl)prop-2-ynyloxy)propyl)amino)-2-oxoacetyl)-6-methoxy-1,2,3,4-tetrahydroisoquinoline-1-carboxylate (8c)

A mixture of 219 mg of 8b, 261 mg of 3a and 390 μl of N-ethyl morpholine in 3.5 ml of DMF was stirred for 5 min. Then, 333 mg of TBTU was added and stirring was prolonged for 2 hr. The reaction mixture was diluted with 15 ml of 5% aq. NH$_4$Cl and stirred for 5 min and then extracted with ethyl acetate. The combined extracts were washed with water, dried, concentrated and the crude material was chromatographed, using a gradient of heptane/ethyl acetate as eluent, providing 295 mg of 8c as colorless amorphous material. R$_f$ (heptane/ethyl acetate 1/1) 0.45.

NMR (CDCl$_3$) δ 1.27 (t, 3, C$_2$H$_5$), 1.55 (s, 9, tertC$_4$H$_9$), 1.98 and 2.10 (2×m, 2, CH$_2$), 2.85 and 2.97 (2×dt, 2, CH$_2$), 3.40-3.60 (bm, 4, 2×CH$_2$), 3.70 (dd, 2, CH$_2$), 3.89 (s, 3, OCH$_3$), 4.17 (m, 2, C$_2$H$_5$), 4.35 (s, 2, CH$_2$), 5.72 (s, 1, C HCOOC$_2$H$_5$), 6.64 and 7.74 (2×s, 2, Ar—H), 7.97 and 8.70 (2×s, 2, thiazole-H).

7-bromo-2-(2-(tert-butyl(3-(3-(thiazol-5-yl)prop-2-ynyloxy)propyl)amino)-2-oxoacetyl)-6-methoxy-1,2,3,4-tetrahydroisoquinoline-1-carboxylic acid (8d)

A solution of 293 mg of 8c in 3 ml of dioxane was mixed with a solution of 100 mg of KOH in 1 ml of water and stirred at 55° C. for 1 hr. After this period all ester had disappeared according to TLC. The reaction mixture was cooled, diluted with 10 ml of water and cold 0.5N HCl was added until pH 3. The product was extracted into ethyl acetate. The combined organic layers were once washed with water, dried and concentrated. The amorphous product 8d thus obtained was used without further purification in the next step.

NMR (CDCl$_3$) δ 1.53 (s, 9, tertC$_4$H$_9$), 1.97 and 2.10 (2×m, 2, CH$_2$), 2.86 and 2.97 (2×dt, 2, CH$_2$), 3.40-3.60 (bm, 4, 2×CH$_2$), 3.68 (m, 2, CH$_2$), 3.88 (s, 3, OCH$_3$), 4.30 (s, 2, CH$_2$), 5.78 (s, 1, CHCOOH), 6.65 and 7.77 (2×s, 2, Ar—H), 8.00 and 8.76 (2×s, 2, thiazole-H).

2-bromo-9-tert-butyl-3-methoxy-15-(1,3-thiazol-5-yl)-5,6,9,10,11,12-hexahydro[1,5]oxazonino[8',7':4,5]pyrrolo[2,1-a]isoquinolin-8(14H)-one (8e)

A mixture of 240 mg of 8d and 250 mg of sodium acetate in 5 ml of acetic anhydride was heated at 100° C. for 30 min. The reaction mixture was cooled, diluted with 10 ml of water and stirred for 1 hr at ambient temperature to hydrolyze excess anhydride. The mixture was then made alkaline with cold conc. aq. NH$_4$OH and the product was extracted with ethyl acetate. The product thus isolated was purified by chromatography over silica gel, using a gradient of heptane/ethyl acetate as eluent. The purified product isolated was treated with diethyl ether and gave 150 mg of crystalline material 8e. R$_f$ (toluene/acetone 7/3) 0.50.

NMR (CDCl$_3$) δ 1.58 (s, 9, tertC$_4$H$_9$), 1.72 and 1.90 (2×m, 2, CH$_2$), 2.95 and 3.13 (2×m, 2, CH$_2$), 3.45 and 3.54 (2×m, 2, CH$_2$), 3.70-3.88 (bm, 3, CH$_2$+CH), 3.90 (s, 3, OCH$_3$), 4.30-4.50 (bm, 3, CH$_2$+CH), 6.76 and 7.38 (2×s, 2, Ar—H), 7.81 and 8.89 (2×s, 2, thiazole-H).

9-tert-butyl-3-methoxy-2-pyridin-3-yl-15-(1,3-thiazol-5-yl)-5,6,9,10,11,12-hexahydro[1,5]oxazonino[8',7':4,5]pyrrolo[2,1-a]isoquinolin-8(14H)-one (8f)

A solution of 75 mg of 8e, 35 mg of pyridine-3-boronic acid, 60 mg of K$_2$CO$_3$ in 2 ml of degassed 90% aq.

dimethoxyethane was heated at 90° C. for 16 h The reaction mixture was cooled, diluted with water and extracted with ethyl acetate. The organic layer was once washed with 1M $K_2CO_3$, once with water, dried and concentrated. The crude material was chromatographed over silica gel using a gradient of toluene/acetone. The isolated material was treated with diethyl ether and provided 70 mg of 8f; Mp 200-201° C.; $R_f$ 0.15 (toluene/acetone 7/3). MS-ESI: [M+1] 529.3.

NMR ($CDCl_3$) δ 1.58 (s, 3, tert$C_4H_9$), 1.73 and 1.90 (2×m, 2, $CH_2$), 3.03 and 3.23 (2×bm, 2, $CH_2$), 3.46 and 3.56 (2×bm, 2, $CH_2$), 3.70-3.88 (bm, 3, $CH_2$ and CH), 3.83 (s, 3, $OCH_3$) 4.30-4.50 (bm, 3, $CH_2$ and CH) 7.22, 7.55, 8.48 and 8.58 (4×m, 4, pyridyl), 6.86, 7.08, 7.81 and 8.85 (4×s, 4, thiazole-H and Ar—H).

hFSHRago (CHO luc) $pEC_{50}$=7.85

9-tert-butyl-3-methoxy-2-pyrazin-2-yl-15-(1,3-thiazol-5-yl)-5,6,9,10,11,12-hexahydro[1,5]oxazonino[8',7':4,5]pyrrolo[2,1-a]isoquinolin-8(14H)-one (8g)

A solution of 75 mg of 8e, 150 mg of 2-tributylstannylpyrazine and 16 mg of $Pd(PPh_3)_4$ in 2 ml of degassed toluene was heated under $N_2$ atmosphere for 24 hr. The reaction mixture was concentrated and the crude material was chromatographed over silica gel, using a gradient of toluene/acetone. The material isolated was treated with diethyl ether and provided 66 mg of 8g; Mp 235-236° C.; MS-ESI: [M+1] 530.3;

$R_f$ (toluene/acetone 7/3) 0.25. NMR ($CDCl_3$) δ 1.57 (s, 9, tert$C_4H_9$) 1.74 and 1.90 (2×m, 2, $CH_2$), 3.05 and 3.24 (2×m, 2, $CH_2$) 3.45 and 3.65 (2×m, 2, $CH_2$), 3.70-3.90 (bm, 3, $CH_2$+CH), 3.90 (s, 3, $OCH_3$), 4.30-4.50 (bm, 3, $CH_2$+CH). 8.38, 8.50 and 8.98 (3×m 3, pyrazine-H), 6.88, 7.63, 7.82 and 8.83 (4×s, 4, thiazole-H and Ar—H).

hFSHRago (CHO luc) $pEC_{50}$=6.92

Example 9

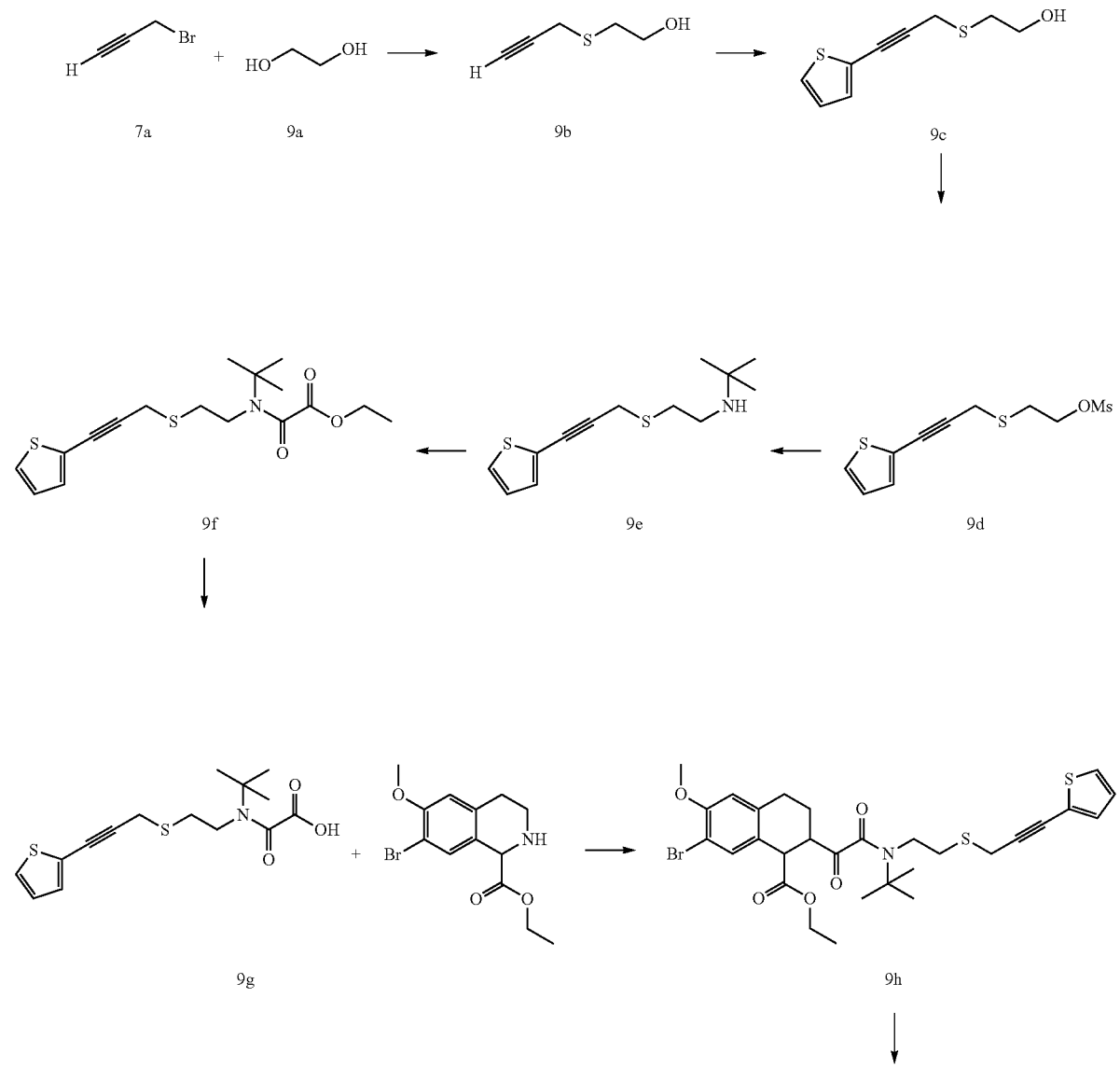

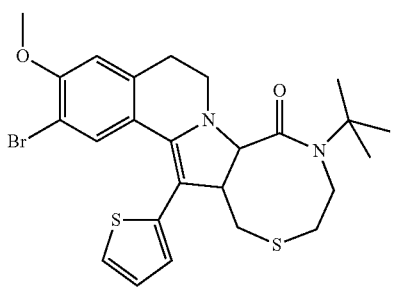

9j

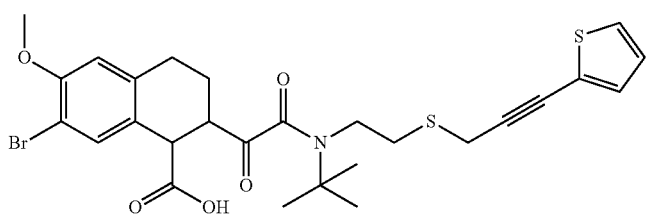

9i

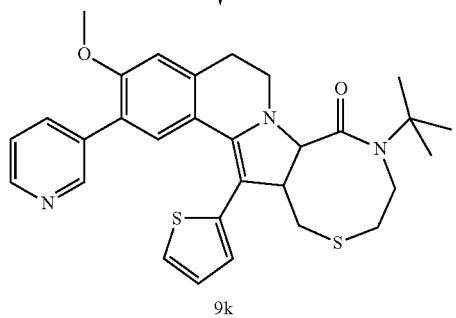

9k

2-(prop-2-ynylthio)ethanol (9b)

To a suspension of 1.7 g of 60% NaH in 20 ml of DMF was added dropwise at 0° C. 3.34 g of 2-mercaptoethanol (9a). After stirring for an additional 10 minutes a solution of 5.09 g of propargyl bromide (7a) in 10 ml of DMF was added dropwise at 0° C. The reaction mixture was allowed to stir at ambient temperature for ½ h and was then poured onto 500 ml of ice-water and extracted with dichloromethane. The combined organic layers were washed twice with sat. aq. NaCl, dried and concentrated, to provide 1.8 g of 9b. $R_f$ (heptane/ethyl acetate 1/1) 0.40.

NMR (CDCl$_3$) δ 2.03 (t, 1, OH), 2.28 (t, 1, acetylene-H), 2.92 (t, 2, CH$_2$), 3.28 (d, 2, CH$_2$), 3.81 (q, 2, CH$_2$).

Adaption of literature: A. Bottini, E. Bonner, *J. Org. Chem.* 31, 385 (1966); L. Skatteboll, B. Boulette, S. Solomon, *J. Org. Chem.* 33, 548 (1968).

2-(3-(thiophen-2-yl)prop-2-ynylthio)ethanol (9c)

A solution of 1.3 g of 9b, 2.4 g of 2-iodothiophene, 2.2 ml of piperidine, 128 mg of CuI and 236 mg of PdCl$_2$(PPh$_3$)$_2$ in 15 ml degassed toluene was stirred under N$_2$ for 16 hr at RT. The reaction mixture was then concentrated and 5% aq. NH$_4$Cl was added and the product was extracted into ethyl acetate. The organic materials were dried, concentrated and the product was chromatographed over silica gel, using a gradient of heptane/ethyl acetate to provide 1.28 g of 9c as an oil;

$R_f$ (heptane/ethyl acetate 1/1) 0.45. NMR (CDCl$_3$) δ 2.08 (t, 1, OH), 2.94 (t, 2, CH$_2$), 3.53 (s, 2, CH$_2$) 3.84 (q, 2, CH$_2$) 6.96, 7.19, 7.23 (3×m, 3, thiophene-H).

2-(3-(thiophen-2-yl)prop-2-ynylthio)ethyl methanesulfonate (9d)

A solution of 1.28 g of 9c and 1.5 ml of triethyl amine in 10 ml of diethyl ether was treated at 0° C. with 0.78 g of methanesulphonyl chloride in 5 ml of diethyl ether. The reaction mixture was stirred for ½ h and then quenched by addition of 20 ml of water. The product was extracted into ethyl acetate and the combined extracts were washed once with 1M K$_2$CO$_3$ and once with water, dried and concentrated, to provide 1.7 g as essentially pure 9d and was used without further purification in the next step.

$R_f$ 0.45 (heptane/ethyl acetate 1/1). NMR (CDCl$_3$) δ 3.05 (s, 3, CH$_3$SO$_2$), 3.08 (t, 2, CH$_2$), 3.58 (s, 2, CH$_2$), 4.46 (t, 2, CH$_2$) 6.97, 7.22, 7.25 (3×m, 3, thiophene-H).

2-methyl-N-(2-(3-(thiophen-2-yl)prop-2-ynylthio)ethyl)propan-2-amine (9e)

A solution of 400 mg of 9d in 8 ml of tert-butyl amine was stirred for 3 days at RT; conversion was completed after that time. The reaction mixture was concentrated and the residue was treated with 30 ml of water and 30 ml of sat. NaHCO$_3$ and the product was extracted into ethyl acetate. The combined organic layers were washed with water, dried and concentrated to provide 354 mg of 9e as essentially pure material, which was used without further purification in the next step. NMR (CDCl$_3$) δ 1.12 (s, 9, tertC$_4$H$_9$), 2.88 (m, 4, 2×CH$_2$), 3.52 (s, 2, CH$_2$), 6.96, 7.18 and 7.22 (3×m, 3, thiophene-H).

ethyl 2-(tert-butyl(2-(3-(thiophen-2-yl)prop-2-ynylthio)ethyl)amino)-2-oxoacetate (9f)

To a solution of 1.63 of 9e in 20 ml of diethyl ether and 1.4 ml of triethyl amine was added, at 0° C., 0.8 ml of ethyloxalyl chloride. The reaction mixture was stirred for ½ h and then poured into water and extracted with ethyl acetate. The extract was washed with 1M aq. K$_2$CO$_3$ and water, dried and concentrated. The residue was chromatographed over silica gel, using a gradient of heptane/ethyl acetate as eluent, to provide 950 mg of 9f.

$R_f$ 0.30 (heptane/ethyl acetate 1/1). NMR (CDCl$_3$) δ 1.34 (t, 3, C$_2$H$_5$), 1.50 (s, 9, tertC$_4$H$_9$), 2.96 (m, 2, CH$_2$), 3.52 (s, 2, CH$_2$), 3.54 (m, 2, CH$_2$), 4.32 (q, 2, C$_2$H$_5$) 6.97, 7.18 and 7.23 (3×m, 3, thiophene-H).

2-(tert-butyl(2-(3-(thiophen-2-yl)prop-2-ynylthio) ethyl)amino)-2-oxoacetic acid (9g)

A solution of 520 mg of 9f in 12 ml of dioxane and a solution of 330 mg of KOH in 2 ml of water were mixed and stirred for 4 h at ambient temperature. The reaction mixture was diluted with 20 ml of water and acidified with cold 0.5 HCl to pH3. The product was extracted into ethyl acetate. The extract was washed once with water, dried and concentrated to provide 480 mg of acid 9g as a colorless oil, which was used without further purification in the next step.

ethyl 7-bromo-2-(2-(tert-butyl-(2-(3-(thiophen-2-yl) prop-2-ynylthio)ethyl)amino)-2-oxoacetyl)-6-methoxy-1,2,3,4-tetrahydroisoquinoline-1-carboxylate (9h)

A mixture of 480 mg of 9g, 570 mg of 3a, 0.56 ml of N-ethyl morpholine and 730 mg of TBTU in 8 ml of DMF was stirred at RT for 16 h. The reaction mixture was diluted with 5% NH$_4$Cl, stirred for 10 min and extracted with ethyl acetate. The extracts was washed with water, dried, concentrated and the residue was chromatographed over silica gel, using a gradient of heptane/ethyl acetate as eluent, to provide 505 mg of 9h as yellowish oil.

$R_f$ 0.48 (heptane/ethyl acetate 1/1). NMR (CDCl$_3$) δ 1.28 (t, 3, CH$_2$CH$_3$), 1.54 (s, 9, tertC$_4$H$_9$), 2.80-3.03 (m, 3, CH$_2$+CH), 3.16 (m, 1, CH), 3.53 (d, 2, CH$_2$), 3.62 (m, 2, CH$_2$), 3.72 (m, 2, CH$_2$), 3.88 (s, 3, OCH$_3$), 4.25 (m, 2, C$_2$H$_5$), 5.75 (s, 1 CHCOOC$_2$H$_5$), 6.38 and 6.73 (2×s, 2, Ar—H) 6.95, 7.19 and 7.22 (3×m, 3, thiophene-H).

7-bromo-2-(2-(tert-butyl-(2-(3-(thiophen-2-yl)prop-2-ynylthio)ethyl)amino)-2-oxoacetyl)-6-methoxy-1,2,3,4-tetrahydroisoquinoline-1-carboxylic acid (9i)

A solution of 505 mg of 9h in 6 ml of dioxane and a solution of 180 mg of KOH in 1 ml of water were mixed and stirred for 3 h at 50° C. The reaction mixture was cooled and diluted with 20 ml of water and acidified to pH 3 by addition of 0.5 N HCl and extracted with ethyl acetate. The extract was once washed with water, dried and concentrated, to provide 480 mg of crude and unstable 9I, which was used without further purification directly in the next step.

2-bromo-9-tert-butyl-3-methoxy-14-(2-thienyl)-5,6,10,11,13,13a-hexahydro-7aH-[1,4]thiazocino[7',6':4,5]pyrrolo[2,1-a]isoquinolin-8(9H)-one (9j)

A mixture of 480 mg of 9I and 600 mg of sodium acetate in 8 ml of acetic anhydride was heated under N$_2$ for 30 min. The mixture was cooled and 15 ml of water was added and stirring was continued for 1 hr to decompose excess anhydride. The mixture was made slightly alkaline by addition of cold conc. aq. NH$_4$OH and was then extracted with ethyl acetate. The extracts were washed with water, dried, concentrated and the product was chromatographed over silica gel, using a gradient of heptane/ethyl acetate. The material thus obtained was triturated with diethyl ether, to provide 20 mg of 9j as white crystalline material; Mp 233-235° C.; $R_f$ 0.20 (heptane/ethyl acetate 1/1).

NMR (CDCl$_3$) δ 1.58 (s, 9, tertC$_4$H$_9$), 2.80-3.20 (bm, 4, 2×CH$_2$), 3.55 (dd, 2, CH$_2$), 3.75 (bm, 1, CH), 3.85-3.97 (bm, 2, CH$_2$), 3.88 (s, 3, OCH$_3$), 4.64 (bm, 1, CH), 6.72, 7.22 (2×s, 2, Ar—H), 6.98, 7.13 and 7.42 (3×m, 3, thiophene-H).

9-tert-butyl-3-methoxy-2-pyridin-3-yl-14-(2-thienyl)-5,6,10,11,13,13a-hexahydro-7aH-[1,4]thiazocino[7',6':4,5]pyrrolo[2,1-a]isoquinolin-8(9H)-one (9k)

A mixture containing 20 mg of 9j, 6 mg of pyridine-3-boronic acid and 10 mg of K$_2$CO$_3$ and 6 mg of Pd(PPh$_3$)$_4$ in 2 ml of degassed 90% aq. dimethoxyethane was heated under N$_2$ for 16 h. The reaction mixture was cooled and diluted with water. The product was extracted with ethyl acetate. The extract was dried, concentrated and the residue was purified by chromatography over silica gel, using heptane/acetone as eluent. The isolated product was treated with ether/ethyl acetate (9/1 v/v) to give 14 mg of white crystalline 9k; $R_f$ 0.50 (heptane/acetone 1/1);

MS-ESI: [M+1] 530.10. Mp 280° C.

NMR (CDCl$_3$) δ 1.58 (s, 9, tertC$_4$H$_9$), 2.80-3.20 (bm, 4, 2×CH$_2$), 3.55 (dd, 2, CH$_2$), 3.75 (bm, 1, CH), 3.85-3.97 (bm, 2, CH$_2$), 3.88 (s, 3, OCH$_3$) 4.64 (bm, 1, CH), 6.72 and 7.22 (2×s, 2, Ar—H), 6.98 and 7.13 and 7.42 (3×m, 3, thiophene-H).

hFSHRago (CHO luc) pEC$_{50}$=9.50

Example 10

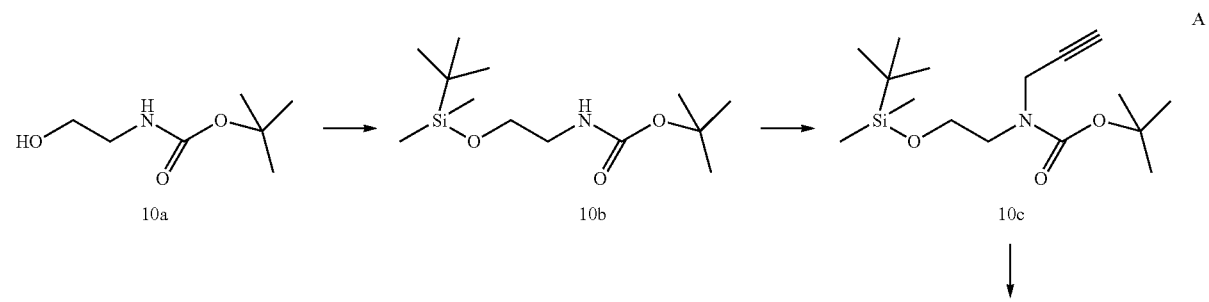

55
-continued
56
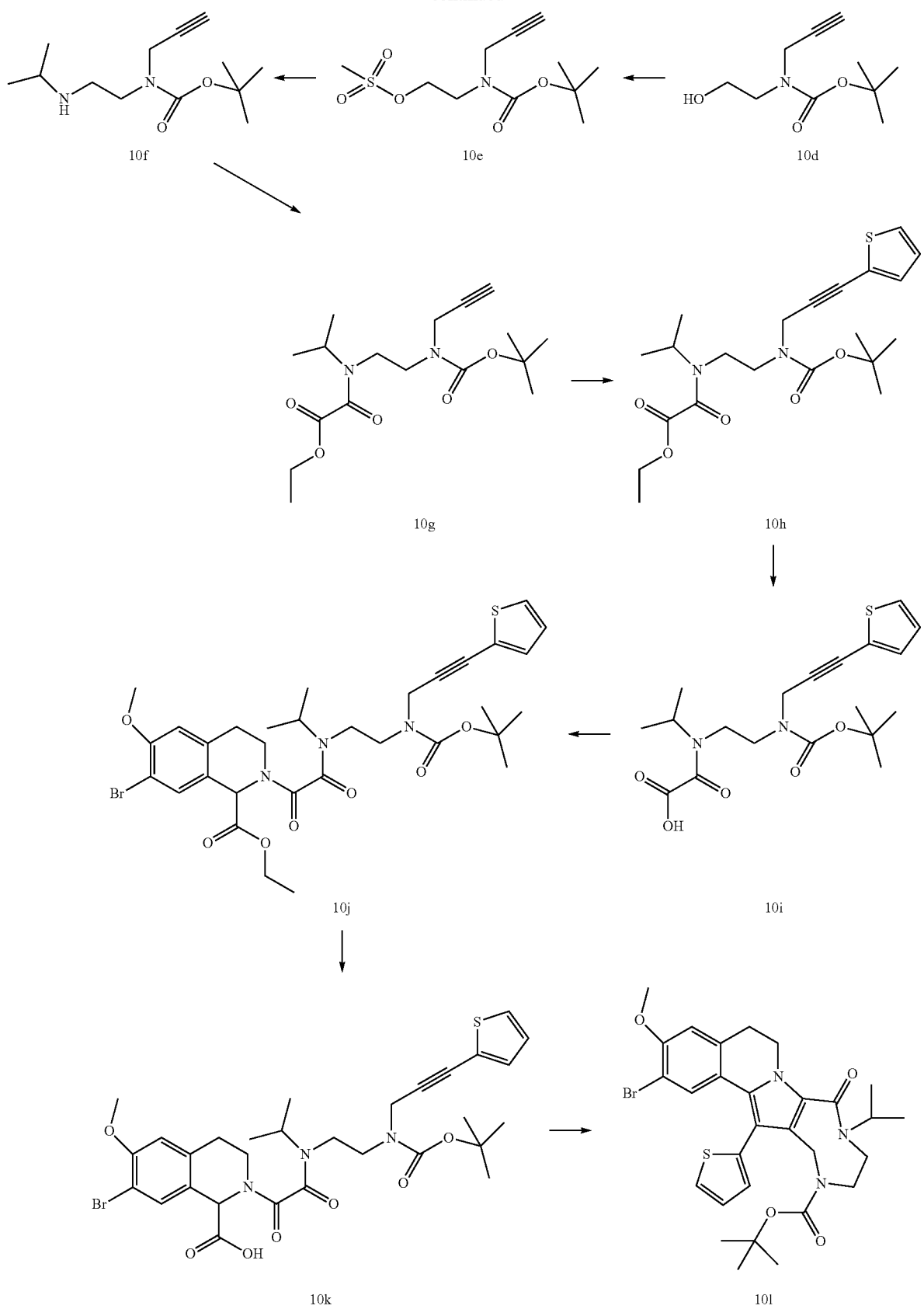

tert-butyl 2-(tert-butyldimethylsilyloxy)ethylcarbamate (10b)

To a solution of 2.6 g of 10a, 2g of imidazole and 0.2 g of DMAP in 30 ml of dichloromethane was added 2.7 g of tertbutyldimethylsilyl chloride. The mixture was stirred overnight. The reaction mixture was quenched by addition of water and the product was extracted into diethyl ether. The organic material was washed once with sat. NaCl, dried and concentrated. The crude product was purified by silica gel chromatography, using a gradient of heptane/ethyl acetate as eluent, to give 3.6 g of 10b as colorless oil. $R_f$ (heptane/ethyl acetate 8/2) 0.40

NMR (CDCl$_3$) δ 0.07 (s, 6, Si(CH$_3$)$_2$), 0.90 (s, 9, tertC$_4$H$_9$Si), 1.45 (s, 9, tertC$_4$H$_9$), 3.25 (m, 2, NCH$_2$), 3.67 (m, 2, OCH$_2$), 4.85 (m, 1, NH).

tert-butyl 2-(tert-butyldimethylsilyloxy)ethyl(prop-2-ynyl)carbamate (10c)

A solution of 800 mg of 10b and 800 µl of propargyl bromide in 8 ml of DMF was treated with 300 mg of NaH (60% dispersion in oil) at 0° C. The mixture was stirred at 0° C. for 1 hr and then for 1 hr at RT (the reaction mixture turned gradually deep brown). Then the mixture was poured onto ice water and the product was extracted with ethyl acetate. The combined organic layers were washed with water, dried and concentrated. The crude material was chromatographed over silica gel, using a gradient of heptane/ethyl acetate as eluent, to provide 650 mg of 10c. $R_f$ (heptane/ethyl acetate 8/2) 0.50.

NMR (CDCl$_3$) δ 0.05 (s, 6, Si(CH$_3$)$_2$), 0.88 (s, 9, tertC$_4$H$_9$Si), 1.47 (s, 9, tertC$_4$H$_9$), 2.18 (m, 1, acetylene-H), 3.25 (m, 2, NCH$_2$), 3.42 (m, 2, CH$_2$), 3.75 (m, 2, CH$_2$), 4.12 (m, 2, CH$_2$).

Described in literature: G. A. Molander, E. P. Cornier, *J. Org. Chem.* 70 (7), 2622 (2005).

tert-butyl 2-hydroxyethyl(prop-2-ynyl)carbamate (10d)

To a solution of 950 mg of 10c in 5 ml of THF was added 5 ml of 1M tetra-n-butyl ammonium fluoride in THF. The mixture was stirred for 1 hr at RT and then poured into 50 ml of water and extracted with ethyl acetate. The crude product thus obtained was chromatographed on silica gel (using a gradient of heptane/ethyl acetateas eluent) and provided 700 mg of 10d, as a colorless oil; $R_f$ 0.35 (heptane/ethyl acetate 1/1);

NMR (CDCl$_3$) δ 1.48 (s, 9, tertC$_4$H$_9$), 2.25 (m, 1, acetylene-H), 3.50 (m, 2, CH$_2$), 3.80 (m, 2, CH$_2$), 4.10 (bs, 2, CH$_2$).

2-(tert-butoxycarbonyl(prop-2-ynyl)amino)ethyl methanesulfonate (10e)

A solution of 700 mg of 10d in 1 ml of triethyl amine and 15 ml of ether was treated at 0° C. with 320 µl of methanesulfonyl chloride in 3 ml of ether. The reaction mixture was stirred for ½ h and then quenched by addition of 20 ml of water and the product was extracted into ether. The organic extract was washed with 1M aq. K$_2$CO$_3$ and once with water, dried and concentrated, to give 900 mg of 10e as a colorless oil, essentially pure according to TLC and NMR, which was used without further purification in the next step. $R_f$ 0.40 (heptane/ethyl acetate 1/1).

NMR (CDCl$_3$) δ 1.49 (s, 9, tertC$_4$H$_9$), 2.25 (m, 1, acetylene-H), 3.02 (s, 3, CH$_3$SO$_2$), 3.68 (t, 2, CH$_2$), 4.10 (m, 2, CH$_2$), 4.38 (bs, 2, CH$_2$).

tert-butyl 2-(isopropylamino)ethyl(prop-2-ynyl)carbamate (10f)

A solution of 900 mg of 10e in 15 ml of isopropyl amine was stirred for 3 days at RT. The reaction mixture was concentrated. The residue was treated with 10 ml of sat. NaHCO$_3$ and extracted with ethyl acetate. After drying and concentration of the organic material 750 mg of essentially pure 10f was obtained as an oil.

NMR (CDCl$_3$) δ 1.05 (d, 6, isoC$_3$H$_7$), 1.48 (s, 9, tertC$_4$H$_9$), 2.20 (m, 1, acetylene-H), 2.80 (m, 3, isoC$_3$H$_7$+CH$_2$), 3.42 (m, 2, CH$_2$), 4.07 (bm, 2, CH$_2$).

ethyl 2-((2-(tert-butoxycarbonyl(prop-2-ynyl)amino)ethyl)(isopropyl)amino)-2-oxoacetate (10g)

To a solution of 900 mg of 10f and 1 ml of triethyl amine in 10 ml of ether was added at 0° C. a solution of 500 µl of ethyloxalyl chloride in 5 ml of ether. The reaction mixture was stirred for ½ h and then quenched by addition of 5% aq. NH$_4$Cl and extracted with ethyl acetate. The organic layers were combined and washed with 1M K$_2$CO$_3$ and water, dried and concentrated, to give 1.03 g of 10g as an oil.

$R_f$ 0.53 (hept/ethyl acetate 1/1).

NMR (CDCl$_3$) δ 1.25 (d, 6, isoC$_3$H$_7$), 1.34 (t, 3, OCH$_2$CH$_3$), 1.49 (s, 9, tertC$_4$H$_9$), 2.25 (m, 1, acetylene-H), 3.40-3.50 (m, 4, CH$_2$CH$_2$), 3.80 bm, 1, isoC$_3$H$_7$), 4.08 (bm, 2, CH$_2$), 4.33 (q, 2, OCH$_2$CH$_3$).

ethyl 2-((2-(tert-butoxycarbonyl(3-(thiophen-2-yl)prop-2-ynyl)amino)ethyl)-(isopropyl)amino)-2-oxoacetate. (10h)

A solution of 340 mg of 10g, 130 µl of 2-iodothiophene, 12 mg of CuI, 21 mg of PdCl$_2$(PPh$_4$)$_2$ and 200 µl of piperidine in 2 ml of degassed toluene was stirred under N$_2$ for 3 h. The mixture was concentrated and applied to a silica column and chromatographed with a gradient of heptane/ethyl acetate, to provide 400 mg of 10h as an orange oil. $R_f$ 0.60 (hept/ethyl acetate 1/1).

NMR (CDCl$_3$) δ 1.15-1.22 (m, 6, isoC$_3$H$_7$), 1.26 (t, 3, OC$_2$H$_5$), 1.45 (s, 9, tertC$_4$H$_9$), 3.73 (m, 1, isoC$_3$H$_7$), 3.40 (bs, 4, CH$_2$CH$_2$), 4.30 (bs+q, 4, OC$_2$H$_5$ and CH$_2$), 7.08, 7.32, 7.60 (3×m, 3, thiophene-H).

2-((2-(tert-butoxycarbonyl(3-(thiophen-2-yl)prop-2-ynyl)amino)ethyl)(isopropyl)amino)-2-oxoacetic acid (10i)

A solution of 400 mg of 10h in 6 ml of dioxane was mixed with a solution of 180 mg of KOH in 1.5 ml of water and stirred for 2 hr at RT. The reaction mixture was diluted with 20 ml of water and acidified to pH3 by addition of 0.5N HCl. The product was extracted into ethyl acetate. The combined organic layers were once washed with water, dried and concentrated, to provide 320 mg of 10i as colorless oil:

MS-ESI: [M+1] 395.09.

ethyl 7-bromo-2-(2-((2-(tert-butoxycarbonyl(3-(thiophen-2-yl)prop-2-ynyl)amino)ethyl)(isopropyl)amino)-2-oxoacetyl)-6-methoxy-1,2,3,4-tetrahydroisoquinoline-1-carboxylate (10j)

A mixture consisting of 200 mg of 10i, 180 mg of 3a, 200 µA of N-ethyl morpholine in 3 ml of DMF was stirred for 5 min and then 230 mg of TBTU was added and stirred for 5 hr.

The reaction mixture was quenched by addition of 30 ml of 5% NH$_4$Cl and extracted with ethyl acetate. The organic layer was washed several times with water, dried, concentrated and the crude material was chromatographed over silica gel, using a gradient of toluene/ethyl acetate, to provide 310 mg of 10j as colorless oil.

R$_f$ 0.60 (toluene/ethyl acetate 1/1). MS-ESI: [M+1] 692.07 and 690.14.

NMR (DMSO-d$^6$), complex due to rotamers, δ 1.15 (t, 3, C$_2$H$_5$), 1.15, 1.25 (bm, 6, isoC$_3$H$_7$), 1.45 (bs, 9, tertC$_4$H$_9$), 3.84 (s, 3, OCH$_3$), 4.12 (q, 2, C$_2$H$_5$) 5.74 (bs, 1, CHCOOC$_2$H$_5$), 2.88 (m, 2, CH$_2$), 3.38-3.70 (bm, 6, 3×CH$_2$), 4.35 (bm, 2, CH$_2$), 6.98+7.02 (2×bs, 1, Ar—H), 7.69, 7.72 (2×bs, 1, Ar—H), 7.60, 7.33, 7.08 (3×bm, 3, thiophene-H).

7-bromo-2-(2-((2-(tert-butoxycarbonyl(3-(thiophen-2-yl)prop-2-ynyl)amino)ethyl)(isopropyl)amino)-2-oxoacetyl)-6-methoxy-1,2,3,4-tetrahydroisoquinoline-1-carboxylic acid (10k)

A solution of 250 mg of 10j in 6 ml of dioxane was mixed with a solution of 120 mg of KOH in 1 ml of water and the reaction mixture was stirred for 5 h at 45° C. The mixture was diluted with 20 ml of water and acidified to pH3 with 0.5N HCl. The product was extracted into ethyl acetate. The organic layer was washed twice with water, dried and concentrated, to give 220 mg of amorphous 10k.

tert-butyl 2-bromo-9-isopropyl-3-methoxy-8-oxo-14-(2-thienyl)-5,6,8,10,11,13-hexahydro[1,4]diazocino[6',7':4,5]pyrrolo[2,1-a]isoquinoline-12(9H)-carboxylate (10l)

A solution of 600 mg of 10k in 8 ml of acetic anhydride and 1g of anhydrous sodium acetate was heated under N$_2$ for 45 min at 100° C. The reaction mixture was cooled and 20 ml of water was added and the mixture was stirred for another 1 hr at ambient temperature. The reaction mixture was then treated with cold conc. aq. NH$_4$OH to make it slightly basic and the product was extracted with ethyl acetate. The crude material thus isolated was purified by chromatography over silica gel, using a gradient of heptane/acetone as eluent. The product isolated, was triturated with diisopropyl ether and provided 350 mg of white crystalline 10l. Mp: 233-234° C., R$_f$ 0.55 (toluene/ethylactetate 1/1). NMR (CDCl$_3$) δ 1.25-1.45 (bs, 15, tertC$_4$H$_9$+isoC$_3$H$_7$), 3.87 (s, 3, OCH$_3$), 4.65 (bm, 1, isoC$_3$H$_7$), 6.72 (bs, 1, Ar—H), 6.93 (bm, 1, thiophene-H), 7.15 (bm, 2, thiophene-H+Ar—H), 7.43 (bm, 1, thiophene-H).

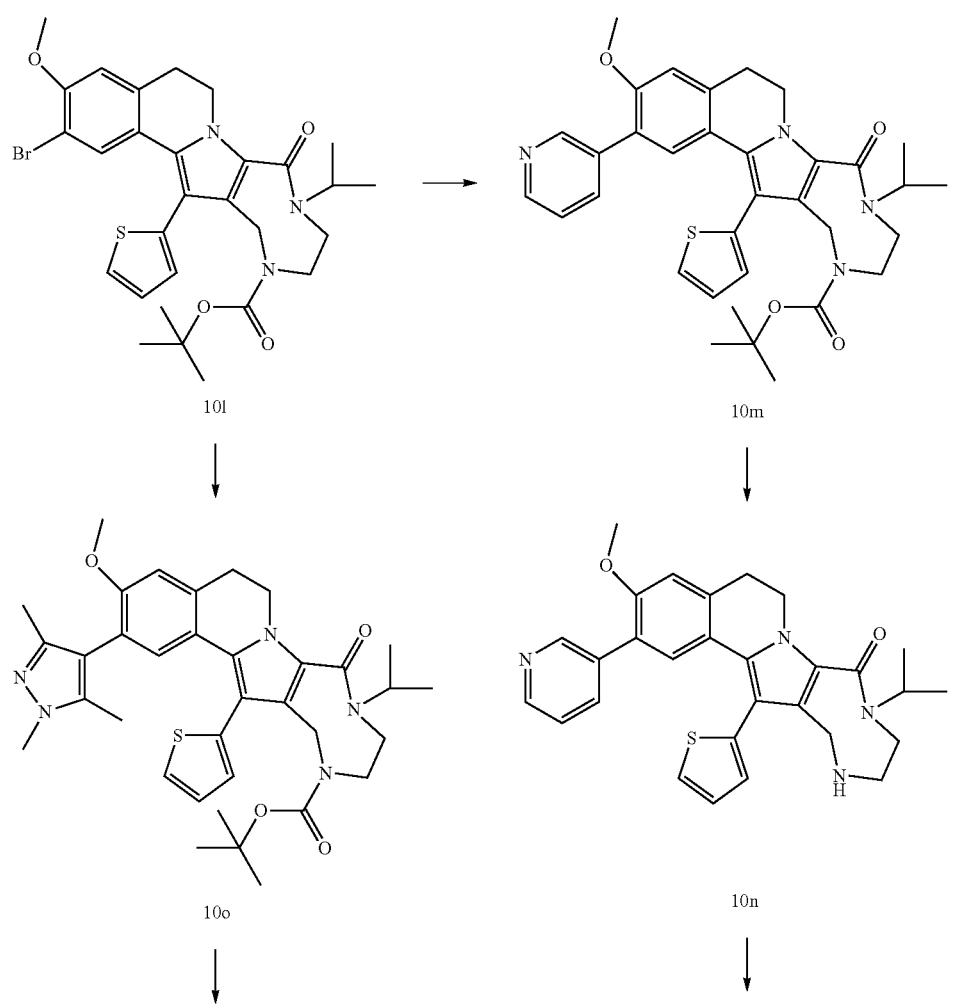

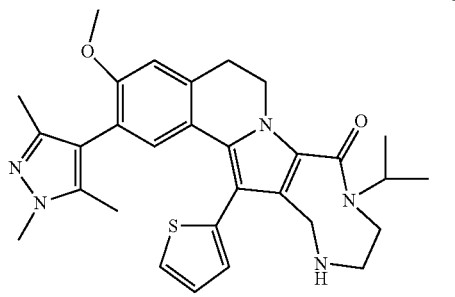

10q

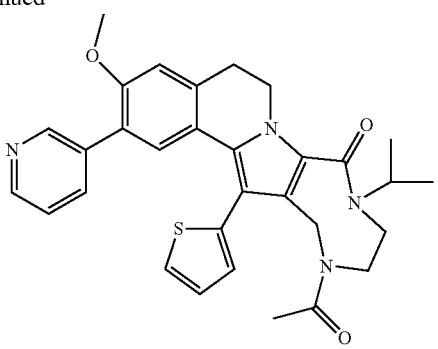

10p

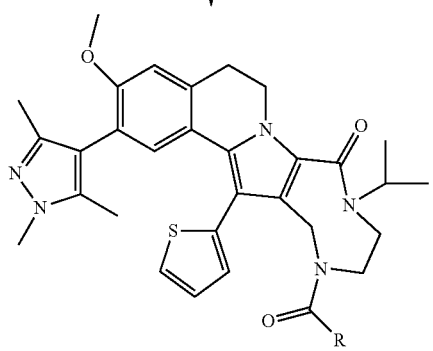

10r R = CH3—
10s R = iso-C3H7—
10t R = CF3CH2CH2— tert-butyl 9-isopropyl-3-methoxy-8-oxo-2-pyridin-3-yl-14-(2-thienyl)-5,6,8,10,11,13-hexahydro[1,4]diazocino[6',7':4,5]pyrrolo[2,1-a]isoquinoline-12(9H)-carboxylate (10m)

A mixture of 60 mg of 10l, 22 mg of 3-pyridylboronic acid, 12 mg of Pd(PPh$_3$)$_4$ and 40 mg of K$_2$CO$_3$ in 3 ml of degassed 90% aq. DME was heated under N$_2$ for 16 h. The reaction mixture was poured onto 1M K$_2$CO$_3$ solution and the product was extracted with ethyl acetate. The organic extract was washed once with sat. NaCl, dried and concentrated. The crude material thus obtained was chromatographed over silica gel, using heptane/acetone in a gradient. The isolated product was triturated with diethyl ether, to give 56 mg of 10m, Mp: 207-208° C.

R$_f$ 0.30 (heptane/acetone 1/1).

NMR (CDCl$_3$) δ 1.30-1.45 (bs, 15, isoC$_3$H$_7$+tertC$_4$H$_9$), 3.80 (s, 3, OCH$_3$), 6.81, 6.98 (2×s, 2, Ar—H), 6.95, 7.13, 7.42 (3×m, 3, thiophene-H), 7.22, 7.60, (2×m, 2, pyridine-H), 8.64 (m, 2, pyridine-H).

9-isopropyl-3-methoxy-2-pyridin-3-yl-14-(2-thienyl)-5,6,10,11,12,13-hexahydro[1,4]diazocino[6',7':4,5]pyrrolo[2,1-a]isoquinolin-8(9H)-one (10n)

To a solution of 50 mg of 10m in 1 ml of dioxane was added 150 μl of 4N HCl in dioxane and a few drops of methanol. The mixture was stirred for 3 hr at RT. The reaction mixture was diluted with 5 ml of 5% aq NaHCO$_3$ and the product was extracted with ethyl acetate. The organic layer was washed with water, dried, concentrated and the residue was treated with diisopropyl ether, to give 35 mg of white crystalline 10n; Mp: 227-229° C.; R$_f$: 0.60 (CH$_2$Cl$_2$/methanol 80/20).

MS-ESI: [M+1] 499.15. NMR (CDCl$_3$) δ 1.31 (d, 6, isoC$_3$H$_7$), 3.82 (s, 3, OCH$_3$), 4.72 (m, 1, isoC$_3$H$_7$), 6.82, 7.05 (2×s, 2, Ar—H), 6.95, 7.11, 7.40 (3×m, 3, thiophene-H), 7.22, 7.60, 8.46, 8.48 (4×m, 4, pyridine-H).

12-acetyl-9-isopropyl-3-methoxy-2-pyridin-3-yl-14-(2-thienyl)-5,6,10,11,12,13-hexahydro[1,4]diazocino[6',7':4,5]pyrrolo[2,1-a]isoquinolin-8(9H)-one (10p)

A solution of 32 mg of 10n in 200 μl of pyridine was treated with 30 μl of Ac$_2$O and 1 mg of DMAP and was stirred at RT for 1 hr. Then, 2 ml of water was added and stirring was continued for 1 hr at RT. The mixture was made slightly alkaline by addition of conc. aq. NH$_4$OH and was extracted with ethyl acetate. The organic layer was washed with a small amount of sat. NaCl, dried, concentrated and treated with diisopropyl ether, to give 30 mg of white crystalline 10p. Mp: 225-226° C.; R$_f$ 0.40 (CH$_2$Cl$_2$/acetone 1/1). MS-ESI: [M+1] 541.12.

NMR (CDCl$_3$) δ 1.33 (bs, 6, isoC$_3$H$_7$), 2.02 (s, 3, CH$_3$CO), 3.83 (s, 3, OCH$_3$), 4.70 (m, 1, isoC$_3$H$_7$), 6.83, 7.00 (2×s, 2, Ar—H), 6.97, 7.14, 7.45 (3×m, 3, thiophene-H), 7.22, 7.61 (2×m, 2, pyridine-H), 8.44, 8.47 (2×m, 2, pyridine-H).

hFSHRago (CHO luc) pEC$_{50}$=8.28.

tert-butyl 9-isopropyl-3-methoxy-8-oxo-14-(2-thienyl)-2-(1,3,5-trimethyl-1H-pyrazol-4-yl)-5,6,8,10,11,13-hexahydro[1,4]diazocino[6',7':4,5]pyrrolo[2,1-a]isoquinoline-12(9H)-carboxylate (10o)

A mixture of 160 mg 10l, 95 mg of 1,3,5-pyrazole-4-boronic acid, 100 mg of $K_2CO_3$, 20 mg of $Pd(PPh_3)_4$, in 6 ml of degassed 90% aq. dimethoxyethane was heated at 90° C. for 48 hr. The reaction mixture was cooled and poured into 30 ml of water, 10 ml of 2N NaOH was added and the product was extracted with ethyl acetate. The crude material thus isolated was purified by chromatography over silica gel, using a gradient of heptane/acetone as eluent. The product isolated was triturated with diethyl ether, to give 110 mg of 10o, as white crystalline material. Mp 232-234° C., $R_f$ 0.30 (heptane./acetone 1/1); MS-ESI: [M+1] 630.22.

NMR (CDCl$_3$) δ 1.47 (bs, 15, isoC$_3$H$_7$+tertC$_4$H$_9$), 1.90 and 1.93 (2×s, 6, CH$_3$ pyrrazole), 3.68 (s, 3, NCH$_3$ pyrrazole), 3.80 (s, 3, OCH$_3$), 6.78 (bs, 1, Ar—H), 6.90 (bs, 2, Ar—H+ thiophene H), 7.07 and 7.33 (2×bm, 2, thiophene).

9-isopropyl-3-methoxy-2-(1,3,5-trimethyl-1H-pyrazol-4-yl)-14-(2-thienyl)-5,6,10,11,12,13-hexahydro[1,4]diazocino[6',7':4,5]pyrrolo[2,1-a]isoquinolin-8(9H)-one (10q)

To a suspension of 110 mg of 10o in 1 ml of dioxane, was added 75 μl of anisole and 500 μl of 4N HCl in dioxane. After 1 hr the reaction mixture was diluted with 10 ml of sat. NaHCO$_3$ and the product was extracted with ethyl acetate. The organic layer was washed once with sat. NaCl, dried and concentrated. The residue was triturated with diethyl ether, to provide 90 mg of 10q as white crystalline material. Mp: 250-252° C.; $R_f$ 0.60 (CH$_2$Cl$_2$/methanol 8/2);

MS-ESI: [M+1] 530.17. NMR (CDCl$_3$) δ 1.31 (d, 6, isoC$_3$H$_7$), 1.90 and 1.94 (2×s, 6, CH$_3$ pyrrazole), 3.70 (s, 3, N—CH$_3$ pyrrazole), 3.80 (s, 3, OCH$_3$), 4.71 (m, 1, isoC$_3$H$_7$), 6.78 and 6.93 (2×s, 2, Ar—H), 6.90, 7.04 and 7.30 (3×m, 3, thiophene).

hFSHRago (CHO luc) pEC$_{50}$=6.59.

12-acetyl-9-isopropyl-3-methoxy-14-(2-thienyl)-2-(1,3,5-trimethyl-1H-pyrazol-4-yl)-5,6,10,11,12,13-hexahydro[1,4]diazocino[6',7':4,5]pyrrolo[2,1-a]isoquinolin-8(9H)-one (10r)

To 32 mg of 10q in 200 μl of pyridine 30 μl of acetic anhydride and 1 mg of DMAP were added. The mixture was stirred for ½ hr, then water and ethyl acetate were added and stirring was continued for ½ hr at RT. The product was extracted into ethyl acetate and washed twice with water, dried, concentrated and the residues were treated with diethyl ether to provide 25 mg of 10r, as white crystalline material. Mp: 178-180° C. $R_f$ 0.15 (heptane/acetone 1/1). NMR (CDCl$_3$) δ 1.33 (bm, 6, N-isoC$_3$H$_7$), 1.90+1.94 (2×s, 6, 2×CH$_3$-pyrrazole), 2.00 (s, 3, N—CH$_3$), 3.70 (s, 3, NCH$_3$), 3.80 (s, 3, OCH$_3$), 4.65 (m, 1, CH isoC$_3$H$_7$), 6.79 and 6.89 (2×s, 2, ArH), 6.93, 7.08 and 7.36 (3×m, 3, thiophene).

hFSHRago (CHO luc) pEC$_{50}$=6.79.

12-isobutyryl-9-isopropyl-3-methoxy-14-(2-thienyl)-2-(1,3,5-trimethyl-1H-pyrazol-4-yl)-5,6,10,11,12,13-hexahydro[1,4]diazocino[6',7':4,5]pyrrolo[2,1-a]isoquinolin-8(9H)-one (10s)

A solution of 20 mg of 10q in 200 μl of pyridine was treated with 30 μl of isobutyric anhydride and 1 mg of DMAP. The mixture was stirred for ½ hr and then water and ethyl acetate were added and stirring was continued for an additional ½ hr. The product was extracted into ethyl acetate. The organic layer was once washed with 0.5 N NaOH and once with water. The material which remained after drying and concentration was triturated with diethyl ether, to provide 15 mg of 10s as crystalline material. Mp: 232-235° C. $R_f$ 0.20 (heptane/ethyl acetate 1/1). MS-ESI: [M+1] 600.23.

NMR (CDCl$_3$) δ 1.00 (d, 6, isoC$_3$H$_7$), 1.32 (bs, 6, isoC$_3$H$_7$), 1.90, 1.93 (2×s, 6, 2×CH$_3$ pyrrazole), 2.58 (m, 1, isoC$_3$H$_7$), 3.70 (s, 3, NCH$_3$), 3.79 (s, 3, OCH$_3$), 6.78 and 6.90 (2×s, 2, Ar—H), 6.39, 7.09 and 7.38 (3×m, 3, thiophene).

hFSHRago (CHO luc) pEC$_{50}$=5.3

9-isopropyl-3-methoxy-14-(2-thienyl)-12-(4,4,4-trifluorobutanoyl)-2-(1,3,5-trimethyl-1H-pyrazol-4-yl)-5,6,10,11,12,13-hexahydro[1,4]diazocino[6',7':4,5]pyrrolo[2,1-a]isoquinolin-8(9H)-one (10t)

A suspension of 26 mg of 10q, 10 mg of trifluorobutyric acid, 15 μl of N-ethyl morpholine and 20 mg of TBTU was stirred at RT for 1 hr. The turbid mixture readily became homogeneous. After one hour, water and ethyl acetate were added and the mixture was stirred for ½ hr. The organic layer was once washed with 1N NaOH and twice with 5% aq. NH$_4$Cl, dried and concentrated. The residue was treated with diethyl ether, from which 25 mg of 10t crystallized, Mp: 256-258° C. $R_f$ 0.25 (heptane/acetone). MS-ESI: [M+1] 654.18

NMR (CDCl$_3$) δ 1.33 (bs, 6, isoC$_3$H$_7$), 1.90, 1.93 (2×s, 6, CH$_3$ pyrrazole), 3.70 (s, 3, NCH$_3$ pyrrazole), 3.80 (s, 3, OCH$_3$), 4.65 (m, 1, N-isoC$_3$H$_7$), 6.78 and 6.89 (2×s, 2, Ar—H), 6.82, 7.09 and 7.38 (3×m, 3, thiophene).

hFSHRago (CHO luc) pEC$_{50}$=6.01.

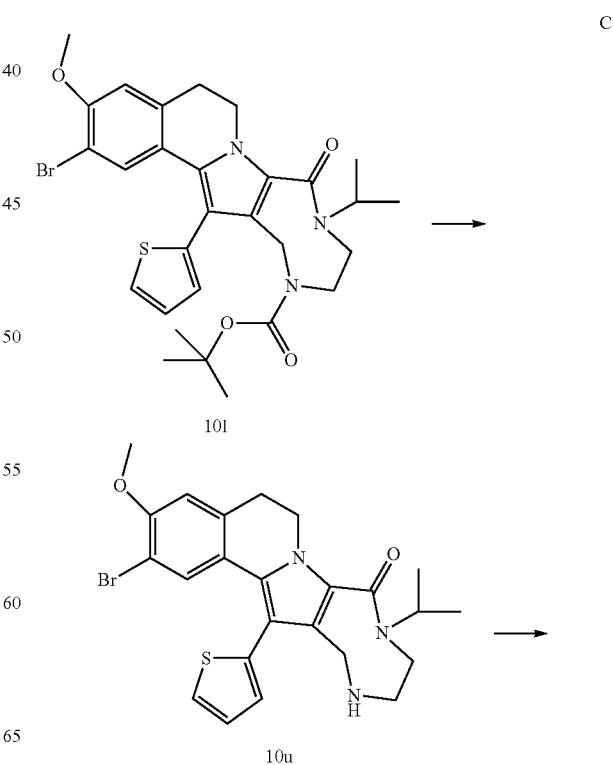

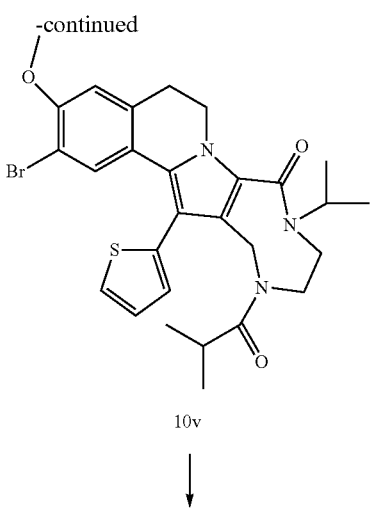

10v

↓

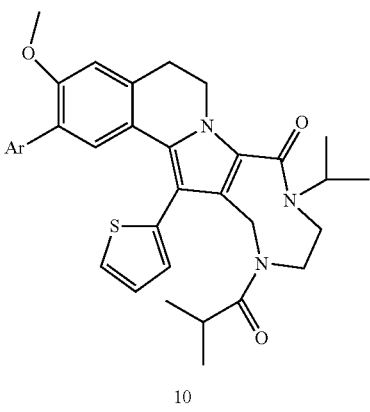

10

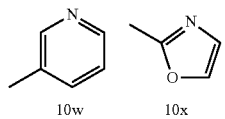

10w    10x 9-isopropyl-3-methoxy-14-(2-thienyl)-2-bromo-5,6,
10,11,12,13-hexahydro[1,4]diazocino[6',7':4,5]pyr-
rolo[2,1-a]isoquinolin-8(9H)-one (10u)

To a solution of 130 mg of 10l, 30 mg of anisole and 100 ul of methanol in 1 ml of dioxane was added 400 µl of 4N HCl in dioxane. The reaction mixture was stirred for 5 h and then quenched by addition of 10 ml of 5% aq. NaHCO₃ and extracted with ethyl acetate. The organic layer was washed once with water, dried and concentrated. The residue was treated with diisopropyl ether, to afford 95 mg of 10u as white crystalline material; Mp 201-203° C.; $R_f$ 0.20 (heptane-acetone 1/1). MS-ESI: [M+1] 499.94 and 501.95. NMR (CDCl₃) 1.30 (d, 6, isoC₃H₇), 3.88 (s, 3, OCH₃), 4.72 (m, 1, isoC₃H₇), 6.70, 7.18 (2×s, 2, Ar—H), 6.93, 7.13, 7.41 (3×m, 3, thiophene-H).

9-isopropyl-3-methoxy-12-isobutyryl-14-(2-thienyl)-
2-bromo-5,6,10,11,12,13-hexahydro[1,4]diazocino
[6',7':4,5]pyrrolo[2,1-a]isoquinolin-8(9H)-one (10v)

To a solution of 90 mg of 10u in 0.6 ml of pyridine was added 1 mg of DMAP and 50 µl of isobutyric anhydride. The reaction mixture was stirred for 1 h and then diluted with 5 ml of water and stirred for ½ h. The product was extracted into ethyl acetate. The organic layer was washed twice with water, dried and concentrated. The residue was treated with diethyl ether and provided 98 mg of 10v as white crystalline material; Mp 248-249° C.; MS-ESI: [M+1] 569.95 and 572.00.

NMR (CDCl₃) δ 1.00 (d, 6, isoC₃H₇), 1.30 (bs, 6, isoC₃H₇), 2.60 (m, 1, CH isoC₃H₇), 3.88 (s, 3, OCH₃), 4.60 (m, 1, isoC₃H₇), 6.72, 7.14 (2×s, 2, Ar—H), 6.97, 7.18, 7.47 (3×m, 3, thiophene-H).

9-isopropyl-3-methoxy-12-isobutyryl-14-(2-thienyl)-
2-pyridin-3-yl-5,6,10,11,12,13-hexahydro[1,4]diazo-
cino[6',7':4,5]pyrrolo[2,1-a]isoquinolin-8(9H)-one
(10w)

A mixture of 52 mg 10v, 20 mg of pyridine-3-boronic acid, 40 mg of K₂CO₃ and 12 mg of Pd(PPh₃)₄ in 3 ml of degassed 90% aq. DME was heated at 95° C. (N₂) for 16 hr.

The reaction mixture was cooled and diluted with 5% aq K₂CO₃ solution and extracted with ethyl acetate. The organic material was dried, concentrated and the crude material thus obtained was chromatographed over silica gel, using a gradient of heptane-acetone as eluent. The product thus obtained was treated with diethyl ether, to provide 36 mg of 10w as white crystals; Mp 178-183° C.;

$R_f$: 0.28 (heptane/acetone 1/1).

MS-ESI: [M+1] 569.17 NMR (CDCl₃) δ 1.00 (d, 6, isoC₃H₇), 1.33 (bs, 6, isoC₃H₇), 2.62 (m, 1, CH isobutyryl), 3.82 (s, 3, OCH₃), 4.61 (m, 1, isoC₃H₇), 6.82, 7.01 (2×s, 2, Ar—H), 6.97, 7.16, 7.46 (3×m, 3, thiophene-H) 7.22, 7.62 (2×m, 2, pyridine-H), 8.45 (m, 2, pyridine-H).

hFSHRago (CHO luc) pEC₅₀=6.12.

9-isopropyl-3-methoxy-12-isobutyryl-14-(2-thienyl)-
2-oxazol-2-yl-5,6,10,11,12,13-hexahydro[1,4]diazo-
cino[6',7':4,5]pyrrolo[2,1-a]isoquinolin-8(9H)-one
(10x)

A solution of 45 mg of 10v, 45 mg of 2-tributylstannyloxazole, 10 mg of Pd(PPh₃)₄ in 2 ml of degassed toluene was heated at 100° C. for 48 hr. The reaction mixture was cooled and applied to a silica column and eluted with a gradient of heptane-acetone. The purified product was treated with diethyl ether to give 25 mg of 10x as crystalline material; Mp 242-243° C.

$R_f$ 0.27 (heptane/acetone 1/1). MS-ESI: [M+1] 559.15.

NMR (CDCl₃) δ 1.00 (d, 6, isoC₃H₇), 1.33 (bs, 6, isoC₃H₇), 2.62 (m, 1, CH isoC₃H₇), 3.98 (s, 3, OCH₃), 4.62 (m, 1, isoC₃H₇), 6.87, 7.20 (2×s, 2, Ar—H), 7.56, 7.67 (2×s, 2, oxazole-H), 7.01, 7.17, 7.45 (3×m, 3, thiophene-H).

hFSHRago (CHO luc) pEC₅₀=5.90.

Example 11
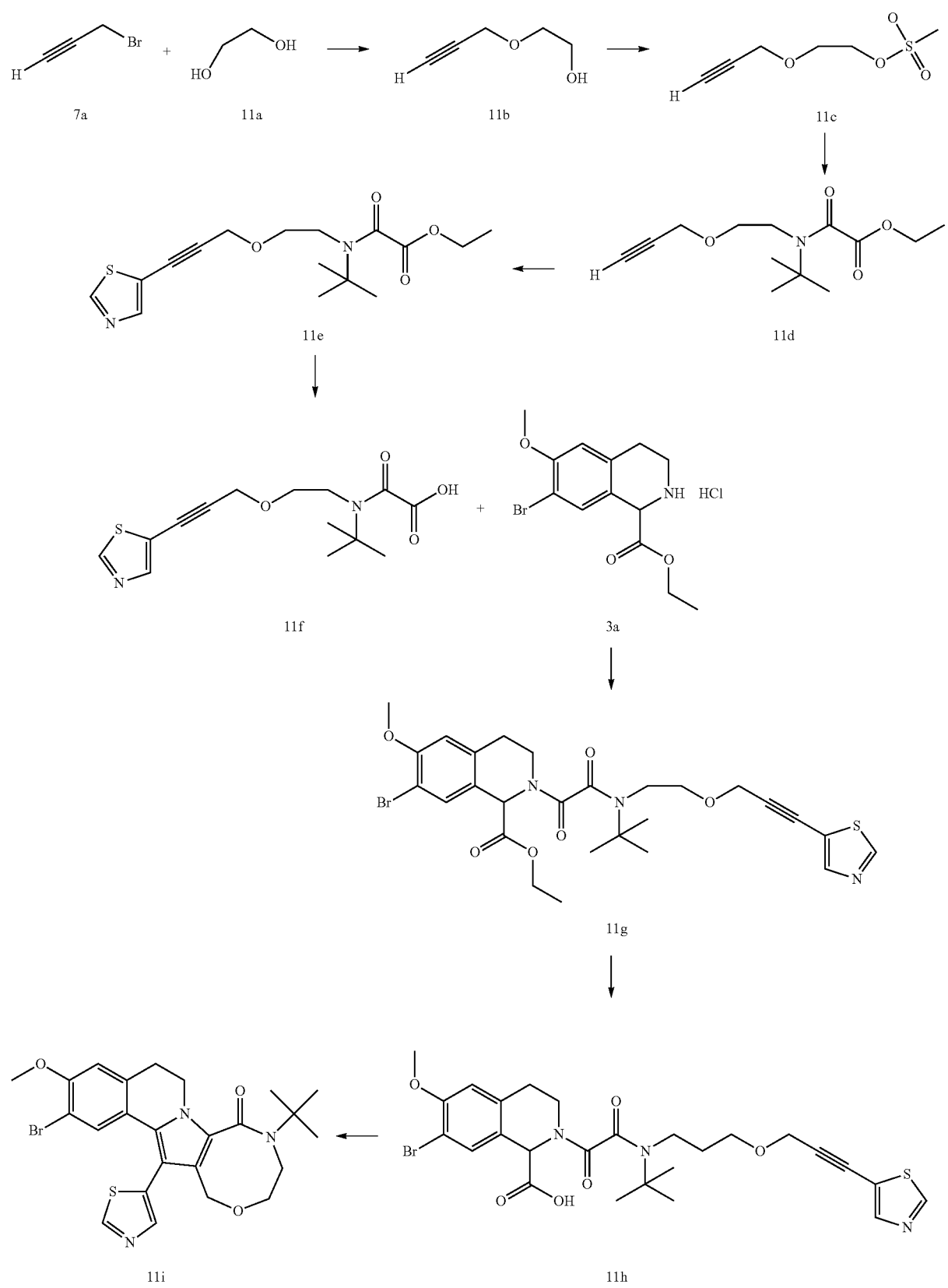

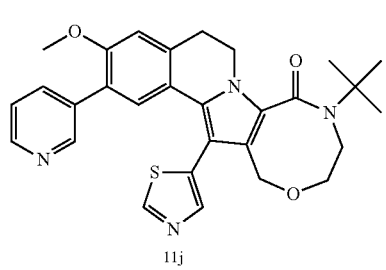 11j

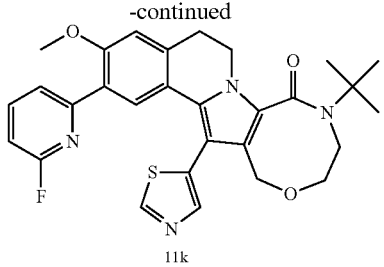 11k

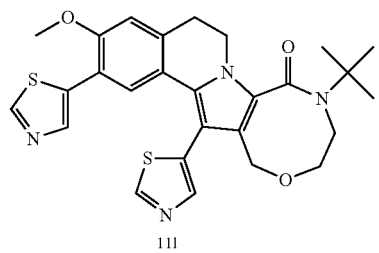 11l 2-(prop-2-ynyloxy)ethanol (11b)

To a mixture of 5 ml of ethylene glycol, 11a and 3.4 ml of propargyl bromide (7a) was added at 0° C. with vigorous stirring 3g of powdered KOH in portions over 5 min. A vigorous reaction ensued after a few minutes which was controlled by external cooling to keep the temperature below 35° C. After stirring for 1 hr at ambient temperature the reaction mixture was diluted with 50 ml of water and the product was extracted 5 times with ethyl acetate. The combined organic layers were once washed with sat. aq. NaCl, dried and concentrated. The product was purified by chromatography over silica, using a gradient of heptane-ethyl acetate as eluent, to provide 1.7 g of 11b as colorless oil; $R_f$ 0.30 (heptane/ethyl acetate 1/1). NMR (CDCl$_3$) δ 2.48 (t, 1, acetylene-H), 2.00 (t, 1, CH$_2$OH), 3.65 (t, 2, CH$_2$), 3.77 (m, 2, CH$_2$), 4.22 (d, 2, CH$_2$).

2-(prop-2-ynyloxy)ethyl methanesulfonate (11c)

A solution of 1.7 g of 11b and 3 ml of triethyl amine in 20 ml of diethyl ether was treated at 0° C. with 1.5 ml of methanesulfonyl chloride. The mixture was stirred for an additional 30 min and then diluted with 35 ml of water and extracted with ethyl acetate. The combined organic layers were washed with 1M aq. K$_2$CO$_3$ solution and water, dried and concentrated, to provide 2.45 of 11c as a colorless oil; $R_f$ 0.45 (heptane/ethyl acetate 1/1).

NMR (CDCl$_3$) δ 2.48 (t, 1, acetylene-H), 3.08 (s, 3, CH$_3$SO$_2$), 3.82 (m, 2, CH$_2$), 4.03 (d, 2, CH$_2$), 4.41 (m, 2, CH$_2$).

ethyl 2-(tert-butyl(2-(prop-2-ynyloxy)ethyl)amino)-2-oxoacetate (11d)

A solution of 2.45 g of 11c in 15 ml of tert-butyl amine was stirred at 45° C. for 24 h. The reaction mixture was concentrated and diluted with 50 ml of sat. aq. NaHCO$_3$ solution. The product was extracted into ethyl acetate. The organic layer was washed once with sat. aq. NaCl solution, dried and concentrated. The residue was dissolved in 70 ml of diethyl ether and 10 ml of triethyl amine and cooled to 0° C. To this was added, dropwise with stirring, 2 ml of ethyloxalyl chloride in 5 ml of diethyl ether. The reaction mixture was stirred for ½ h and then poured into 100 ml of water. The product was extracted with ethyl acetate and the organic layers were combined and washed once with 1M K$_2$CO$_3$ and once with water and then dried and concentrated. The product was purified by passing through a short silica gel column, using heptane/ethyl acetate gradient as eluent, to provide 3.2 g of 11d as a colorless oil;

NMR (CDCl$_3$) δ 1.36 (t, 3, OC$_2$H$_5$), 1.48 (s. 9, tertC$_4$H$_9$), 2.45 (t, 1, acetylene-H), 3.53 (bt, 2, CH$_2$) 3.63 (bt, 2, CH$_2$).

ethyl 2-(tert-butyl(2-(3-(thiazol-5-yl)prop-2-ynyloxy)ethyl)amino)-2-oxoacetate (11e)

A solution of 390 mg of 11d, 290 mg of 5-bromothiazole, 400 µl of diisopropyl amine, 40 mg of PdCl$_2$(PheCN)$_2$, 20 mg of CuI and 300 µl of a 1M solution of tri-tert-butyl phosphine (in toluene) in 4 ml of degassed dioxane, was stirred under N$_2$ for 16 hr. The mixture was poured into 20 ml of 5% aq. NH$_4$Cl solution and extracted with ethyl acetate. The organic layer was dried, concentrated and the product was chromatographed over silica gel, using a gradient of heptane/ethyl acetate, to give 450 mg of 11e as a colorless oil; $R_f$ 0.40 (heptane/ethyl acetate 1/1);

MS-ESI: [M+1] 339.10.

NMR (CDCl$_3$) δ 1.48 (s, 9, tertC$_4$H$_9$), 1.35 (t, 3, C$_2$H$_5$), 4.39 (s, 2, CH$_2$) 3.57 (bt, 2, CH$_2$) 4.32 (q, 2, C$_2$H$_5$) 3.68 (bt, 2, CH$_2$), 8.00, 8.72 (2×s, 2, thiazole-H).

2-(tert-butyl-(2-(3-(thiazol-5-yl)prop-2-ynyloxy)ethyl)amino)-2-oxoacetic acid (11f)

A solution of 450 mg of 11e in 4 ml of dioxane was mixed with a solution of 250 mg of KOH in 2 ml of water and stirred at 55° C. for 1 h. The reaction mixture was then cooled and diluted with 20 ml of water and made acidic to pH3 by addition of 0.5N HCl. The product was extracted with ethyl acetate. The organic extract was washed once with water, dried and concentrated, to give 430 mg of 11f as a colorless oil, which solidified on standing; Mp: 104-105° C.; $R_f$ 0.20 (CH$_2$Cl$_2$/methanol 8/2). MS-ESI:

[M+1] 311.12

NMR (CDCl$_3$) δ 1.50 (s, 9, tertC$_4$H$_9$), 4.40 (s, 2, CH$_2$), 3.71 (t, 2, CH$_2$), 3.99 (bs, 2, CH$_2$), 7.98, 8.78 (2×bs, 2, thiazole-H).

ethyl 7-bromo-2-(2-(tert-butyl(2-(3-(thiazol-5-yl)prop-2-ynyloxy)ethyl)amino)-2-oxoacetyl)-6-methoxy-1,2,3,4-tetrahydroisoquinoline-1-carboxylate (11g)

A solution of 520 mg of 3a, 430 mg of 11f, 900 µl of N-ethylmorpholine, 650 mg of TBTU in 4 ml of DMF was stirred at RT for 16 hr. The reaction mixture was then diluted with 25 ml of 5% aq. NH$_4$Cl, stirred for 10 min and extracted with ethyl acetate. The extract was washed with water, dried, concentrated and the residue was purified by chromatography over silica gel, using a gradient of toluene/ethyl acetate as eluent, to provide 510 mg of 11g as a colorless oil.

$R_f$ 0.55 (toluene/ethyl acetate 1/1).

MS-ESI: [M+1] 606.08 and 608.11.

7-bromo-2-(2-(tert-butyl(2-(3-(thiazol-5-yl)prop-2-ynyloxy)ethyl)amino)-2-oxoacetyl)-6-methoxy-1,2,3,4-tetrahydroisoquinoline-1-carboxylic acid (11h)

A solution of 500 mg of 11g in 6 ml of dioxane was mixed with a solution of 300 mg of KOH in 3 ml of water and heated to 50° C. for 2 h. The reaction mixture was cooled and diluted with water and then acidified to pH3 by addition of 0.5N HCl. The product was extracted with ethyl acetate and the organic extract was washed once with water, dried and concentrated, to provide 480 mg of 11h as colorless amorphous material;
MS-ESI: [M+1] 578.05, 580.06.

The material was used without further purification in the next step.

2-bromo-9-tert-butyl-3-methoxy-14-(1,3-thiazol-5-yl)-5,6,10,11-tetrahydro-9H-[1,4]oxazocino[7',6':4,5]pyrrolo[2,1-a]isoquinolin-8(13H)-one (11i)

A solution of 480 mg of 11h in 7 ml of acetic anhydride and 500 mg of anhydrous sodium acetate was heated at 105° C. for 30 min. The reaction mixture was cooled and treated with 40 ml of ice-water and stirred for 1 hr at ambient temperature to break down excess anhydride. Then, 30 ml of ethyl acetate was added and the stirred mixture was treated with cold conc. aq. NH₄OH, to adjust the pH of the reaction mixture to slightly basic. The materials were extracted into ethyl acetate, washed with water, dried and concentrated. The residue was passed over a short silica column, using a gradient of toluene/ethyl acetate as eluent and the purified material thus obtained was treated with diethyl ether, to give 290 mg of 11i as white crystals; Mp 219-220° C.; $R_f$ 0.35 (toluene/ethyl acetate 1/1). MS-ESI: [M+1] 516.04, 518.05.

NMR (CDCl₃) conformers δ 1.58 (bs, 9, tertC₄H₉), 2.95, 3.10 (2×bs, 2, CH₂), 3.55 (bm, 1, CH₂), 4.43 (dd, 2, CH₂) 4.75 (bs, 1, CH₂) 3.80-4.05 (bm, 4, 2×CH₂), 3.88 (s, 3, OCH₃), 6.75, 7.20 (2×s, 2, Ar—H), 7.78, 8.92 (2×s, 2, thiazole-H).

9-tert-butyl-3-methoxy-2-pyridin-3-yl-14-(1,3-thiazol-5-yl)-5,6,10,11,12,13-hexahydroazocino[4',3':4,5]pyrrolo[2,1-a]isoquinolin-8(9H)-one (11j)

A degassed solution of 40 mg of 11i, 20 mg of pyridyl-3-boronic acid, 30 mg of K₂CO₃, 12 mg Pd(PPh₃)₄ and 3 ml of 90% aq. dimethoxyethane was heated at 90° C. for 16 hr. The reaction mixture was cooled, poured into 20 ml of 1N NaOH and extracted with ethyl acetate. The organic layer was washed with water, dried, concentrated and the residues were passed through a short silica column, using a gradient of toluene/acetone as eluent. The isolated material was treated with diethyl ether and gave 35 mg of 11j as white crystals; Mp: 227-229° C.; $R_f$ 0.35 (toluene/acetone 1/1).

MS-ESI: [M+1] 515.18. NMR (CDCl₃) conformers δ 1.58 (s, 9, tertC₄H₉), 3.82 (s, 3, OCH₃), 6.88, 7.78 (2×s, 2, Ar—H), 7.01, 8.88 (2×s, 2, thiazole-H), 7.22, 7.53, 47, 8.54 (4×m, 4, pyridine-H), 3.85-4.07 (bm, 4, 2×CH₂), 3.06 (bm, 2, CH₂) 3.20 (bm, 1, CH₂), 3.56 (bm, 1, CH₂), 4.80 (bm, 1, CH₂) 4.47 (bd, 2, CH₂).

hFSHRago (CHO luc) pEC₅₀=8.51.

9-tert-butyl-2-(6-fluoropyridin-2-yl)-3-methoxy-14-(1,3-thiazol-5-yl)-5,6,10,11-tetrahydro-9H-[1,4]oxazocino[7',6':4,5]pyrrolo[2,1-a]isoquinolin-8(13H)-one (11k)

A solution of 80 mg of 11i, 90 mg of 2-fluoro-6-tributylstannylpyridine and 25 mg of Pd(PPh₃)₄ in 5 ml of degassed toluene was heated at 110° C., under N₂ atmosphere, during 48 hr. The reaction mixture was applied to a silica gel column and eluted with a gradient of heptane/acetone. The isolated product was treated with diethyl ether and provided 60 mg of 11k as white crystalline material; Mp: 232-234° C.; $R_f$ 0.45 (heptane/acetone 1/1).

MS-ESI: [M+1] 533.14. NMR (CDCl₃): conformers δ 1.57 (s, 9, tertC₄H₉), 3.05, 3.20 (2×bs, 2, CH₂), 3.90 (s, 3, OCH₃), 4.47 (bd, 2, CH₂), 4.80 (bs, 1, CH₂), 3.56 (bd, 1, CH₂), 3.84-4.07 (bm, 4, 2×CH₂) 6.83, 7.56 (2×s, 2, Ar—H), 7.78, 8.92 (2×s, 2, thiazole-H), 6.75 (dd, 1, pyridine-H), 7.58 (dd, 1, pyridine-H), 7.70 (q, 1, pyridine-H).

hFSHRago (CHO luc) pEC₅₀=7.86

9-tert-butyl-3-methoxy-2,14-di-1,3-thiazol-5-yl-5,6,10,11-tetrahydro-9H-[1,4]oxazocino[7',6':4,5]pyrrolo[2,1-a]isoquinolin-8(13H)-one (11l)

A degassed solution of 40 mg of 11i, 45 mg of 5-tributylstannyl thiazole and 15 mg of Pd(PPh₃)₄ in 3 ml of toluene was heated at 110° C. during 5 hr. The reaction mixture was concentrated and the residue was chromatographed over silica gel, using a gradient of toluene/acetone as eluent. The isolated product was treated with diethyl ether, to provide 31 mg of 11l as white crystalline material; Mp: 254-255° C.; $R_f$ 0.30 (heptane/acetone 1/1).

MS-ESI: [M+1] 521.12.

NMR (CDCl₃) conformers δ 1.58 (s, 9, tertC₄H₉), 3.04 and 3.18 (2×bm, 2, CH₂), 3.57 (bm, 1, CH₂), 3.85-4.07 (bm, 4, 2×CH₂), 4.48 (bd, 2, CH₂) 4.78 (bm, 1, CH₂), 3.94 (s, 3, OCH₃), 6.85, 7.35 (2×s, 2, Ar—H) 7.82, 7.88 (2×s, 2, thiazole-H), 8.68, 8.96 (2×s, 2, thiazole-H).

hFSHRago (CHO luc) pEC₅₀=7.9.

Example 12

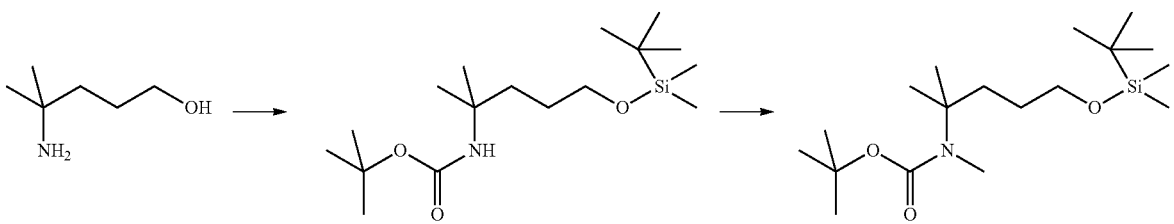

12a 12b 12c

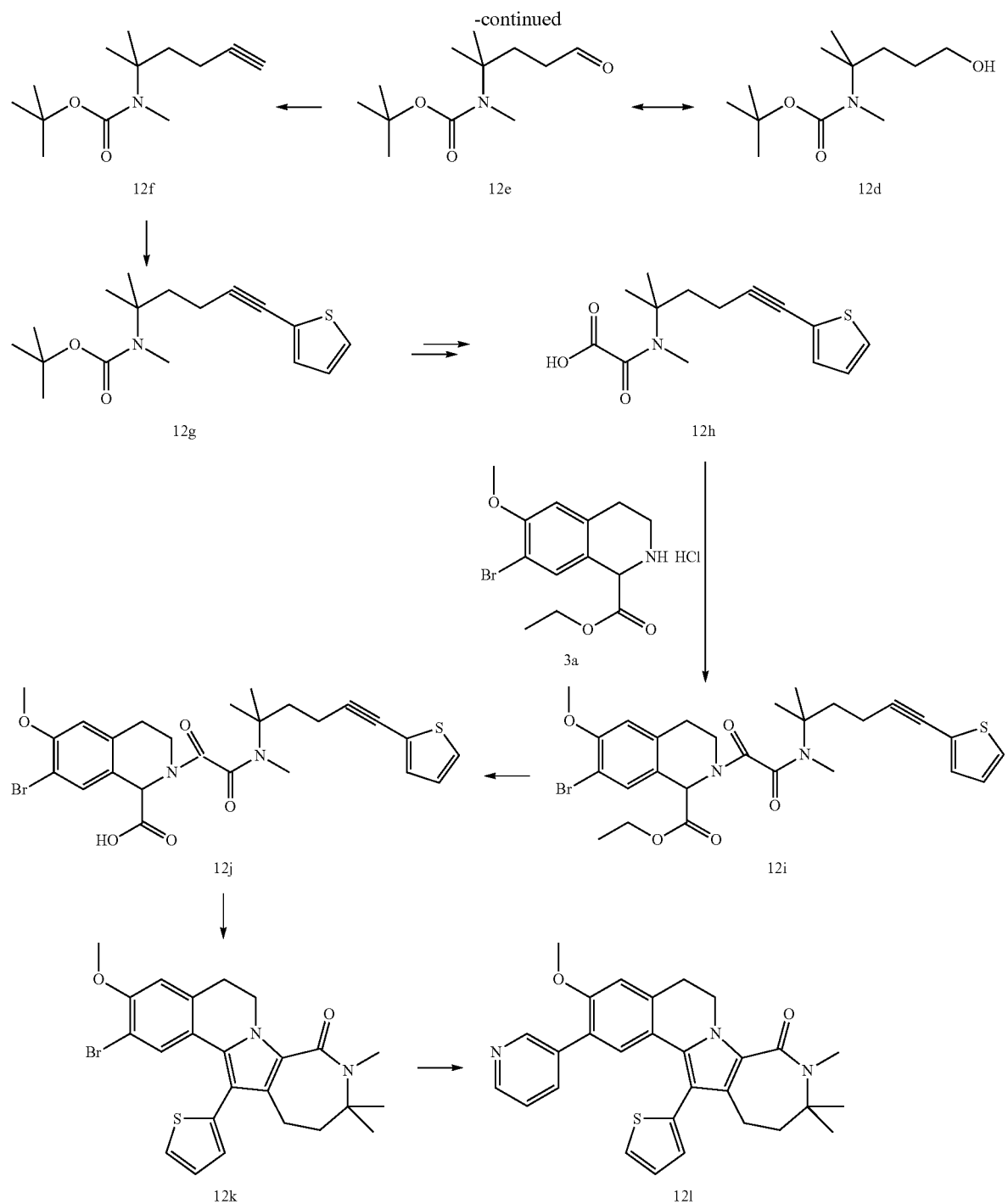

tert-butyl 5-(tert-butyldimethylsilyloxy)-2-methyl-pentan-2-ylcarbamate (12b)

A solution of 1 g of 12a, 2.5 g of NaHCO$_3$ and 2.5 g of di-tert-butyldicarbonate in 20 ml of THF was stirred overnight. The mixture was diluted with 75 ml of water and the product was extracted with ethyl acetate. Subsequently, purification was effected by chromatography over silica gel, using a gradient of heptane/acetone as eluent. This provided 1.05 g of the N-Boc-protected material; R$_f$ 0.50 (heptane/acetone 1/1); NMR (CDCl$_3$) δ 1.27 (s, 6, 2×CH$_3$), 1.42 (s, 9, tertC$_4$H$_9$) 1.50-1.75 (bm, 4, 2×CH$_2$), 3.65 (m, 2, CH$_2$)

The product 12a has been described in literature: G. Sosnovsky, B. D. Paul, *Zeitschrift Naturforschung* (*B*) 38B, 9, 1146 (1983).

The product 12a was dissolved in 10 ml of THF and 1 g of imidazole was added, followed by 0.80 g of tert-butyldimethylsilyl chloride in small portions over 10 min. After stirring for an additional 2 h the reaction mixture was poured into water and the product was extracted with ethyl acetate. The combined organic layers were washed twice with water, dried, concentrated and the crude material was chromatographed over silica gel, using a gradient of heptane/ethyl acetate as eluent, to provide 750 mg of 12b as colorless oil; $R_f$ 0.60 (heptane/ethyl acetate 3/1) NMR (CDCl$_3$) δ 0.06 (s, 6, 2×CH$_3$), 0.90 (s, 9, tertC$_4$H$_9$), 1.28 (s, 6, 2×CH$_3$), 1.43 (s, 9, tertC$_4$H$_9$), 1.40-1.60 (bm, 4, 2×CH$_2$), 3.55 (t, 2, CH$_2$).

tert-butyl 5-(tert-butyldimethylsilyloxy)-2-methylpentan-2-yl(methyl)carbamate (12c)

A solution of 750 mg of 12b in 4 ml of DMF was treated with 200 mg of 60% NaH (dispersion in mineral oil) and heated under N$_2$ at 50° C. for 10 min, after which time evolution of hydrogen gas ceased. The reaction mixture was cooled to 0° C. and 500 μl of methyl iodide was added. The reaction mixture was stirred for an additional 2 hr and quenched by pouring into ice-water (caution excess NaH). The product was extracted with ethyl acetate and the extract was washed with water, dried, concentrated and the crude material was purified by chromatography over silica gel, using a gradient of heptane/ethyl acetate as eluent, to provide 550 mg of 12c as colorless oil; $R_f$ 0.50 (heptane/ethyl acetate 3/1). NMR (CDCl$_3$) δ 0.05 (s, 6, Si(CH$_3$)$_2$), 0.89 (s, 9, tertC$_4$H$_9$Si), 1.32 (s, 6, C(CH$_3$)$_2$) 1.42 (s, 9, tertC$_4$H$_9$+m, 2, CH$_2$), 1.72 (m, 2, CH$_2$), 2.88 (s, 3, NCH$_3$), 3.60 t, 2, CH$_2$).

tert-butyl 5-hydroxy-2-methylpentan-2-yl(methyl)carbamate (12d)

A solution of 550 mg of 12c in 4 ml of 1M tetra-n-butyl ammonium fluoride in THF was stirred at RT for 1 h. The reaction mixture was diluted with 25 ml of 5% aq. NH$_4$Cl and the product was extracted with ethyl acetate. The organic layer was washed twice with sat. aq. NaCl, dried and concentrated. The crude material was purified by chromatography over silica gel, using a gradient of dichloromethane/ethyl acetate gradient as eluent. This provide 250 mg of 12d as a colorless oil. $R_f$ 0.25 (CH$_2$Cl$_2$-ethyl acetate 8/2); MS-ESI: [M+1] 232.3, NMR (CDCl$_3$) δ 1.32 (s, 6, 2×CH$_3$), 1.48 (s, 9, tertC$_4$H$_9$), 1.55 (m, 2, CH$_2$), 1.88 (m, 2, CH$_2$), 2.88 (s, 3, NCH$_3$), 3.02 (m, 2, CH$_2$).

tert-butyl methyl-(2-methyl-5-oxopentan-2-yl)carbamate (12e)

To a mixture of 250 mg of 12d and 500 mg of sodium bicarbonate in 3 ml of THF was added 550 mg of Dess-Martin periodinane reagent. After stirring for 1 h the reaction mixture was diluted with water. A few drops of sat. aq. Na$_2$S$_2$O$_3$ solution were added and stirring was prolonged for 5 min. The product was extracted into diethyl ether. The reaction mixture was filtered over decalite, washed once with 1N NaOH, once with water, dried and concentrated. The residue was purified by chromatography over silica gel, using a gradient of CH$_2$Cl$_2$-diethyl ether as eluent, to provide 160 mg of 12e as colorless oil;
$R_f$ 0.75 (CH$_2$Cl$_2$-ethyl acetate 8/2), NMR (CDCl$_3$) δ 1.38 (s, 6, 2×CH$_3$), 1.47 (s, 9, tertC$_4$H$_9$), 2.18 (m, 2, CH$_2$), 2.38 (m, 2, CH$_2$) 2.83 (s, 3, NCH$_3$), 9.72 (s, 1, CHO).

tert-butyl methyl-(2-methylhex-5-yn-2-yl)carbamate (12f)

To 150 mg of 12e in 3 ml of methanol was added 250 mg of dimethyl 1-diazo-2-oxopropylphosphonate and 250 mg of K$_2$CO$_3$. The mixture was stirred at RT overnight. Then reaction was diluted with water and the product was extracted with ether. The extract was washed once with sat. NaCl, dried, concentrated and filtered over a short silica column, using a pentane-ether gradient as eluent, to give 130 mg of 12f as colorless oil; $R_f$ 0.55 (heptane/ether 3/1). NMR (CDCl$_3$) δ 1.33 (s, 3, 2×CH$_3$), 1.48 (s, 9, tertC$_4$H$_9$), 1.92 (t, 1, acetylene-H), 2.10 (m, 4, CH$_2$CH$_2$), 2.88 (s, 3, NCH$_3$).

tert-butyl methyl-(2-methyl-6-(thiophen-2-yl)hex-5-yn-2-yl)carbamate (12g)

A mixture of 130 mg of 12f, 100 μl of piperidine, 75 μl of 2-iodothiophene, 10 mg of CuI and 14 mg of PdCl$_2$(PPh$_3$)$_2$ in 2 ml of degassed toluene was stirred under N$_2$ for 3 hr. The reaction mixture was diluted with 20 ml of ethyl acetate and washed with water, dried and concentrated. The crude material was purified by chromatography over a silica column, using a gradient of pentane/diethyl ether as eluent. This provided 130 mg of 12g as colorless oil; $R_f$ 0.60 (heptane/ether 3/1).
MS-ESI: [M+1] 308.15
NMR (CDCl$_3$) δ 1.38 (s, 6, 2×CH$_3$), 1.48 (s, 9, tertC$_4$H$_9$), 2.15 (m, 2, CH$_2$), 2.39 (m, 2, CH$_2$), 2.88 (s, 3, NCH$_3$), 6.92, 7.10 and 7.17 (3×m, 3, thiophene).

2-(methyl-(2-methyl-6-(thiophen-2-yl)hex-5-yn-2-yl)amino)-2-oxoacetic acid (12h)

A solution of 120 mg of 12g in 4 ml of dioxane was treated with 2 ml of a 4N HCl solution in dioxane and heated using an oil bath to 45° C. for 1 h. The reaction mixture was cooled, diluted with 30 ml of 5% aq. NaHCO$_3$ and extracted with ethyl acetate. The organic extract was once washed with sat. aq. NaCl, dried and concentrated to give 80 mg of the N-deprotected material as an oil. [LC/MS: M+1 208.14].
This material was dissolved in 2 ml of diethyl ether and 100 μl of triethyl amine and a solution of 50 μl of ethyloxalyl chloride in 1 ml of diethyl ether was added dropwise at 0° C. After stirring for an additional ½ h, 5 ml of water was added and the product was extracted into ethyl acetate. The organic extract was washed once with 1M K$_2$CO$_3$ and once with water, dried and concentrated, to provide 102 mg of oxalate ester as a colorless oil. [$R_f$: 0.60 (heptane/ethyl acetate 1/1)].
This oil was dissolved in 2 ml of dioxane and a solution of 50 mg of KOH in 1 ml of water was added. The mixture was stirred for 1 h at 45° C., after which the ester had been saponified. The reaction mixture was cooled, diluted with 10 ml of water and acidified to pH3 by addition of cold 0.5N HCl. The product was extracted with ethyl acetate. The extract was once washed with sat. aq. NaCl, dried and concentrated, to give 81 mg of 12h;
MS-ESI: [M+1] 280.07.
$R_f$ 0.40 (CH$_2$Cl$_2$/methanol 8/2).

ethyl 7-bromo-6-methoxy-2-(2-(methyl(2-methyl-6-(thiophen-2-yl)hex-5-yn-2-yl)amino)-2-oxoacetyl)-1,2,3,4-tetrahydroisoquinoline-1-carboxylate (12i)

A mixture of 80 mg of 12h, 100 mg of 3a, 100 μl of N-ethyl morpholine and 110 mg of TBTU in 1.5 ml of DMF was stirred for 16 hr. The reaction mixture was diluted with 7 ml of 5% aq. NH$_4$Cl and stirred for an additional 5 min. The product was extracted with ethyl acetate. The extract was washed with water, dried and concentrated. The residue was purified by chromatography over silica gel, using a gradient of heptane/ethyl acetate, to give 110 mg of 12i as amorphous material; $R_f$: 0.38 (heptane/ethyl acetate 1/1).
MS-ESI: [M+1] 575.03 and 577.03.

7-bromo-6-methoxy-2-(2-(methyl(2-methyl-6-(thiophen-2-yl)hex-5-yn-2-yl)amino)-2-oxoacetyl)-1,2,3,4-tetrahydroisoquinoline-1-carboxylic acid (12j)

To a solution of 110 mg of 12i in 3 ml of dioxane a solution of 50 mg of KOH in 1 ml of water was added. The mixture was stirred at 50° C. for 2 hr. After cooling to RT, 15 ml of water was added and the reaction mixture was acidified to pH3 by addition of cold 0.5 N HCl. The product was extracted into ethyl acetate. The extract was once washed with water, dried and concentrated, to provide 100 mg of the acid 12j as colorless amorphous material, used without further purification in the next step; MS-ESI: [M+1] 546.98, 548.98).

9-methyl-2-bromo-3-methoxy-10,10-dimethyl-13-(2-thienyl)-5,6,9,10,11,12-hexahydro-8H-azepino[4',3':4,5]pyrrolo[2,1-a]isoquinolin-8-one (12k)

A mixture of 100 mg of 12j and 150 mg of anhydrous sodium acetate in 4 ml of acetic anhydride was heated at 100-105° C. for 2 h. The mixture was cooled and diluted with 10 ml of water and stirred at ambient temperature for 1 hr in order to decompose excess anhydride. The reaction mixture was neutralized by addition of cold conc. aq. $NH_4OH$ and then extracted with ethyl acetate. The extract was washed twice with water, dried, concentrated and the residue was purified by chromatography over silica gel, using a gradient of heptane/ethyl acetate. The purified product thus isolated was treated with diisopropyl ether, to give 65 mg of crystalline 12k; Mp 173-175° C.; $R_f$ 0.45 (heptane/ethyl acetate 1/1). MS-ESI: [M+1] 484.96, 586.98.

NMR (CDCl$_3$) δ 1.38 s, 6, 2×CH$_3$), 3.13 (s, 3, NCH$_3$), 3.88 (s, 3, OCH$_3$), 2.03 (m, 2, CH$_2$), 2.66 (m, 2, CH$_2$), 2.98 (t, 2, CH$_2$), 4.62 (t, 2, CH$_2$), 6.73 and 7.22 (2×s, 2, Ar—H), 6.93, 7.13 and 7.42 (3×m, 3, thiophene).

9-methyl-2-pyidin3-yl-3-methoxy-10,10-dimethyl-13-(2-thienyl)-5,6,9,10,11,12-hexahydro-8H-azepino[4',3':4,5]pyrrolo[2,1-a]isoquinolin-8-one (12l)

A solution of 50 mg of 12k, 60 mg of K$_2$CO$_3$, 20 mg of 3-pyridylboronic acid and 12 mg of Pd(PPh$_3$)$_4$ in 3.5 ml of degassed 90% aq. dimethoxyethane was heated under N$_2$ at 95° C. for 16 hr. The reaction mixture was cooled, diluted with water and extracted with ethyl acetate. The extract was washed once with 1M K$_2$CO$_3$ and once with water, dried and concentrated. The residue was chromatographed over silica, using a gradient of heptane/acetone, The product thus obtained was treated with ethyl acetate, to give 30 mg of 12l as white crystals; Mp: 219-220° C.; $R_f$ 0.35 (heptane/acetone 1/1). MS-ESI:

[M+1] 484.10.

NMR (CDCl$_3$) δ 1.40 (s, 6, 2×CH$_3$), 3.13 (s, 3, NCH$_3$), 3.83 (s, 3, OCH$_3$), 2.05 (m, 2, CH$_2$) 2.67 (m, 2, CH$_2$), 3.08 (t, 2, CH$_2$), 4.68 (t, 2, CH$_2$), 6.83 and 7.08 (2×s, 2, Ar—H), 6.94+7.12+7.40 (3×m, 3, thiophene), 7.21 and 7.62 (2×m, 2, pyridine), 8.45 (m, 2, pyridine).

hFSHRago (CHO luc) pEC$_{50}$=7.92.

Example 13

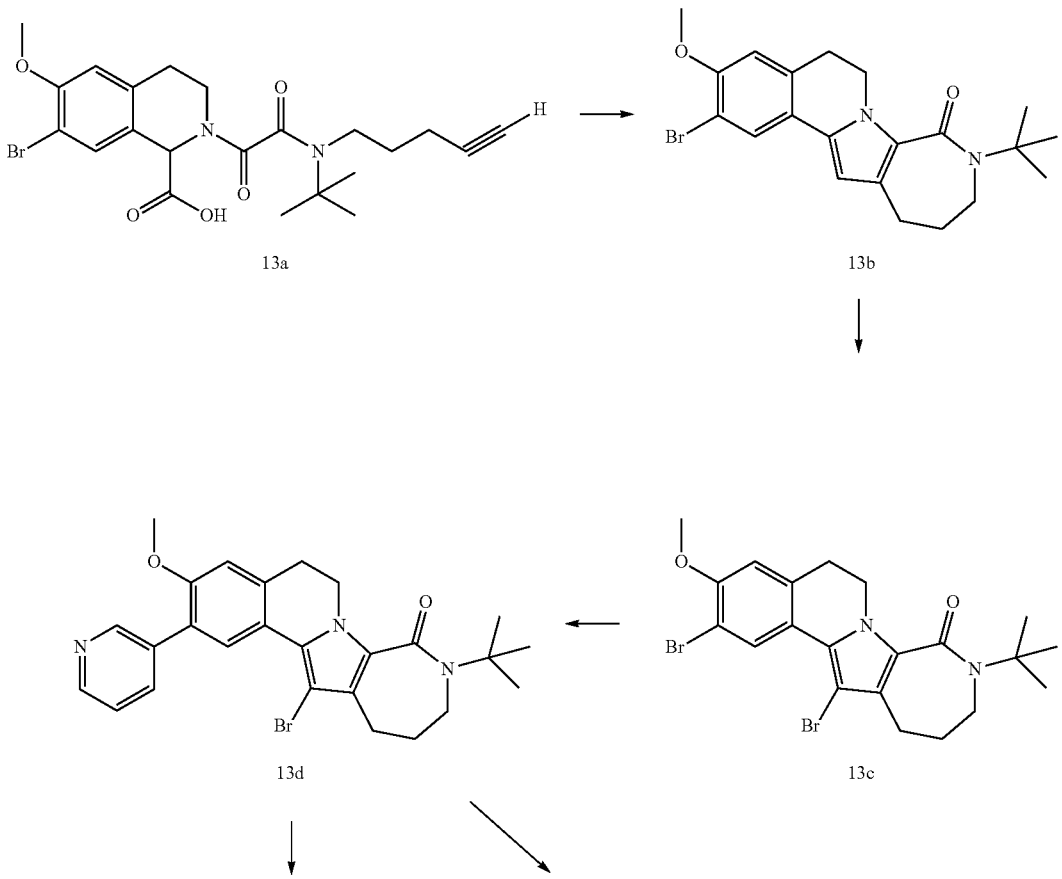

13a

13b

13d

13c

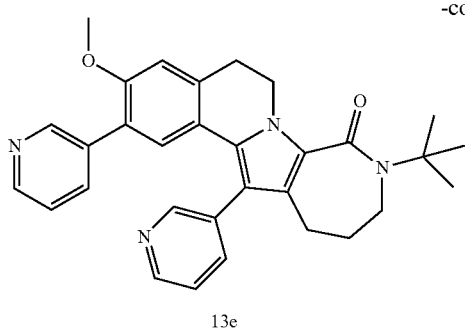

13e

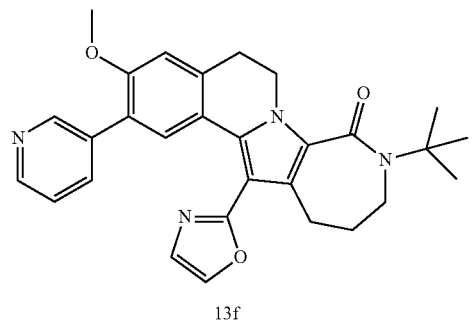

13f

9-tert-butyl-2-bromo-3-methoxy-5,6,9,10,11,12-hexahydro-8H-azepino[4',3':4,5]pyrrolo[2,1-a]isoquinolin-8-one (13b)

A mixture of 1 g of 13a (prepared analogously to compound 3c, starting from 2-(tert-butyl(pent-4-ynyl)amino)-2-oxoacetic acid) and 1 g of sodium acetate in 10 ml of acetic anhydride was heated at 100° C. for 1 hr. The reaction mixture was cooled and 30 ml of water was added and stirred for 1 hr to decompose excess anhydride. The reaction mixture was neutralized by addition of cold conc. NH$_4$OH and the product was extracted with ethyl acetate. The extract was washed with water, dried, concentrated and passed through a short silica column (toluene/ethyl acetate as eluent). The product obtained was triturated with heptane, to provide 0.65 g of 13b as white crystalline material; Mp 163-165° C. MS-ESI: [M+1] 417.13 and 419.17.

NMR (CDCl$_3$) δ 1.52 (s, 9, tertC$_4$H$_9$), 1.92 (m, 2, CH$_2$), 2.68 (t, 2, CH$_2$), 3.00 (t, 2, CH$_2$), 3.40 (t, 2, CH$_2$), 4.47 (t, 2, CH$_2$), 3.90 (s, 3, OCH$_3$), 6.20 (s, 1, pyrrole-H), 6.72, 7.66 (2×s, 2, Ar—H)

9-tert-butyl-2,13-dibromo-3-methoxy-5,6,9,10,11,12-hexahydro-8H-azepino[4',3':4,5]pyrrolo[2,1-a]isoquinolin-8-one (13c)

To a solution of 340 mg of 13b in 3 ml of DMF was added in small portions 160 mg of N-bromosuccinimide. After stirring for an additional 15 minutes the reaction mixture was diluted with 3 ml of water and stirred for an additional 15 minutes. The precipitate was filtered and dried, to give 380 mg of 13c, as white crystalline material. Mp: 218-220° C. MS-ESI: [M+1] 495.06, 497.06, 499.08. NMR (CDCl$_3$) δ 1.53 (s, 9, tertC$_4$H$_9$), 1.95 (m, 2, CH$_2$), 2.71 (t, 2, CH$_2$), 2.97 (t, 2, CH$_2$), 3.38 (t, 2, CH$_2$), 4.45 (t, 2, CH$_2$) 6.77, 8.56 (2×s, 2, Ar—H).

9-tert-butyl-2-pyridin-3-yl-13-bromo-3-methoxy-5,6,9,10,11,12-hexahydro-8H-azepino[4',3':4,5]pyrrolo[2,1-a]isoquinolin-8-one (13d)

A mixture of 150 mg of 13c, 44 mg of pyridine-3-boronic acid, 80 mg of K$_2$CO$_3$ and 22 mg of Pd(PPh$_3$)$_4$ in 3 ml of degassed dimethoxyethane was heated at 90° C., for 16 hr. The reaction mixture was cooled and diluted with 20 ml of water and the product was extracted with ethyl acetate. The extract was washed once with 2N KOH and once with water, dried and concentrated. The crude material was chromatographed over silica gel, using a gradient of heptane/ethyl acetate as eluent. The product isolated was triturated with pentane, to provide 95 mg of 13d as white, crystalline material. Mp 184-186° C. R$_f$ 0.25 (heptane/ethyl acetate 1/1). MS-ESI: [M+1] 494.11 and 496.11.

NMR (CDCl$_3$) δ 1.53 (s, 9, tertC$_4$H$_9$), 3.85 (s, 3, OCH$_3$), 1.95 (m, 2, CH$_2$), 2.73 (t, 2, CH$_2$), 3.07 (t, 2, CH$_2$), 3.38 (t, 2, CH$_2$), 4.50 (t, 2, CH$_2$), 6.85, 8.38 (2×s, 2, Ar—H), 7.35, 8.00, 8.56, 8.83 (4×m, 4, pyridine-H).

hFSHRago (CHO luc) pEC$_{50}$=6.42.

9-tert-butyl-2,13-di-(pyridin3-yl)-3-methoxy-5,6,9,10,11,12-hexahydro-8H-azepino[4',3':4,5]pyrrolo[2,1-a]isoquinolin-8-one (13e)

A mixture of 45 mg of 13d, 20 mg of pyridine-3-boronic acid, 30 mg of K$_2$CO$_3$ and 10 mg of Pd(PPh$_3$)$_4$ in 2 ml of degassed dimethoxyethane was heated at 90° C., for 16 hr. The reaction mixture was cooled, diluted with water and the product was extracted with ethyl acetate. The extract was washed once with 2N KOH and once with water, dried and concentrated. The residue was purified by chromatography over silica gel, using a gradient of toluene/acetone as eluent. The isolated product was triturated with diethyl ether, to provide 31 mg of 13e as white, crystalline material; Mp 310-312° C.

MS-ESI: [M+1] 493.21. R$_f$ 0.25 (toluene/acetone 2/1).

NMR CDCl$_3$) δ 1.55 (s, 9, tertC$_4$H$_9$), 3.82 (s, 3, OCH$_3$), 1.90 (m, 2, CH$_2$), 2.55 (t, 2, CH$_2$), 3.14 (t, 2, CH$_2$), 3.48 (t, 2, CH$_2$), 4.56 (t, 2, CH$_2$), 6.85, 8.87 (2×s, 2, Ar—H), 7.18, 7.36, 7.50, 7.66 (4×m, 4, pyridine-H), 8.43 (m, 2, pyridine-H), 8.58 (m, 2, pyridine-H).

hFSHRago (CHO luc) pEC$_{50}$=7.37.

9-tert-butyl-2-pyridin-3-yl-13-(1,3-oxazolidin-2-yl)-3-methoxy-5,6,9,10,11,12-hexahydro-8H-azepino[4',3':4,5]pyrrolo[2,1-a]isoquinolin-8-one (13f)

A solution of 49 mg of 13d, 50 mg of 2-tributylstannyl oxazole and 10 mg of Pd(PPh$_3$)$_4$ in 3 ml of degassed toluene was heated under N$_2$ at 100° C. for 48 hr. The reaction mixture was cooled and applied to a silica gel column and eluted with a gradient of toluene/ethyl acetate. The product obtained was triturated with diethyl ether to provide 15 mg of 13f as white crystalline material; Mp 218-220° C. R$_f$ 0.20 (toluene/ethyl acetate 1/1). MS-ESI: [M+1] 482.23.

NMR (CDCl$_3$) δ 1.57 (s, 9, tertC$_4$H$_9$), 3.85 (s, 3, OCH$_3$), 1.98 (m, 2, CH$_2$), 2.85 (t, 2, CH$_2$), 3.11 (t, 2, CH$_2$), 3.45 (t, 2, CH$_2$), 4.52 (t, 2, CH$_2$), 6.87, 7.40 (2×s, 2, Ar—H), 7.28, 7.71 (2×d, 2, oxazole-H), 7.29, 7.80, 8.51, 8.67 (4×m, pyridine-H).

hFSHRago (CHO luc) pEC$_{50}$=7.80.

81 82
Example 14
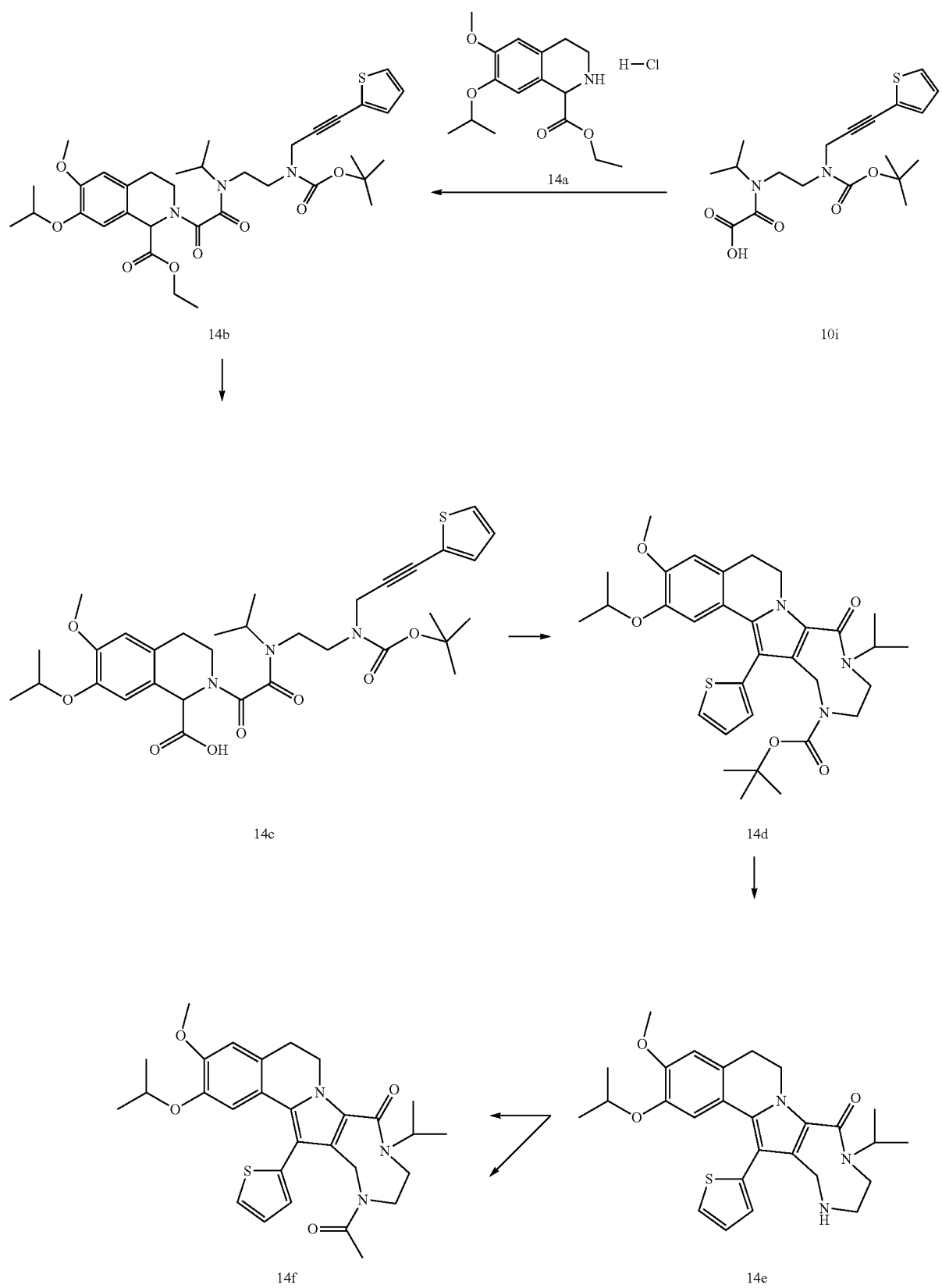

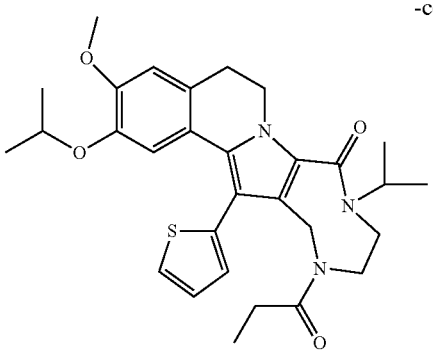

14g ethyl 7-isopropoxy-6-methoxy-1,2,3,4-tetrahydroisoquinoline-1-carboxylate hydrochloride (14a)

A solution of 6-methoxy-7-isopropoxy-tetrahydroisoquinoline-1-carboxylic acid in 15 ml of ethanol was treated at 0° C. with 700 µl of $SOCl_2$ and then heated with stirring at 80-85° C. for 1.5 h. The mixture was concentrated to a small volume and then treated with diethyl ether, to provide 880 mg of ethyl ester hydrochloride, 14a, as a white solid. Mp: 175-176° C. $R_f$ (free base, toluene/acetone 1/1) 0.40. MS-ESI: [M+1] 294.11. NMR (DMSO-d$^6$) δ 1.25 (m, 9, isoC$_3$H$_7$+C$_2$H$_5$), 4.24 (q, 2, C$_2$H$_5$), 4.48 (m, 1, CH isoC$_3$H$_7$), 2.96 (m, 2, CH$_2$), 3.46 (m, 2, CH$_2$), 5.35 (s, 1, CHCOOC$_2$H$_5$), 3.78 (s, 3, OCH$_3$), 6.83 and 6.94 (2×s, 2, Ar—$\overline{H}$).

ethyl 2-(2-(2-(tert-butoxycarbonyl(3-(thiophen-2-yl)prop-2-ynyl)amino)ethyl)-(isopropyl)amino)-2-oxoacetyl)-7-isopropoxy-6-methoxy-1,2,3,4-tetrahydro-isoquinoline-1-carboxylate (14b)

A mixture of 480 mg of 10i, 470 mg of 14a and 520 µl of N-ethyl morpholine in 7 ml of DMF was stirred for 10 min and then 600 mg of TBTU was added. The reaction mixture was stirred overnight. Then, 35 ml of 5% aq. NH$_4$Cl was added and the reaction mixture was extracted with ethyl acetate. The combined extracts were washed twice with water, dried and concentrated. The residue was chromatographed over silica gel, using a gradient of heptane/ethyl acetate, to provide 620 mg of 14b as a colorless foam.

$R_f$ 0.40 (heptane/ethyl acetate 1/1); MS-ESI: [M+1] 670.28; NMR (CDCl$_3$) δ 1.22-1.44 (m, 15, C$_2$H$_5$+2× isoC$_3$H$_7$), 1.52 (bs, 9, tertC$_4$H$_9$), 3.86 (s, 3, OCH$_3$), 4.12 (m, 1, CH isoC$_3$H$_7$), 4.52 (m, 1, isoC$_3$H$_7$) 5.52 (s, 1, C HCOOC$_2$H$_5$), 6.62, 7.18 (2×s, 2, H7+H10), 6.96 (m, 1, thiophene), 7.22 (m, 2, thiophene).

2-(2-((2-(tert-butoxycarbonyl(3-(thiophen-2-yl)prop-2-ynyl)amino)ethyl)(isopropyl)amino)-2-oxoacetyl)-7-isopropoxy-6-methoxy-1,2,3,4-tetrahydroisoquinoline-1-carboxylic acid (14c)

A solution of 620 mg of 14b in 8 ml of dioxane was mixed with 250 mg of KOH in 2 ml of water and stirred for 4 h at 45° C. The ester was saponified after that time. The reaction mixture was cooled and diluted with 35 ml of ice-water and acidified to pH 3 by addition of 0.5N HCl. The product was extracted into ethyl acetate. The extract was washed with water, dried and concentrated to provide 590 mg of 14c as colorless foam, which was used without further purification in the next step. MS-ESI: [M+1] 642.24.

tert-butyl 9-isopropyl-3-methoxy-8-oxo-2-isopropoxy-14-(2-thienyl)-5,6,8,10,11,13-hexahydro[1,4]diazocino[6',7':4,5]pyrrolo[2,1-a]isoquinoline-12(9H)-carboxylate (14d)

A mixture of 580 mg of 14c and 1 g of anhydrous sodium acetate in 8 ml of acetic anhydride was heated at 100° C. for 45 min. The reaction mixture was cooled and 25 ml of water was added and stirring prolonged for 1 h. The product crystallized from the reaction mixture and was filtered, washed with water and dried in vacuo, to give 420 mg of 14d as white crystalline material; Mp 205-206° C.

$R_f$ (heptane/ethyl acetate 1/1) 0.35. MS-ESI: [M+1] 580.21.

NMR (CDCl$_3$) δ 1.13 (s, 6, isoC$_3$H$_7$), 1.30-1.50 (bs, 15, tertC$_4$H$_9$+isoC$_3$H$_7$), 2.97 (bs, 2, CH$_2$), 6.62, 6.68 (2 bs, 2, H7+H10), 6.94, 7.11 and 7.38 (3 bm, 3, thiophene).

9-isopropyl-3-methoxy-2-isopropoxy-14-(2-thienyl)-5,6,10,11,12,13-hexahydro[1,4]diazocino[6',7':4,5]pyrrolo[2,1-a]isoquinolin-8(9H)-one (14e)

To a suspension of 110 mg of 14d in 300 µl of dioxane was added 400 µl of a solution of 4N HCl in dioxane. A clear solution readily formed. The reaction mixture was stirred for 1 h. Then, 3 ml of a 1/1 mixture of ethyl acetate and diethyl ether was added. The precipitate was filtered and dried, to give 95 mg of white crystalline 14e; Mp 242-243° C. MS-ESI: [M+1] 480.14. NMR (CDCl$_3$+CD$_3$OD) δ 1.13 (d, 6,0-isoC$_3$H$_7$), 1.33 (d, 6, isoC$_3$H$_7$), 3.85 (s, 3, OCH$_3$), 3.95 (m, 1, isoC$_3$H$_7$), 4.65 (m, 1, isoC$_3$H$_7$), 6.67 and 6.72 (2×s, H7 and H10), 7.18, 7.21 and 7.44 (3×m, 3, thiophene). hFSHRago (CHO luc) pEC$_{50}$=7.03.

12-acetyl-9-isopropyl-3-methoxy-2-isopropoxy-14-(2-thienyl)-5,6,10,11,12,13-hexahydro[1,4]diazocino[6',7':4,5]pyrrolo[2,1-a]isoquinolin-8(9H)-one (14f)

A solution of 35 mg of 14e in 250 µl of pyridine was treated with 30 µl of acetic anhydride and a catalytic amount of DMAP. After stirring ½ hr the reaction mixture was diluted with 400 µl of water and stirred for an additional 1 h. The precipitate was filtered, washed with water and dried to give 31 mg of crystalline white 14f;

Mp 217-218° C. $R_f$ 0.35 (heptane/acetone 1/1). MS-ESI: [M+1] 522.11

NMR (CDCl$_3$) δ 1.13 (d, 6 isoC$_3$H$_7$), 1.33 (bs, 6, isoC$_3$H$_7$), 2.0 (s, 3, CH$_3$CO), 2.98 (bs, 2, CH$_2$), 3.83 (s, 3, OCH$_3$), 3.94 .

(m, 1, isoC$_3$H$_7$), 4.68 (m, 1, isoC$_3$H$_7$), 6.63 (s, 1, Ar—H), 6.69 (s, 1, Ar—H), 6.98, 7.14 and 7.42 (3×m, 3, thiophene).
hFSHRago (CHO luc) pEC$_{50}$=7.45.

12-propanoyl-9-isopropyl-3-methoxy-2-isopropoxy-14-(2-thienyl)-5,6,10,11,12,13-hexahydro[1,4]diazocino[6',7':4,5]pyrrolo[2,1-a]isoquinolin-8(9H)-one (14g)

A solution of 35 mg of 14e in 250 µl of pyridine was treated with 30 µl of propionic anhydride and a catalytic amount of DMAP. After stirring for ½ hr the reaction mixture was diluted with 400 µl of water and stirred for an additional 1 h. The precipitate was filtered, wshed with water and dried to give 32 mg of crystalline white 14g;
Mp 162-163° C. R$_f$ 0.40 (heptane/acetone 1/1). MS-ESI: [M+1] 536.17.
NMR (CDCl$_3$) δ 1.03 (t, 3, CH$_3$), 1.15 (d, 6, isoC$_3$H$_7$), 1.33 (bs, 6, isoC$_3$H$_7$) 2.28 (bs, 2, CH$_3$CH$_2$CO), 2.98 (bs, 2, CH$_2$), 3.94 (m, 1, isoC$_3$H$_7$), 4.64 (m, 1, isoC$_3$H$_7$), 6.63, 6.68 (2×s, 2, H7 and H10), 6.98, 7.13 and 7.42 (3×m, 3, thiophene).
hFSHRago (CHO luc) pEC$_{50}$=6.66.

Example 15

2-(3,3-diethoxyprop-1-ynyl)thiophene (15a)

To a solution of 3 g of propargyl aldehyde diethylacetal and 9.83 g of 2-iodothiophene in degassed diisopropyl amine was added 0.46 g of Cu(OAc)$_2$ and 0.5 g of Pd(PPh$_3$)$_4$ and the mixture was stirred at 55° C. under N$_2$ for 2 hr. The reaction mixture was concentrated and the residue was purified by chromatography over silica gel, using a gradient of heptane/ethyl acetate as eluent. This provided 4.4 g of 15a as yellowish oil.
NMR (CDCl$_3$) δ 1.27 (t, 6, C$_2$H$_5$), 3.65 and 3.80 (2×m, 4, C$_2$H$_5$) 5.00 (s, 1, CH), 6.97 (m, 1, thiophene), 7.25 (m, 2, thiophene). R$_f$ 0.78 (heptane/ethyl acetate 3/2), starting material R$_f$ 0.88.

ethyl 2-formyl-9-isopropoxy-8-methoxy-1-(thiophen-2-yl)-5,6-dihydropyrrolo[2,1-a]isoquinoline-3-carboxylate (15c)

A mixture of 2.3 g of acetal 15a and 2.02 g of isoquinolinic acid 15b in 20 ml of acetic anhydride was stirred in a microwave reactor at 140° C. for 12 min. The reaction mixture was cooled and concentrated in vacuo. The residue was applied onto a silica gel column and eluted with a gradient of heptane/ethyl acetate, to provide 815 mg of 15c. MS-ESI: [M+1] 440.20.

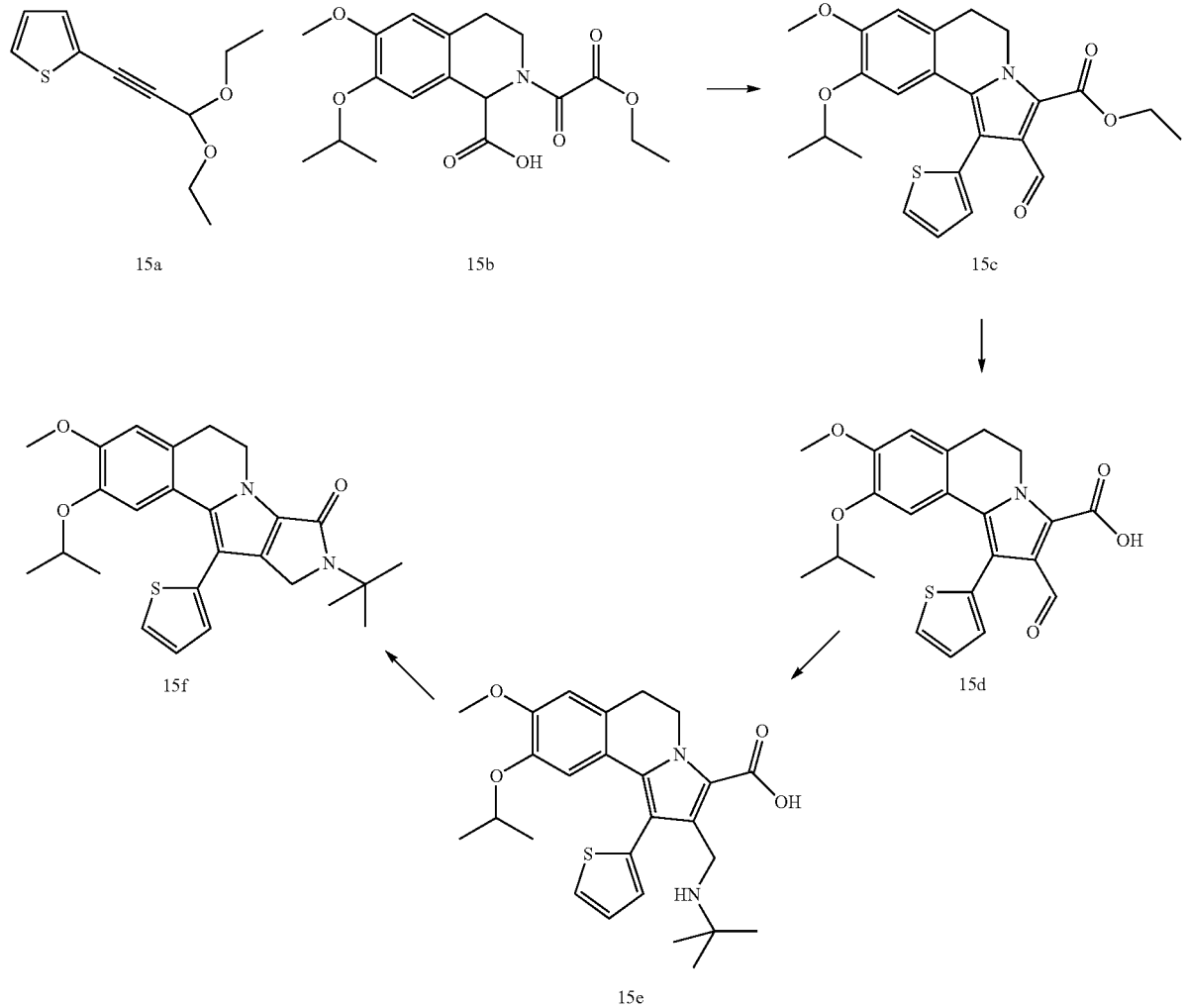

NMR (CDCl$_3$) δ 10.40 (s, 1, CHO), 7.01, 7.12 and 7.42 (3×m, 3, thiophene), 4.62 (t, 2, CH$_2$), 3.02 (t, 2, CH$_2$), 4.45 (q, 2, C$_2$H$_5$), 3.94 (m, 1, isoC$_3$H$_7$), 3.84 (s, 3, OCH$_3$), 1.43 (t, 3, C$_2$H$_5$), 1.10 (d, 6, isoC$_3$H$_7$).

2-formyl-9-isopropoxy-8-methoxy-1-(thiophen-2-yl)-5,6-dihydropyrrolo[2,1-a]isoquinoline-3-carboxylic acid (15d)

A solution of 815 mg of 15c in 40 ml of ethanol was mixed with 18 ml of 2N NaOH. The mixture was stirred for 1 h at 60° C. The mixture was cooled and concentrated to half its original volume and diluted with 30 ml of water, acidified with 0.5N NaOH and extracted with ethyl acetate. The organic extract was washed with water, dried and concentrated to provide 750 mg of 15d as an amorphous material, which was used without further purification in the next step.
MS-ESI: [M+1] 412.15.

2-((tert-butylamino)methyl)-9-isopropoxy-8-methoxy-1-(thiophen-2-yl)-5,6-dihydropyrrolo[2,1-a]isoquinoline-3-carboxylic acid (15e)

To a solution of 500 mg of 15d and 110 mg of tert-butyl amine in 20 ml of methanol and 5 ml of THF was added 140 mg of sodium cyanoborohydride and 90 mg of acetic acid. The mixture was stirred for 3 hr at RT, then 140 mg of sodium cycanoborohydride was added additionally and stirring was prolonged for 16 h. The reaction mixture was concentrated in vacuo and the residue was purified by chromatography over silica gel, using a gradient of dichloromethane and methanol, to provide 520 mg of 15e; MS-ESI: [M+1] 469.23.

9-tert-butyl-2-isopropoxy-3-methoxy-11-(2-thienyl)-5,6,9,10-tetrahydro-8H-pyrrolo[3',4':4,5]pyrrolo[2,1-a]isoquinolin-8-one (15f)

A mixture of 55 mg of 15e and 100 μl of DiPEA in 0.5 ml of THF and 0.1 ml of NMP was treated with 50 mg of HATU. The mixture was stirred overnight and then diluted with 5 ml of water and extracted with ethyl acetate. The extract was washed with water, dried, concentrated and the crude material was purified by chromatography over silica gel, using a gradient of heptane/ethyl acetate, to provide 27 mg of 15f. MS-ESI:
[M+1] 451.28.
NMR (CDCl$_3$) δ 1.20 (d, 6, isoC$_3$H$_7$), 1.52 (s, 9, tertC$_4$H$_9$), 3.01 (t, 2, CH$_2$), 4.33 (t, 2, CH$_2$), 4.05 (m, 1, isoC$_3$H$_7$), 4.25 (s, 2, CH$_2$), 3.86 (s, 3, OCH$_3$), 6.73, 7.05 (2×s, 2, H7+H10), 7.08 (m, 2, thiophene), 7.33 (m, 1, thiophene).
hFSHRago (CHO luc) pEC$_{50}$=6.21.

Example 16

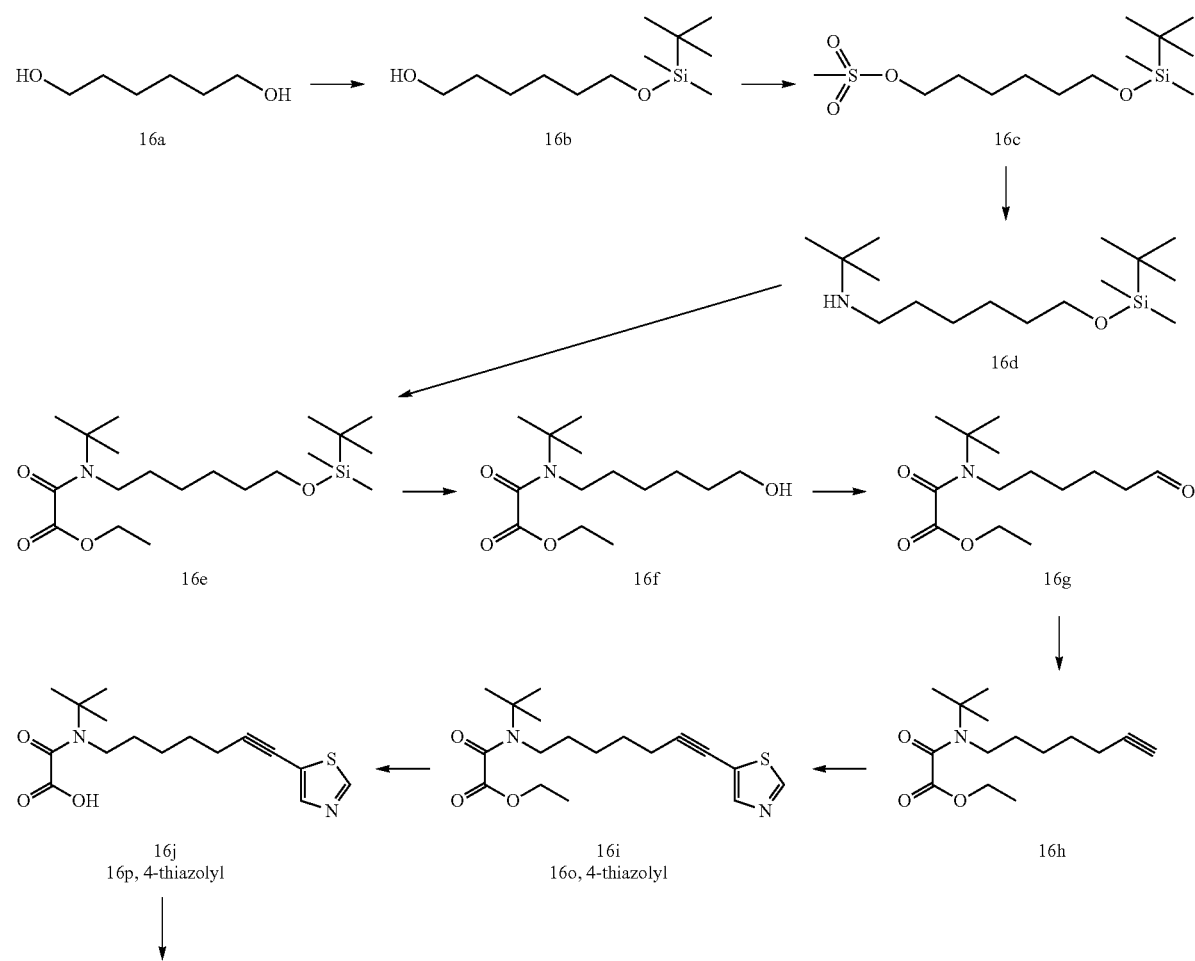

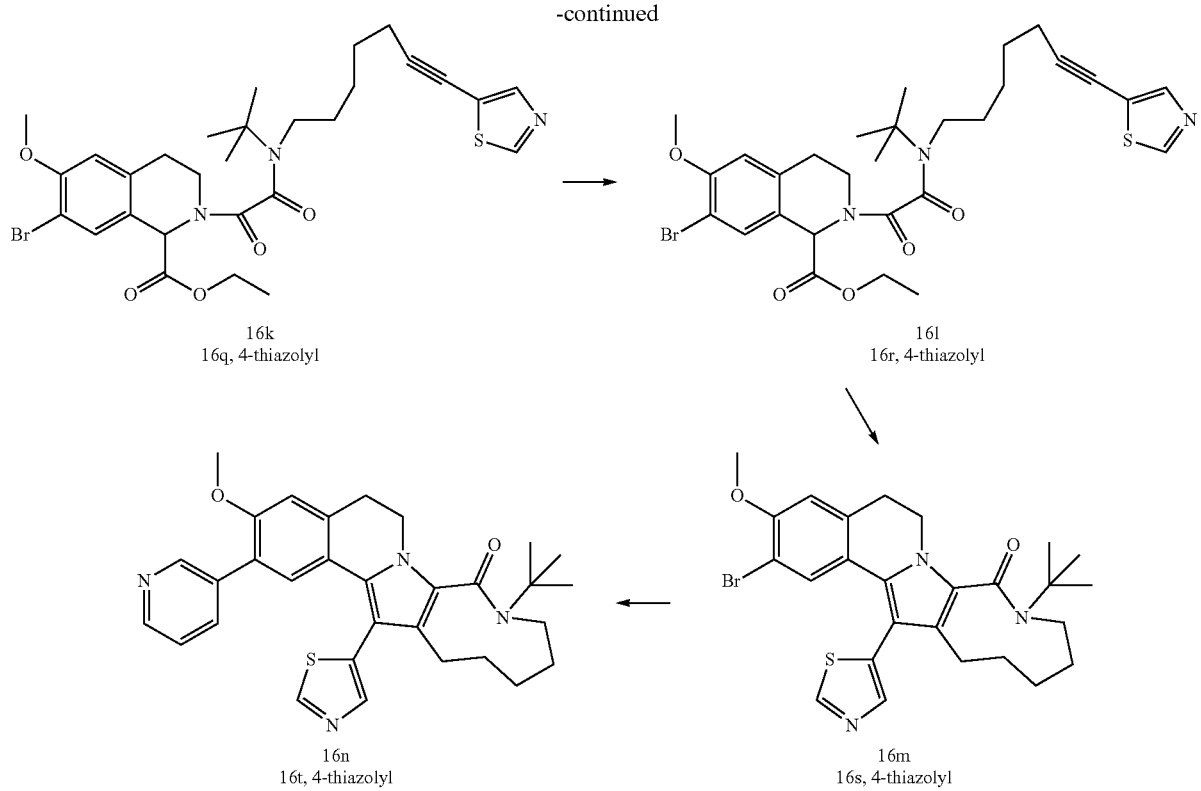

6-(tert-butyldimethylsilyloxy)hexan-1-ol (16b)

To a solution of 5 g of 1,6-hexanediol (16a) in 80 ml of THF was added 6 g of imidazole and then 6.4 g of tBDMSCl in 20 ml of THF at 0° C. The mixture was stirred for 2 hr. A mixture of bis-silylated and mono-silylated material was formed. The reaction mixture was poured into water and extracted with ethyl acetate. The organic layer was washed with water, dried, concentrated and the residue was passed through a silica column, using a gradient of heptane/ethyl acetate as eluent. This gave 5.1 g of 16b as a colorless oil.

$R_f$ (hept/ethyl acetate 1/1) 0.65.

NMR (CDCl$_3$) δ 0.05 (s, 6, (CH$_3$)$_2$Si), 0.89 (s, 9, tertC$_4$H$_9$), 1.31 (t, 1, OH), 1.38 (m, 4, 2×CH$_2$), 1.55 (m, 4, 2×CH$_2$), 3.62 (t, 2, CH$_2$), 3.65 (m, 2, CH$_2$).

6-(tert-butyldimethylsilyloxy)hexyl methanesulfonate (16c)

To a solution of 232 mg of alcohol 16b in 10 ml of ether was added 1 ml of triethyl amine, followed at 0° C. by 80 µl of mesyl chloride. The mixture was stirred at ambient temperature for 1 hr and then poured into water and extracted into ether. The organic extract was washed with water, dried and concentrated, to give 320 mg of 16c as a colorless oil.

$R_f$ 0.68 (heptane/ethyl acetate 1/1), starting material $R_f$ 0.63

NMR (CDCl$_3$) δ 0.05 (s, 6, (CH$_3$)$_2$Si), 0.89 (s, 9, tertC$_4$H$_9$), 1.40 (m, 4, 2×CH$_2$), 1.53 (m, 2, CH$_2$), 1.75 (m, 2, CH$_2$) 3.02 (s, 3, CH$_3$SO$_2$) 3.62 (t, 2, CH$_2$), 4.23 (t, 2, CH$_2$).

N-tert-butyl-6-(tert-butyldimethylsilyloxy)hexan-1-amine (16d)

A solution of 320 mg of 16c in 6 ml of t-butyl amine was stirred in a closed flask for 3 days at RT. The reaction mixture was concentrated and the residue was partitioned between ether and aq. NaHCO$_3$. The organic layer was separated, dried and concentrated, to give 310 mg of amine 16d as a colorles oil, which was used without further purification in the next step.

ethyl 2-(tert-butyl(6-(tert-butyldimethylsilyloxy) hexyl)amino)-2-oxoacetate (16e)

To a solution of 310 mg of 16d in 6 ml of ether and 0.3 ml of triethyl amine a solution of 120 µl of ethyloxalyl chloride in 1 ml of diethyl ether was added dropwise at 0° C. The mixture was stirred for ½ hr at 0° C. The reaction mixture was quenched by addition of 25 ml of 10% NaHCO$_3$ followed by extraction with ethyl acetate. The organic extract was washed with water, dried, concentrated and the crude material was passed through silica gel, using a gradient of heptane/ethyl acetate as eluent, to give 300 mg of 16e as a colorless oil.

$R_f$ 0.40 (heptane/ethyl acetate 2/1).

NMR (CDCl$_3$) δ 0.05 (s, 6, (CH$_3$)$_2$Si), 0.89 (s, 9, tertC$_4$H$_9$), 1.24 (m, 4, 2×CH$_2$), 1.33 (m, 2, CH$_2$), 1.35 (t, 3, C$_2$H$_5$), 1.50 (m, 2, CH$_2$), 1.65 (m, 2, CH$_2$) 3.18 (m, 2 CH$_2$) 3.60 (t, 2, CH$_2$), 4.31 (q, 2, C$_2$H$_5$).

ethyl 2-(tert-butyl(6-hydroxyhexyl)amino)-2-oxoacetate (16f)

A solution of 2g of 16e in 20 ml of THF was treated with 11 ml of 1M tetra-n-butyl ammonium fluoride in THF at 55° C. After stirring for 1 hr the mixture was concentrated, diluted with 50 ml of 5% aq. NH$_4$Cl and 10 ml of sat. NaCl and extracted with ethyl acetate. The organic layer was concentrated to give an oil. This was passed trough a silica pad using a gradient of heptane/ethyl acetate as eluent, to provide 1.5 g of 16f as a colorless oil, which was used without further purification in the next step.

$R_f$ (heptane/ethyl acetate 1/1) 0.45.

ethyl 2-(tert-butyl(6-oxohexyl)amino)-2-oxoacetate (16g)

A solution of 1.1 g of 16f, in a mixture of 30 ml of dichloromethane, 15 ml of DMSO and 3 ml of triethyl amine, was treated with 1 g of Pyr.SO$_3$ at 0° C. The reaction mixture was then stirred at RT for 2 hr. The mixture was partially concentrated and poured into water and the product was extracted with diethyl ether. The organic extract was washed with water, dried, concentrated and the crude material was purified by passing through a short silica column, to give 1.1 g of crude product, which was passed through silica gel, using a gradient of heptane/ethyl acetate as eluent, to provide 0.85 g of 16g as a colorless oil.

R$_f$ 0.45 (heptane/ethyl acetate 1/1).

NMR (CDCl$_3$) δ 9.78 (s, 1, CHO), 1.25 (m, 2, CH$_2$), 1.36 (t, 3, C$_2$H$_5$), 1.48 (s, 9, tertC$_4$H$_9$), 1.65 (m, 4, 2×CH$_2$), 2.46 (m, 2, CH$_2$), 3.18 (m, 2, CH$_2$), 4.30 (q, 2, C$_2$H$_5$).

ethyl 2-(tert-butyl(hept-6-ynyl)amino)-2-oxoacetate (16h)

To a solution of 850 mg of 16g in 12 ml of methanol was added 850 mg of K$_2$CO$_3$, followed at 0° C. by 850 mg of dimethyl 1-diazo-2-oxopropylphosphonate. The mixture was stirred at 0° C. for 2 hr, followed by stirring at RT for 16 hr. The reaction mixture was poured into 5% aq. NH$_4$Cl solution and extracted with ethyl acetate. The extract was washed with water, dried, concentrated and the crude material was purified by chromatography over silica gel, using a gradient of heptane/ethyl acetate as eluent, to give 650 mg of 16h as a colorless oil, as the methyl ester (due to transesterfication in the medium).

R$_f$ 0.65 (heptane/ethyl acetate 1/1). NMR (CDCl$_3$) δ 1.97 (t, 1, acetylene-H), 2.20 (m, 2, CH$_2$), 3.18 (m, 2, CH$_2$), 3.83 (s, 3, OCH$_3$), 1.68 (m, 2, CH$_2$), 1.48 (s, 9, tertC$_4$H$_9$), 1.30-1.55 (m, 4, 2×CH$_2$).

ethyl 2-(tert-butyl(7-(thiazol-5-yl)hept-6-ynyl)amino)-2-oxoacetate (16i)

A solution containing 300 mg of 16h, 180 μl of 5-Br-thiazole, 350 μl of diisopropyl amine, 21 mg of PdCl$_2$(benzonitrile)$_2$, 250 μl of 1M tri-tert-butyl phosphine (in toluene), 12 mg of CuI in 2 ml of degassed dioxane was stirred overnight at RT under a N$_2$ atmosphere. The mixture was poured onto 5% aq. NH$_4$Cl and extracted with ethyl acetate. The extract was dried, concentrated and the crude material was purified by chromatography over silica gel, using a gradient of heptane/ethyl acetate as eluent. This afforded 320 mg 16i as a colorless oil. R$_f$ 0.45 (heptane/ethyl acetate 1/1). MS-ESI: [M+1] 337.17

NMR (CDCl$_3$) δ 8.64 and 7.88 (2×s, 2, thiazole H), 1.40 (m, 2, CH$_2$), 1.48 (s, 9, tertC$_4$H$_9$), 1.64 (m, 4, 2×CH$_2$), 2.46 (t, 2, CH$_2$), 3.20 (m, 2, CH$_2$), 3.83 (s, 3, OCH$_3$).

ethyl 2-(tert-butyl(7-(thiazol-4-yl)hept-6-ynyl)amino)-2-oxoacetate (16o)

Similarly prepared 16o; NMR (CDCl$_3$) δ 3.94 (2×s, 3, OCH$_3$), 7.40 and 8.73 (2×d, 2, thiazole-H), 3.18 (m, 2, CH$_2$), 2.44 (t, 2, CH$_2$), 1.65 (bm, 4, CH$_2$), 1.40 (bm, 2, CH$_2$).

LC/MS M+1 337.17.

2-(tert-butyl(7-(thiazol-5-yl)hept-6-ynyl)amino)-2-oxoacetic acid (16j)

A solution of 310 mg of 16i in 9 ml of dioxane was mixed with a solution of 200 mg of KOH in 3 ml of water and was stirred at 50° C. for 1 hr. The mixture was diluted with water and acidified to pH3 with 0.5N HCl and the product was extracted into ethyl acetate. The organic extract was washed twice with water, dried and concentrated, to give 290 mg of 16j.

NMR (CDCl$_3$) δ 8.72 and 7.88 (2×s, 2, thiazole-H), 1.48 (s, 9, tertC$_4$H$_9$), 1.43 (m, 2, CH$_2$), 1.62 (m, 2, CH$_2$), 2.45 (t, 2, CH$_2$), 3.52 (m, 2, CH$_2$).

MS-ESI: [M+1] 323.13.

ethyl 7-bromo-2-(2-(tert-butyl(7-(thiazol-5-yl)hept-6-ynyl)amino)-2-oxoacetyl)-6-methoxy-1,2,3,4-tetrahydroisoquinoline-1-carboxylate (16k)

A solution of 280 mg of acid 16j, 300 mg of 3a and 250 μl of N-ethylmorpholine was stirred in 3 ml of dry DMF for 5 min. Then, 340 mg of TBTU was added and stirring was prolonged for 3 hr. After 3 hr, 15 ml of water was added and the product was extracted with ethyl acetate. The organic layer was washed with water, dried, concentrated and the remaining material was purified by chromatography over silica gel, using a gradient of heptane/ethyl acetate as eluent, to provide 530 mg of 16k as a colorless oil.

R$_f$ 0.28 (heptane/ethyl acetate 1/1) MS-ESI: [M+1] 618.09 and 620.13.

NMR (CDCl$_3$) δ 7.88 and 8.63 (2×s, 2, thiazole-H), 7.73 and 6.63 (2×s, 2, Ar—H), 5.73 (s, 1, CHCOOC$_2$H$_5$), 4.18 (m, 2, C$_2$H$_5$), 3.89 (s, 3, OCH$_3$), 3.70 (m, 2, CH$_2$), 3.35 (t, 2, CH$_2$), 2.85 and 2.98 (2×dt, 2, CH$_2$), 2.43 (t, 2, CH$_2$), 1.85 (m, 1, CH), 1.58-1.70 (bm, 3, CH+CH$_2$), 1.38 (m, 2, CH$_2$), 1.53 (s, 9, tertC$_4$H$_9$), 1.25 (t, 3, C$_2$H$_5$).

ethyl 7-bromo-2-(2-(tert-butyl(7-(thiazol-4-yl)hept-6-ynyl)amino)-2-oxoacetyl)-6-methoxy-1,2,3,4-tetrahydroisoquinoline-1-carboxylate (16q)

Similarly prepared 16q (o→p→q)

R$_f$ 0.55 (toluene/ethyl acetate 1/1). MS-ESI: [M+1] 618.10, 620.13,

NMR (CDCl$_3$) δ 7.38 and 8.73 (2×d, 2, thiazole-H), 7.73 and 6.63 (2×s, 2, Ar—H), 5.73 (s, 1, CHCOOC$_2$H$_5$), 4.18 (m, 2, CH$_2$CH$_3$), 3.89 (s, 3, OCH$_3$), 3.70 (m, 2, CH$_2$), 3.34 (m, 2, CH$_2$), 2.85 and 2.98 (2×dt, 2, CH$_2$), 2.43 (t, 2, CH$_2$), 1.85 (m, 1, CH), 1.58-1.70 (bm, 3, CH+CH$_2$), 1.40 (bm, 2, CH$_2$), 1.53 (s, 9, tertC$_4$H$_9$), 1.25 (t, 3, C$_2$H$_5$).

7-bromo-2-(2-(tert-butyl(7-(thiazol-5-yl)hept-6-ynyl)amino)-2-oxoacetyl)-6-methoxy-1,2,3,4-tetrahydroisoquinoline-1-carboxylic acid (16l)

A solution of 530 mg of 16k in 9 ml of dioxane was mixed with a solution of 300 mg of KOH in 3 ml of water and stirred at 55° C. for ½ hr. The reaction mixture was diluted with 25 ml of water and acidified with 0.5N HCl to pH3 and the product was extracted with ethyl acetate. The extract was once washed with water, dried and concentrated, to give 480 mg of 16l as colorless oil.

MS-ESI: [M+1] 590.09 and 592.07.

NMR (CDCl$_3$) δ 1.52 (s, 9, tertC$_4$H$_9$), 1.65 and 1.83, (2×bm, 2, CH$_2$), 2.35 (dt, 2, CH$_2$), 2.85 and 2.98 (2×dt, 2, CH$_2$), 3.37 (bt, 2, CH$_2$), 3.70 (m, 2, CH$_2$), 3.88 (s, 3, OCH$_3$).

1.34 and 1.57 (2×m, 4, 2×CH$_2$), 5.79 (s, 1, CHCOOH), 6.64, 7.79, 7.90 and 8.70 (4×s, 4, Ar—H+thiazole-H).

7-bromo-2-(2-(tert-butyl(7-(thiazol-4-yl)hept-6-ynyl)amino)-2-oxoacetyl)-6-methoxy-1,2,3,4-tetrahydroisoquinoline-1-carboxylic acid (16r)

Similarly prepared 16r; MS-ESI: [M+1] 590.09, 592.07. NMR (CDCl$_3$) δ 1.52 (s, 9, tertC$_4$H$_9$), 3.88 (s, 3, OCH$_3$). 5.89 (s, 1, CHCOOH), 6.63, 7.84, (2×s, 2, Ar—H) 7.38 and 8.96 (2×d, 2 thiazole-H).

2-bromo-9-tert-butyl-3-methoxy-15-(1,3-thiazol-5-yl)-5,6,9,10,11,12,13,14-octahydro-8H-azonino[4′,3′:4,5]pyrrolo[2,1-a]isoquinolin-8-one (16m)

A solution of 480 mg of 16l in 15 ml of acetic anhydride and 500 mg of sodium acetate was heated at 105° C. for 1.5 hr. The reaction mixture was cooled and diluted with 40 ml of water and stirred for 1 hr at ambient temperature to decompose excess anhydride. The mixture was then neutralized with cold conc. aq. NH$_4$OH and the product was extracted with ethyl acetate. The extract was washed with water, dried, concentrated and the residue was passed through a short silica column, using a gradient of heptane/ethyl acetate as eluent. The product isolated was triturated with diisopropyl ether, to provide 25 mg of white solid. Further purification was performed by chromatography on reversed phase C18 silica gel, using a gradient of acetonitrile-water, to give 12 mg of 16m as a white solid.

MS-ESI: [M+1] 528.12 and 530.10

R$_f$: 0.35 (heptane/ethyl acetate 1/1).

2-bromo-9-tert-butyl-3-methoxy-15-(1,3-thiazol-4-yl)-5,6,9,10,11,12,13,14-octahydro-8H-azonino[4′,3′:4,5]pyrrolo[2,1-a]isoquinolin-8-one (16s)

Similarly prepared 16s, 4-thiazolyl derivative;

R$_f$ 0.37 (heptane/ethyl acetate 1/1). MS-ESI: [M+1] 528.11, 530.10,

NMR (CDCl$_3$) (complex, conformers) δ 1.53 (s, 9, tertC$_4$H$_9$) 3.86 (s, 3, OCH$_3$), 6.71 and 7.03 (2×s, 2, Ar—H), 7.22 and 8.96 (2×dd, 2, thiazole-H), 4.32 (bm, 1, CH), 3.53 (bm, 2, CH$_2$), 3.25 (bm, 1, CH), 3.00 (bm, 2, CH$_2$), 2.65 (bm, 2, CH$_2$, 1.60-1.80 (bm, 2, CH$_2$), 1.44, (bm, 4, 2×CH$_2$). MS-ESI: [M+1] 527.13.

R$_f$ 0.40 (heptane/acetone 1/1).

2-pyridin-3-yl-9-tert-butyl-3-methoxy-15-(1,3-thiazol-5-yl)-5,6,9,10,11,12,13,14-octahydro-8H-azonino[4′,3′:4,5]pyrrolo[2,1-a]isoquinolin-8-one (16n)

A solution of 12 mg of 16m, 6 mg of pyridine-3-boronic acid, 10 mg of K$_2$CO$_3$, 1.5 ml of degassed dimethoxyethane, 100 µl of water and 5 mg of Pd(PPh$_3$)$_4$ was heated at 90° C. for 4 hr under a N$_2$ atmosphere. The mixture was cooled and poured into 10 ml of 2N NaOH and extracted with ethyl acetate. The extract was washed once with water, dried and chromatographed using a gradient of heptane/acetone as eluent. The material thus isolated was taken up in 200 µl of CH$_2$Cl$_2$ and treated with 0.2N HCl in diethyl ether, to pH slight acidic, to provide 12 mg of 16n as a yellowish HCl salt, MS-ESI:

[M+1] 527.20. R$_f$ (free base) 0.40 (heptane/acetone 1/1).

NMR (DMSO-d$^6$) (complex, conformers) δ 1.48 (s, 9, tertC$_4$H$_9$), 3.82 (s, 3, OCH$_3$), 6.87, 7.20 (2×s, 2, Ar—H), 7.80, 9.18 (2×s, 2, thiazole-H), 7.74, 8.00, 8.58 and 8.67 (4×m, 4, pyridine-H).

hFSHRago (CHO luc) pEC$_{50}$=7.79.

2-pyridin-3-yl-9-tert-butyl-3-methoxy-15-(1,3-thiazol-4-yl)-5,6,9,10,11,12,13,14-octahydro-8H-azonino[4′,3′:4,5]pyrrolo[2,1-a]isoquinolin-8-one (16t)

Similarly prepared 16t, 4-thiazolyl derivative:

NMR (DMSO-d$^6$) (complex, conformers) δ 1.48 (s, 9, tertC$_4$H$_9$) 3.81 (s, 3, OCH$_3$), 6.86 and 7.17 (2×s, 2, Ar—H), 7.65 and 9.21 (2×dd, 2, thiazole-H), 7.70, 7.98, 8.58 and 8.64 (4×m, 4, pyridine-H). R$_f$ 0.40 (heptane/acetone 1/1)

MS-ESI: [M+1] 527.13, hFSHRago (CHO luc) pEC$_{50}$=7.53.

Example 17

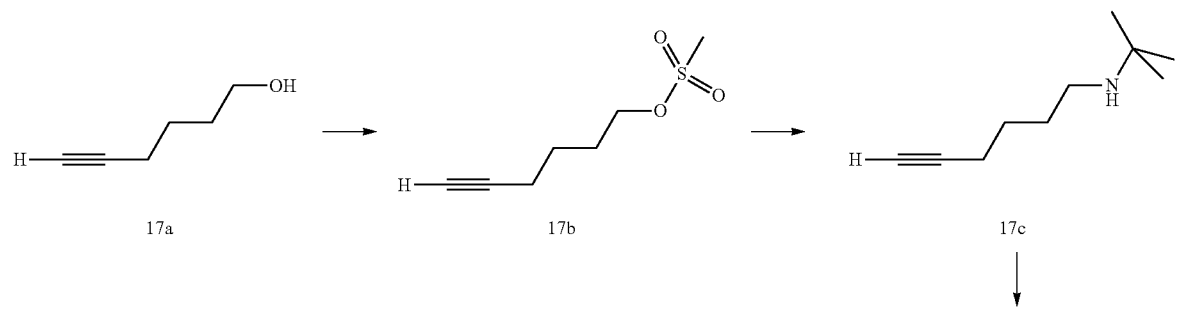

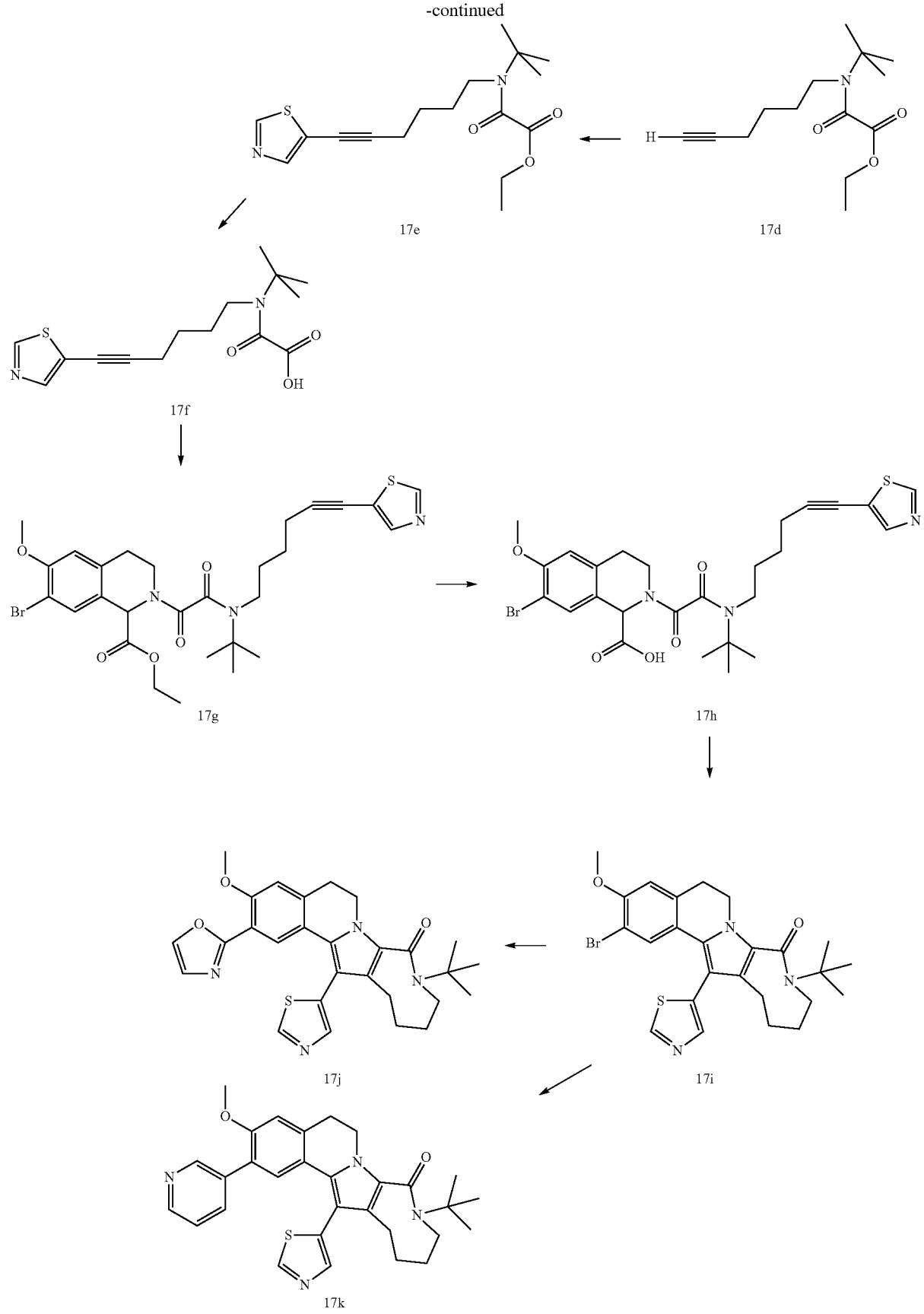

hex-5-ynyl methanesulfonate (17b)

To a solution of 2.3 ml of hexynol 17a, in 15 ml of diethyl ether was added 3 ml of triethyl amine, followed by 1.6 ml of mesyl chloride at 0° C. The mixture was stirred for 1 hr at 0° C., then diluted with 20 ml of water and extracted with diethyl ether. The extract was washed with 1N NaOH, water, dried and concentrated, to give 3.5 g of mesylate 17b as a colorless oil. $R_f$ 0.65 (heptane/acetone 1/1).

NMR (CDCl$_3$) δ 1.90 (m, 2, CH$_2$), 1.98 (t, 1, acetylene-H), 2.28 (dt, 2, CH$_2$), 4.28 (t, 2, CH$_2$), 3.02 (s, 3, OSO$_2$CH$_3$).

N-tert-butylhex-5-yn-1-amine (17c)

A solution of 3.5 g of 17b in 30 ml of tert-butyl amine was stirred at ambient temperature for 24 hrs. The reaction mixture was concentrated and the residues were partitioned between ethyl acetate and 5% NaHCO$_3$. The organic layer was dried and concentrated, to provide 3.0 g of 17c as a colorles oil, which was used without further purification in next step.

NMR (CDCl$_3$) δ 1.09 (s, 9, tertC$_4$H$_9$), 1.55 (m, 4, 2×CH$_2$), 2.20 and 2.55 (2×m, 4, 2×CH$_2$), 1.93 (t, 1, acetylene-H).

ethyl 2-(tert-butyl(hex-5-ynyl)amino)-2-oxoacetate (17d)

To a solution of 1 g of 17c in 10 ml of diethyl ether was added 1.5 ml of triethyl amine, followed, at 0° C., by 0.8 ml of ethyloxalyl chloride. The mixture was stirred for 1/2 hr at 0° C. and then poured into 30 ml of ice water and extracted with diethyl ether. The organic layer was washed with 1N NaOH, 1N HCl, water, dried and concentrated, to give 1.2 g of 17d as an oil. $R_f$ 0.15 (heptane/ethyl acetate 9/1).

NMR (CDCl$_3$) δ 1.35 (t, 3, C$_2$H$_5$), 1.49 (s, 9, tertC$_4$H$_9$), 1.98 (t, 1, CH acetylene), 1.46, 1.75, 2.18, 3.20 (4×m, 8, 4×CH$_2$), 4.30 (q, 2, C$_2$H$_5$).

ethyl 2-(tert-butyl(6-(thiazol-5-yl)hex-5-ynyl) amino)-2-oxoacetate (17e)

A mixture of 180 mg of 17d, 120 mg of purified 5-bromothiazole, 200 µl of diisopropyl amine and 2 ml of degassed dioxane was charged with 150 ml of 1M tri-tert-butyl phosphine (solution in toluene), 20 mg of PdCl$_2$(PheCN)$_2$ and 10 mg of CuI.

The mixture was stirred under N$_2$ for 16 hr, and subsequently the reaction mixture was poured into water and extracted with ethyl acetate. The organic extract was washed with water, dried, concentrated and the residue was purified by chromatography over silica gel (using a gradient of heptane/ethyl acetate as eluent) to provide 185 mg of 17e as colorless oil.

$R_f$ 0.52 (heptane/ethyl acetate 1/1) NMR (CDCl$_3$) δ 1.34 (t, 3, C$_2$H$_5$), 1.52 (s, 9, tertC$_4$H$_9$), 2.48 (t, 2, CH$_2$), 1.80 (m, 2, CH$_2$) 1.55 (m, 2, CH$_2$), 3.26 (m, 2, CH$_2$) 4.32 (q, 2, C$_2$H$_5$), 7.90 and 8.65 (2×s, 2, thiazole-H).

2-(tert-butyl(6-(thiazol-5-yl)hex-5-ynyl)amino)-2-oxoacetic acid (17f)

A solution of 180 mg of 17e in 2 ml of dioxane was mixed with a solution of 120 mg of KOH in 1 ml of water. The mixture was stirred for 1 hr at 50° C. The reaction mixture was cooled and diluted with 10 ml of water, acidified to pH 3 with 1N HCl and the product was extracted into ethyl acetate. The organic extract was washed twice with water, dried and concentrated, to provide 175 mg of 17f as a colorless oil.

NMR (CDCl$_3$) δ 1.50 (s, 9, tertC$_4$H$_9$), 1.59, 1.83, 2.47, 3.65 (4×m, 8, 4×CH$_2$), 7.87 and 8.70 (2×bs, 2, thiazole-H).

ethyl 7-bromo-2-(2-(tert-butyl(6-(thiazol-5-yl)hex-5-ynyl)amino)-2-oxoacetyl)-6-methoxy-1,2,3,4-tetrahydroisoquinoline-1-carboxylate (17g)

A mixture of 170 mg of 17f and 200 mg of 3a in 2 ml of DMF was treated with 350 µl of N-ethylmorpholine and 220 mg of TBTU. The mixture was stirred for 3 hr under N$_2$ atmosphere. 10 ml of water was added and the product was extracted with ethyl acetate. The organic extract was washed with water and 5% NH$_4$Cl, dried and concentrated. The product obtained was purified by chromatography over silica gel (using a gradient of toluene/ethyl acetate as eluent), to provide 310 mg of 17g as a colorless oil. $R_f$ 0.63 (toluene/ethyl acetate. 1/1).

NMR (CDCl$_3$) δ 1.27 (t, 3, C$_2$H$_5$), 1.53, s, 9, tertC$_4$H$_9$), 1.60-2.00 (2×m, 4, 2×CH$_2$), 2.45 (m, 2, CH$_2$) 2.80-3.00 (2×m, 2, CH$_2$) 3.38 (m, 2, CH$_2$) 3.70 (m, 2, CH$_2$), 3.88 (s, 3, OCH$_3$), 4.20 (m, 2, C$_2$H$_5$), 5.73 (s, 1, CHCOOC$_2$H$_5$), 6.63, 7.72, 7.89, 8.63 (4×s, 4, Ar—H and thiazole-H).

MS-ESI: [M+1] 604.16 and 606.13.

7-bromo-2-(2-(tert-butyl(6-(thiazol-5-yl)hex-5-ynyl) amino)-2-oxoacetyl)-6-methoxy-1,2,3,4-tetrahydroisoquinoline-1-carboxylic acid (17h)

A solution of 300 mg of 17g in 3 ml of dioxane was mixed with 130 mg of KOH in 1 ml of water. The mixture was stirred at 50° C. for 1.5 hr, cooled, diluted with 20 ml of water, acidified to pH3 (0.2N HCl) and extracted with ethyl acetate. The extract was washed twice with water, dried and concentrated, to give 240 mg of acid 17h as a colorless foam.

MS-ESI: [M+1] 576.10 and 578.08.

9-tert-butyl-3-methoxy-2-bromo-14-(1,3-thiazol-5-yl)-5,6,10,11,12,13-hexahydroazocino[4',3':4,5]pyrrolo[2,1-a]isoquinolin-8(9H)-one (17i)

A mixture of 220 mg of 17h and 150 mg of sodium acetate in 15 ml of acetic anhydride was stirred at 105° C. for 45 min. The reaction mixture was cooled, diluted with 60 ml of water and stirred at ambient temperature for 1 hr to destroy excess anhydride. The aqueous material was then neutralized by careful addition of cold con. aq. NH$_4$OH. The product was extracted with ethyl acetate. The extract was washed with water, dried, concentrated and the material isolated was chromatographed over silica gel using a gradient of heptane/ethyl acetate as eluent. The material isolated was treated with ether/heptane, to give 85 mg of 17i as white crystals. MS-ESI: [M+1] 514.11 and 516.11.

NMR (CDCl$_3$) δ 1.55 (s, 9, tertC$_4$H$_9$), 1.50-2.00 (bm, 4, 2×CH$_2$), 2.40-2.60 (2×bm, 2, CH$_2$) 2.90-3.15 (2×bm, 2, 2×CH$_2$), 3.55 (bm, 1, CH), 3.80 (bm, 2, CH$_2$), 4.62 (bm, 1, CH), 3.87 (s, 3, OCH$_3$), 6.73, 7.15, 7.73, 8.91 (4×s, 4, Ar—H and thiazole-H).

Mp 180-181° C.

hFSHRago (CHO luc) pEC$_{50}$=8.33.

9-tert-butyl-3-methoxy-2-(1,3-oxazol-2-yl)-14-(1,3-thiazol-5-yl)-5,6,10,11,12,13-hexahydroazocino[4',3':4,5]pyrrolo[2,1-a]isoquinolin-8(9H)-one (17j)

A mixture of 45 mg of 17i.50 mg of 2-tributyltin-oxazole and 10 mg of Pd(PPh$_3$)$_4$ in 3.5 ml of degassed toluene was heated, under N$_2$ atmosphere at 100-105° C. for 48 hr. The reaction mixture was cooled and poured onto a silica gel column and eluted with a gradient of CH$_2$Cl$_2$/ethyl acetate. The product isolated was treated with ether and provided 21 mg of 17j as white crystalline solid. MS-ESI: [M+1] 503.17. Mp: 205-207° C.

NMR (DMSO-d$^6$) δ 1.50 (s, 9, tertC$_4$H$_9$), 1.73 (bm, 4, 2×CH$_2$), 2.35 and 2.45, (2×m, 2, CH$_2$), 3.08 (bt, 2, CH$_2$), 3.57, 3.68, 3.80 and 4.40 (4×bm, 4, 2×CH$_2$), 2.88 (s, 3, OCH$_3$), 7.18, 7.22, 7.48, 7.77, 8.08 and 9.18 (6×s, 6, thiazole-H, oxazole-H and Ar—H).

hFSHRago (CHO luc) pEC$_{50}$=9.01.

9-tert-butyl-3-methoxy-2-pyridin-3-yl-14-(1,3-thiazol-5-yl)-5,6,10,11,12,13-hexahydroazocino[4',3':4,5]pyrrolo[2,1-a]isoquinolin-8(9H)-one (17k)

A mixture of 40 mg of 17l 20 mg of 3-pyridylboronic acid, 30 mg of K$_2$CO$_3$, 12 mg of Pd(PPh$_3$)$_4$, in 2 ml of 90% aq DME was heated at 90-95° C. during 16 h. The reaction mixture was cooled and diluted with water, after which the product was extracted with ethyl acetate. The organic extract was washed once with 1N NaOH and water, dried and concentrated. The isolated material was purified by chromatography (using a gradient of heptane/ethyl acetate as eluent.). The product isolated was taken up in 1 ml of ethyl acetate/ether 1/1 and was treated with 1M HCl in diethyl ether. The HCl salt was filtered and dried, to give 31 mg of 17k. MS-ESI: [M+1] 513.27. R$_f$(toluene/ethyl acetate 1/1).

NMR (DMSO-d$^6$) δ 1.50 (s, 9, tertC$_4$H$_9$), 1.71 (bm, 4, 2×CH$_2$), 2.40-2.60 (bm, 2, CH$_2$) 3.06 (bt, 2, CH$_2$), 3.50-4.40 (bm, 4, 2×CH$_2$), 3.82 (s, 3, OCH$_3$), 6.88, 7.18, 7.80 and 9.20 (4×s, 4, thiazole-H and Ar—H), 7.70, 7.94, 8.55 and 8.63 (4×m, 4, pyridine-H).

hFSHRago (CHO luc) pEC$_{50}$=9.45.

Example 18

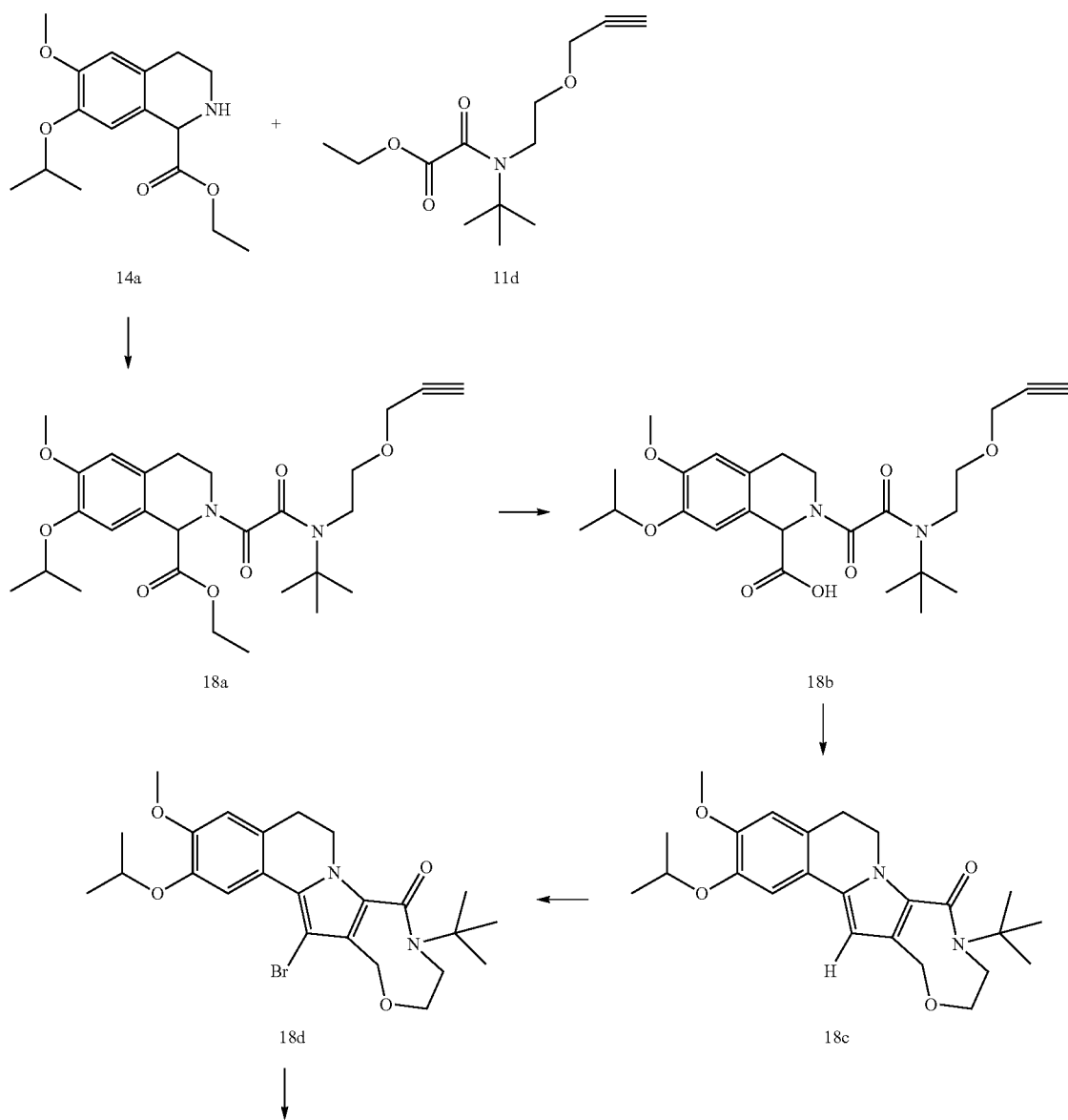

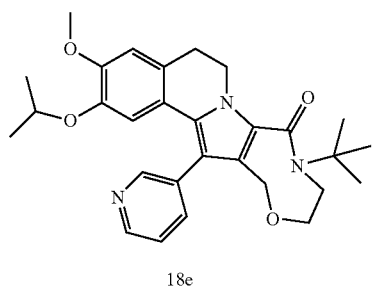 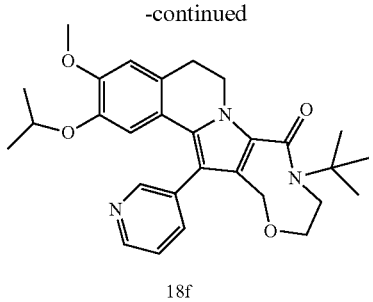 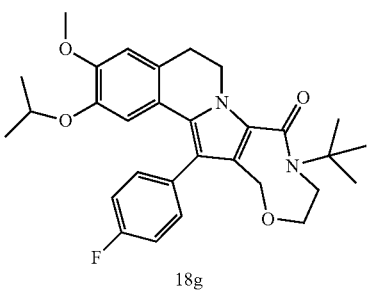

18e 18f 18g ethyl 2-(2-(tert-butyl(2-(prop-2-ynyloxy)ethyl) amino)-2-oxoacetyl)-7-isopropoxy-6-methoxy-1,2,3,4-tetrahydroisoquinoline-1-carboxylate (18a)

A solution of 1 g of 11d in 20 ml of dioxane and a solution of 1.2 g of KOH in 10 ml of water were mixed and stirred at 45° C. for 1 hr. The reaction mixture was cooled and acidified to pH 3 with cold 1N HCl. The product was extracted into ethyl acetate. After once washing with small amount of sat. aq. NaCl, drying and concentration, 0.89 g of the acid was isolated as a colorless oil. To a mixture of 420 mg of 14a and 300 mg of the acid described above, in 2 ml of DMF, was added 480 µl of N-ethyl morpholine and then 430 mg of TBTU. The reaction mixture was stirred for 3 hr and then 8 ml of 5% $NH_4Cl$ was added and stirring was prolonged for 10 min. The product was extracted into ethyl acetate. The organic extract was washed, dried and concentrated. The residue was purified over silica, using a gradient of heptane/ethyl acetate as eluent. The purified product thus obtained was triturated with diethyl ether to give 280 mg of 18a as white crystalline material.

$R_f$ 0.40 (heptane/ethyl acetate 1/1). MS-ESI: [M+1] 503.17.

NMR ($CDCl_3$) δ 1.26 (t, 3, $C_2H_5$), 1.38 (m, 6, iso$C_3H_7$), 1.53 (s, 9, tert$C_4H_9$), 2.42 (t, 1, acetylene-H) 2.82 and 2.94 (2×m, 2, $CH_2$), 3.60-3.80 (bm, 6, 3×$CH_2$), 3.83 (s, 3, $OCH_3$), 4.15-4.24 (bm, $C_2H_5$+$CH_2$), 4.50 (m, 1, CH), 5.20 (s, 1. C H$COOC_2H_5$) 6.01 and 7.08 (2×s, 2, Ar—H). Mp: 108-110° C.

2-(2-(tert-butyl(2-(prop-2-ynyloxy)ethyl)amino)-2-oxoacetyl)-7-isopropoxy-6-methoxy-1,2,3,4-tetrahydroisoquinoline-1-carboxylic acid (18b)

A solution of 280 mg of 18a in 4 ml of dioxane was mixed with 140 mg of KOH in 0.8 ml of water and stirred at 60° C. for 5 hr. The reaction mixture was cooled, diluted with 10 ml of water and acidified with cold 0.5N HCl. The product was extracted with ethyl acetate. The extract was washed twice with water, dried and concentrated, to give 264 mg of 18b as a colorless foam.

$R_f$ 0.15 (heptane/acetone 1/1). MS-ESI: [M+1] 475.19.

9-tert-butyl-3-methoxy-2-isopropoxyl-5,6,10,11-tetrahydro-9H-[1,4]oxazocino[7',6':4,5]pyrrolo[2,1-a]isoquinolin-8(13H)-one (18c)

A solution of 264 mg of 18b and 500 mg of anhydrous sodium acetate in 7 ml of acetic anhydride was heated under $N_2$ at 100° C. for 40 min. The mixture was cooled and diluted with 15 ml of water and stirred for 1 hr at ambient temperature. The mixture was then neutralized by dropwise addition of cold conc. aq. $NH_4OH$ and the product was extracted with ethyl acetate. The organic layer was washed with water, dried, concentrated and the residue was treated with diisopropyl ether to give 180 mg of 18c white crystalline material. Mp 125-127° C. MS-ESI: [M+1] 413.17.

NMR ($CDCl_3$) δ 1.38 (d, 6, iso$C_3H_7$), 1.55 (s, 9, tert$C_4H_9$), 2.97 (bm, 2, $CH_2$), 3.85 (s, 3, $OCH_3$), 3.4-4.10 (bm, 5, 2×$CH_2$+CH), 4.53 (m, 1, iso$C_3H_7$), 4.50-4.60 (bm, 3, CH+$CH_2$), 6.23 (s, 1, pyrrole-H), 6.71 and 7.04 (2×s, 2, Ar—H)

$R_f$ 0.65 (heptane/acetone 1/1).

9-tert-butyl-3-methoxy-2-isopropoxy-14-bromo-5,6,10,11-tetrahydro-9H-[1,4]oxazocino[7',6':4,5]pyrrolo[2,1-a]isoquinolin-8(13H)-one (18d)

To a solution of 180 mg of 18c in 2 ml of DMF was added 85 mg of N-bromosuccinimide. The mixture was stirred for ½ hr at RT. 3 ml of water was added and two drops of sat. aq. $Na_2S_2O_3$ and the mixture was stirred for ½ hr. The precipitate was filtered and washed with water, dried and then triturated with diisopropyl ether, to provide 175 mg of 18d as white crystalline material. Mp 160-162° C.

$R_f$ 0.47 (heptane/ethyl acetate 1/1). MS-ESI: [M+1] 491.03 and 493.08

NMR ($CDCl_3$) δ 1.42 (d, 6, iso$C_3H_7$), 1.56 (s, 9, tert$C_4H_9$), 2.92 and 2.98 (2×m, 2, $CH_2$), 3.50 bm, 1, CH) 3.80-4.0 (bm, 4, 2×$CH_2$), 3.88 (s, 3, $OCH_3$) 4.51 (bm, 1, CH), 4.58 (m, 1, iso$C_3H_7$), 4.65 (d, 2, $CH_2$) 6.73 and 7.96 (2×s, 2, Ar—H).

hFSHRago (CHO luc) p$EC_{50}$=6.90.

9-tert-butyl-3-methoxy-2-isopropoxy-14-pyridin-3-yl-5,6,10,11-tetrahydro-9H-[1,4]oxazocino[7',6':4,5]pyrrolo[2,1-a]isoquinolin-8(13H)-one (18e)

A solution of 50 mg of 18d, 60 mg of $K_2CO_3$, 20 mg of 3-pyridylboronic acid and 15 mg of $Pd(PPh_3)_4$ in 2.5 ml of degassed 90% aq. dimethoxyethane was heated at 95° C. under $N_2$ for 16 hr. The reaction mixture was cooled and poured into 1N NaOH. The product was extracted with ethyl acetate. The organic extract was washed twice with water, dried, concentrated and the residue was chromatographed over silica gel, using a gradient of heptane/acetone as eluent. The product thus isolated was treated with diethyl ether, to provide 28 mg of 18e as white crystalline material. Mp 193-194° C.

MS-ESI: [M+1] 490.17.

NMR ($CDCl_3$) δ 1.08 (d, 6, iso$C_3H_7$), 1.58 (s, 9, tert$C_4H_9$), 2.91 and 3.14 (2×bm, 2, $CH_2$), 3.57 (bd, 1, CH), 3.78-4.05 (bm, 5, 2×$CH_2$+CH), 4.38 (d, 2, $CH_2$), 3.83 (s, 3, $OCH_3$), 4.86 (m, 1, CH), 6.45 and 6.72 (2×s, 2, Ar—H), 7.35, 7.70, 8.59 and 8.63 (4×m, 4, pyridine-H). $R_f$ 0.50 (heptane/acetone 1/1).

hFSHRago (CHO luc) p$EC_{50}$=7.20.

9-tert-butyl-3-methoxy-2-isopropoxy-14-pyridin-4-yl-5,6,10,11-tetrahydro-9H-[1,4]oxazocino[7',6':4,5]pyrrolo[2,1-a]isoquinolin-8(13H)-one (18f)

A solution of 50 mg of 18d, 60 mg of $K_2CO_3$, 30 mg of 4-pyridylboronic acid-pinacolester and 15 mg of $Pd(PPh_3)_4$ in 2.5 ml of degassed 90% aq. dimethoxyethane was heated at 95° C. under $N_2$ for 16 hr. The mixture was cooled and poured onto 1N NaOH and the product was extracted with ethyl acetate. The organic layer was washed twice with water, dried, concentrated and the residue was chromatographed on silica gel (using a gradient of heptane/acetone as eluent). The product was treated with ether, to give 25 mg of 18f as white crystals. Mp: 218-219° C. MS-ESI: [M+1] 490.17.

NMR ($CDCl_3$) 6.1.09 (d, 6, iso$C_3H_7$), 1.58 (s, 9, tert$C_4H_9$), 2.90 and 3.16 (2×bm, 2, $CH_2$), 3.58 (bd, 1, CH), 3.70-4.10 (bm, 5, 2×$CH_2$+CH), 4.38 (d, 2, $CH_2$), 3.83 (s, 3, $OCH_3$), 4.92 (m, 1, CH), 6.55 and 6.72 (2×s, 2, Ar—H), 7.33 and 8.62 (2×dd, 4, pyridine-H). $R_f$ 0.45 (heptane/acetone 1/1).

hFSHRago (CHO luc) $pEC_{50}$=7.32.

9-tert-butyl-3-methoxy-2-isopropoxy-14-(4-fluorophenyl)-5,6,10,11-tetrahydro-9H-[1,4]oxazocino[7',6':4,5]pyrrolo[2,1-a]isoquinolin-8(13H)-one (18g)

A solution of 50 mg of 18d, 60 mg of $K_2CO_3$, 20 mg of 4-fluorophenyl]boronic acid and 10 mg of $Pd(PPh_3)_4$ in 2 ml of degassed 90% aq. dimethoxyethane was heated at 95° C. under $N_2$ for 5 hr. The reaction mixture was cooled, poured into 1N NaOH and extracted with ethyl acetate. The extract was washed twice with water, dried, concentrated and the residue was chromatographed over silica gel, using a gradient of heptane/ethyl acetate as eluent. The purified material was treated with diethyl ether, to give 22 mg of 18g as white crystalline material. Mp 215-217° C.

$R_f$ 0.40 (heptane/ethyl actetate 1/1) MS-ESI: [M+1] 507.17. NMR ($CDCl_3$) δ 1.10 (d, 6, iso$C_3H_7$), 1.57 (s, 9, tert$C_4H_9$), 2.89 and 3.13 (2×bm, 2, $CH_2$), 3.57 (bd, 1, CH), 3.75-4.05 (bm, 5, 2×$CH_2$+CH), 4.38 (d, 2, $CH_2$), 3.82 (s, 3, $OCH_3$), 4.85 (m, 1, CH), 6.51 and 6.70 (2×s, 2, Ar—H), 7.10, 7.33 (2×m, 4, F-phenyl-H)

hFSHRago (CHO luc) $pEC_{50}$=7.70.

Example 19

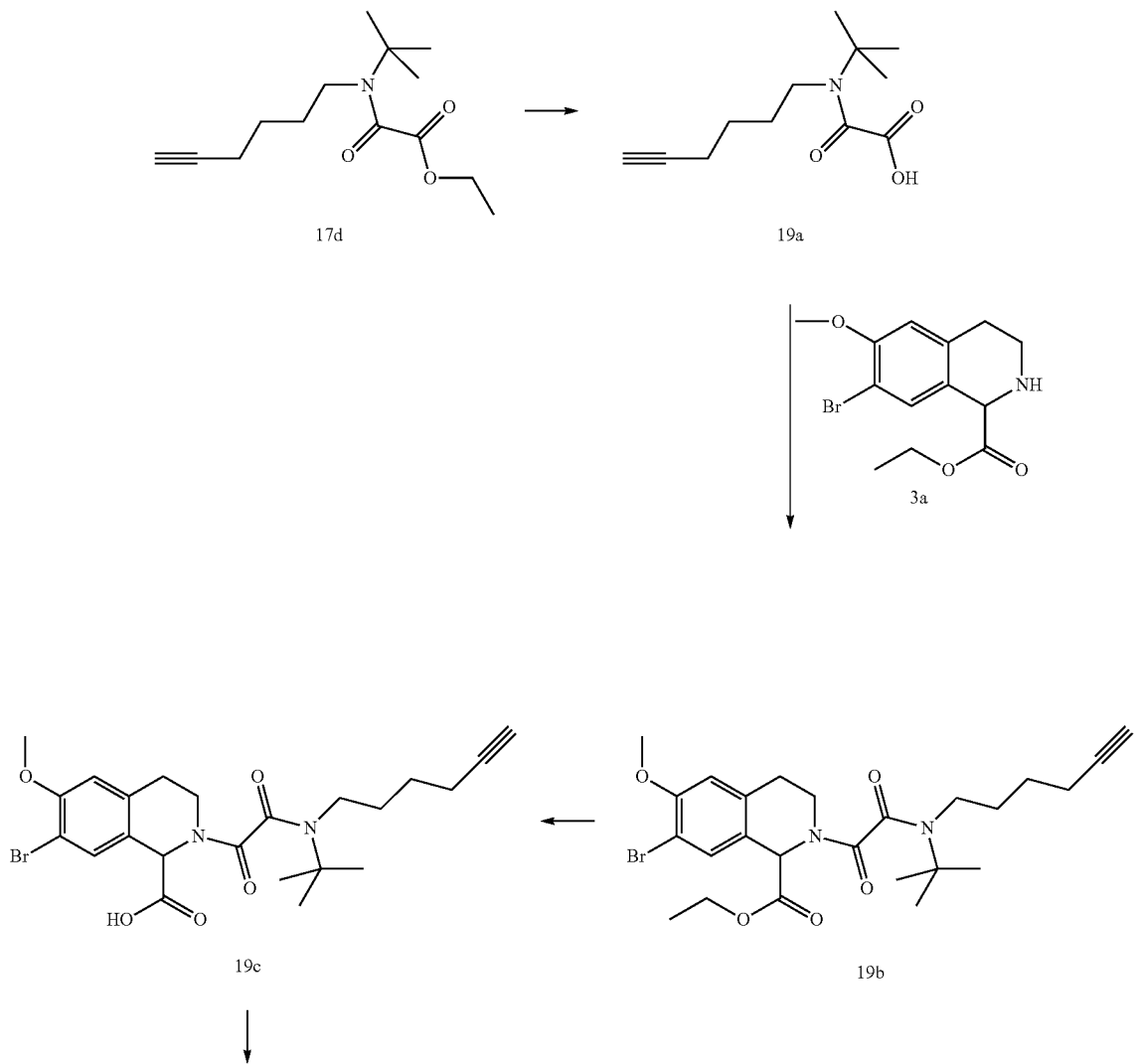

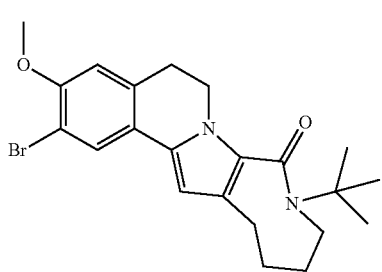

19d

-continued

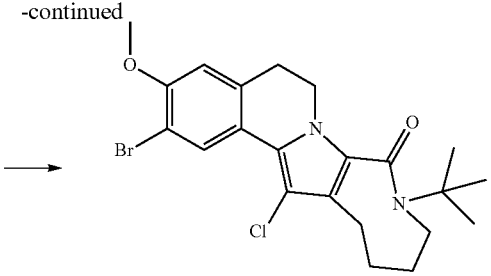

19e

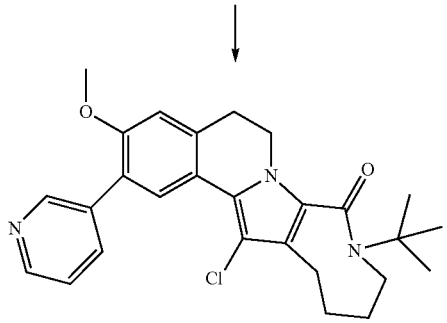

19f

2-(tert-butyl(hex-5-ynyl)amino)-2-oxoacetic acid (19a)

A solution of 0.7 g of 17d in 8 ml of dioxane was mixed with a solution of 0.3 g of KOH in 3 ml of water. The mixture was stirred for 2 h at 50° C. and then diluted with 30 ml of water and acidified to pH3 with 0.5 N HCl. The product was extracted with ethyl acetate. The extract was washed with water, dried and concentrated, to give 0.50 g of 19a as a colorless oil. NMR (CDCl$_3$) δ 1.53 (s and m, 11, tertC$_4$H$_9$ and CH$_2$), 1.78 (m, 2, CH$_2$), 1.97 (t, 1, acetylene), 2.20 (m, 2, CH$_2$), 3.56 (m, 2, CH$_2$).

ethyl 7-bromo-2-(2-(tert-butyl(hex-5-ynyl)amino)-2-oxoacetyl)-6-methoxy-1,2,3,4-tetrahydroisoquinoline-1-carboxylate (19b)

A mixture of 350 mg of 3a, 250 mg of 19a, 380 mg of TBTU and 300 μl of N-ethyl morpholine in 5 ml of DMF was stirred for 16 h. The reaction mixture was diluted with 30 ml of water, stirred for 15 min and then extracted with ethyl acetate. The extract was washed twice with water, dried, concentrated and the residue was chromatographed over silica gel, using a gradient of toluene/ethyl acetate as eluent. This provided 480 mg of 19b as a colorless oil; MS-ESI: [M+1] 523.17 and 521.17. R$_f$ (heptane/etyl acetate 1/1) 0.45. NMR (CDCl$_3$) δ 1.29 (t, 3, CH$_3$), 1.47 (m, 2, CH$_2$), 1.53 (s, 9, tertC$_4$H$_9$), 1.58-1.93 (bm, 2, CH$_2$), 2.20 (m, 2, CH$_2$), 2.36 (t, 1, acetylene), 2.86 and 2.97 (2×m, 2, CH$_2$), 3.34 (m, 2, CH$_2$), 3.89 (s, 3, OCH$_3$), 4.20 (m, 2, OCH$_2$), 5.73 (s, 1, CH), 6.64 (s, 1, ArH), 7.73 (s, 1, ArH).

7-bromo-2-(2-(tert-butyl(hex-5-ynyl)amino)-2-oxoacetyl)-6-methoxy-1,2,3,4-tetrahydroisoquinoline-1-carboxylic acid (19c)

A solution of 480 mg of 19b in 10 ml of dioxane was mixed with 200 mg of KOH in 2 ml of water. The mixture was stirred at rt for 3 h and then diluted with 40 ml of water and acidified to pH 3 with 0.5 N HCl. The product was extracted with ethyl acetate. The organic layer was washed with water, dried and concentrated, to provide 420 mg of 19c as white amorphous material; MS-ESI: [M+1] 495.19 and 493.18. NMR (CDCl$_3$) δ 1.43 (m, 2, CH$_2$), 1.53 (s, 9, tertC$_4$H$_9$), 1.68-1.90 (bm, 2, CH$_2$), 1.92 (t, 1, CH), 2.16 (m, 2, CH$_2$), 2.80-3.00 (bm, 2, CH$_2$), 3.22-3.45 (bm, 2, CH$_2$), 3.68 (m, 2, CH$_2$), 3.88 (s, 3, OCH$_3$), 5.74 (s, 1, CH), 6.65 (s, 1, ArH), 7.73 (s, 1, ArH).

9-tert-butyl-3-methoxy-2-bromo-5,6,10,11,12,13-hexahydroazocino[4',3':4,5]pyrrolo[2,1-a]isoquinolin-8(9H)-one (19d)

A mixture of 420 g of 19c and 500 mg of sodium acetate and 8 ml of acetic anhydride was heated at 105° C. for 3 h. The reaction mixture was cooled and diluted with 20 ml of water and stirred for 1 h to decompose the acetic anhydride. Then a solution of cold conc. ammonia was added to pH 8. The product was extracted with ethyl acetate. The organic layer was washed, dried, concentrated and the crude material was chromatographed over silica gel, using a gradient of heptane/ethyl acetate as eluent. The material thus isolated was treated with heptane/diisopropyl ether (1/1) to provide 95 mg of 19d as white crystalline material; Mp 127-129° C.

MS-ESI: [M+1] 431.18 and 433.17; R$_f$ (heptane/ethyl acetate 1/1) 0.60. NMR (CDCl$_3$) δ 1.58 (s, 9, tertC$_4$H$_9$), 1.62-2.00 (bm, 4, 2×CH$_2$), 2.65-2.80 (bm, 2, CH$_2$), 2.90-3.05 (bm, 2, CH$_2$), 3.40-4.00 (bm, 3, CH$_2$+CH), 3.89 (s, 3, OCH$_3$), 4.30-4.60 (bm, 1, CH), 6.12 (s, 1, CH-pyrrole), 6.72 (s, 1, ArH), 7.63 (s, 1, ArH).

9-tert-butyl-3-methoxy-2-bromo-14-chloro-5,6,10,11,12,13-hexahydroazocino[4',3':4,5]pyrrolo[2,1-a]isoquinolin-8(9H)-one (19e)

To a solution of 66 mg of 19d in 1 ml of DMF was added at 0° C. 27 mg of N-chlorosuccinimide. The mixture was stirred for 2 h. Then, 5 ml of water was added and 1 drop of a sat. Na₂S₂O₃ solution. Stirring was continued for 5 min and the product was extracted into ethyl acetate. The extract was washed with water, dried, concentrated and the residue was treated with cold pentane, to provide 65 mg of 19e as a white crystalline material; Mp 203-205° C. MS-ESI: [M+1] 464.12, 465.10, 466.09, 467.08, 468.08 and 469.07.

NMR (CDCl₃) δ 1.58 (s, 9, tertC₄H₉), 1.60-1.77 (bm, 2, CH₂), 1.80-2.04 (bm, 2, CH₂), 2.58-2.75 (bm, 2, CH₂), 2.84- 3.07 (bm, 2, CH₂), 3.43-3.58 (bm, 1, CH), 3.72-3.88 (bm, 2, CH₂), 3.91 (s. 3, OCH₃), 4.38-4.50 (bm, 1, CH), 6.76 (s, 1, ArH), 8.40 (s, 1, ArH).

9-tert-butyl-3-methoxy-2-pyridin-3-yl-14-chloro-5,6, 10,11,12,13-hexahydroazocino[4',3':4,5]pyrrolo[2,1-a]isoquinolin-8(9H)-one (19f)

A mixture of 65 mg of 19e, 25 mg of 3-pyridine-boronic acid, 45 mg of K₂CO₃ and 12 mg of Pd(PPh₃)₄ in 3 ml of degassed 90% aq. dimethoxyethane was heated under a nitrogen atmosphere for 16 h at 90° C. The mixture was diluted with water, extracted with ethyl acetate, dried and concentrated. The residues were purified by chromatography over silica gel, using a gradient of heptane/ethyl acetate as eluent. The material thus obtained was triturated with pentane, to provide 45 mg of white crystalline 19f; Mp: 190-192° C. MS-ESI: [M+1] 464.17, 465.17 and 466.17. NMR (CDCl₃) δ 1.58 (s, 3, tertC₄H₉), 1.62-1.77 (bm, 2, CH₂), 1.80-2.05 (bm, 2, CH₂), 2.60-2.77 (bm, 2, CH₂), 2.970-3.18 (bm, 2, CH₂), 3.50 bm, 1, CH), 3.76-3.92 (bm, 2, CH₂), 3.86 (s, 3, OCH₃), 4.50 (bm, 1, CH), 6.87 (s, 1, ArH), 8.20 (s, 1, ArH), 7.36, 7.89, 8.57, 8.83 (4×m, 4, pyridine-H).

hFSHRago (CHO luc) pEC₅₀=7.91.

Example 20

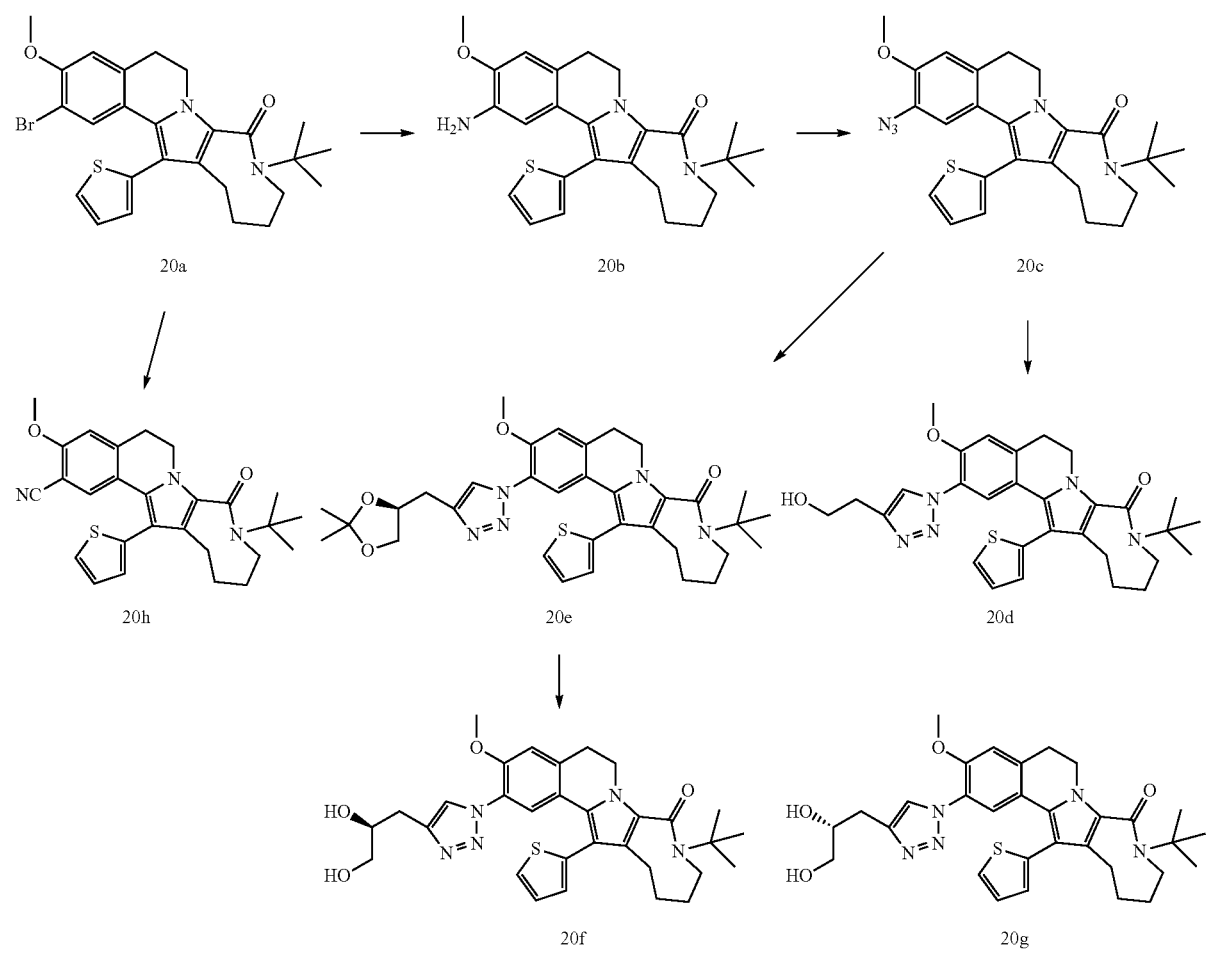

9-tert-butyl-14-(thien-2-yl)-2-amino-3-methoxy-5,6,10, 11,12,13-hexahydroazocino[4',3':4,5]pyrrolo[2,1-a]isoquinolin-8(9H)-one (20b)

To a solution of 800 mg of 20a (prepared in an analogous way as 17i, starting from 17d and 2-iodo or 2-bromothiophene) in degassed toluene was added 540 mg of triphenylsilylamine, 13 mg of dicyclohexyl-(2',6'-dimethoxybiphenyl-2-yl)phosphine, followed by 1.95 ml of a 1M solution of lithiumbistrimethylsilylamide and 14 mg of Pd₂(dba)₃. The reaction mixture was heated for 5 hr at 100° C. under nitrogen atmosphere. The mixture was cooled and poured onto saturated NaHCO₃ solution and extracted with ethyl acetate. The organic extract was washed once with water, dried and concentrated, to provide 1.3 g of solid. This was suspended in 4 ml of 80% aqueous acetic acid, to provide a homogeneous solution after being stirred for 1 hr at 50° C. The mixture was diluted with water, and neutralized by addition of solid NaHCO₃. The product was extracted with ethyl acetate. The organic layer was washed with water, dried and concentrated, to provide 565 mg of 20b as a light yellow solid; LCMS-ESI: [M+1] 450.1

NMR (CDCl$_3$). δ 7.36, 7.08, and 6.90 (3×m, 3, thienyl-H), 6.6 and 6.42 (2×s, Ar—H), 4.60 and 3.85 (2×br.m, 2, CH$_2$), 3.82 (s, 3, OCH$_3$), 3.76, and 3.50 (2×br.m, 2, H$_2$), 3.44 (bs, 2, NH$_2$), 3.03 and 2.85 (2×br.m, 2, CH$_2$), 1.60-2.00 (br.m, 4, 2×CH$_2$) 1.85 (s, 9, tertC$_4$H$_9$).

hFSHRago (CHO luc) pEC$_{50}$=7.40.

9-tert-butyl-14-(thien-2-yl)-2-azido-3-methoxy-5,6,10,11,12,13-hexahydroazocino[4',3':4,5]pyrrolo[2,1-a]isoquinolin-8(9H)-one (20c)

To a solution of 1.75 g of 20b in 40 ml of acetonitrile was added dropwise at 0° C. 0.54 g of trimethylsilyl azide, followed by 0.6 gr of tertbutyl nitrite. The reaction was stirred for ½ hr at ambient temperature, and then diluted with water and extracted with ethyl acetate. The extract was washed with water, dried and concentrated. The remainder was chromatographed on silicagel (using a gradient of heptane/ethyl acetate as eluent), to provide 1.14 g of 20c. LCMS-ESI: [M+1] 476.17.

NMR (CDCl$_3$) δ 7.40 (d, 1, thienyl H), 7.12 (dd, 1, thienyl-H), 6.91 (d, 1, thienyl-H), 6.73 and 6.70 (2×s, Ar—H), 4.60 and 3.83 (2×br.m, 2, CH$_2$, 3.84 (s, 3, OCH$_3$) 3.10 and 2.95 (2×br.m, 2, CH$_2$), 2.55 (br.m, 2, CH$_2$), 1.6-2.0 (br.m, 4, 2×CH$_2$), 1.57 (s, 9, tertC$_4$H$_9$).

9-tert-butyl-14-(thien-2-yl)-2-(4-(2-hydroxyethyl)-1H-1,2,3-triazol-1-yl)-3-methoxy-5,6,10,11,12,13-hexahydroazocino[4',3':4,5]pyrrolo[2,1-a]isoquinolin-8(9H)-one (20d)

In a microwave tube were mixed 52 mg of azide 20c, 10 ul of 3-butyn-1-ol, 2 ml of water, 2 ml of ethanol, 3.5 mg of CuSO4, 11 mg of sodium ascorbate and 11 mg of tris(benzyltriazolylmethyl)amine. The mixture was heated at 100° C. for 30 min., and then cooled and diluted with water. The product was extracted into ethyl acetate. The organic layer was washed, dried and concentrated, and the residue was purified by silicagel chromatography (using a gradient of heptane/ethyl acetate as eluent), and provided 29 mg of product 20d. LCMS-ESI: [M+1] 564.2.

NMR (CDCl$_3$) δ 7.34, 7.08, 6.92 (3×m, 3, thienyl H), 7.34, 7.65, and 6.89 (3×s, 3, Ar—H), 4.70 and 3.85 (2×m, 2, 2H), 3.98 (m, 2, CH$_2$O), 2.98 (t, 2, CH$_2$CH$_2$OH), 3.85 (s, 3, OCH$_3$), 3.80 and 3.55 (2×bm, 2, CH$_2$), 3.18 and 3.02 (2×bm, 2, CH$_2$), 2.52 (bm+t, 3, CH2+OH) 1.60-2.0 (bm, 4, CH$_2$) 1.55 (s, 9, tertC$_4$H$_9$).

hFSHRago (CHO luc) pEC$_{50}$=9.23.

(S)-9-tert-butyl-14-(thien-2-yl)-2-(4-((2,2-dimethyl-1,3-dioxolan-4-yl)methyl)-1H-1,2,3-triazol-1-yl)-3-methoxy-5,6,10,11,12,13-hexahydroazocino[4',3':4,5]pyrrolo[2,1-a]isoquinolin-8(9H)-one (20e)

Analogous to the synthesis of compound 20d, compound 20e (30 mg) was prepared from 70 mg of 20c and 20 mg of (S)-2,2-dimethyl-4-(prop-2-ynyl)-1,3-dioxolane (Y. Kishi et al., *Tetr. Letters,* 33 (12) 1553 (1992), 4 mg of CuSO$_4$, 15 mg of sodium ascorbate, and 15 mg of tris(benzyltriazolylmethyl)amine (V. Fokin et al., *Org. Lett.,* 6 (17) 2004).

LCMS-ESI: [M+1] 616.4.

(S)-9-tert-butyl-14-(thien-2-yl)-2-(4-(2,3-dihydroxypropyl)-1H-1,2,3-triazol-1-yl)-3-methoxy-5,6,10,11,12,13-hexahydroazocino[4',3':4,5]pyrrolo[2,1-a]isoquinolin-8(9H)-one (20f)

Compound 20e (30 mg) was dissolved in 2 ml of 80% acetic acid and stirred for 2 days at RT. The mixture was diluted with ice-water and neutralized by addition of conc. NH$_4$OH. The product was extracted with ethyl acetate. The organic extract was washed with water, dried and concentrated, and the remainder purified by chromatography over silica gel, (using a gradient of heptane/acetone as eluent), to provide 12 mg of 20f.

LCMS-ESI: [M+1] 576.3.

NMR (CDCl$_3$) δ 7.69, 7.35, 6.88 (3×s, 3, Ar—H), 7.36, 7.09, 6.93 (3×m, 3, thienyl H) 4.68 and 3.85 (2×br.m, 2, CH$_2$), 3.85 (s, 3, OCH$_3$), 4.10 (m, 1, CHOH), 3.74 and 3.62 (2×m, 2, CH$_2$OH), 3.82, and 3.57 (2×m, 2, CH$_2$), 2.92 (d, 2, triazol-CH$_2$), 2.53 (bm, 2, CH2), 1.60-2.00 (bm, 4, 2×CH$_2$), 1.58 (s, 9, tertC$_4$H$_9$).

hFSHRago (CHO luc) pEC$_{50}$=8.39.

(R)-9-tert-butyl-14-(thien-2-yl)-2-(4-(2,3-dihydroxypropyl)-1H-1,2,3-triazol-1-yl)-3-methoxy-5,6,10,11,12,13-hexahydroazocino[4',3':4,5]pyrrolo[2,1-a]isoquinolin-8(9H)-one (20g)

The other enantiomer 20g was prepared analogous to 20f, starting from (R)-2,2-dimethyl-4-(prop-2-ynyl)-1,3-dioxolane.

LCMS-ESI: [M+1] 576.3.

hFSHRago (CHO luc) pEC$_{50}$=8.49.

Enantiomeric purity of enantiomers 20f and 20g thus prepared was unevoqualy determined by chiral analytical column chromatography on Chiralcel-AD column, using 20% ethanol in heptane as eluent: t$_R$ 8.87 min (20f) vs 9.45 min (20g)

9-tert-butyl-14-(thien-2-yl)-3-methoxy-5,6,10,11,12,13-hexahydroazocino[4',3':4,5]pyrrolo[2,1-a]isoquinolin-8(9H)-one-2-carbonitrile (20h)

To a solution of 200 mg of 20a in 5 ml of degassed DMF was added 91 mg of ZnCN and 45 mg of tetrakis(triphenylphosphine)palladium(0). The mixture was heated in a microwave oven at 150° C. for 1 hr in a sealed nitrogen flushed vessel. The reaction was cooled and diluted with 1N NaOH and the product was extracted with ethyl acetate. The organic material was washed with water, dried and concentrated, and the crude product was purified by chromatography on a preparative reversed phase C18 silica column, using a gradient of acetonitrile-water. This provided 112 mg of 20h.

LCMS-ESI: [M+1] 460.2.

NMR (CDCl$_3$) δ 7.18 and 6.78 (2×s, 2, Ar—H), 7.40, 7.12, and 6.90 (3×m, 3, thiophene-H), 4.61, 3.80, 3.55 (3×m, 4, 2×CH$_2$), 2.99 and 3.15 (2×m, 2, CH$_2$), 1.50-2.00 (b.m, 4, 2×CH$_2$), 1.55 (s, 9, tertC$_4$H$_9$).

hFSHRago (CHO luc) pEC$_{50}$=8.75.

Example 21

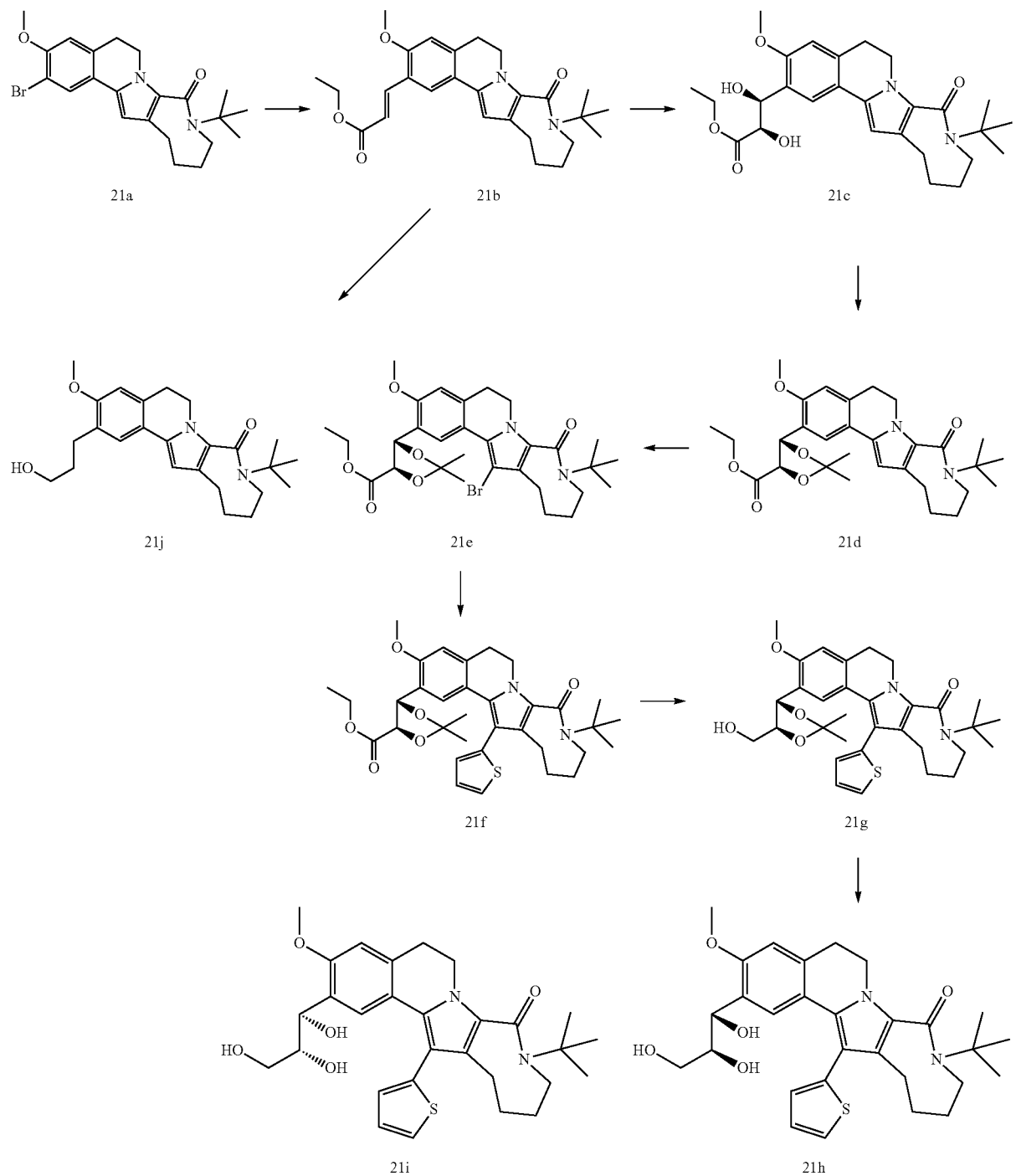

Ethyl (E)-(9-tert-butyl-12,12-dimethyl-3-methoxy-5,6,10,11,12,13-hexahydroazocino[4',3':4,5]pyrrolo[2,1-a]isoquinolin-8(9H)-on-2-yl)acrylate (21b)

A mixture of 2.8 gr of 21a, 1.7 g of ethoxycarbonylvinylboronic acid pinacolester and 1.8 g of $K_2CO_3$, and 0.3 gr of tetrakis(triphenylphosphine)palladium(0) in 120 ml of degassed 90% aq. DME was heated under $N_2$ atmosphere for 16 hr. The mixture was concentrated, diluted with water and extracted with ethyl acetate. The organic extracts were washed, dried and concentrated and the residue purified by chromatography over silicagel (using a gradient of heptane-ethylacetate as eluent). This provided 2.1 g of 21b. [M+1] 451.15. NMR (CDCl$_3$) δ 7.95 and 6.52 (2×dd, 2, trans double bond), 6.17, 6.72, 7.61 (3×s, 3, Ar—H), 4.25 (q, 2, ethyl ester), 1.32 (t, 3, ethyl ester), 3.88 (s, 3, OCH$_3$). R$_f$ (heptane/ethyl acetate 1/1) 0.57.

(2R,3S) 3-(9-tert-butyl-12,12-dimethyl-3-methoxy-5,6,10,11,12,13-hexahydroazocino[4',3':4,5]pyrrolo[2,1-a]isoquinolin-8(9H)-on-2-yl)-2,3-dihydroxypropanoic acid ethyl ester (21c)

To a suspension of 1.06 g of 21b in 40 ml of 1/1 t-butanol/water was added 3.29 g of AD-MIX-BETA. The mixture was stirred for 15 min. Then 0.2 g of methanesulfonamide was added and stirring was prolonged for 16 h. A solution of 0.5 g of sodiumsulfite was added and after stirring for an additional 15 min. the mixture was diluted with water, and the product extracted with ethyl acetate. The extract was washed, dried and concentrated, and the remainder was chromatographed over silicagel (using a gradient of heptane-ethylacetate as eluent). This provided 868 mg of 21c. $R_f$ (heptane/ethyl acetate 1/1) 0.19. NMR (CDCl$_3$) δ 7.51, 6.70 and 6.18 (3×s, 3, Ar—H) 5.27 (dd, 1, CHOH), 4.48 (dd, 1, CHOH), 3.87 (s, 3, OCH$_3$), 4.28 (m, 2, ethyl ester), 1.28 (t, 3, ethyl ester), 1.57 (s, 9, tertC$_4$H$_9$).

(4R,5S)-ethyl 5-(9-tert-butyl-12,12-dimethyl-3-methoxy-5,6,10,11,12,13-hexahydroazocino[4',3':4,5]pyrrolo[2,1-a]isoquinolin-8(9H)-on-2-yl)-2,2-dimethyl-1,3-dioxolane-4-carboxylate (21d)

A solution of 868 mg of 21c in 10 ml of acetone, 2.2 ml of 2,2-dimethoxypropane, and 17 mg of p-toluenesulfonic acid was stirred for 2 hr. The reaction was treated with 0.8 ml of triethylamine, stirred for 5 min, and then concentrated to a small volume and diluted with 30 ml of 5% NaHCO$_3$ solution. The product was extracted with ethyl acetate and the extracts were washed with water, dried and concentrated, to provide 940 mg of product 21d, which was used as is in the next step; $R_f$ (heptane/ethyl acetate 1/1) 0.57.

NMR (CDCl$_3$) δ 7.60, 6.68, 6.18 (3×s, 3, Ar—H), 5.50 (d, 1, CHO), 4.25 (m, 3, CHO+OCH$_2$—), 3.78 (s, 3, OCH$_3$), 1.28 (q, 3, ethyl ester), 1.61 (s, 6, dimethyl-ketal), 1.57 (s, 9, tertC$_4$H$_9$).

(4R,5S)-ethyl 5-(9-tert-butyl-14-bromo-3-methoxy-5,6,10,11,12,13-hexahydroazocino[4',3':4,5]pyrrolo[2,1-a]isoquinolin-8(9H)-on-2-yl)-2,2-dimethyl-1,3-dioxolane-4-carboxylate (21e)

A solution of 0.95 g of 21d in 10 ml of DMF was treated with 0.32 g of NBS. The reaction was stirred for 1 hr and then poured into water and extracted with ethyl acetate. The extract was washed with water, dried and concentrated and the product filtered through silica gel (using a gradient of heptane-ethylacetate as eluent), to provide 1.08 gr of 21e; LC-MS-ESI: [M+1] 603.13, 605.13. NMR (CDCl$_3$) δ 8.57 and 6.70 (2×s, 2, Ar—H), 5.51 (d, 1, CHO), 4.20 (m, 2, CHO and ethyl ester), 1.25 (t, 3, ethyl ester), 4.32+3.80 (2×m, 2, CH$_2$), 3.78 (3, 3, OCH$_3$), 3.75 (and 3.50 (2×m, 2, CH$_2$), 2.95 and 3.05 (2×m, 2, CH$_2$), 2.65 and 2.70 (2×m, 2, CH$_2$) 1.65-2.0 (bm, 4, 2×CH$_2$) 1.62 and 1.64 (2×s, 6, dimethylketal) 1.57 (s, 9, tertC$_4$H$_9$)

(4R,5S)-ethyl 5-(9-tert-butyl-14-(thien-2-yl)-3-methoxy-5,6,10,11,12,13-hexahydroazocino[4',3':4,5]pyrrolo[2,1-a]isoquinolin-8(9H)-on-2-yl)-2,2-dimethyl-1,3-dioxolane-4-carboxylate (21f)

A mixture of 750 mg of 21e, 550 mg of 2-(tributylstannyl)-thiophene and 28 mg of tetrakis(triphenylphosphine)palladium(0) in 14 ml of degassed toluene was heated under N$_2$ atmosphere for 16 hr at 110° C. The reaction mixture was cooled, 15 ml of sat. aq. KF was added, and stirring prolonged for 2 hr. The reaction was filtered through Celite, and the product was extracted with ethyl acetate. The organic layer was washed, dried and concentrated and the product purified by chromatography over silicagel (using a gradient of heptane-ethylacetate as eluent). This provided 630 mg of 21f; LC-MS-ESI: [M+1] 607.26. NMR (CDCl$_3$) δ 7.35, 7.08, and 6.93 (3×m, 3, thienyl-H), 6.67 and 7.30 (2×s, 2, Ar—H) 5.35 (d 1, CHO), 3.95 (d, 1, CHO), 3.75 (s, 3, OCH$_3$), 0.20 (m, 2, ethyl ester), 1.28 (t, 3, ethyl ester), 4.60, and 3.80 (2×bm, 2, CH$_2$), 3.55 and 4.15 (2×br.m, 2, CH$_2$), 2.92 and 3.13 (2×b.m, 2, CH$_2$) 1.6-2.0 (bm, 4, 2×CH$_2$), 1.32 and 1.50 (2×s, 6, dimethylketal), 1.57 (s, 9, tertC$_4$H$_9$).

((4R,5S)-5-(9-tert-butyl-14-(thien-2-yl)-3-methoxy-5,6,10,11,12,13-hexahydroazocino[4',3':4,5]pyrrolo[2,1-a]isoquinolin-8(9H)-on-2-yl)-2,2-dimethyl-1,3-dioxolan-4-yl)methanol (21g)

To a solution of 680 mg of 21f in 20 ml of THF and 0.5 ml of ethanol was added dropwise 0.56 ml of a 2M solution of LiBH$_4$ in THF. The reaction was stirred for 3 hr. The reaction was poured onto 5% NH$_4$Cl solution, and the product was extracted into ethylacetate. The extract was dried and concentrated to provide 620 mg of product 21g which was used as is in the next step; $R_f$ (Hept./ethyl acetate 1/1) 0.21. NMR (CDCl$_3$) δ 7.35, 7.10, and 6.92 (3×m, 3, thienyl-H), 6.70 and 7.33 (2×s, 2, Ar—H); 5.10 (bd, 1, CHO), 4.65 (bm, 1, CH), 3.50-3.90 (bm, 6, CHO+CH$_2$O+CH+CH$_2$), 3.82 (s, 3, OCH$_3$), 2.90+3.12 (2×bm, 2, CH$_2$) 2.50 (b.m, 2, CH$_2$) 1.60-2.05 (bm, 4, 2×CH$_2$) 1.42 and 1.25 (2×s, 6, 2×CH$_3$) 1.56 (s, 9, tertC$_4$H$_9$).

(1S,2S)-1-(9-tert-butyl-14-(thien-2-yl)-3-methoxy-5,6,10,11,12,13-hexahydroazocino[4',3':4,5]pyrrolo[2,1-a]isoquinolin-8(9H)-on-2-yl)propane-1,2,3-triol (21h)

A solution of 588 mg of 21g in 14 ml of 80% aq acetic acid was stirred at rt for 24 hr. The mixture was diluted with water, and neutralized by addition of cold ammonia. The product was extracted with ethyl acetate. The organic extract was washed, dried and concentrated and the isolated material was purified by chromatography over SiO$_2$, using a gradient of heptane-acetone as eluent. The material isolated that way was passed through a reversed phase column (LUNA-C18, using a gradient of acetonitrile-water) to provide, after concentration and freeze-drying of the pure fractions, 275 mg of 21h.

NMR (CDCl$_3$) δ 7.38, 7.12, and 6.91 (3×m, 3, thienyl-H), 6.72 and 6.96 (2×s, 2, Ar—H); 5.40 (b.d, 1, CHO), 4.65 and 3.90 (2×b.m, 2, CH$_2$), 4.60 (m, 1, CHO), 3.40-3.80 (bm, 5, CHO+CH$_2$O+CH$_2$), 3.50-3.90 (bm, 5, CHO+CH$_2$O+CH$_2$), 3.85 (s, 3, OCH$_3$), 2.95+3.15 (2×bm, 2, CH$_2$) 2.54 (bm, 2, CH$_2$) 1.60-2.0 (bm, 4, 2×CH$_2$), 1.58 (s, 9, tertC$_4$H$_9$).

hFSHRago (CHO luc) pEC$_{50}$=8.26.

Chiral integrity check was done by LC on analytical Chiracel-OD column, 20% ethanol in heptane as eluent. Retention Time 6.32 min for 21 h, and 8.13 min for 21i $α_D$ (c=0.2 ethanol)−25.1.

The synthesis of 21i is fully identical to that of 21h, except that in the conversion of 21b to 21c ADMix-alpha is used instead, leading to the other enantiomer; $α_D$ (c=0.2 ethanol)+24.6.

Compound 21i: hFSHRago (CHO luc) pEC$_{50}$=8.28.

3-(9-tert-butyl-14-(thien-2-yl)-3-methoxy-5,6,10,11,12,13-hexahydroazocino[4',3':4,5]pyrrolo[2,1-a]isoquinolin-8(9H)-on-2-yl)propan-1-ol (21j)

To a solution of 115 mg of 21b in 2 ml of dichloromethane was added 0.5 ml of a 2M solution of LiBH$_4$ in THF. The reaction mixture was stirred overnight, and then diluted with 5 ml of 2M citric acid solution, followed by 10 ml of water and extraction with ethyl acetate. The extract was dried and concentrated and the remainder was chromatographed over silicagel (using a gradient of heptane/ethyl acetate as eluent), to provide 75 mg of 21j. R$_f$ (heptane/ethyl acetate 1/1) 0.30. LC-MS-ESI: [M+1] 493.3. NMR (CDCl$_3$) δ7.38, 7.12 and 6.91 (3×m, 3, thiophene-H), 6.80 and 6.66 (2×s, 2, Ar—H), 4.60 and 3.85 (2×b.m, 2, CH$_2$), 3.55 and 3.80 (2×bm, 2, CH$_2$), 3.81 (s, 3, OCH$_3$), 3.45 (m, 2, CH$_2$O), 2.95 and 3.10 (2×b.m, 2, CH$_2$) 2.55 (bm, 2, CH$_2$), 2.45 (m, 2, propyl CH$_2$), 1.60 (m, 2, propyl CH$_2$), 1.55-2.05 (bm, 4, 2×CH$_2$), 1.58 (s, 3, tertC$_4$H$_9$).

hFSHRago (CHO luc) pEC$_{50}$=9.60.

Example 22

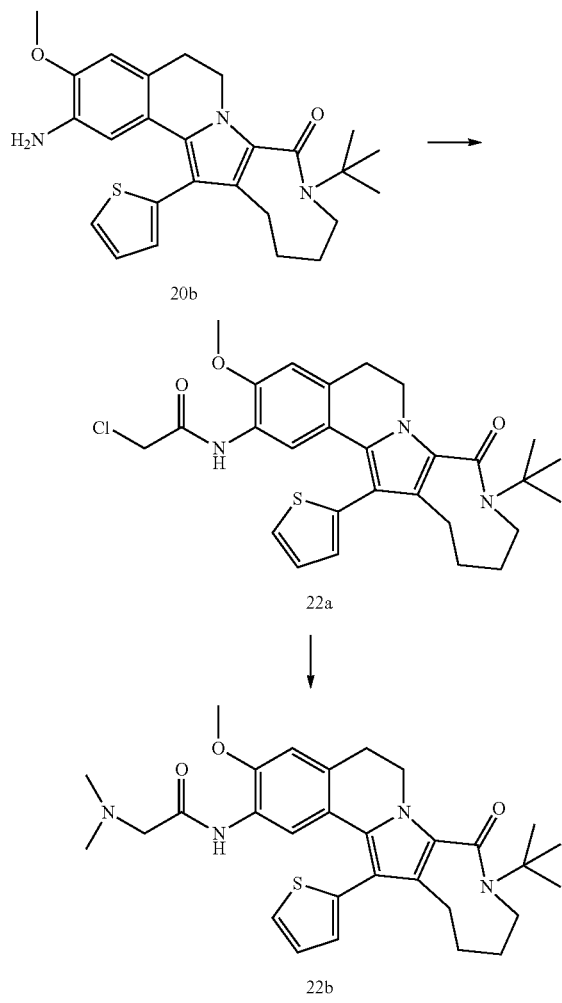

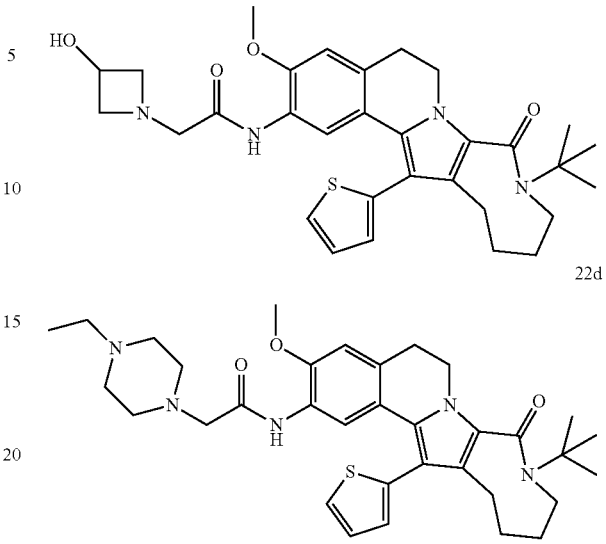

2-chloro-N-(9-tert-butyl-14-(thien-2-yl)-3-methoxy-5,6,10,11,12,13-hexahydroazocino[4',3':4,5]pyrrolo[2,1-a]isoquinolin-8(9H)-on-2-yl)acetamide (22a)

To a solution of 365 mg of 20b and 160 ul of triethylamine in 1 ml of CH$_2$Cl$_2$ was added at 0° C. 90 ul of chloroacetylchloride in ½ ml of CH$_2$Cl$_2$. The reaction was stirred for 15 min, and then diluted with water and extracted with ethyl acetate. The extract was washed several times with water, and then dried and concentrated. The residue was treated with diethylether, to provide, after decantation of the supernatant and drying 390 mg of light grey solid 22a; R$_f$ (heptane/ethyl acetate) 0.50 (R$_f$ 20b: 0.60). NMR (CDCl$_3$) δ 8.73 (bs, 1, NH), 7.42, 7.18, and 6.96 (3×m, 3, thienyl-H), 6.72 and 8.12 (2×s, 2, Ar—H), 4.62 and 3.88 (2×bm, 2, CH$_2$), 4.08 (s, 2, CH$_2$Cl), 3.87 (s, 3, OCH$_3$), 3.90 and 3.50 (2×bm, 2, CH$_2$), 2.90+3.10 (2×b.m, 2, CH$_2$), 2.52 (b.m, 2, CH$_2$), 1.60-2.0 (b.m, 4, 2×CH$_2$), 1.57 (s, 9, tertC$_4$H$_9$).

2-dimethylamino-N-(9-tert-butyl-14-(thien-2-yl)-3-methoxy-5,6,10,11,12,13-hexahydroazocino[4',3':4,5]pyrrolo[2,1-a] isoquinolin-8(9H)-on-2-yl)acetamide (22b)

A suspension of 392 mg of 22a in 3 ml of DMF was treated with 0.5 ml of triethylamine and 2 ml of a 2M solution of dimethylamine in THF. The reaction mixture was sealed and heated at an oil bath at 60° C. for 40 min. The clear solution was poured onto water and extracted with ethyl acetate. The extract was washed, dried and concentrated and the residue was purified by chromatography over silicagel, using a gradient of CH$_2$Cl$_2$-methanol. The material thus isolated was triturated with diethylether, to provide 438 mg of crystalline material.

LC-MS-ESI: [M+1] 535.4. NMR (CDCl$_3$) δ 9.31 (bs, 1, NH), 7.42, 7.18, and 6.97 (3×m, 3, thienyl-H), 6.70 and 8.11 (2×s, 2, Ar—H), 4.62 and 3.90 (2×b.m, 2, CH$_2$), 2.97 (s, 2, CH$_2$N) 3.87 (s, 3, OCH$_3$), 3.77 and 3.51 (2×b.m, 2, CH$_2$), 2.90+3.10 (2×bm, 2, CH$_2$) 2.52 (bm, 2, CH$_2$), 2.30 (s, 6, N—CH$_3$), 1.60-2.0 (bm, 4, 2×CH$_2$), 1.57 (s, 9, tertC$_4$H$_9$).

hFSHRago (CHO luc) pEC$_{50}$=8.33.

In a similar way were prepared:

2-(3-hydroxyazetidin-1-yl)-N-(9-tert-butyl-14-(thien-2-yl)-3-methoxy-5,6,10,11,12,13-hexahydroazocino[4',3':4,5]pyrrolo[2,1-a]isoquinolin-8(9H)-on-2-yl)acetamide (22c)

LC-MS-ESI: [M+1] 563.3. NMR (CDCl$_3$) δ 9.08 (b.s, 1, NH), 8.10 (s, 1, Ar—H), 6.70 (s, 1, Ar—H), 7.42, 7.18, 6.96 (3×m, 3, thiophene-H), 4.60 and 3.90 (2×b.m, 2, CH$_2$), 4.50 (m, 1, CHOH), 3.89 (s, 3, OCH$_3$), 3.20 (br.s, 2, CH$_2$), 3.55 and 2.90 (2×bm, 2, CH$_2$), 3.70 (bm, 2, CH$_2$), 3.08 (bm, 2, CH$_2$), 2.50 (bm, 2, CH$_2$), 1.50-2.00 (bm, 4, 2×CH$_2$), 1.57 (s, 9, tertC$_4$H$_9$).

hFSHRago (CHO luc) pEC$_{50}$=8.90.

2-(4-ethylpiperazin-1-yl)-N-(9-tert-butyl-14-(thien-2-yl)-3-methoxy-5,6,10,11,12,13-hexahydroazocino[4',3':4,5]pyrrolo[2,1-a]isoquinolin-8(9H)-on-2-yl)acetamide (22d)

LC-MS-ESI: [M+1] 604.13. NMR (DMSO-d6) δ 9.50 (s, 1, NH), 8.00 and 6.98 (2×s, 2, Ar—H), 6.91, 7.10 and 7.53 (3×m, 3, thiophene-H), 4.38, 3.70 and 3.55 (3×b.m, 4, 2×CH$_2$), 3.87 (s, 3, OCH$_3$), 2.97 (m, 4, 2×CH$_2$), 2.35 (q, 2, N-ethyl), 2.30-2.60 (b.m, 10, 5×CH$_2$), 1.50-1.80 (bm, 4, 2×CH$_2$) 1.52 (s, 9, tertC$_4$H$_9$), 1.00 (t, 3, N-ethyl).

hFSHRago (CHO luc) pEC$_{50}$=8.48.

Example 23

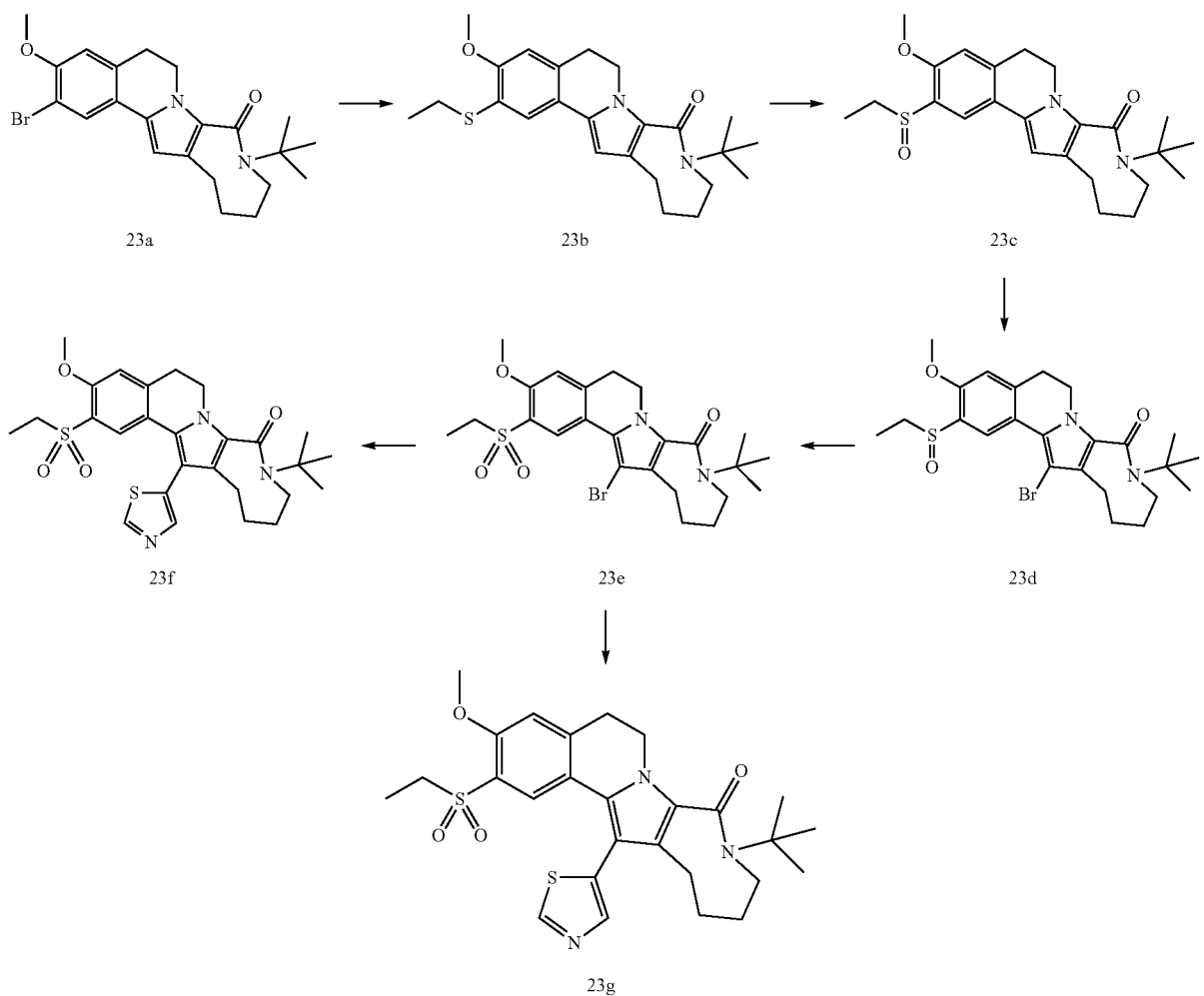

9-tert-butyl-2-ethylthio-3-methoxy-5,6,10,11,12,13-hexahydroazocino[4',3':4,5]pyrrolo[2,1-a]isoquinolin-8(9H)-one (23b)

To a solution of 430 mg of 23a in 6 ml of dry THF was added 700 ul of 1.6N BuLi in heptane at −60° C. The mixture was stirred for 15 min and then 200 mg of diethyldisulfide in 1 ml of THF was added dropwise in 1 min. The cooling was removed and the mixture was stirred for 1 hr at ambient temperature. The reaction was quenched with water and 3 ml of 2M NaOH. The product was extracted with ethyl acetate. The organic extract was dried and concentrated, and the residue was purified by chromatography over silicagel, (using a gradient of heptane/ethyl acetate) to give a colorless oil. This solidified on trituration with heptane, to provide 360 mg of 23b as white crystalline material. Mp: 124-125° C. $R_f$ (heptane/ethyl acetate 1/1): 0.56 (starting material $R_f$ 0.54)

LC-MS-ESI: [M+1] 413.11. NMR (CDCl$_3$) δ 1.30 (t, 3, ethyl); 2.90 (q, 2, ethyl), 1.56 (s, 9, tertC$_4$H$_9$), 3.90 (s, 3, OCH$_3$), 6.15, 6.68 and 7.40 (3×s, 3, Ar—H), 3.40-4.80 (.bm, 4, 2×CH$_2$), 2.72 and 3.00 (2×b.m, 4, 2×CH$_2$), 1.50-2.20 (bm, 4, 2×CH$_2$).

9-tert-butyl-2-ethylsulfinyl-3-methoxy-5,6,10,11,12, 13-hexahydroazocino[4',3':4,5]pyrrolo[2,1-a]isoquinolin-8(9H)-one (23c)

A solution of 350 mg of 23b in 15 ml of methanol was treated with a solution of 210 mg of NaIO$_4$ in 1.5 ml of water. The mixture was stirred for 16 hr and then diluted with 60 ml of water and extracted with ethyl acetate. The organic extract was washed with water, dried and concentrated.

The remaining oil was treated with heptane, to provide 370 mg of white crystalline 23c.

$R_f$ 0.18 (heptane/ethyl acetate 1/1). Mp: 185-187° C. LC-MS-ESI: [M+1] 429.10.

NMR (CDCl$_3$) δ 1.20 (t, 3, ethyl); 2.80 and 3.07 (2×m, 2, ethyl), 1.56 (s, 9, tertC$_4$H$_9$), 3.82 (s, 3, OCH$_3$), 6.31, 6.73 and 7.83 (3×s, 3, Ar—H), 3.30-4.60, (b.m, 4, 2×CH$_2$), 3.00-3.15 and 2.65-2.85 (2×b.m, 4, 2×CH$_2$), 1.50-2.00 (b.m, 4, 2×CH$_2$).

9-tert-butyl-14-bromo-2-ethylsulfinyl-3-methoxy-5, 6,10,11,12,13-hexahydroazocino[4',3':4,5]pyrrolo[2, 1-a]isoquinolin-8(9H)-one (23d)

A solution of 350 mg of 23c in 4 ml of DMF was treated with 155 mg of NBS. After stirring for 10 min. the reaction was diluted with 25 ml of water and extracted with ethyl acetate. The organic extract was washed with water, dried and concentrated, and the residue was treated with diisopropyl ether, to give 360 mg of 23d, Mp: 140-145° C. $R_f$ 0.18 (heptane/ethyl acetate 1/1). LC-MS-ESI: [M+1] 506.97 and 524.99. NMR (CDCl$_3$) δ 1.24 (t, 3, ethyl), 2.82 and 3.08 (2×m, 2, ethyl), 3.88 (s, 3, OCH$_3$), 6.77, 8.78 (2×s, 2, Ar—H).

hFSHRago (CHO luc) pEC$_{50}$=6.61.

9-tert-butyl-14-bromo-2-ethylsulfonyl-3-methoxy-5, 6,10,11,12,13-hexahydroazocino[4',3':4,5]pyrrolo[2, 1-a]isoquinolin-8(9H)-one (23e)

A solution of 350 mg of 23d, and 20g of Mn(III)TPPP (OAc) and 75 mg of imidazole in 20 ml of dichloromethane were treated with tetrabutylammonium oxone, according to a described procedure; D. Mohajer et al., *Tetr. Letters,* 45, 3811 (2004). This provide after work-up, and chromatographic purification on silicagel (using a gradient of CH$_2$Cl$_2$ and ethyl acetate as eluent) 160 mg of crystalline 23e (triturated with diisopropyl ether); Mp 227° C. $R_f$ (CH$_2$Cl$_2$-ethyl acetate 1/1) 0.61. LC-MS-ESI: [M+1] 522.97 and 524.99. NMR (CDCl$_3$) δ 1.28 (t, 3, ethyl), 3.38 (q, 2, ethyl), 1.58 (s, 9, tertC$_4$H$_9$), 4.00 (s, 3, OCH$_3$), 8.89 and 6.89 (2×s, 2, Ar—H), 4.50 and 3.85 (2×m, 2, CH$_2$), 3.80 and 3.50 (2×m, 2, CH$_2$), 3.05 (m, 2, CH$_2$), 2.70 (m, 2, CH$_2$) 1.90-1.65 (2×m, 4, 2×CH$_2$).

hFSHRago (CHO luc) pEC$_{50}$=6.81.

9-tert-butyl-14-(thien-2-yl)-2-ethylsulfonyl-3-methoxy-5,6,10,11,12,13-hexahydroazocino[4',3':4,5] pyrrolo[2,1-a]isoquinolin-8(9H)-one (23f)

A solution of 50 mg of 23e, 60 mg of 2-tributylstannylthiophene and 10 mg of tetrakis(triphenylphosphine)palladium (0) in 2 ml of toluene was heated at 125° C. for 16 hr under a nitrogen atmosphere. Reaction was cooled and applied onto silica gel column and eluted with a gradient of toluene/acetone. The fractions containing the product were pooled and concentrated and the remainder crystallized from ethylacetate/ether, providing 34 mg of 23f; Mp: 223-224° C. $R_f$ 0.55 (toluene/acetone 2/1). LC-MS-ESI: [M+1] 527.08. NMR (CDCl$_3$) δ 6.82 and 7.63 (2×s, Ar—H), 6.92, 7.16 and 7.41 (3×m 3, thienyl-H), 1.12 (t, 3, ethyl), 3.22 (m, 3, ethyl), 3.94 (s, 3, OCH$_3$), 4.70 (bm, 1, CH$_2$,) 3.80 (bm, 2, CH$_2$), 3.55 (bm, 1, CH$_2$), 3.02 and 3.20 (2×b.m, 2, CH$_2$), 2.55 (b.m, 2, CH$_2$), 1.60-2.00 (b.m, 4, CH$_2$), 1.56 (s, 9, tertC$_4$H$_9$).

hFSHRago (CHO luc) pEC$_{50}$=8.74.

9-tert-butyl-14-(thiazol-5-yl)-2-ethylsulfonyl-3-methoxy-5,6,10,11,12,13-hexahydroazocino[4',3':4, 5]pyrrolo[2,1-a]isoquinolin-8(9H)-one (23g).

Prepared in a similar way from 23e and 5-(tributylstannyl) thiazole, 23g, (crystallized from ethyl acetate), Mp 258-260° C. $R_f$ 0.35 (toluene/acetone 2/1)). LC-MS-ESI: [M+1] 527.99. NMR (CDCl$_3$) δ 6.87, 7.59, 7.70, and 8.91 (4×s, 4, Ar—H), 1.12 (t, 3, ethyl), 3.20 (m, 3, ethyl), 3.95 (s, 3, OCH$_3$), 4.70 (bm, 1, CH$_2$), 3.80 (bm, 2, CH$_2$), 3.55 (bm, 1, CH$_2$), 3.02 and 3.20 (2×bm, 2, CH$_2$) 2.50 (2×bm, 2, CH$_2$), 1.60-2.00 (bm, 4, CH$_2$), 1.58 (s, 9, tertC$_4$H$_9$).

hFSHRago (CHO luc) pEC$_{50}$=7.97.

Example 24

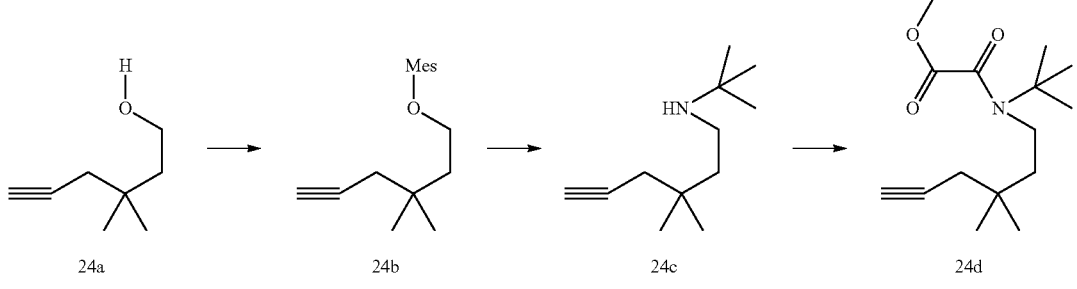

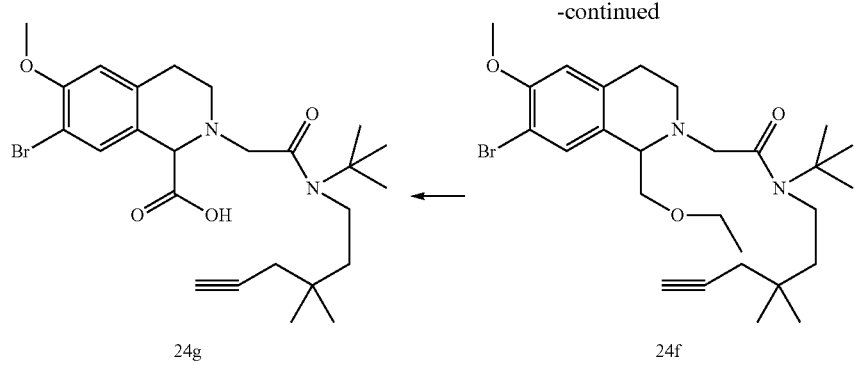

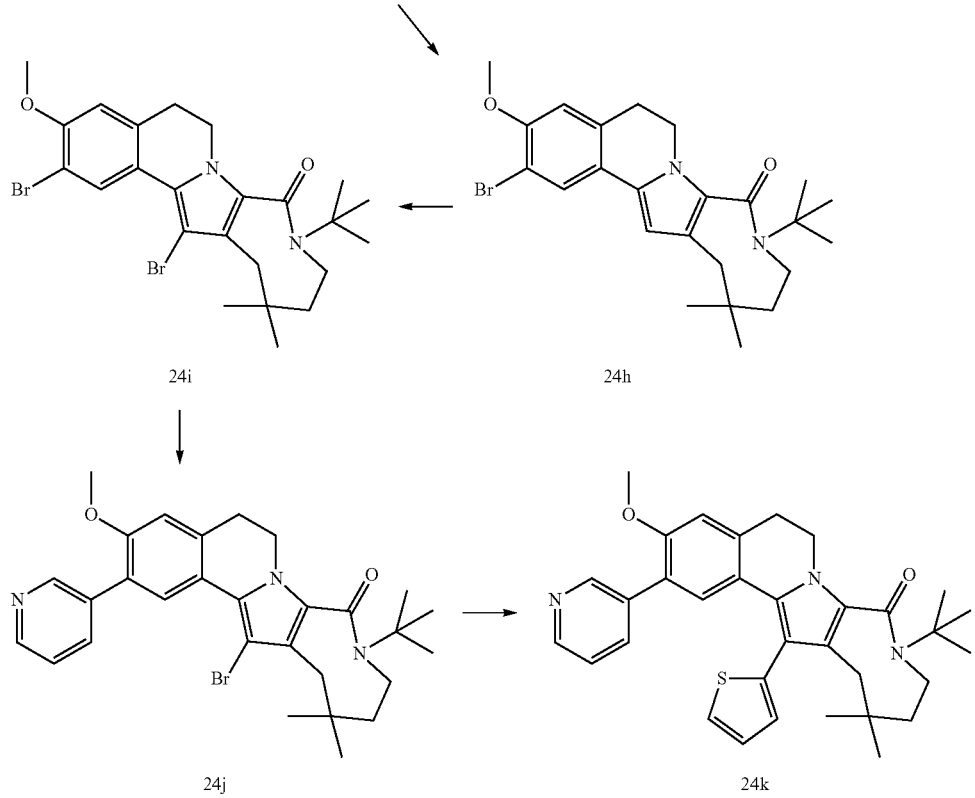

3,3-dimethylhex-5-ynyl methanesulfonate (24b)

To a solution of 900 mg of 24a (3,3-dimethylhex-5-yn-1-ol, G. B. Dudley et al., J. Amer. Chem. Soc., 128, 499 (2006)) in 15 ml of diethylether and 2 ml of triethylamine, was added at 0° C., 800 ul of methanesulfonylchloride. The reaction stirred for 15 min and then 20 ml of water was added. The product was extracted into ethyl acetate. The organic extract was washed with water and 1M $K_2CO_3$ and dried and concentrated to provide 1.3 g of 24b; $R_f$ (toluene/ethyl acetate 3/1) 0.60 ($R_f$ 24a: 0.40). NMR ($CDCl_3$) δ 1.05 (s, 6, 2×$CH_3$), 1.81 (t, 2, $CH_2$), 2.03 (t, 1, acetylene), 2.13 (d, 2, $CH_2$), 3.12 (s, 3, mesylate), 4.31 (t, 2, $CH_2$).

N-tert-butyl-3,3-dimethylhex-5-yn-1-amine (24c)

A solution of 1.3 g of 24b in 15 ml of tert.butylamine, was heated in a closed vessel at an oil bath at 70° C. for 4 days. The reaction was concentrated (rotavap, 150 mB, 40° C.) and then diluted with water and acidified with 1N HCl. The organic layer was washed twice with ether. The aqueous phase was made alkaline (2N NaOH) and extracted with diethylether. The organic material was dried and concentrated (100 mm, 40° C.) to give 960 mg of amine 24c, as a colorless oil. NMR ($CDCl_3$) δ 1.00 (s, 6, 2×$CH_3$), 1.11 (s, 9, tert$C_4H_9$), 1.47 (m, 2, $CH_2$), 1.98 (t, 1, acetylene), 2.10 (d, 2, $CH_2$), 2.55 (m, 2, $CH_2$).

ethyl 2-(tert-butyl(3,3-dimethylhex-5-ynyl)amino)-2-oxoacetate (24d)

To a solution of 310 mg of 24c and 500 ul of triethylamine in 7 ml of diethylether was added at 0° C., 300 ul of ethyloxalylchloride. The mixture was stirred for ½ hr and then diluted with water and acidified to pH 3 with 1N HCl. The organic material was extracted into ether; the organic layer was once washed with 1N NaOH, water, dried and concentrated, to give 450 mg of 24d, as yellowish oil. $R_f$ (heptane/ethyl acetate 1/1) 0.65. NMR ($CDCl_3$) δ 0.95 (s, 6, 2×$CH_3$), 1.38 (t, 3, ethyl ester), 4.30 (q, 2, ethyl ester), 1.48 (s, 9, tertC$_4$H$_9$), 1.70 (m, 2, CH$_2$), 2.02 (t, 1, acetylene), 2.08 (d, 2, CH$_2$), 3.30 (m, 2, CH$_2$).

2-(tert-butyl(3,3-dimethylhex-5-ynyl)amino)-2-oxoacetic acid (24e)

A mixture of 250 mg of 24d, 250 mg of KOH, 3 ml of dioxane and 1 ml of water was heated at oil bath at 50° C. for 1 hr. The mixture was poured onto water and extracted once with heptane/ether 1/1. The aqueous phase was acidified with cold 1N HCl to pH3 and extracted with ethyl acetate. The organic extract was once washed with sat. NaCl and dried and concentrated, to give 240 mg of 24e, as colorless oil. NMR (CDCl$_3$) δ 1.00 (s, 6, 2×CH$_3$), 1.50 (s, 9, tertC$_4$H$_9$), 2.00 (t, 1, acetylene), 1.70 (m, 2, CH$_2$), 2.10 (m, 2, CH$_2$), 3.71 (m, 2, CH$_2$).

2-(7-bromo-1-(ethoxymethyl)-6-methoxy-3,4-dihydroisoquinolin-2(1H)-yl)-N-tert-butyl-N-(3,3-dimethylhex-5-ynyl)acetamide (24f)

A mixture of 260 mg of 3a, 360 mg of 24e, 360 ul of NEM in 2 ml of DMF was stirred for 5 min. Then 370 mg of TBTU was added, and stirred for 16 hr. Then 20 ml of water and 2 ml of sat NH$_4$Cl and 30 ml of ethyl acetate were added and stirring prolonged for 15 min. The product was extracted into ethyl acetate.

The organic layer was washed with 2N NaOH and water, dried and concentrated

The material isolated was purified by chromatography over silicagel (using a gradient of heptane/ethyl acetate as eluent), to give 430 mg 24f, as a white foam.

R$_f$ (heptane/ethylacetate 1/1) 0.50. NMR (CDCl$_3$) δ 0.95 (s, 6, 2×CH$_3$), 3.89 (s, 3, OCH$_3$), 1.58 (s, 9, tertC$_4$H$_9$, 1.98 (t, 1, acetylene), 1.25 (t, 3, ethyl ester), 4.20 (m, 2, ethyl ester), 5.80 (s, 1, CH), 7.70 and 6.61 (2×s, 2, Ar—H).

7-bromo-2-(2-(tert-butyl-(3,3-dimethylhex-5-ynyl)amino)-2-oxoethyl)-6-methoxy-1,2,3,4-tetrahydroisoquinoline-1-carboxylic acid (24g)

A mixture of 430 mg of 24f, 300 mg of KOH, 10 ml of dioxane and 1.5 ml of water was warmed at 60° C. for 1 hr. Reaction was cooled and diluted with 30 ml of water and acidified to pH3 with 0.5 N HCl. The product was extracted into ethyl acetate. The organic extract was washed twice with water, dried and concentrated, to leave 390 mg of 24g, as a colorless oil. R$_f$ (toluene/acetone 1/1) 0.55. NMR (CDCl$_3$) δ 7.70 and 6.65 (2×s, 2, Ar—H), 5.79 (s, 1, CH), 3.90 (s, 3, OCH$_3$), 1.97 (t, 1, acetylene), 0.90 (s, 6, 2×CH$_3$), 1.55 (s, 9, tertC$_4$H$_9$).

9-tert-butyl-2-bromo-12,12-dimethyl-3-methoxy-5,6,10,11,12,13-hexahydroazocino[4',3':4,5]pyrrolo[2,1-a]isoquinolin-8(9H)-one (24h)

A solution of 350 mg of 24g in 5 ml of acetic anhydride and 300 mg of sodium acetate, was heated at 90-100° C. for 3 h. The reaction was cooled to rt and 10 ml of water was added and stirring at ambient temperature was prolonged for 1 hr. The mixture was neutralized by addition of cold conc. NH$_4$OH and the product was extracted with ethyl acetate. The organic extract was washed with water, dried and concentrated, and the remainders chromatographed over silicagel (using a gradient of heptane/ethyl acetate as eluent), to give 70 mg 24h (white crystalline material, triturated with heptane); Mp 175-177° C. R$_f$ (heptane/ethyl acetate 1/1) 0.75.
LC-MS-ESI: [M+1] 459.12 and 461.11. NMR (CDCl$_3$) δ 7.67, 6.73, 6.12 (3×s, 3, Ar—H),
0.90 (b.s, 6, 2×CH$_3$), 3.90 (s, 3, OCH$_3$).

9-tert-butyl-2,14-dibromo-12,12-dimethyl-3-methoxy-5,6,10,11,12,13-hexahydroazocino[4',3':4,5]pyrrolo[2,1-a]isoquinolin-8(9H)-one (24i)

To a solution of 70 mg of 24h in 1 ml of DMF was added 27 mg of NBS. The reaction was stirred for ½ hr at rt and then poured onto water, and extracted with ethyl acetate, The organic extract was washed, dried and concentrated and the material thus isolated was filtered through a short silica column (using heptane/ethyl acetate 1/1 as eluent).

The residue was triturated with pentane, to provide 55 mg of white crystalline dibromide 24i.

R$_f$ (heptane/ethyl acetate 2/1) 0.41 (R$_f$ 24h: 0.47). LC-MS-ESI: [M+1] 537.04, 539.04 and 541.04. NMR (CDCl$_3$) δ 8.60, 6.78 (2×s, 2, Ar—H), 0.88 and 1.08 (2×b.s, 6, 2×CH$_3$), 3.91 (s, 3, OCH$_3$), 1.56 (s, 9, tertC$_4$H$_9$).

9-tert-butyl-12,12-dimethyl-3-methoxy-2-pyridin-3-yl-14-bromo-5,6,10,11,12,13-hexahydroazocino[4',3':4,5]pyrrolo[2,1-a]isoquinolin-8(9H)-one (24j)

A solution of 55 mg of 241.18 mg of 3-pyridylboronic acid, 35 mg of K$_2$CO$_3$, and 10 mg of tetrakis(triphenylphosphine) palladium(0) in 2 ml of degassed 90% aq. DME was heated under N$_2$ for 16 hr. The reaction was cooled and diluted with 5% NaHCO$_3$ and extracted with ethyl acetate. The organic extract was washed with water, dried and concentrated and the residue was chromatographed over silicagel (using heptane/ethyl acetate 1/1 as eluent), to provide 30 mg of yellowish oil, 24j, which solidified on standing.

R$_f$ 0.30 (heptane/ethyl acetate 1/1). LC-MS-ESI: [M+1] 533.18 and 536.18. NMR (CDCl$_3$) δ 8.84, 8.57, 7.91, 7.35 (4×m, 4, pyridyl-H), 8.41, 6.87 (2×s, 2, Ar—H), 0.88 and 1.05 (2×b.s, 6, 2×CH$_3$), 3.85 (s, 3, OCH$_3$), 1.58 (s, 9, tertC$_4$H$_9$), 4.40-4.70 (b.m, 1, CH$_2$), 3.80-4.05 (b.m, 1, CH$_2$), 2.60 (b.m, 2, CH$_2$), 3.09 (b.m, 2, CH$_2$), 3.30-3.60 (b.m, 2, CH$_2$).

9-tert-butyl-12,12-dimethyl-3-methoxy-2-pyridin-3-yl-14-(2-thienyl)-5,6,10,11,12,13-hexahydroazocino[4',3':4,5]pyrrolo[2,1-a]isoquinolin-8(9H)-one (24k)

A solution of 31 mg of 24j, 35 ul of 2-(tributylstannyl)1-thiophene, 10 mg of tetrakis(triphenylphosphine)palladium (0), in 2 ml of toluene, was heated at 120° C. under N2 during 16 hr. The reaction was applied on a silica column using a gradient of toluene/ethyl acetate as eluent. This provided 30 mg of 24k.

Material was further purified on reversed phase C18 silica gel, employing a gradient of 50 to 100% acetonitrile. Fractions were pooled, concentrated and residue triturated with pentane/ether, to provide 15 mg of 24k as white crystalline material. R$_f$: 0.35 (toluene/ethyl acetate 2/1);

Mp: 142-144° C. LC-MS-ESI: [M+1] 540.20. NMR (CDCl$_3$) δ 8.48 (2×m, 2, pyridyl-H), 7.62, 7.23 (2×m, 2, pyridyl-H) 6.82, 6.89 (2×s, 2, Ar—H), 6.92, 7.12, 7.42 (3×m, 3, thienyl-H), 0.80 (bs, 6, 2×CH$_3$), 3.85 (s, 3, OCH$_3$), 1.58 (s, 9, tertC$_4$H$_9$), 4.25 (b.m, 1, CH$_2$), 3.50 (bm, 2, CH$_2$), 3.10 (t, 2, CH$_2$), 2.50 (s, 2, CH$_2$), 3.30-3.60 (bm, 2, CH$_2$).

hFSHRago (CHO luc) pEC$_{50}$=6.41.

Example 25

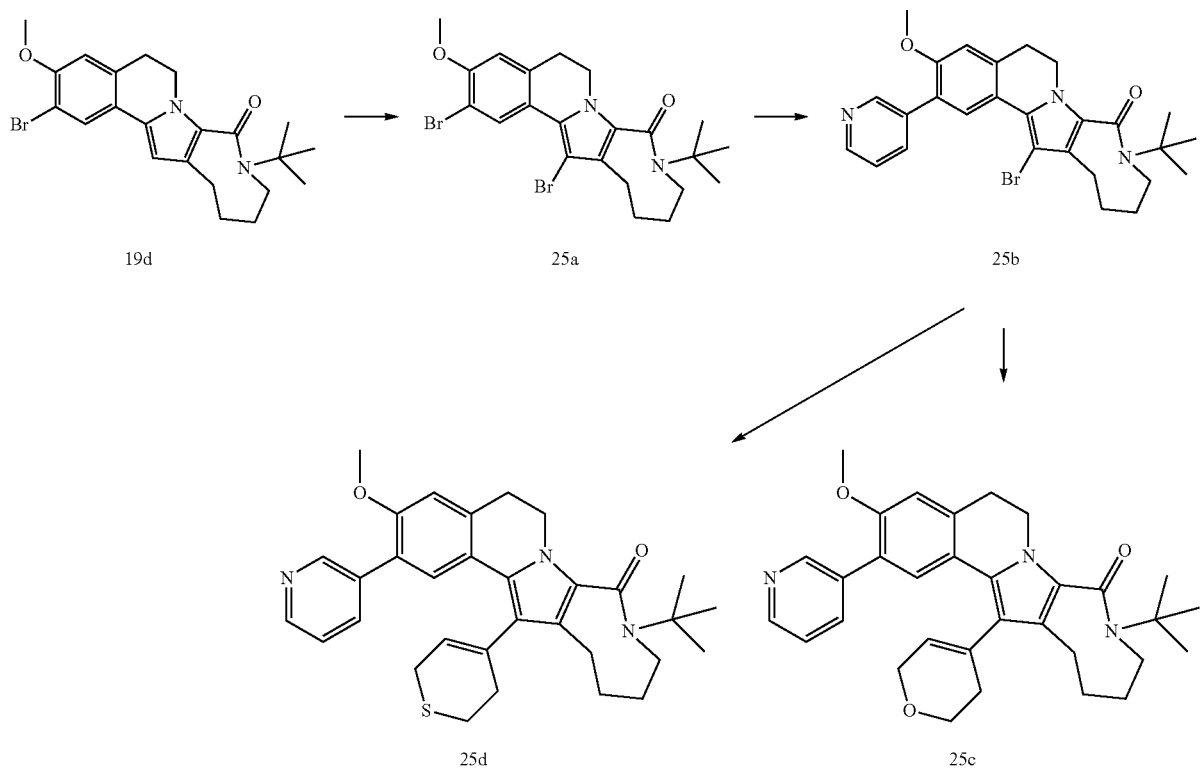

9-tert-butyl-2,14-dibromo-3-methoxy-5,6,10,11,12,13-hexahydroazocino[4',3':4,5]pyrrolo[2,1-a]isoquinolin-8(9H)-one (25a)

A solution of 506 mg of 19d in 4 ml of DMF was treated with 210 mg of NBS. The reaction was stirred for 45 min, then diluted with water, and stirred for an additional 15 min. The white precipitate was filtered and dried, to provide 543 mg of dibromide 25a.

NMR (CDCl$_3$) δ 8.55 and 6.77 (2×s, 2, Ar—H), 4.43, 3.80, 3.50 (3×b.m, 4, 2×CH$_2$), 3.91 (s, 3, OCH$_3$), 1.85 (s, 9, tertC$_4$H$_9$), 2.96 (b.m, 2, CH$_2$), 2.63 (b.m, 2, CH$_2$) 1.92 (b.m, 2, CH$_2$), 1.68 (b.m, 2, CH$_2$).

9-tert-butyl-2-(3-pyridyl)-14-bromo-3-methoxy-5,6,10,11,12,13-hexahydroazocino[4',3':4,5]pyrrolo[2,1-a]isoquinolin-8(9H)-one (25b)

A mixture of 250 mg of 25a, 72 mg of pyridine-3-boronic acid, 135 mg of K$_2$CO$_3$ and 5 ml of degassed 90% aqueous DME was heated under N$_2$ for 16 h at 90° C. The reaction was then cooled and diluted with water, and the product was extracted with ethyl acetate. The organic extract was washed with water, dried and concentrated, and the remainder was chromatographed over silica gel (using a gradient of heptane/ethyl acetate as eluent). The product isolated was triturated with diethylether, to provide 183 mg of 25b; NMR (CDCl$_3$) δ 8.85, 8.56, 7.91, and 7.35 (4×m, 4, pyridyl-H), 8.37 and 6.87 (2×s, 2, Ar—H), 4.45 and 3.40-3.90 (br.m, 4, 2×CH$_2$), 3.05 (bm, 2, CH$_2$), 2.60 (br.m, 2, CH$_2$), 1.90 and 1.70 (2×br.m, 4, 2×CH$_2$), 1.58 (s, 9, tertC$_4$H$_9$).

9-tert-butyl-2-(3-pyridyl)-14-(3,6-dihydro-2H-pyran-4-yl)-3-methoxy-5,6,10,11,12,13-hexahydroazocino[4',3':4,5]pyrrolo[2,1-a]isoquinolin-8(9H)-one (25c)

A mixture of 75 mg of 25b, 37 mg of 2-(3,6-dihydro-2H-pyran-4-yl)-4,4,5,5,-tetramethyl-1,3,2-dioxaborolane, 41 mg of K$_2$CO$_3$ and 17 mg of tetrakis(triphenylphosphine)palladium(0) in 3 ml of degassed DMF was heated under N$_2$ atmosphere at 125° C. for 2 hr. The reaction was cooled and diluted with 15 ml of water. The product was extracted with ethyl acetate. The organic extract was washed with water, dried and concentrated. The remainder was chromatographed over silcagel (using a gradient of heptane/acetone as eluent). The product isolated was triturated with diethyl ether, providing 57 mg of white crystalline 25c; Mp 208-210° C. LC-MS-ESI: [M+1] 512.13. NMR (CDCl$_3$) δ 8.70, 8.58, 7.88, and 7.37 (4×m, 4, pyridine-H), 7.68 and 6.87 (2×s, 2, Ar—H), 1.60 (s, 9, tertC$_4$H$_9$), 3.87 (s, 3, OCH$_3$), 5.75 (m, 1, CH), 4.30 (m, 2, CH$_2$O), 4.70 (bm, 1, CH$_2$), 3.55 (bm, 1, CH), 3.85 (bm, 4, 2×CH$_2$) 3.00 and 3.20 (2×bm, 2, CH$_2$), 2.63 (bm, 2, CH$_2$), 2.35 (m, 2, CH$_2$), 1.70-2.05 (bm, 4, 2×CH$_2$).

hFSHRago (CHO luc) pEC$_{50}$=8.20.

9-tert-butyl-2-(3-pyridyl)-14-(3,6-dihydro-2H-thiopyran-4-yl)-3-methoxy-5,6,10,11,12,13-hexahydroazocino[4',3':4,5]pyrrolo[2,1-a]isoquinolin-8(9H)-one (25d)

Compound 25d was synthesized in a similar way as 25c, starting from 40 mg 25b and 21.4 mg 2-(3,6-dihydro-2H-thiopyran-4-yl)-4,4,5,5,-tetramethyl-1,3,2-dioxaborolane to give 1.4 mg of compound 25d.

LC-MS-ESI: [M+1] 528.3 hFSHRago (CHO luc) pEC$_{50}$=7.97.

Example 26

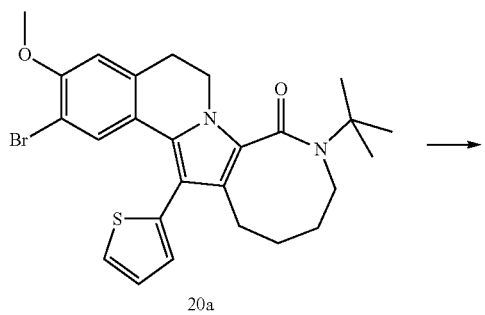
20a

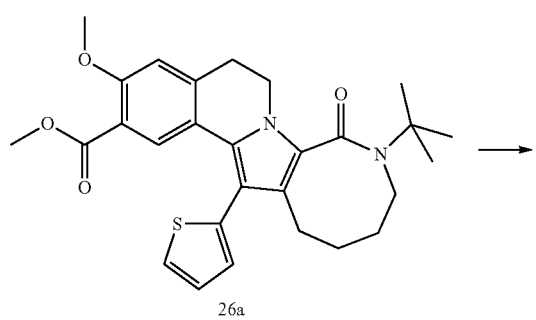
26a

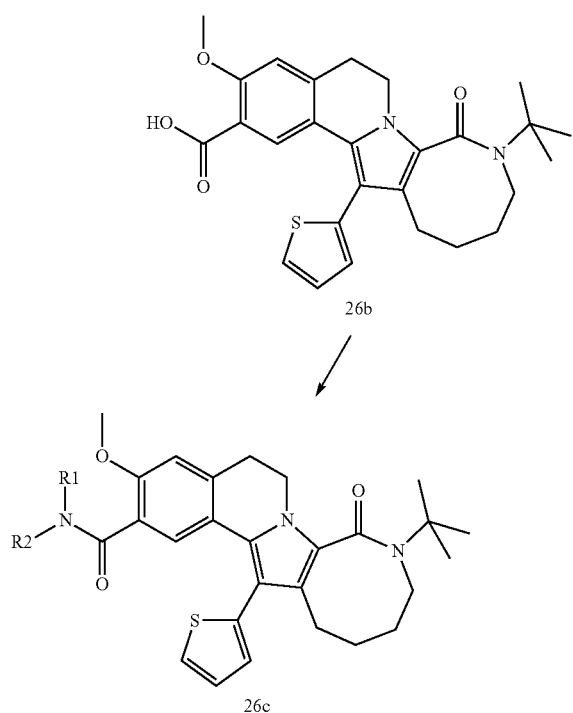
26b

26c

—NR1R2 =

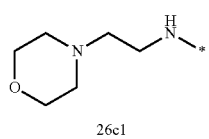
26c1

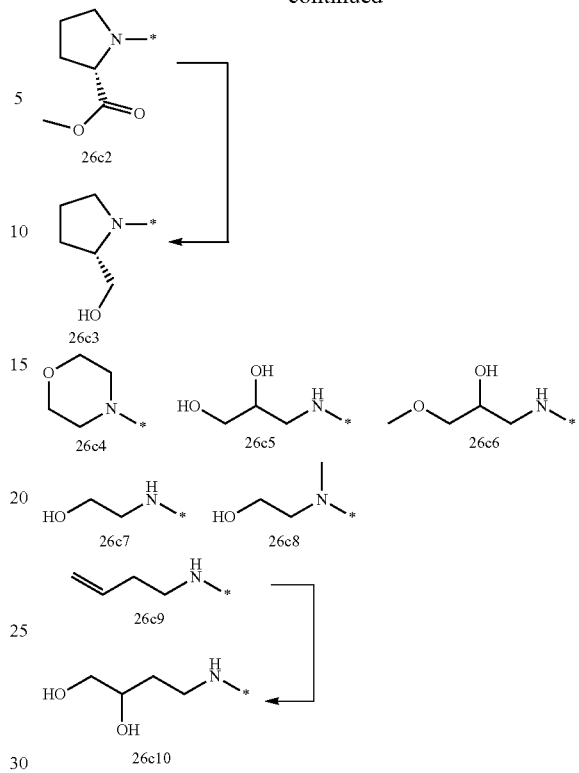

methyl 9-tert-butyl-3-methoxy-14-(thiophen-2-yl)-5,6,10,11,12,13-hexahydroazocino[4',3':4,5]pyrrolo[2,1-a]isoquinolin-8(9H)-one-2-carboxylate (26a)

To a degassed solution of 5.71 g 20a, 1.22 g 1,3-bis(diphenylphosphino)propane and 4.80 mL triethylamine in 150 mL DMF/methanol (2:1) was added 0.719 g Pd(II)OAc. The mixture was degassed and flushed with carbon monoxide and was then stirred at 100° C. under 2 bar carbon monoxide for 16 h. The reaction mixture was cooled to room temperature, 100 mL water was added and the mixture was extracted with 2×100 mL ethyl acetate. The combined organic layers were washed with 2×50 mL water, 50 mL brine, dried and concentrated to give 6.00 g of a yellow oil. Trituration with diisopropyl ether provided 5.74 g of 26a as a yellow solid that was used without further purification in the subsequent step.

MS-ESI: [M+1] 493.3

NMR (CDCl$_3$) δ 1.58 (s, 9H, tertC$_4$H$_9$), 1.70, 1.82, 2.57 (m, br, 6H, 3×CH$_2$), 3.00, 3.14 (m, br, 2×1H, CH$_2$), 3.56 (m, br, 1H, CH$_2$), 3.70 (s, 3H, OCH$_3$), 3.84 (m, br, 2×1H, CH$_2$+CH$_2$), 3.88 (s, 3H, CO$_2$CH$_3$), 4.64 (m, br, 1H, CH$_2$), 6.78 (s, 1H, ArH), 6.93, 7.13, 7.40 (3×m, 3H, 3×thiophene-H), 7.52 (s, 1H, ArH).

hFSHRago (CHO luc) pEC$_{50}$=9.00.

9-tert-butyl-3-methoxy-14-(thiophen-2-yl)-5,6,10,11,12,13-hexahydroazocino[4',3':4,5]pyrrolo[2,1-a]isoquinolin-8(9H)-one-2-carboxylic acid (26b)

To a solution of 480 mg 26a in 10 mL methanol was added a solution of 164 mg potassium hydroxide in 10 mL water. The mixture was stirred at 80° C. for 5 h and then at 50° C. for 16 h. The reaction mixture was poured into a 2M solution of citric acid in water and was extracted with 2×50 mL dichloromethane. The combined organic layers were washed with brine, dried (MgSO$_4$) and concentrated to give 460 mg of compound 26b.

MS-ESI: [M+1] 479.09

NMR (CDCl$_3$) δ 1.58 (s, 9H, tertC$_4$H$_9$), 1.73, 1.82, 2.57 (m, br, 6H, 3×CH$_2$), 3.04, 3.17 (m, br, 2×1H, CH$_2$), 3.55 (m, br, 1H, CH$_2$), 3.83 (m, br, 2×1H, CH$_2$+CH$_2$), 4.04 (s, 3H, OCH$_3$), 4.68 (m, br, 1H, CH$_2$), 6.86 (s, 1H, ArH), 6.95, 7.17, 7.43 (3×m, 3H, 3×thiophene-H), 7.86 (s, 1H, ArH), 10.38 (s, br, 1H, CO$_2$H).

hFSHRago (CHO luc) pEC$_{50}$=7.35

9-tert-butyl-3-methoxy-N$^2$-(2-morpholinoethyl)-14-(thiophen-2-yl)-5,6,10,11,12,13-hexahydroazocino[4',3':4,5]pyrrolo[2,1-a]isoquinolin-8(9H)-one-2-carboxamide (26c1)

General Method

To a solution of 440 mg 26b in 5 mL DMF was added 0.111 mL N-methylmorpholine, 137 mg 1-hydroxybenzothiazole (HOBt) and 194 mg 1-(3-dimethylaminopropyl)-3-ethylcarbodiimidehydrochloride (EDCI). The reaction mixture was stirred at room temperature for 2 h and was then poured into a water/ethyl acetate mixture. The organic layer was washed with 2× water, dried (MgSO$_4$) and concentrated. The crude product was stirred with diethyl ether and the solid was filtered to give 400 mg of the HOBt ester as yellow solid.

25 mg of the crude HOBt ester was dissolved in 2 mL methylene chloride and 14 μL diisopropylethylamine (DIPEA) and 11 μL N-(2-aminoethyl)morpholine was added. The reaction mixture was stirred at room temperature for 1 h. The reaction mixture was then washed with 2× water, dried (MgSO$_4$) and concentrated. The crude product was purified by preparative HPLC on a reversed phase C18 column to give 6.3 mg of compound 26c1.

MS-ESI: [M+1] 591.15

NMR (DMSO-d6) δ 1.52 (s, 9H, tertC$_4$H$_9$), 1.71, 1.75 (m, br, 4H, 2×CH$_2$), 2.42 (m, br, 8H, 4×CH$_2$), 3.04 (m, br, CH$_2$), 3.30 (t, br, 2H, CH$_2$), 3.56 (m, br, 1H, CH$_2$), 3.60 (t, br, 4H, 2×CH$_2$O), 3.68 (m, br, 1H, CH$_2$), 3.75 (m, br, 1H, CH$_2$), 3.83 (s, 3H, OCH$_3$), 4.40 (m, br, 1H, CH$_2$), 7.07 (s, 1H, ArH), 6.93, 7.13, 7.35 (3×m, 3H, 3×thiophene-H), 7.66 (s, 1H, ArH), 8.17 (t, br, 1H, NH).

hFSHRago (CHO luc) pEC$_{50}$=8.75.

(S)-9-tert-butyl-3-methoxy-14-(thiophen-2-yl)-5,6,10,11,12,13-hexahydroazocino[4',3':4,5]pyrrolo[2,1-a]isoquinolin-8(9H)-one-2-carbonyl(1-pyrrolidinyl-2-carboxylate) methyl ester (26c2)

Similarly prepared as compound 26c1.
MS-ESI: [M+1] 590.13
hFSHRago (CHO luc) pEC$_{50}$=7.43.

(S)-9-tert-butyl-3-methoxy-2-(2-hydroxymethyl-1-pyrrolidinylcarbonyl)-14-(thiophen-2-yl)-5,6,10,11,12,13-hexahydroazocino[4',3':4,5]pyrrolo[2,1-a]isoquinolin-8(9H)-one (26c3)

To a solution of 23.1 mg 26c2 in 2 mL methylene chloride was added 0.157 mmol lithium borohydride. The reaction mixture was stirred at room temperature for 3 h. The reaction mixture was washed with 2× water, dried (MgSO4) and concentrated. The crude product was purified by preparative HPLC on a reversed phase C18 column to give 10.4 mg of compound 26c3.

MS-ESI: [M+1] 562.4

NMR (CDCl$_3$) δ 1.59 (s, 9H, tertC$_4$H$_9$), 1.67, 1.76, 1.87, 2.09 (4×m, br, 8H, 4×CH$_2$), 2.54 (m, br, 2H, CH$_2$), 2.96, 3.04 (m, br, 2×1H, CH$_2$), 3.17 (m, br, 2H, CH$_2$), 3.54 (m, 2×1H, CH$_2$+CH$_2$), 3.77 (m, br, 2×1H, CH$_2$+CH$_2$), 3.83 (s, 3H, OCH$_3$), 3.85 (m, br, 1H, CH$_2$), 4.25 (m, br, 1H, CH$_2$), 4.70 (m, br, 2×1H, CH$_2$+OH), 6.76 (s, 1H, ArH), 6.85 (s, 1H, ArH), 6.91, 7.08, 7.34 (3×m, 3H, 3×thiophene-H).

hFSHRago (CHO luc) pEC$_{50}$=7.56.

9-tert-butyl-3-methoxy-2-(4-morpholinylcarbonyl)-14-(thiophen-2-yl)-5,6,10,11,12,13-hexahydroazocino[4',3':4,5]pyrrolo[2,1-a]isoquinolin-8(9H)-one (26c4)

Similarly prepared as compound 26c1.
MS-ESI: [M+1] 548.2
NMR (CDCl$_3$) δ 1.60 (s, 9H, tertC$_4$H$_9$), 1.73, 1.88, (2×m, br, 4H, 2×CH$_2$), 2.52 (m, br, 2H, CH$_2$), 2.95, 3.15, 3.40, 3.56, 3.76 (m, br, 9H, 4×CH$_2$+CH$_2$), 3.82 (s, 3H, OCH$_3$), 4.76 (m, br, 1H, CH$_2$), 6.76 (s, 1H, ArH), 6.86 (s, 1H, ArH), 6.89, 7.08, 7.35 (3×m, 3H, 3×thiophene-H).
hFSHRago (CHO luc) pEC$_{50}$=8.01.

9-tert-butyl-3-methoxy-2-(2,3-dihydroxy-1-propylaminocarbonyl)-14-(thiophen-2-yl)-5,6,10,11,12,13-hexahydroazocino[4',3':4,5]pyrrolo[2,1-a]isoquinolin-8(9H)-one (26c5)

Similarly prepared as compound 26c1.
MS-ESI: [M+1] 552.08
NMR (CDCl$_3$) δ 1.59 (s, 9H, tertC$_4$H$_9$), 1.74, 1.87, (2×m, br, 4H, 2×CH$_2$), 2.56 (m, br, 2H, CH$_2$), 3.00, 3.08, 3.18, 3.53, 3.77, 3.86 (m, br, 11H, 4×CH$_2$+CH$_2$+2×OH), 3.94 (s, 3H, OCH$_3$), 4.66 (m, br, 1H, CH$_2$), 6.78 (s, 1H, ArH), 6.95, 7.17, 7.43 (3×m, 3H, 3×thiophene-H), 7.87 (s, 1H, ArH), 7.96 (t, br, 1H, NH).
hFSHRago (CHO luc) pEC$_{50}$=9.06.

9-tert-butyl-3-methoxy-2-(2-hydroxy-3-methoxy-1-propylaminocarbonyl)-14-(thiophen-2-yl)-5,6,10,11,12,13-hexahydroazocino[4',3':4,5]pyrrolo[2,1-a]isoquinolin-8(9H)-one (26c6)

Similarly prepared as compound 26c1.
MS-ESI: [M+1] 566.11
NMR (CDCl$_3$) δ 1.58 (s, 9H, tertC$_4$H$_9$), 1.74, 1.88, (2×m, br, 4H, 2×CH$_2$), 2.56 (m, br, 2H, CH$_2$), 3.00, 3.15, 3.28-3.43, 3.55, 3.64, 3.82, 3.92 (m, br, 11H, 4×CH$_2$+CH$_2$+2×OH), 3.37 (s, 3H, OCH$_3$), 3.94 (s, 3H, OCH$_3$), 4.65 (m, br, 1H, CH$_2$), 6.78 (s, 1H, ArH), 6.95, 7.17, 7.43 (3×m, 3H, 3×thiophene-H), 7.90 (s, 1H, ArH), 8.03 (t, br, 1H, NH).
hFSHRago (CHO luc) pEC$_{50}$=8.97.

9-tert-butyl-2-(2-hydroxyethylaminocarbonyl)-3-methoxy-14-(thiophen-2-yl)-5,6,10,11,12,13-hexahydroazocino[4',3':4,5]pyrrolo[2,1-a]isoquinolin-8(9H)-one (26c7)

Similarly prepared as compound 26c1.
MS-ESI: [M+1] 522.2
NMR (CDCl$_3$) δ 1.58 (s, 9H, tertC$_4$H$_9$), 1.74, 1.85, (2×m, br, 4H, 2×CH$_2$), 2.56 (m, br, 2H, CH$_2$), 2.76, 3.00, 3.15, 3.55, 3.75, 3.84 (m, br, 10H, 4×CH$_2$+CH$_2$+OH), 3.84 (s, 3H, OCH$_3$), 4.64 (m, br, 1H, CH$_2$), 6.78 (s, 1H, ArH), 6.95, 7.17, 7.43 (3×m, 3H, 3×thiophene-H), 7.92 (s, 1H, ArH), 8.04 (t, br, 1H, NH).
hFSHRago (CHO luc) pEC$_{50}$=9.37.

9-tert-butyl-2-(N-2-hydroxyethyl,N-methylaminocarbonyl)-3-methoxy-14-(thiophen-2-yl)-5,6,10,11,12,13-hexahydroazocino[4',3':4,5]pyrrolo[2,1-a]isoquinolin-8(9H)-one (26c8)

Similarly prepared as compound 26c1.

MS-ESI: [M+1] 536.2

NMR (CDCl$_3$) δ 1.58 (s, 9H, tertC$_4$H$_9$), 1.74, 1.85, (2×m, br, 4H, 2×CH$_2$), 2.55 (m, br, 2H, CH$_2$), 2.77 (s, 3H, NCH$_3$), 2.97, 3.15 (m, 2×1H, 2×CH$_2$), 3.56 (m, br, 1H, CH$_2$), 3.62 (m, 2H, CH$_2$N), 3.79 (m, br, 4H, CH$_2$+2×CH$_2$), 3.83 (s, 3H, OCH$_3$), 4.66 (m, br, 1H, CH$_2$), 4.77 (s, br, 1H, OH), 6.75 (br, 1H, ArH), 6.84 (s, br, 1H, ArH), 6.90, 7.08, 7.35 (3×m, 3H, 3×thiophene-H).

hFSHRago (CHO luc) pEC$_{50}$=8.27.

9-tert-butyl-2-(4-butenylaminocarbonyl)-3-methoxy-14-(thiophen-2-yl)-5,6,10,11,12,13-hexahydroazocino[4',3':4,5]pyrrolo[2,1-a]isoquinolin-8(9H)-one (26c9)

Similarly prepared as compound 26c1.

MS-ESI: [M+1] 532.2

NMR (CDCl$_3$) δ 1.58 (s, 9H, tertC$_4$H$_9$), 1.74, 1.86, 2.29, 2.56 (m, br, 8H, 4×CH$_2$), 2.99, 3.13 (m, br, 2×1H, CH$_2$), 3.46 (m, 2H, CH$_2$), 3.54 (m, br, 1H, CH$_2$), 3.82 (m, br, 2×1H, CH$_2$+CH$_2$), 3.89 (s, 3H, OCH$_3$), 4.64 (m, br, 1H, CH$_2$), 5.12 (2×m, 2H, CH$_2$), 5.80 (m, 1H, =CH), 6.77 (s, 1H, ArH), 6.96, 7.18, 7.44 (3×m, 3H, 3×thiophene-H), 7.72 (t, br, 1H, NH), 7.93 (s, 1H, ArH).

hFSHRago (CHO luc) pEC$_{50}$=9.33.

9-tert-butyl-2-(3,4-dihydroxybutylaminocarbonyl)-3-methoxy-14-(thiophen-2-yl)-5,6,10,11,12,13-hexahydroazocino[4',3':4,5]pyrrolo[2,1-a]isoquinolin-8(9H)-one (26c10)

To a solution of 50 mg 26c9 in a mixture of 11 mL acetone/ethanol/water (5:5:1) was added 23 mg 4-methylmorpholine-N-oxide and 59.8 mg osmium tetraoxide. The reaction mixture was stirred at room temperature for 2 h. Another 10 mL ethanol was added and the mixture was stirred for another 16 h. Then a 10% solution of KHSO$_4$ in water was added and the mixture was stirred for 30 min. Ethyl acetate was added and the organic phase was washed with water, saturated aqueous NH$_4$Cl solution, water and brine. The organic phase was dried (MgSO$_4$) and concentrated. The crude product was purified over a 4g silica SPE column and was then purified further by preparative HPLC on a reversed phase C18 column to give 17.4 mg of compound 26c10.

MS-ESI: [M+1] 566.23

NMR (CDCl$_3$) δ 1.57 (s, 9H, tertC$_4$H$_9$), 1.62, 1.75, 1.86, 2.23, 2.56 (m, br, 8H, 4×CH$_2$), 3.00, 3.13 (m, br, 2×1H, CH$_2$), 3.23 (m, 2H, CH$_2$N), 3.47 (m, 1H, CHOH), 3.58 (m, br, 3×1H, CH$_2$+CH$_2$OH+OH), 3.83 (m, br, 3×1H, CH$_2$+CH$_2$+CH$_2$OH), 3.93 (s, 3H, OCH$_3$), 4.32 (s, br, 1H, OH), 4.66 (m, br, 1H, CH$_2$), 6.77 (s, 1H, ArH), 6.95, 7.16, 7.43 (3×m, 3H, 3×thiophene-H), 7.83 (m, br, 1H, NH), 7.86 (s, 1H, ArH).

hFSHRago (CHO luc) pEC$_{50}$=8.71.

Example 27

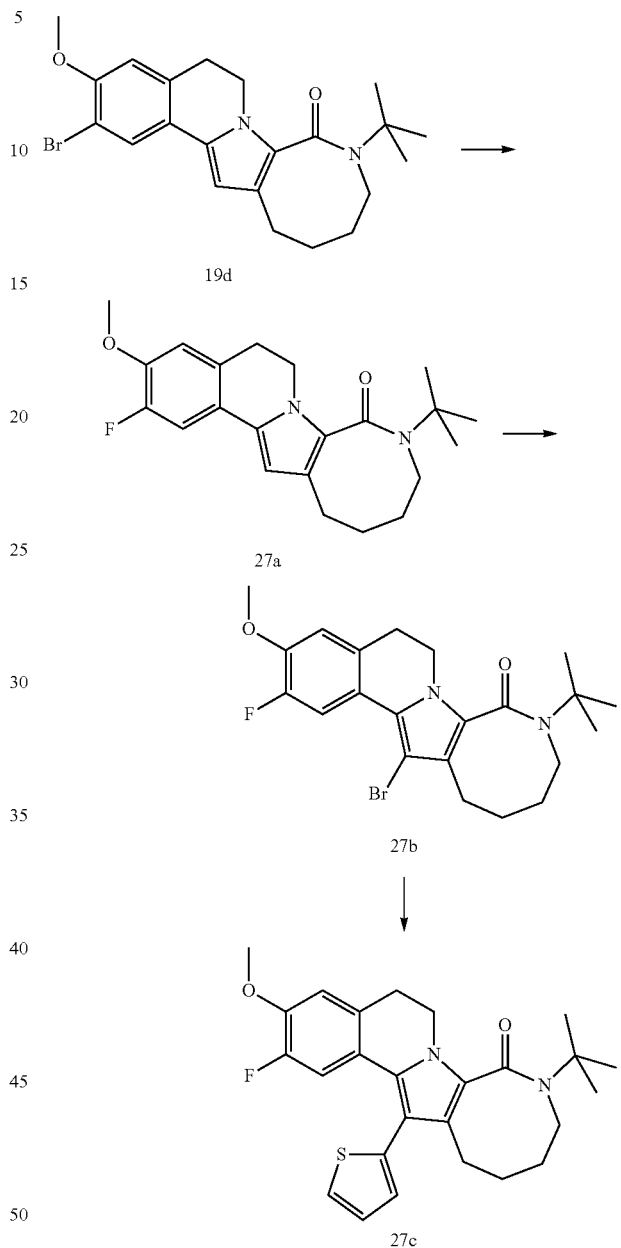

9-tert-butyl-2-fluoro-3-methoxy-5,6,10,11,12,13-hexahydroazocino[4',3':4,5]pyrrolo[2,1-a]isoquinolin-8(9H)-one (27a)

To a cooled (−60° C.) solution of 800 mg 19d in 10 mL THF was added 2.04 mmol n-butyllithium. After stirring at −60° C. for 30 min 877 mg N-fluorobenzenesulfonimide was added. The mixture was allowed to reach room temperature and was stirred for another 2 h. Water was added and the mixture was extracted with 2×ethyl acetate. The combined organic phases were dried and concentrated. The crude product by column chromatography over silica to afford an oil, which was crystallized from heptane/diisopropyl ethyl ether to give compound 340 mg of 27a as a pale yellow solid.

MS-ESI: [M+1] 371.17.

14-bromo-9-tert-butyl-2-fluoro-3-methoxy-5,6,10,11,12,13-hexahydroazocino[4',3':4,5]pyrrolo[2,1-a]isoquinolin-8(9H)-one (27b)

To a solution of 250 mg 27a in 7 mL dimethylformamide was added 120 mg N-bromosuccinimide. The reaction mixture was stirred at room temperature for 1 h. Water was added and the mixture was extracted with 2×ethyl acetate. The combined organic phases were washed with water and brine, dried and concentrated. The crude product was triturated with heptane/diisopropyl ethyl ether (1:1) to afford 230 mg of 27b as a white solid.

MS-ESI: [M+1] 449.04/451.02.

9-tert-butyl-2-fluoro-3-methoxy-14-(thiophen-2-yl)-5,6,10,11,12,13-hexahydroazocino[4',3':4,5]pyrrolo[2,1-a]isoquinolin-8(9H)-one (27c)

To a degassed solution of 50 mg 27b and 62.3 mg 2-(tributylstannyl)thiophene in 3 mL toluene was added 12.9 mg tetrakis(triphenylphosphine)palladium(0). The mixture was stirred at reflux for 16 h. The crude reaction mixture purified by column chromatography over silica and was then triturated with diisopropyl ethyl ether/pentane (1:1) to give 38 mg 27c as a yellow solid.

MS-ESI: [M+1] 453.11

NMR (CDCl$_3$) δ 1.58 (s, 9H, tertC$_4$H$_9$), 1.72, 1.86, 2.53 (m, br, 6H, 3×CH$_2$), 2.93, 3.07 (m, br, 2×1H, CH$_2$), 3.54 (m, br, 1H, CH$_2$), 3.80 (m, br, 2×1H, CH$_2$+CH$_2$), 3.86 (s, 3H, OCH$_3$), 4.61 (m, br, 1H, CH$_2$), 6.75 (d, J=13 Hz, 1H, ArH), 6.77 (d, J=9 Hz, 1H, ArH), 6.91, 7.12, 7.38 (3×m, 3H, 3×thiophene-H).

hFSHRago (CHO luc) pEC$_{50}$=7.52.

Example 28

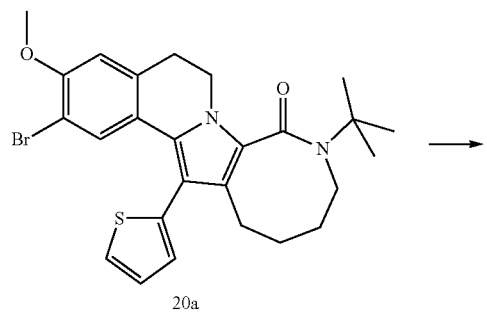

20a

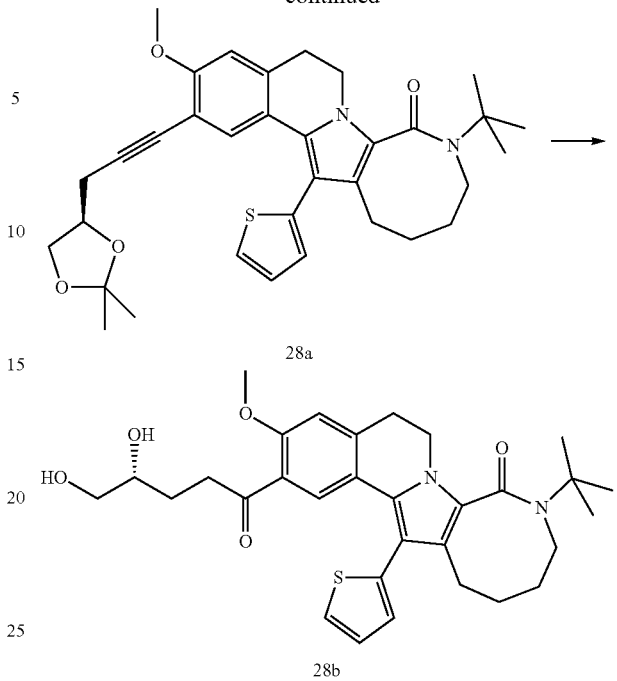

28a

28b (R)-9-tert-butyl-2-((2,2-dimethyl-1,3-dioxolan-4-yl)prop-1-ynyl)-3-methoxy-14-(thiophen-2-yl)-5,6,10,11,12,13-hexahydroazocino[4',3':4,5]pyrrolo[2,1-a]isoquinolin-8(9H)-one (28a)

To a suspension of 30 mg 20a in 0.4 mL diisopropylamine was added 6.8 mg tetrakis(triphenylphosphine)palladium(0), 2.2 mg copper(I) iodide and 12.3 mg (R)-2,2-dimethyl-4-(prop-2-ynyl)-1,3-dioxolane. The reaction mixture was stirred at 80° C., under a nitrogen atmosphere for 3 h. Ethyl acetate was added and the mixture was washed with water and brine, dried (Na$_2$SO$_4$) and concentrated. The crude product was purified by column chromatography over silica to afford 47 mg of 28a.

MS-ESI: [M+1] 573.18.

(R)-9-tert-butyl-2-(4,5-dihydroxypentanoyl)-3-methoxy-14-(thiophen-2-yl)-5,6,10,11,12,13-hexahydroazocino[4',3':4,5]pyrrolo[2,1-a]isoquinolin-8(9H)-one (28b)

A solution of 40 mg of 28a in 1 mL 80% acetic acid was stirred at room temperature for 16 h. Then water was added and the mixture was made alkaline with ammonia. The mixture was extracted with 2×ethyl acetate. The combined organic phases were dried and concentrated. The crude product was purified by preparative HPLC on a reversed phase C18 column to give 8.8 mg of compound 28b.

MS-ESI: [M+1] 551.3

NMR (CDCl$_3$) δ 1.62 (s, 9H, tertC$_4$H$_9$), 1.68 (m, br, 2H, CH$_2$), 1.80 (m, 1H, CH2), 1.92 (m, br, 2H, CH$_2$), 2.07 (m, 1H, CH$_2$) 2.58 (m, br, 2H, CH$_2$), 2.91 (m, 2H, CH$_2$C=O), 3.03, 3.17 (m, br, 2×1H, CH$_2$), 3.45 (m, 1H, CHOH), 3.56 (m, br, 1H, CH$_2$), 3.63 (m, 1H, CH$_2$), 3.67 (br, 1H, OH), 3.85 (m, br, 3×1H, CH$_2$+CH$_2$+OH), 3.86 (s, 3H, OCH$_3$), 3.86 (m, 1H, CH$_2$), 4.68 (m, br, 1H, CH$_2$), 6.82 (s, 1H, ArH), 6.96, 7.17, 7.44 (3×m, 3H, 3×thiophene-H), 7.45 (s, 1H, ArH).

hFSHRago (CHO luc) pEC$_{50}$=8.58.

Example 29

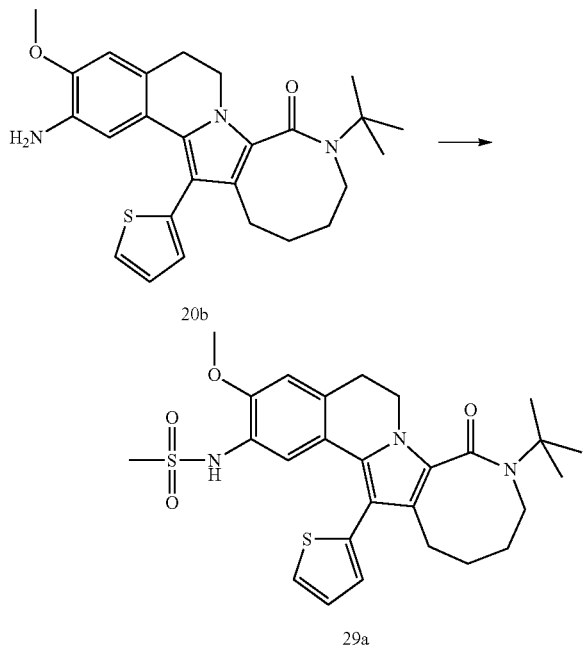

9-tert-butyl-3-methoxy-2-(methylsulfonamido)-14-(thiophen-2-yl)-5,6,10,11,12,13-hexahydroazocino[4',3':4,5]pyrrolo[2,1-a]isoquinolin-8(9H)-one (29a)

To a solution of 12.5 mg 20b in 2 mL methylene chloride was added 3.2 µL methanesulphonyl chloride and 9.2 µL N,N-diisopropylethylamine. The mixture was stirred at room temperature. After 1 h the mixture was diluted with methylene chloride and was washed with water. The organic phase was dried and concentrated. The crude product was purified by preparative HPLC on a reversed phase C18 column to give 1.8 mg of compound 29a.

MS-ESI: [M+1] 528.2

NMR (CDCl$_3$) δ 1.59 (s, 9H, tertC$_4$H$_9$), 1.76, 1.88 (m, br, 4H, 2×CH$_2$), 2.53 (m, br, 2H, CH$_2$), 2.97, 3.17 (m, br, 2×1H, 2×CH$_2$), 3.27 (m, br, 3H, SO$_2$CH$_3$), 3.55 (m, br, 1H, CH$_2$), 3.78 (m, 2H, 2×CH$_2$), 3.89 (s, 3H, OCH$_3$), 4.71 (m, br, 1H, CH$_2$), 6.83 (s, 1H, ArH), 6.92 (s, 1H, ArH), 6.95, 7.09, 7.34 (3×m, 3H, 3×thiophene-H).

hFSHRago (CHO luc) pEC$_{50}$=8.71

Example 30

Agonistic Activity of Compounds at the Human FSH Receptor Expressed in CHO Cells Agonistic activity of the compounds at the human FSH receptor was determined in Chinese Hamster Ovary (CHO) cells stably transfected with the human FSH receptor and cotransfected with a cAMP responsive element (CRE)/promotor directing the expression of a firefly luciferase reporter gene. Binding of the compounds to the Gs protein-coupled FSH receptor will result in an increase of cAMP, which in turn will induce an increased transactivation of the luciferase reporter. Cells (7,500 cells/well of a 384 well plate) were incubated in Dulbecco' minimal essential F12 modified medium (Invitrogen), supplemented with 1 µg/ml bovine insulin, 5 µg/ml human apo-transferrin, 80 U/ml penicillin G and 80 µg/ml streptomycin with the test compounds (concentration between 0.0316 nM and 10.0 µM) in duplicate in a humidified atmosphere (95%) at 5-7% CO2 and 37° C. The final concentration of DMSO was 1%. After 4 hours of incubation, plates were allowed to adjust to room temperature for 1 hour. Then, Luclite (PerkinElmer) solution was added to the wells and cells were allowed to lyse for at least 1 hour at room temperature. Subsequently, luciferase activity was measured in a luminescence counter. The signal is expressed as counts per second (cps). The EC$_{50}$ (concentration of the test compound that elicits half-maximal (50%) luciferase stimulation compared to the compound's maximally attainable effect) and efficacy values (maximal effect of the test compound as percentage of the maximal effect of recombinant human FSH) of the compounds were determined using the software program MathIQ (version 2.0, ID Business Solutions Limited). pEC$_{50}$ data (pEC$_{50}$ is −log EC$_{50}$) are indicated at the synthesis examples.

The invention claimed is:
1. A ring-annulated dihydropyrrolo[2,1-a]isoquinoline derivative according to formula I

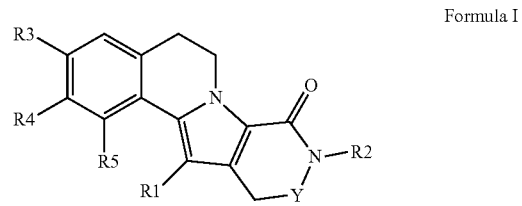

Formula I or a pharmaceutically acceptable salt thereof wherein
R1 is phenyl, (2-5C)heteroaryl, (3-6C)cycloalkyl, (1-6C)alkyl, (2-5C)heterocycloalkyl or (2-5C)heterocycloalkenyl, each optionally substituted with one or more (1-3C)alkyl or halogen; or
R1 is halogen;
R2 is H or (1-4C)alkyl;
R3 is hydroxyl, (1-3C)alkoxy; (1-3C)alkylthio or (1-4C)alkyl;
R4 is (1-5C)heteroaryl, (2-5C)heterocycloalkyl or (2-5C)heterocycloalkenyl, each optionally substituted with one or more hydroxy, cyano, halogen, (1-3C)alkoxy or (1-6C)alkyl, the alkyl group optionally substituted with one or more hydroxy or fluorine; or
R4 is halogen, nitro, cyano, amino, carboxylic acid or N-hydroxy-imidamide; or
R4 is (1-6C)alkyl, (2-6C)alkenyl, (2-6C)alkynyl, (3-6C)cycloalkyl, (1-6C)alkoxy, (1-6C)alkylthio, (1-6C)alkylOC(O)(1-6C)alkyl, each optionally substituted with one or more hydroxy, oxo, cyano or fluorine; or
R4 is —NH(CO)R6, —NHSO2R6, —NHR6, —C(O)N(R7)R8, —C(O)OR6, —S(O)R6 or —SO2R6;
R5 is H or halogen;
R6 is (1-6C)alkyl, (2-6C)alkenyl or (2-5C)heteroaryl, each optionally substituted with one or more (1-3C)alkyl, (1-3C)alkoxy, hydroxy or halogen; or
R6 is (di)[(1-4C)alkyl]amino(1-4C)alkyl, (di)[(1-4C)alkyl]aminoC(O)(1-4C)alkyl or (2-5C)heterocycloalkyl (1-4C)alkyl, the heterocycloalkyl group optionally substituted with one or more (1-4C)alkyl, oxo, hydroxy, fluorine or (di)[(1-4C)alkyl]amino(1-4C)alkyl;

Y is a bond, Y is $(CH_2)_n$ or Y is $X(CH_2)_m$, wherein one or more of the hydrogen atoms in the $(CH_2)_n$ or $(CH_2)_m$ groups in Y may optionally be substituted with (1-3C) alkyl, fluorine or hydroxy;

X is O, S or NR9;

R7 is H or (1-6C)alkyl, optionally substituted with one or more hydroxyl groups;

R8 is H, or (1-6C)alkyl, (1-6C)alkenlyl or (2-5C)heteroaryl, each optionally substituted with one or more (1-3C)alkyl, (1-3C)alkoxy, hydroxy or halogen; or R8 is (2-5C)heterocycloalkyl(1-4C)alkyl, the heterocycloalkyl group optionally substituted with (1-4C)alkyl or (di)[(1-4C)alkyl]amino(1-4C)alkyl; or R7 and R8 can form, together with the interconnecting nitrogen, a (2-5)heterocycloalkyl group, optionally substituted with hydroxy, (1-6C)alkoxycarbonyl or (1-6C) alkyl, the alkyl group optionally substituted with one or more hydroxy or fluorine;

R9 is hydrogen or R10-carbonyl;

R10 is (1-3C)alkyl, optionally substituted with halogen;

n is 0-4;

m is 2 or 3.

2. The compound according to claim 1 wherein R4 is (1-5C) heteroaryl, optionally substituted with (1-3C)alkyl or halogen; or R4 is nitro, (1-6C)alkyl, (1-6C)alkoxy, (1-6C) alkylthio, or —NH(CO)R6.

3. The compound according to claim 1 wherein R5 is H.

4. The compound according to claim 1 wherein R6 is (1-3C)alkyl.

5. The compound according to claims 1 wherein R3 is (1-3C)alkoxy.

6. The compound according to claims 1 wherein Y is $(CH_2)_n$ or Y is $X(CH_2)_m$, wherein one or more of the hydrogen atoms in the $(CH_2)_n$ or $(CH_2)_m$ groups in Y may optionally be substituted with (1-3C)alkyl.

7. The compound according to claim 1 wherein Y is $(CH_2)_3$.

8. The compound according to claim 1 wherein Y is $X(CH_2)_2$.

9. The compound according to claim 1 wherein R1 is thienyl or thiazolyl.

10. A pharmaceutical composition made by combining a compound according to claim 1, or a pharmaceutically acceptable salt thereof and one or more pharmaceutically acceptable excipients.

11. A pharmaceutical composition which comprises a compound according to claim 1 or a pharmaceutically acceptable salt thereof and one or more pharmaceutically acceptable excipients.

12. A pharmaceutical composition according to claim 11, which further comprises at least one additional therapeutically active agent.

* * * * *